US011654036B2

(12) United States Patent
Sirhan et al.

(10) Patent No.: US 11,654,036 B2
(45) Date of Patent: May 23, 2023

(54) ANTICOAGULANT COMPOUNDS AND METHODS AND DEVICES FOR THEIR USE

(71) Applicant: Elixir Medical Corporation, Milpitas, CA (US)

(72) Inventors: Motasim Sirhan, Los Altos, CA (US); Xiaoxia Zheng, Fremont, CA (US); Vinayak D. Bhat, Cupertino, CA (US); John Yan, Los Gatos, CA (US)

(73) Assignee: Elixir Medical Corporation, Milpitas, CA (US)

( * ) Notice: Subject to any disclaimer, the term of this patent is extended or adjusted under 35 U.S.C. 154(b) by 52 days.

(21) Appl. No.: 17/402,357

(22) Filed: Aug. 13, 2021

(65) Prior Publication Data

US 2022/0039976 A1    Feb. 10, 2022

Related U.S. Application Data

(63) Continuation of application No. PCT/US2021/034108, filed on May 25, 2021.
(Continued)

(51) Int. Cl.
*A61K 31/5377* (2006.01)
*A61F 2/82* (2013.01)
(Continued)

(52) U.S. Cl.
CPC .............. *A61F 2/844* (2013.01); *A61F 2/82* (2013.01); *A61F 2/848* (2013.01);
(Continued)

(58) Field of Classification Search
None
See application file for complete search history.

(56) References Cited

U.S. PATENT DOCUMENTS

| 5,506,241 A | 4/1996 | Mano et al. |
| 6,500,855 B1 | 12/2002 | Lam et al. |

(Continued)

FOREIGN PATENT DOCUMENTS

| CA | 2464290 A1 | 5/2003 |
| EP | 1849434 A1 | 10/2007 |

(Continued)

OTHER PUBLICATIONS

Becker et al. "Antithrombotic Drugs: Pharmacology and Implication for Dental Practice" Anesth Prog. 2013, 60(2) pp. 72-80. (Year: 2013).*

(Continued)

*Primary Examiner* — Carlos A Azpuru
*Assistant Examiner* — Casey S Hagopian
(74) *Attorney, Agent, or Firm* — Wilson Sonsini Goodrich & Rosati

(57) ABSTRACT

Devices, systems, and methods are provided including a structure having one or more surfaces configured for internal use within a patient's body and one or more therapeutic compositions comprising one or more active substances including a direct factor Xa inhibitor, and a direct factor IIa inhibitor disposed in or on the structure. The structure is configured to be positioned adjacent an injury site in the patient's body. The one or more active substances optionally include an anti-proliferative agent. The therapeutic composition is formulated to release the one or more active substances to the injury site to provide one or more of inhibit clot formation, promote clot dissolution, inhibit or dissolute inflammation, inhibit vessel injury, increase time before clotting, and/or inhibit cell proliferation.

48 Claims, 17 Drawing Sheets

Related U.S. Application Data

(60) Provisional application No. 63/030,203, filed on May 26, 2020, provisional application No. 63/174,496, filed on Apr. 13, 2021.

(51) Int. Cl.

| | | |
|---|---|---|
| *A61L 27/50* | (2006.01) | |
| *A61L 27/54* | (2006.01) | |
| *A61L 31/16* | (2006.01) | |
| *A61L 33/00* | (2006.01) | |
| *A61L 27/20* | (2006.01) | |
| *A61L 27/34* | (2006.01) | |
| *A61L 31/04* | (2006.01) | |
| *A61L 31/10* | (2006.01) | |
| *A61L 33/08* | (2006.01) | |
| *A61K 31/4545* | (2006.01) | |
| *A61L 27/58* | (2006.01) | |
| *A61F 2/844* | (2013.01) | |
| *A61K 31/727* | (2006.01) | |
| *A61F 2/848* | (2013.01) | |
| *A61K 31/4709* | (2006.01) | |

(52) U.S. Cl.
CPC ...... *A61K 31/4545* (2013.01); *A61K 31/4709* (2013.01); *A61K 31/5377* (2013.01); *A61K 31/727* (2013.01); *A61L 27/20* (2013.01); *A61L 27/34* (2013.01); *A61L 27/507* (2013.01); *A61L 27/54* (2013.01); *A61L 31/04* (2013.01); *A61L 31/042* (2013.01); *A61L 31/10* (2013.01); *A61L 31/16* (2013.01); *A61L 33/0011* (2013.01); *A61L 33/08* (2013.01); *A61F 2210/0004* (2013.01); *A61F 2220/0008* (2013.01); *A61F 2250/0035* (2013.01); *A61F 2250/0068* (2013.01); *A61L 27/58* (2013.01)

(56) References Cited

U.S. PATENT DOCUMENTS

| | | | |
|---|---|---|---|
| 7,018,990 | B2 | 3/2006 | Wong et al. |
| 8,409,272 | B2 | 4/2013 | Omura et al. |
| 8,946,219 | B2 | 2/2015 | Conley et al. |
| 9,687,529 | B2 | 6/2017 | Sullenger et al. |
| 10,668,015 | B2 | 6/2020 | Narasimhan et al. |
| 2002/0045613 | A1 | 4/2002 | Pauls et al. |
| 2003/0017211 | A1 | 1/2003 | Steiner et al. |
| 2003/0158120 | A1 | 8/2003 | Mattsson |
| 2004/0092477 | A1 | 5/2004 | Bernat et al. |
| 2005/0064006 | A1 | 3/2005 | Perzborn et al. |
| 2005/0169908 | A1 | 8/2005 | Murakami et al. |
| 2006/0014698 | A1 | 1/2006 | O'Connor et al. |
| 2007/0098753 | A1* | 5/2007 | Falotico ............... A61L 31/16 514/291 |
| 2008/0241215 | A1 | 10/2008 | Falotico et al. |
| 2009/0048667 | A1 | 2/2009 | Mochizuki et al. |
| 2009/0075949 | A1 | 3/2009 | Eisert |
| 2010/0003542 | A1 | 1/2010 | Perzborn et al. |
| 2010/0130543 | A1 | 5/2010 | Gant et al. |
| 2010/0184729 | A1 | 7/2010 | Reilly et al. |
| 2012/0202232 | A1 | 8/2012 | Braun et al. |
| 2013/0115363 | A1* | 5/2013 | Omura ............... A61P 7/00 427/2.25 |
| 2013/0199527 | A1 | 8/2013 | Smutney et al. |
| 2014/0083421 | A1 | 3/2014 | Smutney et al. |
| 2015/0056604 | A1 | 2/2015 | Sehgal |
| 2016/0199205 | A1 | 7/2016 | Cottone |
| 2016/0213499 | A1 | 7/2016 | Zheng et al. |
| 2017/0056518 | A1 | 3/2017 | Chang et al. |
| 2017/0291892 | A1 | 10/2017 | Rohrig et al. |
| 2018/0000490 | A1 | 1/2018 | Kaplan et al. |
| 2018/0000750 | A1* | 1/2018 | Tseng ............... A61K 31/519 |
| 2018/0008540 | A1 | 1/2018 | Narasimhan et al. |
| 2020/0138852 | A1 | 5/2020 | Chattaraj et al. |

FOREIGN PATENT DOCUMENTS

| | | |
|---|---|---|
| WO | WO-2005077344 A2 | 8/2005 |
| WO | WO-2007056218 A2 | 5/2007 |
| WO | WO-2008033956 A2 | 3/2008 |
| WO | WO-2009114010 A1 | 9/2009 |
| WO | WO-2010040064 A1 | 4/2010 |
| WO | WO-2012047813 A1 | 4/2012 |
| WO | WO-2013007840 A1 | 1/2013 |
| WO | WO-2022031758 A1 | 2/2022 |

OTHER PUBLICATIONS

Lipinski et al., Comparison of acute thrombogenicity for magnesium versus stainless steel stents in a porcine arteriovenous shunt model, Euro Intervention 2019;vol. 14, No. 13, pp. 1420-1427, published online May 2018.
Otsuka et al., Acute Thrombogenicity of a Durable Polymer Everolimus-Eluting Stent Relative to Contemporary Drug-Eluting Stents With Biodegradable Polymer Coatings Assessed Ex Vivo in a Swine Shunt Model, JACC: Cardiovascular Interventions, vol. 8, Issue 9, Aug. 17, 2015, pp. 1248-1260.
PCT/US2021/034108 International Search Report and Written Opinion ofthe International Searching Authority dated Sep. 23, 2021.
Schwartz et al., Drug-Eluting Stents in Preclinical Studies: Recommended Evaluation From a Consensus Group, Circulation, vol. 106, Issue 14, Oct. 1, 2002; pp. 1867-1873.
Schwartz et al., Restenosis and the Proportional Neointimal Response to Coronary Artery Injury: Results in a Porcine Model, Journal of the American College of Cardiology, vol. 19, Issue 2, Feb. 1992, pp. 267-274.
Waksman et al., Comparison of Acute Thrombogenicity for Metallic and Polymeric Bioabsorbable Scaffolds: Magmaris Versus Absorb in a Porcine Arteriovenous Shunt Model, Circulation: Cardiovascular Interventions, vol. 10, Issue 8, Aug. 2017.
PCT/US2021/049964 International Search Report and Written Opinion ofthe International Searching Authority dated Dec. 20, 2021.
Gould et al., Inhibitors of blood coagulation factors Xa and IIa synergize to reduce thrombus weight and thrombin generation in vivo and in vitro, Journal of Thrombosis and Haemostasis,Apr. 2006;4(4); pp. 834-841.
Lyon et al., Evaluation of the thrombin inhibitor D-phenylalanyl-L-prolyl-L-arginine chloromethylketone (PPACK) with the factor Xa inhibitor 1,5-dansyl-L-glutamyl-Lglycyl-L-arginine chloromethylketone (GGACK) as anticoagulants for critical care clinical chemistry specimens, Clinica Chimica Acta Feb. 1999; 280(1-2):91-99.
PCT/US2021/044414 International Search Report and Written Opinion dated Jan. 11, 2022.
Robertson, Lindsay et al. Oral direct thrombin inhibitors or oral factor Xa inhibitors for the treatment of pulmonary embolism. The Cochrane database of systematic reviews vol. 2015,12CD010957. Dec. 4, 2015, doi:10.1002/14651858.CD010957.pub2.

* cited by examiner

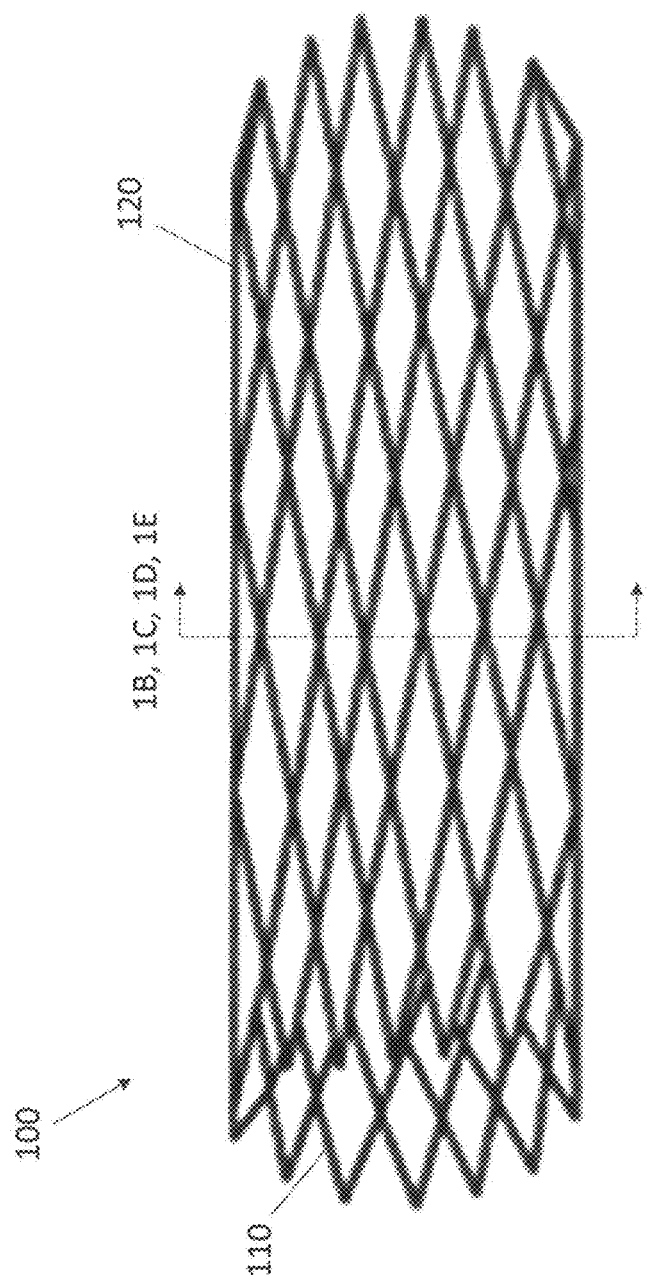

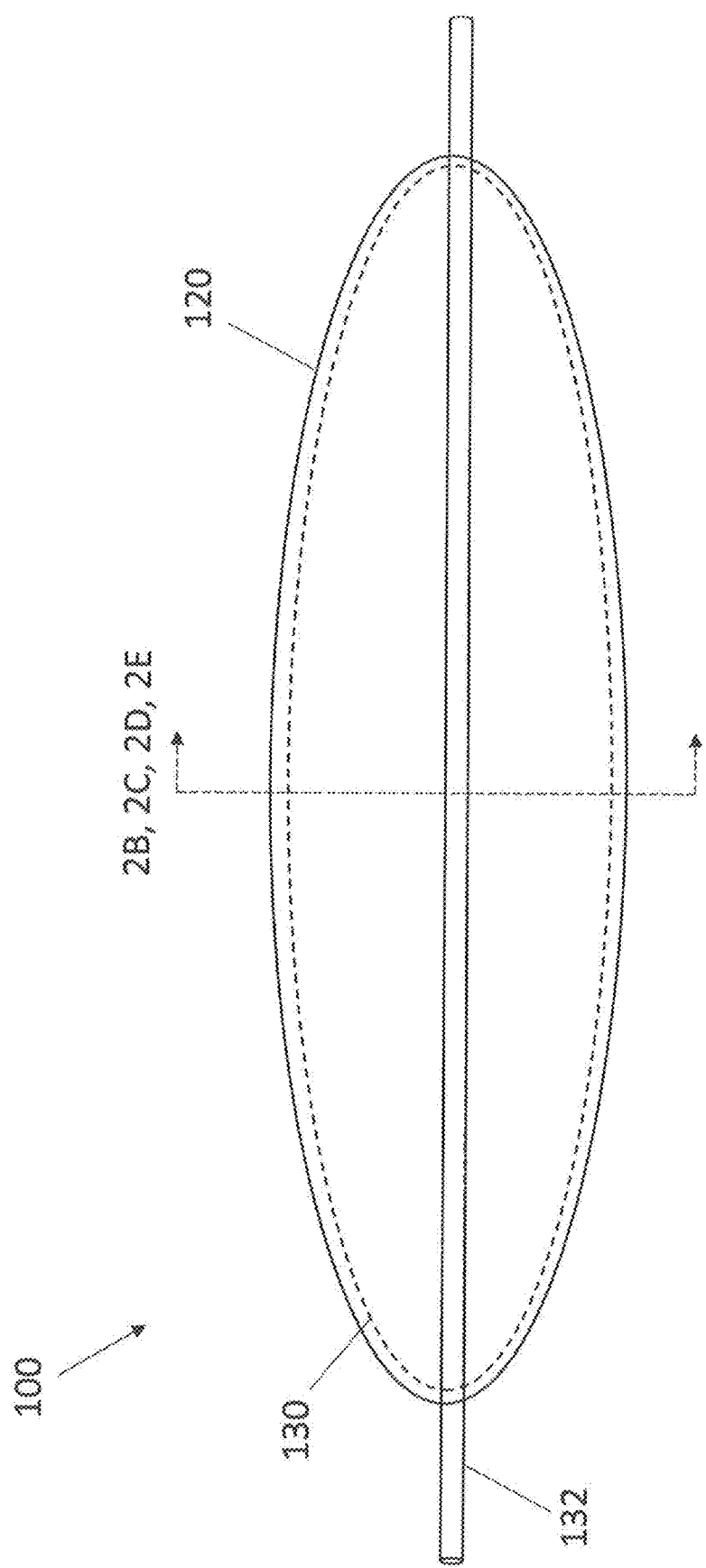

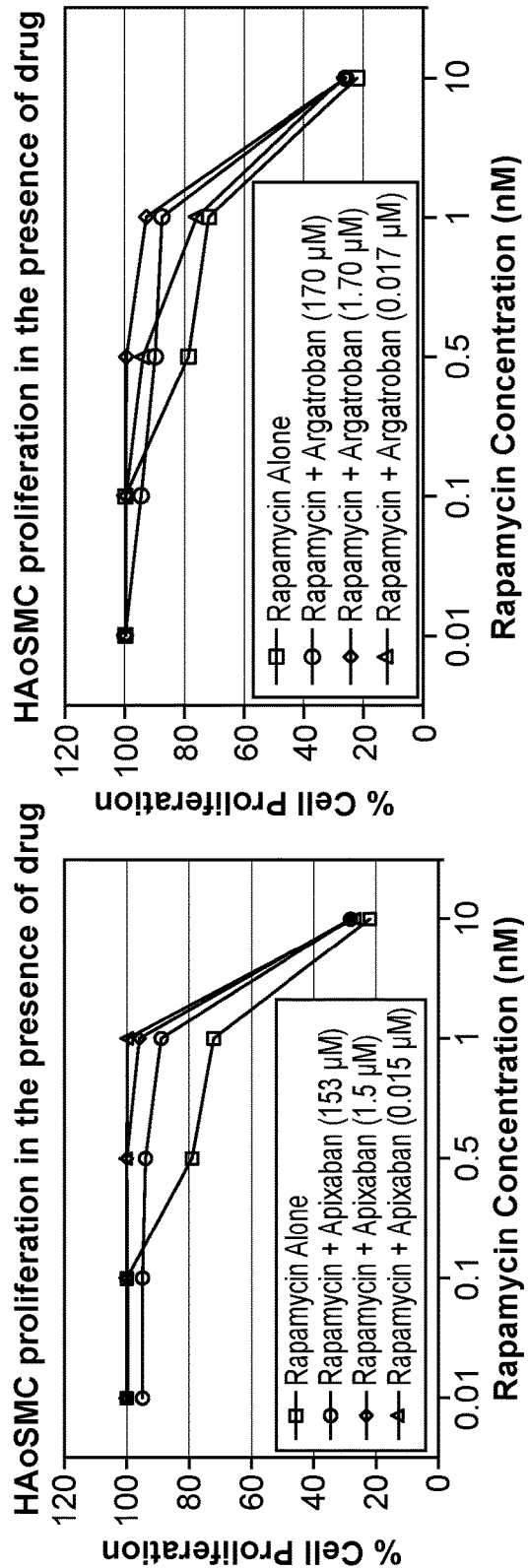
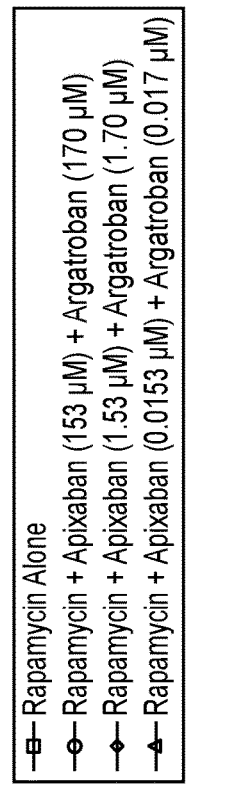
FIG. 6A
FIG. 6B
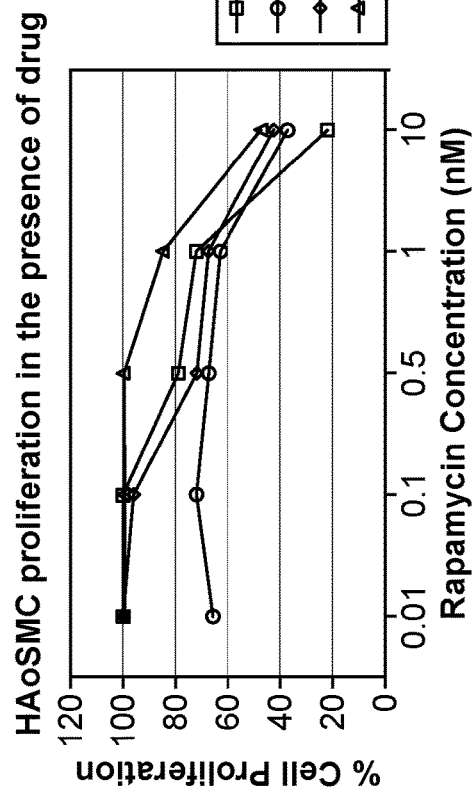
FIG. 6C

ANTICOAGULANT COMPOUNDS AND METHODS AND DEVICES FOR THEIR USE

CROSS-REFERENCE

This application is a continuation of PCT Application No. PCT/US2021/034108, filed May 25, 2021, which claims the benefit of U.S. Provisional No. 63/030,203, filed May 26, 2020; U.S. Provisional No. 63/174,496, filed Apr. 13, 2021, the entire content of which are fully incorporated herein by reference.

BACKGROUND

Field of the Disclosure

The present disclosure relates to anticoagulants and derivatives thereof and their use in therapeutic applications, and in particular with devices.

Coagulation is a process designed to stop bleeding from a damaged blood vessel. Disorders of coagulation can lead to obstructive clotting (thrombosis) or occlusion of the blood vessel.

Damage to a blood vessel can be caused by, e.g., injurious contact of a device employed in a surgery or intervention with the blood vessel (e.g., a surgical knife cutting a tissue containing the blood vessel, or a deployed stent embedding into the wall of the blood vessel). Damage to the blood vessel can lead to abnormal or undesired recruitment, activation, and/or proliferation of proteins (e.g., fibrin) and cells (e.g., platelets) involved in the coagulation process and other processes at the site of injury, which can result in obstructive clotting or occlusion of the blood vessel.

Anticoagulants can be used to prevent the formation of blood clots. Some are used for the prevention or treatment of disorders characterized by abnormal blood clots and emboli. By reducing blood clotting, anticoagulants can prevent deep vein thrombosis, pulmonary embolism, myocardial infarction, and ischemic stroke. Anticoagulant drugs act by inactivating thrombin and several other clotting factors that are required for a clot to form Systemic administration of an anticoagulant may be ineffective in preventing or treating disorders associated with coagulation. For example, the concentration of the anticoagulant at or adjacent the site of injury may be insufficient at the appropriate time to prevent or treat disorders associated with coagulation. Furthermore, deficiencies of systemic administration of an anticoagulant can be exacerbated where the patient has a condition (e.g., cardiovascular disease, hypercholesterolemia, or diabetes) that renders the patient more susceptible to a vaso-occlusive event.

Previous attempts to provide local administration of an anticoagulant have had limited to no success in preventing coagulation disorders and/or preventing thrombus (clot) formation particularly after local tissue injury. Furthermore, local injury to a tissue is commonly associated with additional injury to the tissue adjacent (e.g., proximal, distal, etc.) the site of the first injury.

To reduce the partial or total occlusion of the artery by plaque or the collapse of the arterial lining and to reduce the chance of restenosis, a stent or drug coated balloon may be used in the artery to keep the artery open. Drug delivery stents for anti-proliferative agents such as mTOR inhibitors and Taxol have reduced neointimal hyperplasia and/or incidence of in-stent restenosis. An alternative to a drug-delivery stent is a drug coated balloon (DCB). A drug-coated or coating containing a drug is formed on the exterior of a balloon or infused through a balloon. When the balloon is inflated, and the balloon walls contact the vessel walls, the drug is released or infused through the balloon walls over a period of time. These agents unfortunately may delay the healing period of the injured tissue, increase tissue factor which may generate or amplify thrombin, fibrin, and/or clot formation, especially within the first 3 hours to 72 hours or more.

There is still a need to develop specialized therapeutic compositions for medical devices that can rapidly and/or extended release of therapeutic agents, drugs, or bioactive materials directly into a localized tissue area during or following a medical procedure, so as to treat or prevent vascular and nonvascular diseases or conditions such as restenosis or thrombosis. The device should release the therapeutic agent in an effective and efficient manner at the desired target location, where the therapeutic agent should rapidly permeate the target tissue at a local therapeutic level, preferably prior to the coagulation amplification cascade resulting in clot formation, and/or extended release to inhibit one or more of thrombin, fibrin, platelet aggregation, platelet activation, and/or clot formation.

It would therefore be desirable to provide devices that locally deliver thrombin/clot formation-inhibiting agents, deliver a clot inhibiting agent that additionally inhibits or promotes dissolution of one or more of inflammation, fibrin, injury, cell proliferation, platelet aggregation, platelet activation, and optionally other kinds of biologically active agents (e.g., anti-proliferative agents, anti-inflammatory agents, etc.), to the site of injury of a body part or to an area adjacent thereto such us proximal or distal segments, before, during, and/or after injury. The disclosure also provides methods of using such devices and other forms of therapy for one or more of the following: inhibiting clotting, inhibiting clot formation, improving or promoting wound healing, inhibiting and/or resolving inflammation, inhibiting or attenuating vessel injury such as IEL injury, inhibiting cell proliferation, inhibiting smooth cell proliferation, accelerate or promote fibrin dissolution, inhibiting platelet activation, inhibiting platelet aggregation, at the injury site or at an area or segment adjacent thereto. The following inventions satisfy at least some of these desirable needs.

Listing of Background Art

Relevant background art includes U.S. Pat. Nos. 6,500,855; 8,409,272; 8,946,219; US2003/0158120; US2005/0064006; US2009/0075949; US201010003542; US2010/0130543; US2010/0184729; US2018/0000490; EP1849434; CA2464290; and WO2013/007840.

The subject matter of this application is also related to that of the following commonly owned applications: U.S. Provisional No. 63/030,203, filed May 26, 2020; International Patent Application No. PCT/US2007/078317, filed Sep. 12, 2007, entitled "Macrocyclic lactone compounds and methods for their use"; International Patent Application No. PCT/US2008/056501, filed Mar. 11, 2008, entitled "Macrocyclic lactone compounds and methods for their use"; International Patent Application No. PCT/US2009/059396, filed Oct. 2, 2009, entitled "Macrocyclic lactone compounds and methods for their use"; International Patent Application No. PCT/US20111054637, filed Oct. 3, 2011, entitled "Macrocyclic lactone compounds and methods for their use"; each of which are incorporated herein by reference for all purposes in their entireties.

SUMMARY OF THE INVENTION

In a first aspect, the present invention provides an implantable scaffold comprising a scaffold structure having a surface configured to be expanded in the patient's body. A first therapeutic composition is coated, layered, bonded, or otherwise affixed to the scaffold and comprises a first drug formulation including at least one drug selected from the group consisting of a direct factor IIa inhibitor and a direct factor Xa inhibitor. A second therapeutic composition is also coated, layered, bonded, or otherwise affixed to the scaffold structure and or the first therapeutic composition and comprises a second drug formulation including at least one drug selected from the group consisting of a direct factor IIa inhibitor and a direct factor Xa inhibitor. The first therapeutic composition is formulated for a rapid release of the first drug formulation into a vascular environment and the second therapeutic composition is formulated for an extended release of the second drug formulation into the vascular environment.

The implantable scaffold may have any conventional or novel structure intended for implantation in a patient's vasculature, including, the arterial and venous coronary, peripheral and cerebral vasculature. The scaffolds may be intended for direct implantation, for example comprising or consisting of vascular stents intended to maintain patency in in a vascular lumen. Additionally, the scaffolds may be part of assemblies including additional components, such us vascular grafts, prosthetic valves, and the like. Depending on the intended purpose, the scaffold may be non degradable in the vascular environment, for example being formed from or otherwise comprising a metal or a polymer which is non-degradable in the vascular environment. In other instances, the scaffold may be degradable in the vascular environment, for example being formed from or otherwise comprising a metal or polymer which is degradable in the vascular environment.

In addition to such implantable scaffolds, the therapeutic compositions and drug formulations described below may also find use with a wide variety of other implantable and non-implantable devices and tools which may be subject to unwanted clotting, as described elsewhere herein.

The rapid release of the first drug formulation and extended release of the second drug formulation will typically act in combination to accelerate dissolution of one or more of inflammation, cell proliferation, internal elastic lamina (IEL) injury, thrombin, fibrin formation, platelet aggregation, platelet activation, and clot or thrombus formation; and/or inhibit one or more of inflammation, cell proliferation, internal elastic lamina (IEL) injury, thrombin, fibrin formation, platelet aggregation, platelet activation, and clot or thrombus formation; and/or increase or prolong time before blood forms clot or thrombus.

In specific instances, at least one of the first drug formulation and the second drug formulation may comprise both a direct factor IIa inhibitor and a direct factor Xa inhibitor. In other instances, the first drug formulation and the second drug formulation may each comprise both a direct factor IIa inhibitor and a direct factor Xa inhibitor.

In specific instances, the at least one drug of the first (rapid release) drug formulation is released from the first therapeutic composition over a first time period (duration) is in a range front 3 hours to 28 days after implantation, usually from 3 hours to 7 days after implantation, and preferably from 3 hours to 3 days after implantation. The first therapeutic composition is typically configured to release the at least one drug of the first drug formulation at a mean rate in the range from 1 µg/hour to 10 µg/hour, usually from 1 µg/hour to 5 µg/hour, preferably from 2 µg/hour to 4 µg/hour over a 24 hour period following exposure to the vascular environment, where the mean rate may be determined based on the amount (weight) of drug released over the total duration of the release.

In specific instances, the at least one drug of the second drug formulation (sustained release) is released from the second therapeutic composition over a second time period is in a range from 30 days to 12 months after implantation, usually from 30 days to 9 months after implantation, and preferably front 30 days to 6 months after implantation. The second therapeutic composition is typically configured to delay release the at least one drug of the second drug formulation for at least one 24-hour period following exposure to the vascular environment. The second therapeutic composition is typically configured to release the at least one drug of the second drug formulation at a mean rate not exceeding 2 µg/hour, usually 1 µg/hour, preferably 0.5 µg/hour, and more preferably 0.1 µg/hour after the 24 hour period following exposure to the vascular environment, where the mean rate may be determined based on the amount (weight) of drug released over the total duration of the release.

The first and second therapeutic composition will typically but not necessarily comprise a polymer to sequester and control the release rate and duration of the drugs. In some instances the drugs may be coated, layered, or otherwise deposited on or in surfaces or receptacles on the implantable structure without a polymer but optionally with excipients, carriers, coating agents, and other conventional drug coating materials.

In some instances, one of the first and second therapeutic compositions may comprises a polymer while the other is free from polymer. For example, the first therapeutic (rapid release) composition may free from polymer and the second (sustained release) therapeutic composition may comprises a polymer to maintain or control the release rate and duration. For example, the first therapeutic composition may be coated on the scaffold structure or over the second therapeutic composition to effect a burst release.

In instances where the first and second therapeutic compositions each comprise a polymer, the first therapeutic composition will have a first drug-to-polymer weight ratio and the second therapeutic composition will a second drug-to-polymer weight ratio. The ratios may be the same but will more often be different. For example, the first drug-to-polymer weight ratio may be in a range from 5:1 to 1:3, usually from 5:2 to 1:2, and preferably from 5:3 to 1:1, and the second drug-to-polymer weight ratio may in a range from 5:2 to 1:5, usually from 5:3 to 2:5, and preferably from 1:1 to 1:2. The first drug-to-polymer weight ratio is usually greater than the second drug-to-polymer weight ratio (greater loading can enhance the burst effect in the first therapeutic composition), but in some instances the first drug-to-polymer weight ratio may less than the second drug-to-polymer weight ratio (greater loading can also enhance duration of release).

While drug release from the first and second therapeutic compositions may commence simultaneously, in many instances the first therapeutic composition and the second therapeutic composition are configured to delay start of release of the second drug formulation for a time period after release of the first drug formulation has started. For example, the first therapeutic composition may be layered over the second therapeutic composition to delay release of the second drug formulation, e.g. the first therapeutic composition may initially cover at least a portion of the second therapeutic composition and may be configured to dissolve over the time period in the vascular environment to expose the second therapeutic composition and allow release of the second drug formulation.

Alternatively, a sacrificial layer may present over at least one of the first therapeutic composition and the second therapeutic composition or between the first therapeutic composition and the second therapeutic composition to delay release of one or more drugs from either or both of the first therapeutic composition and the second therapeutic compositions.

Alternatively, a diffusion-rate controlling layer may be present over at least one of the first therapeutic composition and the second therapeutic composition or between the first therapeutic composition and the second therapeutic composition to control a release rate of one or more drugs from either or both of the first therapeutic composition and the second therapeutic compositions.

The polymer(s) may be configured to release the first and/or second drug formulation at least partly by dissolution of the polymer when exposed to the vascular environment. For example, the polymer of the first therapeutic composition may dissolve at a faster rate than dissolution of the second therapeutic composition in the vascular environment. Alternatively, the polymer may be configured to release the first and/or second drug formulation at least partly by a diffusion mechanism through the polymer when exposed to the vascular environment. Alternatively, the polymer may be configured to release the first and/or second drug formulation through a combination of dissolution of and diffusion through the polymer when exposed to the vascular environment.

Usually, but not necessarily, one or more polymer will be porous where the first and/or second drug formulation are sequestered in pores of the polymer(s). Often, a release rate of the first and/or second drug formulation may at least partly determined by a pore size of the polymer. In some instances, the polymers of the first and second drug formulations may have different pore sixes which provide different release rates.

In other instances, the first and second drug formulations may be at least partially separated in different regions within the porous polymer. Alternatively or additionally, the first and second drug formulations may at least partially present in overlapping regions of the porous polymer.

In preferred instances, the implantable scaffold of the present invention will further comprise an anti-proliferative drug. The anti-proliferative drug is present in either or both of the first and second drug formulations or may be present in a third drug formulation or may be separately coated, coupled, bonded or attached to the scaffold. For example, the anti-proliferative drug may present in a third therapeutic composition formulated to release the anti-proliferative drug into a vascular environment when the scaffold is present in the vascular environment.

The first, second, and optionally third or additional therapeutic compositions of the present invention may be positioned on an external, internal, edge, and/or other surface of the implantable scaffold. Optionally but not necessarily, the scaffold surfaces will be roughened, scored, etched, or otherwise treated to enhance attachment of the therapeutic compositions. In some instances, the therapeutic compositions may be sequestered in wells, indentations or other receptacles formed on or in the scaffold surfaces.

Exemplary direct factor IIa inhibitors of the present invention include argatroban, dabigatran, ximelagatran, melagatran, efegatran, inogatran, atecegatran metoxil (AZD-0837), hirudin, hirudin analogs, bivalirudin, desirudin, and lepirudin, which may be used individually or in combination. Preferred direct factor IIa inhibitors comprise argatroban, or a salt, isomer, solvate, analog, derivative, metabolite, or prodrugs thereof.

Exemplary direct factor Xa inhibitors of the present invention include apixaban, betrixaban, edoxaban, otamixaban, razaxaban, rivaroxaban, (r)-n-(2-(4-(1-methylpiperidin-4-yl)piperazin-1-yl)-2-oxo-1-phenylethyl)-1h-indole-6-carboxamide (LY-517717), daraxaban (YM-150), 2-[(7-carbamimidoylnaphthalen-2-yl)methyl-[4-(1-ethanimidoylpiperidin-4-yl)oxyphenyl]sulfamoyl]acetic acid (YM-466 or YM-60828), or eribaxaban (PD 0348292), carbamimidoyl-2-hydroxy-phenyl) 4-[5-(2,6-dimethyl-piperidin-1-yl)-pentyl]-3-oxo-3,4-dihydro-quinoxaline-6-carboxylic acid (PD0313052), which may be used individually or in combination. Preferred direct factor Xa inhibitor comprise (1) apixaban, or a salt, isomer, solvate, analog, derivative, metabolite, or prodrugs thereof and (2) rivaroxaban, or a salt, isomer, solvate, analog, derivative, metabolite, or prodrugs thereof.

Exemplary anti-proliferative agents of the present invention include mTOR inhibitors selected from a group consisting of sirolimus, biolimus, everolimus, myolimus, novolimus, ridaforolimus, temsirolimus, zotarolimus, or salts, isomers, solvates, analogs, derivatives, metabolites, or prodrugs thereof, which may be used individually or in combination. Preferred anti-mTOR proliferative agents comprise sirolimus, or a salt, isomer, solvate, analog, derivative, metabolite, or prodrugs thereof.

Exemplary anti-proliferative agents of the present invention also include paclitaxel, or a salts, isomer, solvate, analog, derivative, metabolite, or prodrug thereof.

In addition to the first, second, and optional third therapeutic compositions as discuss above, the implantable scaffolds of the present invention may further comprise at least one additional drug, typically an antiplatelet drug. The additional drug will not necessarily be incorporated as a drug formulation or as part of a therapeutic composition.

In specific examples of the present invention, the direct factor IIa inhibitor comprises argatroban and the direct factor Xa inhibitor comprises apixaban or rivaroxaban. In other specific examples of the present invention, the direct factor IIa inhibitor comprises argatroban or an analogue of argatroban, the direct factor Xa inhibitor comprises apixaban or rivaroxaban or an analogue of apixaban or rivaroxaban, and the anti-proliferative agent comprises sirolimus or an analogue of sirolimus.

In some instances, at least one of the therapeutic compositions may comprises an excipient, an adjuvant, a carrier, a wetting agent. In some instances, the first and second therapeutic compositions may be formed contiguously. In some instances, the first and second therapeutic compositions are separated by barrier, for example a polymer layer.

In some examples, a third therapeutic composition comprises a third drug formulation including at least one drug selected from the group consisting of a direct factor IIa inhibitor and a direct factor Xa inhibitor. The third drug formulation may comprise any one of the previously discussed drugs and/or an additional drug. The third therapeutic composition may be disposed at least partially over the first therapeutic composition which may disposed at least partially over the second therapeutic composition, where the third therapeutic composition may be configured to effect a burst release which is more rapid than the release of either the first or second therapeutic compositions.

In specific examples, the first and second therapeutic compositions may comprise polymer and the third therapeutic composition may be free from polymer and coated or otherwise deposited over at least a portion of the first therapeutic composition.

In specific examples, the additional drug may be unique, i.e. not found in either the first or second drug formulations. Often, the additional drug will have the same release rate as at least one of the other drugs but alternatively may have a different release rate than at least one of the other drugs In other examples, the third drug formulation may comprises at least one polymer, where at least one polymer in the third formulation may be the same and/as or different from at least one polymer in the first and second drug formulations. For example, the at least one polymer in the third formulation may provide a different release rate than provided by at least one polymer in the first and second drug formulations. In other examples, the at least one polymer in the third formulation provides substantially the same release rate as provided by at least one polymer in the first and second drug formulations.

In specific instances, the first, second, or optional third therapeutic compositions may comprise a plurality of drug different formulations for at least one drug. For example, a single drug type may be sequestered in formulations with polymers have different release rates and/or drug loadings, allowing further control of the drug release characteristics.

In a second aspect, the present invention provides an implantable scaffold comprising a scaffold structure having a surface configured to be expanded in the patient's body. A first therapeutic composition comprising a first drug formulation including at least argatraban, at least one of apixaban and rivaroaxaban, and sirolimus is present in a polymer configured to rapidly release the first drug formulation into a vascular environment. A second therapeutic composition comprises a second drug formulation including at least argatraban, at least one of apixaban and rivaroaxaban, and sirolimus present in a polymer configured for extended release of the second drug formulation into the vascular environment.

The polymer comprises will typically be biodegradable polymer, for example being selected from the group consisting of polyesters, including polylactic acids, polyglycolic acids, polylactic acid-co-glycolic acids, polylactic acid-co-caprolactones, polyethylene glycol-block-poly caprolactone, and polyurethanes; poly(methyl methacrylate) (PMMA); poly N-(2-Hydroxypropyl) methacrylamides; polyethylenimine (PET), dextran, dextrin, chitosans, poly (L-lysine); poly(aspartamides), polyethylenes; polypropylenes; polyamides; polyethylene glycols (PEG); silicones; poly(anhydrides); and poly ortho esters.

An exemplary biodegradable polymer comprises poly (lactic-co-glycolic acid) (PLGA), where the PLGA is present at 5 µg to 13 µg per mm of scaffold structure length in the first therapeutic composition and from and from 5 µg to 20 µg per mm of scaffold structure length in the second therapeutic composition.

Alternatively, the polymer may comprises a non-degradable polymer, for example being selected from the group consisting of polyacrylates, polymethacrylates, poly(n-butyl methacrylate), poly(hydroxyethylmethacrylate), polyamides, nylons, nylon 12, dacron, polyethylene terephthalate, poly(ethylene glycol), polyethylene oxide (PEO), polydimethylsiloxane, polyvinylpyrrolidone, ethylene-vinyl acetate, phosphorylcholine-containing polymers, poly(2-methacryloyloxyethylphosphorylcholine), poly(2-methacryloyloxyethylphosphorylcholine-co-butyl methacrylate), and copolymers thereof.

In specific examples, the argatraban, at least one of apixaban and rivaroaxaban, and the sirolimus may be sequestered in a porous structure of the PLGA, and the release of the argatraban, the direct factor Xa inhibitor including at least one of apixaban and rivaroaxaban, and the sirolimus into the vascular environment occurs through a combination of diffusion and dissolution.

In a particular example, (1) the argatraban may be present in the first therapeutic composition at a concentration in a range from 0.5 µg to 3 µg per mm of scaffold structure length, the direct factor Xa inhibitor including at least one of apixaban and rivaroaxaban may be present at a concentration in a range from 0.5 µg to 3 µg per mm of scaffold structure length, and the sirolimus may be present at a concentration in a range from 0.5 µg to 3 µg per mm of scaffold structure length in the first therapeutic composition and (2) the argatraban may be present at a concentration in a range from 2 µg to 10 µg per mm of scaffold structure length, the direct factor Xa inhibitor including at least one of apixaban and rivaroaxaban may be present at a concentration in a range from 2 µg to 10 µg per mm of scaffold structure length, and the sirolimus may be present at a concentration in a range from 2 µg to 10 µg per mm of scaffold structure length in the second therapeutic composition.

In other examples, the first therapeutic composition may be coated on one or more surfaces of the scaffold structure and the second therapeutic composition may be coated over at least a portion of the first therapeutic composition. For example, the first and second therapeutic compositions cover at least 75% of the area of inner and outer surfaces of the scaffold structure.

In a third aspect, the present invention comprises a method for treating a vascular tissue injury in a patient. The method comprises expanding a scaffold structure at a target location in the patient's vasculature proximate a tissue injury. A first drug formulation including at least one of a drug selected from the group consisting of a direct factor IIa inhibitor and a direct factor Xa is released from a first therapeutic composition on the scaffold, and a second drug formulation including at least one drug selected from the group consisting of a direct factor IIa inhibitor and a direct factor Xa is released from a second therapeutic composition on the scaffold to the location of injury. The first therapeutic composition may be formulated to rapidly release the first drug formulation into a vascular environment, and the second therapeutic composition may be formulate to provide an extended release of the second drug formulation into the vascular environment.

In different instances of the methods of the present invention, the therapeutic composition, may be positional on an external surface of the implantable scaffold, on an internal surface of the implantable scaffold, or on both external and internal surfaces of the implantable scaffold.

While the tissue injury will frequently be caused by expanding the scaffold at the location, in other cases the tissue injury may preexist, deploying the structure at the location.

In specific instances, at least one of the first drug formulation and the second drug formulation may comprise either or both a direct factor IIa inhibitor and a direct factor Xa inhibitor.

In specific instances, the first (rapid release) drug formulation may release drug from the first therapeutic composition over a first time period is in a range from 3 hours to 28 days after implantation, usually from 3 hours to 7 days after implantation, preferably from 3 hours to 3 days after implantation, where the at least one drug of the first drug formulation is typically at a mean rate in the range from 1 µg/hour to 10 µg/hour, usually from 1 µg/hour to 5 µg/hour, preferably from 2 µg/hour to 4 µg/hour over a 24 hour period following exposure to the vascular environment, where the mean rate may be determined based on the amount (weight) of drug released over the total duration of the release.

In specific instances, the at least one drug of the second drug formulation is released from the second (sustained release) therapeutic composition over a second time period is in a range from 30 days to 12 months after implantation, usually from 30 days to 9 months alter implantation, preferably from 30 days to 6 months after implantation, where the second therapeutic composition is typically configured to release the at least one drug of the second drug formulation for at a mean rate not exceeding 2 µg/hour, usually 1 It hour, preferably 0.5 µg/hour, and more preferably 0.1 µg/hour after the 24 hour period following exposure to the vascular environment, where the mean rate may be determined based on the amount (weight) of drug released over the total duration of the release.

In preferred instances, the therapeutic compositions are formulated to locally release the first and second drug formulation Xa to the injury site at a rate or a concentration sufficient to begin to inhibit one or more of inflammation, cell proliferation, internal elastic lamina (IEL) injury, fibrin formation, and clot formation within about 3 hours to about 7 days after the structure is deployed.

Exemplary direct factor IIa inhibitors comprise at least one of argatroban, dabigatran, ximelagatran, melagatran, efegatran, inogatran, atecegatran metoxil (AZD-0837), hirudin, hirudin analogs, bivalirudin, desirudin, and lepirudin, with preferred direct factor IIa inhibitor comprises argatroban, or a salt, isomer, solvate, analog, derivative, metabolite, or prodrugs thereof.

Exemplary direct factor Xa inhibitors comprise at least one of apixaban, betrixaban, edoxaban, otamixaban, razaxaban, rivaroxaban, (r)-n-(2-(4-(1-methylpiperidin-4-yl)piperazin-1-yl)-2-oxo-1-phenylethyl)-1h-indole-6-carboxamide (LY-517717), daraxaban (YM-150), 2-[(7-carbamimidoylnaphthalen-2-yl)methyl-[4-(1-ethanimidoylpiperidin-4-yl)oxyphenyl]sulfamoyl]acetic acid (YM-466 or YM-60828), or eribaxaban (PD 0348292), carbamimidoyl-2-hydroxy-phenyl) 4-[5-(2,6-dimethyl-piperidin-1-yl)-pentyl]-3-oxo-3,4-dihydro-quinoxaline-6-carboxylic acid (PD0313052), with preferred direct factor Xa inhibitor comprise (1) rivaroxaban, or a salt, isomer, solvate, analog, derivative, metabolite, or prodrugs thereof and (2) apixaban, or a salt, isomer, solvate, analog, derivative, metabolite, or prodrugs thereof.

In some instances, the methods may farther comprise releasing an anti-proliferative agent from at least one of the first therapeutic composition and the second therapeutic composition on the scaffold to the location of injury. Exemplary anti-proliferative agents include (1) TOR inhibitors selected from a group consisting of sirolimus, biolimus, everolimus, myolimus, novolimus, ridaforolimus, temsirolimus, zotarolinius, or salts, isomers, solvates, analogs, derivatives, metabolites, or prodrugs thereof, preferably comprising sirolimus, or a salt, isomer, solvate, analog, derivative, metabolite, or prodrugs thereof and (2) paclitaxel, or a salts, isomer, solvate, analog, derivative, metabolite, or prodrug thereof.

In other instances, the methods may further comprise releasing an antiplatelet drug from at least one of the first and second therapeutic compositions.

In a fourth aspect, the present invention provides an implantable scaffold comprising a scaffold structure having a surface configured to be expanded in the patient's body. At least one therapeutic composition comprising a drug formulation including at least one drug selected from the group consisting of a direct factor IIa inhibitor and a direct factor Xa inhibitors coated, layered, or otherwise bonded or affixed to the scaffold, wherein the therapeutic composition is formulated for an extended release of the drug formulation into a vascular environment.

Often, the drug formulation includes both a direct factor IIa inhibitor and a direct factor Xa inhibitor, and in some instances, the drug formulation may include one or more additional drugs as described elsewhere herein.

Usually, the drug formulation comprises a polymer, and the drug(s) are incorporated into the polymer. The polymer is typically non-degradable in the vascular environment, where the drugs are loaded into a porous structure of the polymer and released by diffusion over an extended period. Alternatively, the polymer may be degradable in the vascular environment, and the drugs may be released by a combination of diffusion through and dissolution of the polymer.

Typically, the scaffold comprises a metal or a polymer which is non-degradable in the vascular environment, but in other instances the scaffold may be partly of wholly degradable, particularly when the polymer of the drug formulation is also degradable.

In specific examples, at least one drug of the drug formulation is released from the therapeutic composition over a time period of at least 28 days after implantation, usually at least 3 months after implantation, and preferably at least one year after implantation.

In other examples the therapeutic composition may be configured to release the at least one drug of the drug formulation at a mean rate not exceeding 2 µg/hour, usually 1 µg/hour, preferably 0.5 µg/hour, and more preferably 0.1 µg/hour following exposure to the vascular environment.

In many or all instances, the extended release of the drug formulation acts to accelerate dissolution of one or more of inflammation, cell proliferation, internal clastic lamina (IEL) injury, thrombin, fibrin formation, platelet aggregation, platelet activation, and clot or thrombus formation; and/or inhibit one or more of inflammation, cell proliferation, internal elastic lamina (IEL) injury, thrombin, fibrin formation, platelet aggregation, platelet activation, and clot or thrombus formation; and/or increase or prolong time before blood forms clot or thrombus.

In one aspect, a medical device may comprise a structure having at least one surface configured for internal use within a patient's body and a therapeutic composition comprising one or more active substances. These active substances include but not limited to a direct factor Xa inhibitor such as Apixaban, Betrixaban, Edoxaban, Otamixaban, Rivaroxaban, Razaxaban, (r)-n-(2-(4-(1-methylpiperidin-4-yl)piperazin-1-yl)-2-oxo-1-phenylethyl)-1h-indole-6-carboxamide (LY-517717), Daraxaban (YM-150), 2-[(7-carbamimidoylnaphthalen-2-yl)methyl-[4-(1-ethanimidoylpiperidin-4-yl)oxyphenyl]sulfamoyl]acetic acid (YM-466 or YM-60828), or eribaxaban (PD 0348292), or 2-(5-carbamimidoyl-2-hydroxy-phenyl) 4-[5-(2,6-dimethyl-piperidin-1-yl)-pentyl]-3-oxo-3,4-dihydro-quinoxaline-6-carboxylic acid (PD0313052) or others; and/or a direct IIa inhibitor such as Hirudin, Bivalirudin such as Angiomax, Desirudin, Lepirudin, atecegatran metoxil (AZD-0837), Argatroban, Dabigatran, Efegatran, Inogatran, Melagatran, Ximelagatran, or others; Vitamin k antagonist such as Acenocoumarol, Coumatetralyl, Dicoumarol, Ethyl biscoumacetate, Phenprocoumon, Warfarin, Clorindione, Diphenadione, Phenindione, Tioclomarol, or others; and/or other anti-coagulant drug such as Antithrombin III, Defibrotide, Protein C (Drotrecogin alfa), Ramatroban, REG1, or others; and/or an antiplatelet drug such as Abciximab, Eptifibatide, Orbofiban, Roxifiban, Sibrafiban, Tirofiban, Clopidogrel, Prasugrel, Cangrelor, Elinogrel, Ticagrelor, Beraprost, Iloprost, Prostacyclin, Treprostinil, Acetylsalicylic acid/Aspirin, Aloxiprin, Carbasalate calcium, Indobufen, Triflusal, Dipyridamole/aspirin, Picotamide, Terbogrel, Terutroban, Cilostazol, Dipyridamole, Triflusal, Cloricromen, Ditazole, Vorapaxar, Ticlopidine, or others; and/or thrombolytic drugs/fibrinolytics drug such as Plasminogen activators r-tPA, Alteplase, Reteplase, Tenecteplase, Desmoteplase, Saruplase, Urokinase, Antistreplase, Monteplase, Streptokinase, Ancrod, Brinase, Fibrinolysin, or others; and/or Citrate, EDTA, Oxalate; and/or an inhibitor for intrinsic pathway of coagulation and thrombosis such as FXIa inhibitor, protein Z-dependent protease inhibitor; and/or anti-proliferative drug such as Paclitaxel (Taxol), or salts, isomers, solvates, analogs, derivatives, metabolites, or prodrugs, and/or an m-TOR inhibitor such as sirolimus, biolimus, everolimus, myolimus, novolimus, ridaforolimus, temsirolimus, zotarolimus, or salts, isomers, solvates, analogs (including deuterated analogs), derivatives, metabolites, or prodrugs, and combinations thereof in a preferred example, a medical device comprising a structure having at least one surface configured for internal use within a patient's body and a therapeutic composition comprising one or more active substances, wherein the one or more active substances comprises one of Apixaban, Rivaroxaban, or Argatroban. In a preferred example, a medical device comprising a structure having at least one surface configured for internal use within a patient's body and a therapeutic composition comprising one or more active substances, wherein the one or more active substances comprises Apixaban and Argatroban, Apixaban and an anti-platelet agent, Rivaroxaban and an anti-platelet agent, or Argatroban and an anti-platelet agent. In a preferred example, a medical device comprising a structure having at least one surface configured for internal use within a patient's body and a therapeutic composition comprising one or more active substances, wherein the one or more active substances comprises one of Apixaban or Rivaroxaban or an analogue thereof, and Argatroban or an analogue of it. In another preferred example, a medical device comprising a structure having at least one surface configured for internal use within a patient's body and a therapeutic composition comprising one or more active substances, wherein the one or more active substances comprises one of Apixaban or Rivaroxaban or an analogue thereof, Argatroban or its analogue, and one of Taxol or sirolimus or an analogue thereof analogues.

In another aspect, a medical device may comprise a structure having an external surface configured for internal use within a patient's body and a therapeutic composition comprising one or more active substances including a direct factor IIa inhibitor disposed on at least one surface, preferably disposed on the entire external surface of the structure. In some examples, the external surface of the structure is configured to be positioned adjacent to an injury site in the patient's body, preferably expanding such site to a larger configuration. In some example, the therapeutic composition is formulated to locally release the one or more active substances to the injury site at a rate sufficient to generate a tissue concentration of about 2 ng/mg tissue to about 200 ng/mg tissue of the one or more active substances at the injury site within about 3 hours after the external surface of the structure is positioned adjacent the injury site. For example, the therapeutic composition is preferably formulated to locally release the one or more active substances to the injury site at a rate sufficient to generate a tissue concentration of about 20 ng/mg tissue to about 200 ng/mg tissue, or more preferably about 40 ng/mg tissue to about 200 ng/mg tissue, of the one or more active substances at the injury site within about 3 hours after the external surface of the structure is positioned adjacent the injury site. In another example of this aspect, the medical device structure has an internal (inner) surface, wherein one or more agents are coated on at least one region of the inner structure surface, preferably coated on the entire inner structure surfaces. In yet another example of this aspect, the medical device structure has more than two surfaces, and wherein the one or more agents are coated on all or some of these surfaces. In yet another example of this aspect, the coating thickness may be uniform between surfaces or vary between surfaces of the structure. In yet another example of this aspect, the device may have a partial or full covering or a sleeve on one or more surfaces of the device (such as PTFE, Dacron, or other type material) wherein said material comprises the one or more agents. In some examples, the therapeutic composition is formulated to release substantially all of the one or more active substances within about 1 to about 90 days. In some examples, the therapeutic composition is formulated to release substantially all of the one or more active substances about 90 to about 180 days or more. In some examples, the therapeutic composition is formulated to locally release the one or more active substances to the injury site at a rate sufficient to generate a tissue concentration of 0.1 ng/mg or more for a period ranging from 3 hours to 90 days, 3 hours to 180 days, or 3 hours to 270 days or more.

In one aspect, a medical device may comprise a structure having an external surface configured for internal use within a patient's body and a therapeutic composition comprising one or more active substances including a direct factor Xa inhibitor disposed on at least one surface, preferably disposed on the entire external surface of the structure. In some examples, the external surface of the structure is configured to be positioned adjacent to an injury site in the patient's body, preferably expanding such site to a larger configuration. In some examples, the therapeutic composition is formulated to locally release the one or more active substances to the injury site at a rate sufficient to generate a tissue concentration of about 2 ng/mg tissue to about 200 ng/mg tissue of the one or more active substances at the injury site within about 3 hours after the external surface of the structure is positioned adjacent the injury site. For example, the therapeutic composition is preferably formulated to locally release the one or more active substances to the injury site at a rate sufficient to generate a tissue concentration of about 20 ng/mg tissue to about 200 ng/mg tissue, or more preferably about 40 ng/mg tissue to about 200 ng/mg tissue, of the one or more active substances at the injury site within about 3 hours after the external surface of the structure is positioned adjacent the injury site. In another example of this aspect, the medical device structure has an internal (inner) surface, wherein one or more agents are coated on at least one region of the inner structure surface, preferably coated on the entire inner structure surfaces. In yet another example of this aspect, the medical device structure has more than two surfaces, and wherein the one or more agents are coated on all or some of these surfaces. In yet another example of this aspect, the coating thickness may be uniform between surfaces or vary between surfaces of the structure. In yet another example of this aspect, the device may have a partial or full covering or a sleeve on one or more surfaces of the device (such as FIFE, Dacron, or other type material) wherein said material comprise the one or more agents.

In some examples, the therapeutic composition further comprises an anti-proliferative agent. In some examples, the direct factor Xa inhibitor comprises apixaban, betrixaban, edoxaban, otamixaban, razaxaban, rivaroxaban, (r)-n-(2-(4-(1-methylpiperidin-4-yl)piperazin-1-yl)-2-oxo-1-phenyl-ethyl)-1h-indole-6-carboxamide (LY-517717), daraxaban (YM-150), 2-[(7-carbamimidoylnaphthalen-2-yl)methyl-[4-(1-ethanimidoylpiperidin-4-yl)oxyphenyl]sulfamoyl]acetic acid (YM-466 or YM-60828), or eribaxaban (PD 0348292), or 2-(5-carbamimidoyl-2-hydroxy-phenyl) 4-[5-(2,6-dimethyl-piperidin-1-yl)-pentyl]-3-oxo-3,4-dihydro-quinoxaline-6-carboxylic acid (PD0313052), or a salt, isomer, solvate, analog (including deuterated analog), derivative, metabolite, or prodrugs thereof. In some other examples, the direct factor Xa inhibitor comprises rivaroxaban, or a salt, isomer, solvate, analog (including deuterated analog), derivative, metabolite, or prodrugs thereof. In some examples, the direct factor Xa inhibitor comprises apixaban, or a salt, isomer, solvate, analog (including deuterated analog), derivative, metabolite, or prodrugs thereof. In some examples, the anti-proliferative agent comprises Paclitaxel (Taxol), or salts, isomers, solvates, analogs, derivatives, metabolites, or prodrugs thereof. In some examples, the anti-proliferative agent comprises an m-TOR inhibitor. In some examples, the anti-proliferative agent comprises sirolimus, biolimus, everolimus, myolimus, novolimus, ridaforolimus, temsirolimus, zotarolimus, or salts, isomers, solvates, analogs (including deuterated analogs), derivatives, metabolites, or prodrugs thereof. In some examples, the anti-proliferative agent comprises sirolimus, or a salt, isomer, solvate, analog (including deuterated analog), derivative, metabolite, or prodrugs thereof. In some examples, the direct factor Xa inhibitor comprises apixaban and the anti-proliferative agent comprises sirolimus. In some other examples, the factor Xa inhibitor is Apixaban and the antiproliferative agent is Sirolimus or an analogue of sirolimus. In some other examples, the factor Xa inhibitor is Apixaban and the antiproliferative agent is Taxol or an analogue of Taxol. In some other examples, the factor Xa inhibitor is Rivaroxaban and the antiproliferative agent is Sirolimus or an analogue of sirolimus. In some other examples, the factor Xa inhibitor is Rivaroxaban and the antiproliferative agent is Taxol or an analogue of Taxol.

In some examples, the therapeutic composition is formulated to release the one or more active substances at a rate of 1 μg/second/mm device to about 50 μg/day/mm device, preferably at a rate of 1 μg/min/mm device to about 30 μg/day/mm device, more preferably at a rate of 1 μg/hour/mm device to about 30 μg/day/mm device. In some examples, the therapeutic composition is formulated to begin releasing the one or more active substances within about 5, about 15, or about 30 minutes after the device or the external surface of the device structure is positioned adjacent the injury site. In some examples, the therapeutic composition is formulated to begin releasing the one or more active substances before the device or the external surface of the device structure is positioned adjacent the injury site. In some examples, the therapeutic composition is formulated to release substantially all of the one or more active substances within about 1 to about 90 days. In some examples, the therapeutic composition is formulated to release substantially all of the one or more active substances within about 90 to about 180 days or more. In some examples, the therapeutic composition is formulated to release substantially all of the one or more active substances within about 7 days or about 28 days. In some examples, the therapeutic composition is formulated to release substantially all of the one or more active substances within about 3 hours or about 6 hours or about 12 hours or about 1 day or about 3 days. In some examples, the therapeutic composition is formulated to release at least 50% or at least 60% or at least 70% of the one or more active substances within about 3 hours or about 6 hours or about 12 hours or about 1 day or about 3 days. In some examples, the therapeutic composition is formulated to release the direct factor Xa inhibitor faster than the anti-proliferative agent. In some examples, the therapeutic composition is formulated to release the direct factor Xa inhibitor slower than the anti-proliferative agent. In some examples, the therapeutic composition is formulated to release in at least two phases wherein the first phase is a faster release rate, and wherein the second phase is a slower release rate. In such example, the need to address an acute burst release rate is met with the first phase, while a longer duration of drug release is achieved at least in part by the second phase.

In some examples, the therapeutic composition is formulated to release the one or more agents, configured to release the two or more agents, or is configured to release the three or more agents, in one or more of the following: a burst release phase and an extended release phase, wherein the release of a first phase comprises a faster release rate than a second release phase, or other.

In some examples, the therapeutic composition is formulated to release the one or more agents, wherein the therapeutic composition comprises a first therapeutic composition formulated to release said agents at a faster rate, and a second therapeutic composition formulated to release said agents at a slower release rate.

In some examples, the device comprises one therapeutic composition formulated to release one or more of direct factor Xa inhibitor, direct factor IIa inhibitor, and/or an anti-proliferative, wherein the formulation formulated to release the drugs over an extended period of at least 7 days, preferably at least 14 days, more preferably at least 21 days, and most preferably 1 year or more from exposure to vascular environment. Exemplary ranges are from 7 days to 1 year or more, preferably from 14 days to 1 year, more preferably from 21 days to 1 year, and most preferably from 30 days to 1 year from exposure to vascular environment. Optionally, the formulation is configured to have a bolus drug release rate within the first 1 hour, 3 hours, or first 24 hours, from exposure to vascular environment.

In some examples, the therapeutic composition is formulated to release the one or mon active substances at a rate sufficient to generate a tissue concentration at the injury site within a range of about 2 ng/mg to about 800 ng/mg within about 3 hours. In some examples, the therapeutic composition is formulated to release the one or more active substances at a rate sufficient to generate a tissue concentration at the injury site within a range of about 10 ng/mg to about 100 ng/mg within about 3 hours.

In some examples, the therapeutic composition is formulated to release the one or more active substances at a rate sufficient to generate a tissue concentration at the injury site within a range of about 2 ng/mg to about 100 ng/mg within about 24 hours. In some examples, the therapeutic composition is formulated to release the one or more active substances at a rate sufficient to generate a tissue concentration at the injury site within a range of about 3 ng/mg to about 50 ng/mg within about 24 hours. In some examples, the therapeutic composition is formulated to release the one or more active substances at a rate sufficient to generate a tissue concentration at the injury within a range of about 4 ng/mg to about 25 ng/mg within about 24 hours.

In some examples, the therapeutic composition is formulated to release the one or more active substances at a rate sufficient to generate a tissue concentration at the injury site within a range of about 1 ng/mg to about 30 ng/mg within about 7 days. In some examples, the therapeutic composition is formulated to release the one or more active substances at a rate sufficient to generate a tissue concentration at the injury site within a range of about 1.5 ng/mg to about 20 ng/mg within about 7 days. In some examples, the therapeutic composition is formulated to release the one or more active substances at a rate sufficient to generate a tissue concentration at the injury site within a range of about 2 ng/mg to about 25 ng/mg within about 7 days.

In some examples, the therapeutic composition is formulated to release the one or more active substances at a rate sufficient to generate a tissue concentration at the injury site within a range of about 0.5 ng/mg to about 30 ng/mg within about 28 days. In some examples, the therapeutic composition is formulated to release the one or more active substances at a rate sufficient to generate a tissue concentration at the injury site within a range of about 1 ng/mg to about 20 ng/mg within about 28 days. In some examples, the therapeutic composition is formulated to release the one or more active substances at a rate sufficient to generate a tissue concentration at the injury site within a range of about 1.5 ng/mg to about 25 ng/mg within about 28 days.

In some examples, the therapeutic composition is formulated to release the one or more active substances at a rate sufficient to generate a tissue concentration at the injury site within a range of about 0.1 ng/mg to about 10 ng/mg within about 90 days or about 180 days.

In some examples, the therapeutic composition is formulated to release the one or more active substances at a rate sufficient to generate a tissue concentration at a location proximal or distal a proximal end of the structure or a distal end of the structure, respectively, within a range of about 0.5 ng/mg to about 500 ng/mg within about 3 hours. In some examples, the therapeutic composition is formulated to release the one or more active substances at a rate sufficient to generate a tissue concentration at the locution proximal or distal the proximal end of the structure or the distal end of the structure, respectively, within a range of about 1 ng/mg to about 35 ng/mg within about 3 hours. In some examples, the therapeutic composition is formulated to release the one or more active substances at a rate sufficient to generate a tissue concentration at the location proximal or distal the proximal end of the structure or the distal end of the structure, respectively, within a range of about a range of about 1.5 ng/mg to about 30 ng/mg within about 3 hours. In some examples, the therapeutic composition is formulated to release the one or more active substances at a rate sufficient to generate a tissue concentration at the location proximal or distal to the proximal end of the structure or the distal end of the structure (e.g., within =5 mm proximal or distal to an end of the structure), respectively, within a range of about 0.1 ng/mg to about 50 ng/mg, about 0.25 ng/mg to about 20 ng/mg, about 1 ng/mg to about 50 ng/mg, or about 3 ng/mg to about 50 ng/mg within about 3 hours.

In some examples, the therapeutic composition is formulated to release the one or more active substances at a rate sufficient to generate a tissue concentration at a location proximal or distal a proximal end of the structure or a distal end of the structure, respectively, within a range of about 0.2 ng/mg to about 25 ng/mg, about 2 ng/mg to about 25 ng/mg, or about 4 ng/mg to about 25 ng/mg within about 24 hours. In some examples, the therapeutic composition is formulated to release the one or more active substances at a rate sufficient to generate a tissue concentration at a proximal segment (proximal to the proximal end of the device or device structure) or distal segment (distal to the distal end of the device or device structure) (e.g., within ±5 mm proximal or distal to an end of the structure), to the injury site respectively, ranging from about 0.1 ng/mg to about 50 ng/mg, from about 0.25 ng/mg to about 20 ng/mg, from about 1 ng/mg to about 50 ng/mg, or from about 3 ng/mg to about 50 ng/mg within about 24 hours. In some examples, the therapeutic composition is formulated to release the one or more active substances at a rate sufficient to generate a tissue concentration at a segment proximal or distal to the device (within ±5 mm from the device end), respectively, within a range of about 0.3 ng/mg to about 10 ng/mg within about 24 hours.

In some examples, the therapeutic composition is formulated to release a larger dose of the direct factor Xa inhibitor than the anti-proliferative agent. In some examples, the dose of the direct factor Xa inhibitor is about 1 to about 6 times larger, about 1.25 to about 5 times larger, about 1.5 to about 3 times larger, or about 1.5 to about 2.5 times larger than a dose of the anti-proliferative agent.

In some examples, the therapeutic composition is formulated to release a dose of the direct factor Xa inhibitor sufficient to generate a blood concentration of the direct factor Xa inhibitor which is smaller than a median maximum serum concentration ($C_{max}$) of the direct factor Xa inhibitor generated by systemic delivery of the direct factor Xa inhibitor to achieve the same tissue concentration at the injury site. In other examples, the therapeutic composition is formulated to release a dose of the direct factor Xa inhibitor sufficient to generate a blood concentration of the direct factor Xa inhibitor which is smaller than a median maximum serum concentration ($C_{max}$) of the direct factor Xa inhibitor generated by systemic delivery of the direct factor Xa inhibitor when taking one or more oral dose of said factor Xa inhibitor. In some examples, the systemic delivery comprises a single oral dose, a daily oral dose, or a smallest oral dose of the direct factor Xa inhibitor. In some examples, the blood concentration is larger than a median minimum serum concentration ($C_{min}$) of the direct factor Xa inhibitor generated by systemic delivery of a single oral dose. In some examples, the blood concentration is smaller than a median minimum serum concentration ($C_{min}$) of the direct factor Xa inhibitor generated by systemic delivery of a single oral dose. In some examples, the $C_{max}$ is measured using one of plasma blood, scrum blood, or whole blood, in other examples, the median $C_{max}$ is 80 ng/ml, or 123 ng/ml, or 171 ng/ml, or 321 ng/ml, or 480 ng/ml of blood.

In some examples, the therapeutic composition is formulated to release a dose of the direct factor Xa inhibitor sufficient to generate a plasma drug level area under the curve (AUC (0-24) or AUC (0-∞)) in ng·h/ml which is smaller than a median AUC (AUC (0-24) or AUC (0-∞)) in ng·h/ml of the direct factor Xa inhibitor generated by systemic delivery of the direct factor Xa inhibitor to achieve the same tissue concentration at the injury site. In other examples, the therapeutic composition is formulated to release a dose of the direct factor Xa inhibitor sufficient to generate a plasma drug level area under the curve (AUC (0-24) or AUC (0-∞)) in ng·h/ml which is less than a median (AUC (0-24) or AUC (0-∞)) in ng·h/ml of the direct factor Xa inhibitor generated by systemic delivery of the direct factor Xa inhibitor when taking one or more oral dose of said factor Xa inhibitor. In some examples, the systemic delivery comprises a single oral dose, a daily oral dose, or a smallest oral dose of the direct factor Xa inhibitor. In some examples, the (AUC (0-24) or AUC (0-∞)) is measured using one of plasma blood, serum blood, or whole blood. In other examples, the median (AUC (0-24) or AUC (0-∞)) is 724 ng·h/ml, or 1437 ng·h/ml, or 2000 ng·h/ml, or 4000 ng·h/ml.

In some examples, the therapeutic composition is formulated to release a dose of the anti-proliferative agent sufficient to generate a blood concentration of the anti-proliferative agent which is smaller than a median maximum serum concentration ($C_{max}$) of the anti-proliferative agent generated by systemic delivery of the anti-proliferative agent to achieve the same tissue concentration at the injury site. In other examples, the therapeutic composition is formulated to release a dose of the direct factor Xa inhibitor sufficient to generate a blood concentration of the anti-proliferative agent which is smaller than a median maximum serum concentration ($C_{max}$) of the anti-proliferative agent generated by systemic delivery of the anti-proliferative agent when taking one or more oral or IV dose of said anti-proliferative agent. In some examples, the systemic delivery comprises a single oral or IV dose, a daily oral dose, or a smallest oral dose of the anti-proliferative agent. In some examples, the blood concentration is larger than a median minimum serum concentration ($C_{min}$) of the anti-proliferative agent generated by systemic delivery of such agent. In some examples, the blood concentration is smaller than a median minimum serum concentration ($C_{min}$) of the anti-proliferative agent generated by systemic delivery of an oral or IV systemic therapeutic dose. In some examples, the therapeutic composition is formulated to release a dose of the anti-proliferative agent sufficient to generate a plasma drug level area under the curve (AUC (0-∞)) in ng·h/ml which is smaller than a median AUC (0-∞) in ng·h/ml of the anti-proliferative agent generated by systemic delivery of the anti-proliferative agent to achieve the same tissue concentration at the injury site.

In some examples, the therapeutic composition is formulated to release the one or more active substances at a rate within a range of about 2 μg/mm device to about 100 μg/mm device, about 5 μg/mm device to about 100 μg/mm device, about 7 μg/mm device to about 100 μg/mm device, or about 10 μg/mm device to about 100 μg/mm device within about 3 hours, 12 hours, 1 day, 3 days, 7 days, 28 days, 90 days, or 180 days. In some examples, the therapeutic composition is formulated to release the one or more active substances at a rate within a range of about 5 μg/mm device to about 100 μg/mm device within about 3 hours. In some examples, the therapeutic composition is formulated to release the one or more active substances at a rate within a range of about 5 μg/mm device to about 100 μg/nm device within about 12 hours. In some examples, the therapeutic composition is formulated to release the one or more active substances at a rate within a range of about 5 μg/mm device to about 100 μg/mm device within about 7 days. In some examples, the therapeutic composition is formulated to release the one or more active substances at a rate within a range of about 5 μg/mm device to about 100 μg/mm device within about 28 days.

In some examples, the therapeutic composition is formulated to release the one or more active substances at a dose within a range of about 0.5 μg/mm$^2$ device to about 15 μg/mm$^2$ device, or of about 1 μg/mm$^2$ device to about 12 μg/mm$^2$ device, or of about 2 μg/mm$^2$ device to about 12 μg/mm$^2$ device, or of about 5 μg/mm$^2$ device to about 12 μg/mm$^2$ device, or of about 7 μg/mm$^2$ device to about 12 μg/mm$^2$ device, within about 3 hours or about 12 hours or about 1 day or about 3 days or about 7 days. In some examples, the therapeutic composition is formulated to release the one or mote active substances at a dose within a range of about 1 μg/mm$^2$ device to about 12 μg/mm$^2$ device within about 3 hours. In some examples, the therapeutic composition is formulated to release the one or more active substances at a dose within a range of about 1 μg/mm$^2$ device to about 12 μg/mm$^2$ device within about 12 hours. In some examples, the therapeutic composition is formulated to release the one or more active substances at a dose within a range of about 1 μg/mm$^2$ device to about 12 μg/mm$^2$ device within about 7 days. In some examples, the therapeutic composition is formulated to release the one or more active substances at a dose within a range of about 1 μg/mm$^2$ device to about 12 μg/mm$^2$ device within about 28 days.

In some examples, the therapeutic composition is formulated to release the one or more active substances at a rate sufficient to generate a tissue concentration of about 1 ng/mg at about 14 mm from the external surface of the structure within about 28 days.

In some examples, the therapeutic composition is formulated to release the one or more active substances at a rate sufficient to generate a tissue concentration of about 0.5 ng/mg to about 10 ng/mg of tissue adjacent to the device structure within about 28 days or about 90 days or about 180 days.

In some examples, the therapeutic composition is formulated to release the direct factor Xa inhibitor and the anti-proliferative agent at the same rate. In some examples, the therapeutic composition is formulated to release the direct factor Xa inhibitor, and the anti-proliferative agent at different rates. In other examples, the therapeutic composition is formulated to release the direct factor Xa inhibitor at a faster rate than the anti-proliferative agent within the first 3 hours, 1 day, or 72 hour. In yet another example, the therapeutic composition is formulated to release the direct factor Xa inhibitor at a slower rate than the anti-proliferative agent within the first 3 hours, 1 day, or 72 hour.

In some examples, the release rate ratio of the direct factor Xa inhibitor to the anti-proliferative agent is within a range of about 3:2 to about 6:1, or about 2.2:2 to about 6:1, or about 2.5:2 to about 6:1. In some examples, the release rate ratio of the direct factor Xa inhibitor to the anti-proliferative agent is within a range of about 3:2 to about 6:1, about 2.2:2 to about 6:1, or about 2.5:2 to about 6:1 within about 3 hours, about 24 hours, about 7 days, or about 28 days. In some other examples, the release rate ratio of the direct factor Xa inhibitor to the anti-proliferative agent is within a range of about 1:1 to about 2:1 within about 3 hours, 1 day, about 3 days, about 7 days, or about 28 days.

In some examples, the therapeutic composition is formulated to release the anti-proliferative agent at a rate of about 1 μg/second/mm device to about 50 μg/day/mm device, of about 1 μg/min/mm device to about 10 μg/day/mm device, or of about 1 μg/hour/mm device to about 7 μg/day/mm device within about 3 hours, about 1 day, or about 3 days.

In some examples, the therapeutic composition is formulated to release the anti-proliferative agent at a rate of about 1 μg/hour/mm device to about 4 μg/day/mm device.

In some examples, the weight compositional ratio of the direct factor Xa inhibitor to the anti-proliferative agent in the therapeutic composition is about 5:2, about 2:1, about 1.25:1, or about 1:1. In some examples, the weight compositional ratio of the direct factor Xa inhibitor to the anti-proliferative agent in the therapeutic composition is within a range of about 5:1 to about 3:1 or about 5:1 to about 1:1.

In some examples, the therapeutic composition comprises a coating disposed on one or more surfaces of the device structure, and the coating comprises a first layer and a second layer, in some examples, the first layer comprises the direct factor Xa inhibitor. In some examples, the first layer comprises the anti-proliferative agent and the second layer comprises the direct factor Xa inhibitor. In some examples, the therapeutic composition further comprises a top layer or coat of the same or different material as the first layer or the second layer. In some examples, the tint layer comprises the direct factor Xa inhibitor and the anti-proliferative agent. In some examples, the second layer comprises a top layer or coat of the same or different material as the first layer. In some examples, the therapeutic composition comprises a coating disposed on one or more surfaces the device structure, and the coating further comprises a biodegradable polymer carrier. In some examples, the first and second layer comprise a drug/polymer matrix of the one or more agents. In one example, the first layer is configured for a burst release of the one or more agents, while the second layer is configured for an extended release of the one or more agents. In yet another example, the first and/or second layer are topcoat covering one or more drug agents wherein the one or more drug agents are formulated with un excipient or are formulated in a drug polymer matrix under said first and/or second layer coating. The coating of the matrix and the first or second layers maybe the same or different.

In some examples, the weight compositional ratio of the biodegradable polymer carrier to the one or more alive substances is about 1:5 to about 3:2, about 0.5:1 to about 1:1, or about 1:5 to about 1.25:1. In a preferred example, the polymer is biodegradable.

In some other examples, the weight compositional ratio of the carrier to the one or more active substances is about 1:5 to about 3:2, about 0.5:1 to about 1:1, or about 1:5 to about 1.25:1. In one example the carrier is one or more excipients.

In some examples, the therapeutic composition is disposed on at least one surface of the device, preferably on at least the external and/or the inner surfaces of the structure. In some examples, the therapeutic composition is disposed on the external surface (abluminal) of the structure, on the interior surface (lumina) of the structure, and on the side surfaces of the structure. In yet other examples, the therapeutic composition is disposed on one or more surfaces of the structure. In yet other examples, the therapeutic composition is disposed on all surfaces of the structure. In yet other examples, the therapeutic composition is disposed in a reservoir on or in the structure. In some examples, the therapeutic composition is disposed on the external surface of the structure.

In some examples, the therapeutic composition comprises a coating disposed on the external surface of the structure, and the coating further comprises a non-degradable polymer carrier. In some examples, the therapeutic composition comprises a coating disposed on the external surface of the structure, and the coating comprises at least one layer of a polymeric material containing the direct factor Xa inhibitor. In some examples, the therapeutic composition comprises a coating disposed on the external surface of the structure, and the coating consists of a single layer of a polymeric material which releasably contains the direct factor Xa inhibitor, in some examples, the therapeutic composition further comprises a top layer or coat comprising the same or different polymeric material. In some examples, the direct factor Xa inhibitor is uniformly distributed in the polymeric material. In some examples, the direct factor Xa inhibitor is non-uniformly distributed in the polymeric material.

In some examples, the therapeutic composition comprises a coating disposed on at least on surface of the structure, and the coating comprises at least one layer of a polymeric material holding one or more of the direct factor Xa inhibitor and the anti-proliferative agent. In some examples, the therapeutic composition comprises a coating disposed on the external surface of the structure, and the coating consists of a single layer of a polymeric material which releasably contains the direct factor Xa inhibitor and the anti-proliferative agent. In some examples, the therapeutic composition further comprises a top layer or coat comprising the same or different polymeric material. In some examples, the direct factor Xa inhibitor, and the anti-proliferative agent are uniformly distributed in the polymeric material. In some examples, the direct factor Xa inhibitor, and the anti-proliferative agent are non-uniformly distributed in the polymeric material. In some examples, the one or more active substances is present in the polymeric material at weight ratios within a range of about 1:1 to about 6:1 of direct factor Xa inhibitor to anti-proliferative agent.

In some examples, the polymeric material is porous. In some examples, the polymeric material has a porosity within a range of about 10 nm to about 10 µm. In some examples, the polymeric material is non-degradable. In some examples, the polymeric material is biodegradable. In some examples, the polymeric material has a degradation rate within a range of about 1 month to about 36 months. In some examples, the polymeric material comprises a material selected from a group consisting of polyesters, polylactide, polyglycolide, poly(ε-caprolactone), polydioxanone, poly (hydroxyalkanoates), poly(L-lactide-co-D-lactide), poly(L-lactide-co-D,L-lactide), poly(D-lactide-co-D,L-lactide), poly(lactide-co-glycolide) (including 70:30 to 99:1 PLA-co-PGA, such as 85:15 PLA-co-PGA), poly(lactide-co-ε-caprolactone) (including 70:30 to 99:1 PLA-co-PCL, such as 90:10 PLA-co-PCL), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), and copolymers and combinations thereof, wherein lactide includes L-lactide, D-lactide and D,L-lactide. In some examples, the polymeric material comprises a material selected from a group of non-degradable polymeric materials consisting of polyacrylates, polymethacrylates, poly(n-butyl methacrylate), poly(hydroxyethylmethacrylate), polyamides, nylons, nylon 12, Dacron, Polyethylene terephthalate, polyethylene glycol), polyethylene oxide (PEO), polydimethylsiloxane, polyvinylpyrrolidone, ethylene-vinyl acetate, phosphorylcholine-containing polymers, poly(2-methacryloyloxyethylphosphorylcholine), poly(2-methacryloyloxyethylphosphorylcholine-co-butyl methacrylate), and copolymers and combinations thereof.

In some examples, the therapeutic composition is disposed within a drug reservoir fluidly coupled to the external surface of the structure.

In some examples, the structure causes an injury at the injury site and the therapeutic composition is formulated to release the one or more active substances before the injury occurs. In some examples, the structure forms at least a portion of an implantable device. In some examples, the structure forms at least a portion of a surgical tool. In some examples, the structure forms at least a portion of a temporary or non-temporary device which is selected from the group consisting of access devices, infusion devices, tools, surgical instruments and tools, implants, bodily implants, hip implants, shoulder implants, knee implants, organ implants, luminal implants, vascular implants, stem-delivery systems, stents, stent-gratis, catheters, balloons, grail implants, gratis, aneurysm coils, valves, valve implants, shunts, left atrial appendage implants, foramen implants, leads, closure devices, clips, wound-closure devices and implants, sutures, patches, injection devices, guidewires, guiding catheters, needles inserted in the body, and needles inserted from outside the body. In some examples, the device comprising the structure is a stem. In some examples, the device comprising the structure is a balloon catheter.

In some examples, the device is a drug-coated balloon or a balloon reservoir. In some examples, the therapeutic composition is formulated to release the one or more active substances at a rate of 1 μg/minute/mm device to about 100 μg/minute/mm device. In some examples, the device is a catheter. In some examples, the catheter is a diffusion catheter, infusion catheter, balloon-catheter, or weeping catheter. In some examples, the device is a stent. In some examples, the device is a surgical instrument or tool. In some examples, the surgical instrument or tool is a surgical cutting instrument or knife. In some examples, the device is expandable against the injury site. In some examples, the device is configured to treat a blockage at the injury site. In some examples, the injury site comprises one or more of a body part, a duct, an atrium of the heart, a ventricle of the heart, a heart, a heart valve, a valve, an aorta, a coronary artery, a vein, an artery, a tissue, a surface, a lumen wall, a vessel wall, a hip, a shoulder, or a knee.

In another aspect, a medical device may comprise a structure having at least one surface configured for internal use within a patient's body and a therapeutic composition comprising two or more active substances including a direct factor Xa inhibitor and a direct factor IIa inhibitor. In some examples, the at least one surface of the structure is configured to be positioned adjacent an injury site in the patient's body. In some examples, the therapeutic composition is formulated to locally release the two or more active substances to the injury site at a rate or a concentration sufficient to reduce cell proliferation at the injury site within about 3 hours to about 7 days, or within about 28 days to about 12 months, after the external surface of the structure is positioned adjacent the injury site. For example, the therapeutic composition is preferably formulated to locally release the two or more active substances to the injury site at a rate sufficient to generate a tissue concentration of about 20 ng/mg tissue to about 200 ng/mg tissue, or more preferably about 40 ng/mg tissue to about 200 ng/mg tissue, of the one or more active substances at the injury site within about 3 hours after the external surface of the structure is positioned adjacent the injury site. In some examples, the therapeutic composition is formulated to locally release the two or more active substances to the injury site at a rate sufficient to generate a tissue concentration of about 2 ng/mg tissue to about 200 ng/mg tissue of the one or more active substances at the injury site within about 3 hours after the external surface of the structure is positioned adjacent the injury site. For example, the therapeutic composition is preferably formulated to locally release the one or more active substances to the injury site at a rate sufficient to generate a tissue concentration of about 20 ng/mg tissue to about 200 ng/mg tissue, or more preferably about 40 ng/mg tissue to about 200 ng/mg tissue, of the one or more active substances at the injury site within about 3 hours after the external surface of the structure is positioned adjacent the injury site.

In some examples, the therapeutic composition further comprises an anti-proliferative agent. In some examples, the direct factor IIa inhibitor comprises argatroban, dabigatran, ximelagatran, melagatran, efegatran, inogatran, atecegatran metoxil (AZD-0837), hirudin, hirudin analogs, bivalirudin, desirudin, or lepirudin. In some examples, the direct factor IIa inhibitor comprises argatroban, or a salt, isomer, solvate, analog (including deuterated analog), derivative, metabolite, or prodrugs thereof. In some examples, the direct factor IIa inhibitor comprises dabigatran, or a salt, isomer, solvate, analog (including deuterated analog), derivative, metabolite, or prodrugs thereof.

In some examples, the direct factor Xa inhibitor comprises apixaban, betrixaban, edoxaban, otamixaban, razaxaban, rivaroxaban, (r)-n-(2-(4-(1-methylpiperidin-4-yl)piperazin-1-yl)-2-oxo-1-phenylethyl)-1h-indole-6-carboxamide (LY-517717), daraxaban (YM-150), 2-[(7-carbamimidoylnaphthalen-2-yl)methyl-[4-(1-ethanimidoylpiperidin-4-yl)oxyphenyl]sulfamoyl]acetic acid (YM-466 or YM-60828), or eribaxaban (PD 0348292), or 2-(5-carbamimidoyl-2-hydroxy-phenyl) 4-[5-(2,6-dimethyl-piperidin-1-yl)-pentyl]-3-oxo-3,4-dihydro-quinoxaline-6-carboxylic acid (PD0313052). In some examples, the direct factor Xa inhibitor comprises rivaroxaban, or a salt, isomer, solvate, analog (including deuterated analog), derivative, metabolite, or prodrugs thereof. In some examples, the direct factor Xa inhibitor comprises apixaban, or a salt, isomer, solvate, analog (including deuterated analog), derivative, metabolite, or prodrugs thereof. In some examples, the anti-proliferative agent comprises Paclitaxel (Taxol), or salts, isomers, solvates, analogs, derivatives, metabolites, or prodrugs thereof. In some examples, the anti-proliferative agent comprises an m-TOR inhibitor. In some examples, the anti-proliferative agent comprises sirolimus, biolimus, everolimus, myolimus, novolimus, ridaforolimus, temsirolimus, zotarolimus, or salts, isomers, solvates, analogs (including deuterated analogs), derivatives, metabolites, or prodrugs thereof. In some examples, the anti-proliferative agent comprises sirolimus, or a salt, isomer, solvate, analog (including deuterated analog), derivative, metabolite, or prodrugs thereof.

In some examples, the direct factor IIa inhibitor comprises Argatroban and the direct factor Xa inhibitor comprises apixaban. In some examples, the direct factor IIa inhibitor comprises Argatroban, the direct factor Xa inhibitor comprise apixaban, and the anti-proliferative agent comprises sirolimus. In yet another examples the therapeutic composition comprises one of Apixaban, Rivaroxaban, or an analogue thereof, and one of Sirolimus or an analogue of Sirolimus.

In some examples, the therapeutic composition of a direct factor IIa inhibitor and a direct factor Xa inhibitor is formulated to reduce cell proliferation compared to either the direct factor IIa inhibitor or the direct factor Xa inhibitor alone. In some examples, the therapeutic composition is formulated to reduce, inhibit, and/or maintain reduced cell proliferation at the injury site at about 28 days after the external surface of the structure is positioned adjacent the injury site to about 12 months. In some examples, the therapeutic composition is formulated to reduce smooth muscle cell proliferation at the injury site. In some examples, the therapeutic composition of a direct factor IIa inhibitor and a direct factor Xa inhibitor and an antiproliferative is formulated to reduce cell proliferation compared to an antiproliferative alone. In some examples, the therapeutic composition is formulated to reduce, inhibit, and/or maintain reduced cell proliferation at the injury site at about 28 days after the external surface of the structure is positioned adjacent the injury site to about 12 months. In some examples, the therapeutic composition is formulated to reduce smooth muscle cell proliferation at the injury site. In some examples, the therapeutic composition is formulated to enhance an anti-proliferative activity (or enhance anti-proliferative efficacy) of the anti-proliferative agent by about 10% to about 30% in human smooth muscle compared to the anti-proliferative agent alone. In some examples, the direct factor IIa inhibitor and the direct factor Xa inhibitor synergistically increase clotting time as measured by ACT at a concentration of about 0.2 ng/mg or greater. In other examples, the therapeutic composition comprising a direct factor IIa inhibitor and a direct factor Xa inhibitor is formulated to release said agents at a rate sufficient to generate a tissue concentration at the injury site of about 0.2 ng/mg or greater for each of said agents within about 3 hours, about 12 hours, about 1 day, about 3 days, about 7 days, about 28 days, about 90 days, or about 180 days.

In some examples, the direct factor IIa inhibitor and the direct factor Xa inhibitor combined dose synergistically increase clotting time as measured by ACT by a range of about 3-7 times the ACT of the factor IIa at a dose equal to the combined dose, or by a range of about 1.5 to 2 times the ACT of the factor Xa inhibitor at a dose equal to the combined dose.

In some examples, the direct factor IIa inhibitor and the direct factor Xa inhibitor combined dose synergistically increase clotting time as measured by ACT by a range of about 2-3 times the ACT of the factor IIa at a dose equal to the combined dose and the ACT of the factor Xa inhibitor at a dose equal to the combined dose.

In other examples, the therapeutic composition comprising a direct factor IIa inhibitor and a direct factor Xa inhibitor is formulated to release said agents at a rate and/or concentration sufficient to accelerate dissolution or to inhibit one or more of inflammation, smooth muscle cell proliferation, cell proliferation, thrombin formation, fibrin formation, platelet aggregation, platelet activation, vessel injury, or clot formation, within about 3 hours to about 28 days or longer, or within about 3 hours to about 3 months or longer.

In other examples, the therapeutic composition comprising a direct factor IIa inhibitor and a direct factor Xa inhibitor is formulated to release said agents to accelerate dissolution of or to inhibit one or more of inflammation, smooth muscle cell proliferation, cell proliferation, thrombin formation, fibrin formation, platelet aggregation, platelet activation, vessel injury, or clot formation, within about 3 hours to about 28 days or longer, or within about 3 hours to about 3 months or longer.

In other examples, the therapeutic composition comprising a direct factor IIa inhibitor and a direct factor Xa inhibitor formulated to have a weight composition ratio of factor Xa inhibitor to factor IIa inhibitor in the ratio ranging from about 1:1 to about 10:1. In other examples, the therapeutic composition comprising a direct factor IIa inhibitor and a direct factor Xa inhibitor formulated to have a weight composition ratio of factor Xa inhibitor to factor IIa inhibitor in the ratio ranging from about 0.5:1 to about 5:1.

In some examples, the therapeutic composition is formulated to reduce one or more of cell proliferation or fibrin formation within 7 days or longer.

In some examples, the direct factor IIa inhibitor and the direct factor Xa inhibitor synergistically reduce cell proliferation as measured using late lumen loss (LLL) compared to the direct factor IIa inhibitor alone, or the direct factor Xa inhibitor alone, or low molecular weight heparin alone.

In some examples, the therapeutic composition is formulated to release the two or more active substances at a rate of 1 µg/second/mm device to about 50 µg/day/mm device, preferably at a rate of 1 µg/min/mm device to about 30 µg/day/mm device, more preferably at a rate of 1 µg/hour/mm device to about 30 µg/day/mm device. In some examples, the therapeutic composition is formulated to begin releasing the two or more active substances prior to positioning of the device adjacent to the injury site, or immediately after, or within about 5, about 15, or about 30 minutes after the at least one surface of the structure is positioned adjacent the injury site. In some examples, the therapeutic composition is formulated to begin releasing the two or more active substances before the external surface of the structure is positioned adjacent the injury site. In some examples, the therapeutic composition is formulated to release substantially all of the two or more active substances within about 1 to about 90 days or more. In some examples, the therapeutic composition is formulated to release substantially all of the two or more active substances within about 90 to about 180 days or more. In some examples, the therapeutic composition is formulated to release substantially all of the two or more active substances within about 7 days or about 28 days. In some examples, the therapeutic composition is formulated to release substantially all of the two or more active substances within about 3 hours or about 6 hours or about 12 hours or about 1 day or about 3 days. In some examples, the therapeutic composition is formulated to release at least 50% or at least 60% or at least 70% of the two or more active substances within about 3 hours or about 6 hours or about 12 hours or about 1 day or about 3 days or about 7 days or about 28 days.

In some examples, the therapeutic composition is formulated to release the two or more active substances at a rate sufficient to generate a tissue concentration at the injury site within a range of about 2 ng/mg to about 100 ng/mg within about 24 hours. In some examples, the therapeutic composition is formulated to release the two or more active substances at a rate sufficient to generate a tissue concentration at the injury site within a range of about 3 ng/mg to about 50 ng/mg within about 24 hours. In some example, the therapeutic composition is formulated to release the two or more active substances at a rate sufficient to generate a tissue concentration at the injury within a range of about 4 ng/mg to about 25 ng/mg within about 24 hours.

In some examples, the therapeutic composition is formulated to release the two or more active substances at a rate sufficient to generate a tissue concentration at the injury site within a range of about 1 ng/mg to about 30 ng/mg within about 7 days. In some examples, the therapeutic composition is formulated to release the two or more active substances at a rate sufficient to generate a tissue concentration at the injury site within a range of about 1.5 ng/mg to about 20 ng/mg within about 7 days. In some examples, the therapeutic composition is formulated to release the two or more active substances at a rate sufficient to generate a tissue concentration at the injury site within a range of about 2 ng/mg to about 25 ng/mg within about 7 days.

In some examples, the therapeutic composition is formulated to release the two or more active substances at a rate sufficient to generate a tissue concentration at the injury site within a range of about 0.5 ng/mg to about 30 ng/mg within about 28 days. In some examples, the therapeutic composition is formulated to release the two or more active substances at a rate sufficient to generate a tissue concentration at the injury site within a range of about 1 ng/mg to about 20 ng/mg within about 28 days. In some examples, the therapeutic composition is formulated to release the two or more active substances at a rate sufficient to generate a tissue concentration at the injury site within a range of about 1.5 ng/mg to about 25 ng/mg within about 28 days.

In some examples, the therapeutic composition is formulated to release the two or more active substances at a rate sufficient to generate a tissue concentration at the injury site within a range of about 0.1 ng/mg to about 10 ng/mg within about 90 days or about 180 days.

In some examples, the therapeutic composition is formulated to release the two or more active substances at a rate sufficient to generate a tissue concentration at a location proximal or distal a proximal end of the structure or a distal end of the structure, respectively, within a range of about 0.5 ng/mg to about 500 ng/mg within about 3 hours. In some examples, the therapeutic composition is formulated to release the two or more active substances at a rate sufficient to generate a tissue concentration at the location proximal or distal the proximal end of the structure or the distal end of the structure, respectively, within a range of about 1 ng/mg to about 35 ng/mg within about 3 hours. In some examples, the therapeutic composition is formulated to release the two or more active substances at a rate sufficient to generate a tissue concentration at the location proximal or distal the proximal end of the structure or the distal end of the structure, respectively, within a range of about a range of about 1.5 ng/mg to about 30 ng/mg within about 3 hours. In some examples, the therapeutic composition is formulated to release the two or more active substances at a rate sufficient to generate a tissue concentration at the location proximal or distal to the proximal end of the structure or the distal end of the structure (e.g., within 0.1:5 mm proximal or distal to an end of the structure), respectively, within a range of about 0.1 ng/mg to about 50 ng/mg, about 0.25 ng/mg to about 20 ng/mg, about 1 ng/mg to about 50 ng/mg, or about 3 ng/mg to about 50 ng/mg within about 3 hours.

In some examples, the therapeutic composition is formulated to release the two or more active substances at a rate sufficient to generate a tissue concentration at a location proximal or distal a proximal end of the structure or a distal end of the structure, respectively, within a range of about 0.2 ng/mg to about 25 ng/mg, about 2 ng/mg to about 25 ng/mg, or about 4 ng/mg to about 25 ng/mg within about 24 hours. In some examples, the therapeutic composition is formulate to release the two or more active substances at a rate sufficient to generate a tissue concentration at the location proximal or distal to the proximal end of the structure or the distal end of the structure (e.g., within ±5 mm proximal or distal to an end of the structure), respectively, within a range of about 0.1 ng/mg to about 50 ng/mg about 0.25 ng/mg to about 20 ng/mg, about 1 ng/mg to about 50 ng/mg, or about 3 ng/mg to about 50 ng/mg within about 24 hours. In some examples, the therapeutic composition is formulated to release the two or more active substances at a rate sufficient to generate a tissue concentration at the location proximal or distal the proximal end of the structure or the distal end of the structure, respectively, within a range of about 0.3 ng/mg to about 10 ng/mg within about 24 hours.

In some examples, the therapeutic composition is formulated to release a dose of the direct factor Xa inhibitor (of the two or more active substances) sufficient to generate a blood concentration of the direct factor Xa inhibitor which is smaller than a median maximum serum concentration ($C_{max}$) of the direct factor Xa inhibitor generated by systemic delivery of the direct factor Xa inhibitor to achieve the same tissue concentration at the injury site. In other examples, the therapeutic composition is formulated to release; a dose of the direct factor Xa inhibitor sufficient to generate a blood concentration of the direct factor Xa inhibitor which is smaller than a median maximum serum concentration ($C_{max}$) of the direct factor Xa inhibitor generated by systemic delivery of the direct factor Xa inhibitor when taking one or more oral dose of said factor Xa inhibitor. In some examples, the systemic delivery comprises a single oral dose, a daily oral dose, or a smallest oral dose of the direct factor Xa inhibitor. In some examples, the blood concentration is larger than a median minimum serum concentration ($C_{min}$) of the direct factor Xa inhibitor generated by systemic delivery. In some examples, the blood concentration is smaller than a median minimum serum concentration ($C_{min}$) of the direct factor Xa inhibitor generated by systemic delivery. In some examples, the $C_{max}$ is measured using one of plasma blood, serum blood, or whole blood. In other examples, the median $C_{max}$ (is 80 ng/ml, or 123 ng/ml, or 171 ng/ml, or 321 ng/ml, or 480 ng/ml of blood.

In some examples, the therapeutic composition is formulated to release a dose of the direct factor Xa inhibitor sufficient to generate a plasma drug level area under the curve (AUC (0-24) or AUC (0-∞)) in ng·h/ml which is smaller than a median AUC (AUC (0-24) or AUC (0-∞)) in ng·h/ml of the direct factor Xa inhibitor generated by systemic delivery of the direct factor Xa inhibitor to achieve the same tissue concentration at the injury site. In other examples, the therapeutic composition is formulated to release a dose of the direct factor Xa inhibitor sufficient to generate a plasma drug level area under the curve (AUC (0-24) or AUC (0-∞)) in ng·h/ml which is less than a median (AUC (0-24) or AUC (0-∞)) in ng·h/ml of the direct factor Xa inhibitor generated by systemic delivery of the direct factor Xa inhibitor when taking one or more oral dose of said factor Xa inhibitor. In some examples, the systemic delivery comprises a single oral dose, a daily oral dose, or a smallest oral dose of the direct factor Xa inhibitor. In some examples, the (AUC (0-24) or AUC (0-∞)) is measured using one of plasma blood, serum blood, or whole blood. In other examples, the median (AUC (0-24) or AUC (0-∞)) is 724 ng·h/ml, or 1437 ng·h ml, or 2000 ng/ml, or 4000 ng·h/ml.

In some examples, the therapeutic composition is formulated to release a dose of the direct factor IIa inhibitor (of the two or more active substances) sufficient to generate a blood concentration of the direct factor IIa inhibitor which is smaller than a median maximum serum concentration of the direct factor tin inhibitor generated by systemic delivery of the direct factor IIa inhibitor to achieve the same tissue concentration at the injury site. In other examples, the therapeutic composition is formulated to release a dose of the direct factor IIa inhibitor sufficient to generate a blood concentration of the direct factor IIa inhibitor which is smaller than a median maximum serum concentration ($C_{max}$) of the direct factor IIa inhibitor generated by systemic delivery of the direct factor IIa inhibitor when taking one or more oral dose of said factor IIa inhibitor. In some examples, the systemic delivery comprises a single oral dose, a daily oral dose, or a smallest oral dose of the direct factor IIa inhibitor. In some examples, the blood concentration is larger than a median minimum serum concentration ($C_{min}$) of the direct factor IIa inhibitor generated by systemic delivery. In some examples, the blood concentration is smaller than a median minimum serum concentration ($C_{min}$) of the direct factor IIa inhibitor generated by systemic delivery. In some examples, the is measured using one of plasma blood, serum blood, or whole blood. In other examples, the median $C_{max}$ is 80 ng/ml, or 123 ng/ml, or 171 ng/ml, or 321 ng/ml, or 480 ng/ml of blood.

In some examples, the therapeutic composition is formulated to release a dose of the direct factor IIa inhibitor sufficient to generate a plasma drug level area under the curve (AUC (0-24) or AUC (0-∞)) in ng/ml which is smaller than a median AUC (AUC (0-24) or AUC (0-∞)) in ng·h/ml of the direct factor IIa inhibitor generated by systemic delivery of the direct factor IIa inhibitor to achieve the same tissue concentration at the injury site. In other examples, the therapeutic composition is formulated to release a dose of the direct factor IIa inhibitor sufficient to generate a plasma drug level area under the curve (AUC (0-24) or AUC 10-∞)) in ng·h/ml which is less than a median (AUC (0-24) or AUC (0-∞)) in ng·h/ml of the direct factor IIa inhibitor generated by systemic delivery of the direct factor IIa inhibitor when taking one or more oral dose of said factor 11a inhibitor. In some examples, the systemic delivery comprises a single oral dose, a daily oral dose, or a smallest oral dose of the direct factor IIa inhibitor. In some examples, the (AUC (0-24) or AUC (0-∞)) is measured using one of plasma blood, serum blood, or whole blood. In other examples, the median (AUC (0-24) or AIX (0-∞)) is 724 ng·h/ml, or 1437 ng·h/ml, or 2000 ng/ml, or 4000 ng/ml.

In some examples, the therapeutic composition is formulated to release a dose of the anti-proliferative agent (of the two or more active substances) sufficient to generate a blood concentration of the anti-proliferative agent which is smaller than a median maximum serum concentration ($C_{max}$) of the anti-proliferative agent generated by systemic delivery of the anti-proliferative agent to achieve the same tissue concentration at the injury site.

In some examples, the systemic delivery comprises a single oral dose, a daily oral dose, or a smallest oral dose of the anti-proliferative agent. In some examples, the blood concentration is larger than a median minimum serum concentration ($C_{min}$) of the anti-proliferative agent generated by systemic delivery. In some examples, the blood concentration is smaller than a median minimum serum concentration ($C_{min}$) of the anti-proliferative agent generated by systemic delivery.

In some examples, the therapeutic composition is formulated to release a dose of the anti-proliferative agent sufficient to generate a plasma drug level area under the curve (AUC (0-∞)) in ng·h/ml which is smaller than a median AUC (0-∞) in ng·h/ml of the anti-proliferative agent generated by systemic delivery of the anti-proliferative agent to achieve the same tissue concentration at the injury site.

In some examples, the therapeutic composition is formulated to release the two or more active substances at a rate within a range of about 2 μg/mm device to about 100 μg/mm device, about 5 μg/mm device to about 100 μg/mm device, about 7 μg/mm device to about 100 μg/mm device, or about 10 μg/mm device to about 100 μg/mm device within about 3 hours, 12 hours, 1 day, 3 days, 7 days, 28 days, 90 days, or 180 days. In some examples, the therapeutic composition is formulated to release the two or more active substances at a rate within a range of about 5 μg/mm device to about 100 μg/mm device within about 3 hours. In some examples, the therapeutic composition is formulated to release the two or more active substances at a rate within a range of about 5 μg/mm device to about 100 μg/mm device within about 12 hours. In some examples, the therapeutic composition is formulated to release the two or more active substances at a rate within a range of about 5 μg/mm device to about 100 μg/nm device within about 7 days. In some examples, the therapeutic composition is formulated to release the two or more active substances at a rate within a range of about 5 μg/mm device to about 100 μg/mm device within about 28 days.

In some examples, the therapeutic composition is formulated to release the two or more active substances at a dose within a range of about 0.5 $\mu g/mm^2$ device to about 15 $\mu g/mm^2$ device, or of about 1 $\mu g/mm^2$ device to about 12 $\mu g/mm^2$ device, or of about 2 $\mu g/mm^2$ device to about 12 $\mu g/mm^2$ device, or of about 5 $\mu g/mm^2$ device to about 12 $\mu g/mm^2$ device, or of about 7 $\mu g/mm^2$ device to about 12 $\mu g/mm^2$ device, within about 3 hours or about 12 hours or about 1 day or about 3 days or about 7 days. In some examples, the therapeutic composition is formulated to release the two or more active substances at a dose within a range of about 1 $\mu g/mm^2$ device to about 12 $\mu g/mm^2$ device within about 3 hours. In some examples, the therapeutic composition is formulated to release the two or more active substances at a dose within a range of about 1 $\mu g/mm^2$ device to about 12 $\mu g/mm^2$ device within about 12 hours. In some examples, the therapeutic composition is formulated to release the two or more active substances at a dose within a range of about 1 $\mu g/mm^2$ device to about 12 $\mu g/mm^2$ device within about 7 days. In some examples, the therapeutic composition is formulated to release the two or more active substances at a dose within a range of about 1 $\mu g/mm^2$ device to about 12 $\mu g/mm^2$ device within about 28 days.

In some examples, the therapeutic composition is formulated to release the two or more active substances at a rate sufficient to generate a tissue concentration of about 1 ng/mg at about 14 mm from the external surface of the structure within about 28 days. In some examples, the therapeutic composition is formulated to release the two or more active substances at a rate sufficient to generate a tissue concentration of about 0.5 ng/mg to about 10 ng/mg of tissue adjacent to the device structure within about 28 days or about 90 days or about 180 days.

In some examples, the therapeutic composition is formulated to release the direct factor IIa inhibitor and the direct factor Xa inhibitor at about the same rate. In some examples, the therapeutic composition is formulated to release the direct factor IIa inhibitor and the direct factor Xa inhibitor at different rates. In some examples, the release rate ratio of the direct factor IIa inhibitor to the direct factor Xa inhibitor is within a range of about 0.7:1 to about 2:1. In some examples, the release rate ratio of the direct factor IIa inhibitor to the direct factor Xa inhibitor is within a range of about 0.7:1 to about 2:1 within about 3 hours, about 24 hours, or about 7 days.

In some examples, the therapeutic composition is formulated to release the direct factor IIa inhibitor, the direct factor Xa inhibitor, and the anti-proliferative agent at about the same rate. In some examples, the therapeutic composition is formulated to release the direct factor Xa inhibitor and the direct factor IIa inhibitor faster than the anti-proliferative agent. In some examples, the dose of the direct factor Xa inhibitor or the direct factor IIa inhibitor is about 1 to about 6 times larger, about 1.25 to about 5 times larger, about 1.5 to about 3 times larger, or about 1.5 to about 2.5 times larger than a dose of the anti-proliferative agent. In some examples, the therapeutic composition is formulated to release the direct factor IIa inhibitor, the direct factor Xa inhibitor, and the anti-proliferative agent at different rates.

In some examples, the therapeutic composition is formulated to release the anti-proliferative agent at a rate of about 1 μg/second-mm device to about 50 μg/day/mm device, of about 1 μg/min/mm device to about 10 μg/day/mm device, or of about 1 µg/hour/mm device to about 7 µg/day/mm device within about 3 hours, about 1 day, or about 3 days.

In some examples, the release rate ratio of the direct factor IIa inhibitor to the direct factor Xa inhibitor to the anti-proliferative agent is within a range of about 1:1:1 to about 4:4:1. In some examples, the therapeutic composition is formulated to release the direct factor IIa inhibitor at a rate of about 4 µg/hour/him device to about 14 µg/day/mm device. In some examples, the therapeutic composition is formulated to release the direct factor Xa inhibitor at a rate of about 4 µg/hour/mm device to about 14 µg/day/mm device. In some examples, the therapeutic composition is formulated to release the anti-proliferative agent at a rate of about 1 µg/hour/mm device to about 4 µg/day/mm device.

In some examples, the weight compositional ratio of the direct factor 0.1.1a inhibitor to the direct factor Xa inhibitor in the therapeutic composition is about 1:1. In some examples, the weight compositional ratio of the direct factor IIa inhibitor to the direct factor Xa inhibitor in the therapeutic composition is within a range of about 3:1 to about 1:3, for example about 1:1. In some examples, the weight compositional ratio of the direct factor IIa inhibitor to the direct factor Xa inhibitor to the anti-proliferative agent in the therapeutic composition is about 5:5:2. In some examples, the weight compositional ratio of the direct factor IIa inhibitor to the direct factor Xa inhibitor to the anti-proliferative agent in the therapeutic composition is within a range of about 6:6:1 to about 1:3:1.

In some other examples, the weight compositional ratio of the carrier to the two or more active substances is about 1:5 to about 3:1, about 0.5:1 to about 1:1, or about 1:5 to about 1.25:1. In one example the carrier is one or more excipients.

In some examples, the therapeutic composition is disposed on the external surface of the structure and on the internal (inner) surface of the structure. In some examples, the therapeutic composition is disposed on the external surface (abluminal) of the structure, on the interior surface (luminal) of the structure, and on the side surfaces of the structure. In yet other examples, the therapeutic composition is disposed on one or more surfaces of the structure. In yet other examples, the therapeutic composition is disposed on all surfaces of the structure. In yet other examples, the therapeutic composition is disposed in a reservoir on or in the structure. In some examples, the therapeutic composition is disposed on the external surface of the structure.

In some examples, the therapeutic composition comprises a coating disposed on at least one surface of the structure, and the coating comprises a first layer and a second layer. In some examples, the first layer comprises the direct factor IIa inhibitor and the direct factor Xa inhibitor. In some examples, the first layer comprises the direct factor IIa inhibitor and the second layer comprises the direct factor Xa inhibitor. In some examples, the therapeutic composition further comprises a top layer or coat of the same or different material as the first layer or the second layer.

In some examples, the therapeutic composition comprises a coating disposed on at least one surface of the structure, and the coating comprises a first layer and a second layer. In some examples, the first layer comprises the anti-proliferative agent, the dim factor IIa inhibitor, and the direct factor Xa inhibitor. In some examples, the second layer comprises a top layer or coat of the same or different material as the first layer. In some examples, the first layer comprises the anti-proliferative agent and the second layer comprises the direct factor IIa inhibitor and the direct factor Xa inhibitor. In some examples, the first layer comprises the anti-proliferative agent and the direct factor Xa inhibitor and the second layer comprises the direct factor IIa inhibitor. In some examples, the first layer comprises the direct factor IIa inhibitor and the direct factor Xa inhibitor and the second layer comprises the anti-proliferative agent. In some examples, the first layer comprises apixaban and argatroban and the second layer comprises sirolimus. In some examples, the therapeutic composition further comprises a top layer or coat of the same or different material as the first layer or the second layer.

In some examples, the coating further comprises a third layer. In some examples, the first layer comprises the direct factor IIa inhibitor, the second layer comprises the direct factor Xa inhibitor, and the third layer comprises the anti-proliferative agent. In some examples, the therapeutic composition further comprises a top layer or coat of the same or different material as the first layer, the second layer, or the third layer.

In some examples, the therapeutic composition comprises a coating disposed on at least one surface of the structure, and the coating further comprises a biodegradable polymer carrier. In some examples, the weight compositional ratio of the biodegradable polymer carrier to the two or more active substances is about 1:5 to about 3:2. In some examples, the therapeutic composition comprises a coating disposed on the external surface of the structure, and the coating comprises at least one layer of a polymeric material holding one or more of the direct factor IIa inhibitor and the direct factor Xa inhibitor.

In some examples, the therapeutic composition comprises a coating disposed on at least one surface of the structure, and the coating consists of a single layer of a polymeric material which releasably holds each of the direct factor IIa inhibitor and the direct factor Xa inhibitor. In some examples, the therapeutic composition further comprises a top layer or coat comprising the same or different polymeric material. In some examples, the direct factor IIa inhibitor and the direct factor Xa inhibitor are uniformly distributed in the polymeric material. In some examples, the direct factor IIa inhibitor and the direct factor Xa inhibitor are non-uniformly distributed in the polymeric material.

In some examples, the therapeutic composition comprises a coating disposed on at least one surface of the structure, and the coating comprises at least one layer of a polymeric material holding one or more of the direct factor IIa inhibitor, the direct factor Xa inhibitor, and the anti-proliferative agent. In some examples, the therapeutic composition comprises a coating disposed on at least one surface of the structure, and the coating consists of a single layer of a polymeric material which releasably holds each of the direct factor IIa inhibitor, the direct factor Xa inhibitor, and the anti-proliferative agent. In some examples, the therapeutic composition further comprises a top layer or coat comprising the same or different polymeric material. In some examples, the direct factor IIa inhibitor, the direct factor Xa inhibitor, and the anti-proliferative agent are uniformly distributed in the polymeric material. In some examples, the direct factor IIa inhibitor, the direct factor Xa inhibitor, and the anti-proliferative agent are non-uniformly distributed in the polymeric material.

In some examples, the two or more active substances are present in the polymeric material at weight ratios of about 1:3:1; about 3:2:1; about 2:2:1; about 2:3:1; about 3:3:1; about 5:5:1; or about 6:6:1 of direct factor IIa inhibitor to direct factor Xa inhibitor to anti-proliferative agent.

In some examples, the polymeric material is porous. In some examples, the polymeric material has a porosity within a range of about 10 nm to about 10 µm. In some examples, the polymeric material is non-degradable. In some examples, the polymeric material is biodegradable. In some examples, the polymeric material has a degradation rate within a range of about 1 month to about 36 months. In some examples, the polymeric material comprises a material selected from a group consisting of polyesters, polylactide, polyglycol ide, poly(ε-caprolactone), polydioxanone, poly(hydroxyalkanoates), poly(L-lactide-co-D-lactide), poly(L-lactide-co-D,L-lactide), poly(D-lactide-co-D,L-lactide), poly(lactide-co-glycolide) (including 70:30 to 99:1 PLA-co-PGA, such as 85:15 PLA-co-PGA), poly(lactide-co-ε-caprolactone) (including 70:30 to 99:1 PLA-co-PCL, such as 90:10 PLA-co-PCL), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), block polymers and copolymers and combinations thereof, wherein lactide includes L-lactide, D-lactide and D,L-lactide. In some examples, the polymeric material comprises a material selected from a group of non-degradable polymeric materials consisting of polyacrylates, polymethacrylates, poly(n-butyl methacrylate), poly(hydroxyethylmethacrylate), poly(styrene-b-isobutylene-b-styrene), phosphorylcholine polymer, poly(ethylene-co-vinyl acetate), poly(n-butyl methacrylate), blend of thermoplastic Silicone-Polycarbonate-urethane with poly n-butyl methacrylate, poly(vinylidene-co-hexafluoropropylene), Blend of polyvinylpyrrolidone, poly(hexylmethacrylate)-co-polyvinylpyrrolidone-co-poly vinyl acetate, and poly(n-butyl methacrylate)-co-polyvinyl acetate), Poly(styrene-butylene styrene), poly(tyrosine-derived polycarbonate), polyamides, nylons, nylon 12, Dacron, Polyethylene terephthalate, polyethylene glycol), polyethylene oxide (PEO), polydimethylsiloxane, polyvinylpyrrolidone, ethylene-vinyl acetate, phosphorylcholine-containing polymers, poly(2-methacryloyloxyethyl phosphorylcholine), poly(2-methacryloyloxyethylphosphorylcholine-co-butyl methacrylate), polyvinylpyridine block with poly methyl methacrylate (PIMA), poly N-(2-Hydroxypropyl) methacrylamide, Polyethylenimine (PEI), dextran, dextrin, chitosans, poly(L-lysine), and poly(aspartamides), polyamides, Polyethylene glycol (PEG), Silicones, poly(anhydride), poly ortho esters, polystyrene-b-polyvinylpyridine, poly(styrene)-poly(butadiene)-polyvinyl pyridine), poly(styrene-poly(methacrylic acid), poly(styrene)-poly(ethylene oxide), poly(vinyl pyridine)-poly(butadiene)-polyvinyl pyridine), and poly(styrene)-polyvinyl pyridine)-polyethylene oxide) and copolymers and combinations thereof.

In some examples, the therapeutic composition is disposed within a drug reservoir fluidly coupled to the external surface of the structure.

In some examples, the structure causes an injury at the injury site and the therapeutic composition is formulated to release the two or more active substances before the injury occurs. In some examples, the structure forms at least a portion of a temporary or non-temporary device which is selected from the group consisting of access devices, infusion devices, tools, surgical instruments and tools, implants, bodily implants, hip implants, shoulder implants, knee implants, organ implants, luminal implants, vascular implants, stent-delivery systems, stents, stem-grafts, catheters, balloons, graft implants, grafts, aneurysm coils, valves, valve implants, shunts, left atrial appendage implants, foramen implants, leads, closure devices, clips, wound-closure devices and implants, sutures, patches, injection devices, needles inserted in the body, and needles inserted from outside the body. In some examples, the device is a drug-coated balloon or a balloon reservoir. In some examples, the device is a scaffold (stent).

In some examples, the therapeutic composition is formulated to release the two or more active substances at a rate of 1 µg/minute/mm device to about 100 µg/minute/mm device. In some examples, the device is a catheter. In some examples, the catheter is a diffusion catheter, infusion catheter, balloon-catheter, or weeping catheter. In some examples, the device is a stmt. In some examples, the device is a surgical instrument or tool. In some examples, the surgical instrument or tool is a surgical cutting instrument or knife. In some examples, the device is expandable against the injury site. In some examples, the device is configured to treat a blockage at the injury site.

In some examples, the injury site comprises one or more of a body part, a duct, an atrium of the heart, a ventricle of the heart, a heart, a heart valve, a valve, an aorta, a coronary artery, a vein, an artery, an artery wall, a tissue, a surface, a lumen wall, a vessel wall, a hip, a shoulder, or a knee.

In another aspect, a method of treating one or more of inflammation, cell proliferation, smooth muscle cell proliferation, or clotting in a patient may comprise providing a structure having an external surface; deploying the structure at a target location in the patient's body so as to cause an injury at the location; and releasing from at least one surface of the deployed structure to the locution of injury in the patient's body therapeutically effective amounts of a therapeutic composition including at least a direct factor IIa inhibitor, a direct factor Xa inhibitor, and an anti-proliferative agent.

In other examples, the therapeutic composition comprising a direct factor IIa inhibitor and a direct factor Xa inhibitor and an anti-proliferative is formulated to release said agents at a rate sufficient to inhibit one or more of inflammation, smooth muscle cell proliferation, cell proliferation, thrombin formation, fibrin formation, or clot formation, within about 3 hours to about 28 days or longer, or within about 3 hours to about 3 months or longer.

In another example, the therapeutic composition is formulated to release the two or more active substances, wherein the two or more substances comprise a direct 11a inhibitor, a direct Xa inhibitor, and an antiproliferative, to an injury site in a body lumen. In another example, the therapeutic composition is formulated to release the two or more active substances, wherein the two or more substances include a direct IIa inhibitor, a direct Xa inhibitor, and an antiproliferative, to an injury site in a body lumen. In another example, the therapeutic composition is formulated to release the two or more active substances, wherein the two or more substances include a direct IIa inhibitor, and an antiproliferative, to an injury site in a body lumen. In another example, the therapeutic composition is formulated to release the two or more active substances, wherein the two or more substances include a direct IIa inhibitor, a direct Xa inhibitor, to an injury site in a body lumen. In another example, the therapeutic composition is formulated to release the two or more active substances, wherein the two or more substances include a direct Xa inhibitor and an anti-proliferative, to an injury site in a body lumen.

In some examples, the direct factor IIa inhibitor comprises argatroban, the direct factor Xa inhibitor comprises apixaban, and the anti-proliferative agent comprises sirolimus.

In some examples, the direct factor IIa inhibitor comprises argatroban, the direct factor Xa inhibitor comprises Rivaroxaban, and the anti-proliferative agent comprises sirolimus.

In some examples, the therapeutic composition comprises a coating on the external surface of the structure or at least one surface of the structure and releasing the therapeutic composition comprises releasing the therapeutic composition from the coating. In some examples, the coating comprises one or more layers. In some examples, the coating comprises a biodegradable porous polymeric material, a degradable polymeric material, or a non-degradable polymeric material. In some examples, the direct factor IIa inhibitor and the direct factor Xa inhibitor are released faster than the anti-proliferative agent. In some examples, the direct factor IIa inhibitor and the direct factor Xa inhibitor enhance an anti-proliferative effect of the anti-proliferative agent. In some examples, the therapeutic composition is disposed within a drug reservoir fluidly coupled to the external surface of the structure and releasing the therapeutic composition comprises delivering the therapeutic from the drug reservoir to the external surface of the deployed structure.

In some examples, the injury is at least partially caused before deployment of the structure. In some examples, deployment of the structure causes the injury and the therapeutic composition is formulated to release the direct factor IIa inhibitor, the direct factor Xa inhibitor, or the anti-proliferative agent before the injury occurs.

In some examples, the structure forms at least a portion of a temporary or non-temporary device which is selected from the group consisting of access devices, infusion devices, tools, surgical instruments and tools, implants, bodily implants, hip implants, shoulder implants, knee implants, organ implants, luminal implants, vascular implants, stent-delivery systems, stents, stent-grafts, catheters, balloons, graft implants, grafts, aneurysm coils, valves, valve implants, shunts, left atrial appendage implants, foramen implants, leads, closure devices, clips, wound-closure devices and implants, sutures, patches, injection devices, needles inserted in the body, and needles inserted from outside the body. In some examples, the device is a drug-coated balloon or a balloon reservoir. In some examples, the therapeutic composition is formulated to release the one or more active substances at a rate of 1 µg/minute/mm device to about 100 µg/minute/mm device.

In some examples, the device is a catheter. In some examples, the catheter is a diffusion catheter, infusion catheter, balloon-catheter, or weeping catheter. In some examples, the device is a scent. In some examples, the device is a surgical instrument or tool. In some examples, the surgical instrument or tool is a surgical cutting instrument or knife. In some examples, deploying the structure comprises expanding the structure against the injury site. In some examples, the target location comprises a blockage, and the method further comprises treating the blockage with the structure. In some examples, the injury site comprises one or more of a body part, a duct, an atrium of the heart, a ventricle of the heart, a heart, a heart valve, a valve, an aorta, a coronary artery, a vein, an artery, a tissue, a surface, a lumen wall, a vessel wall, a hip, a shoulder, or a knee.

In some examples, a device comprising an expandable stent configured to expand from a crimped configuration to a deployed configuration, wherein said stem comprises a plurality of circumferential rings, each ring comprises struts joined by crowns, and each ring is connected to an adjacent ring, said stent comprises a therapeutic composition comprises a factor Xa inhibitor, an m-TOR inhibitor, and a factor IIa inhibitor, said composition is coated on all surfaces of the stent. In one example, the coating comprise a polymeric material wherein the three agents are contained in the said polymeric material. In one example, the coating is substantially uniform. In another example, the coating thickness is larger on the abluminal surface compared to the thickness of the coating on the luminal surface. In another example, the coating comprises the three drugs and a carrier. In one example, the stent is formed from a tube, bend wire, rolled flat sheet, or printed. In one example, the stent is substantially tubular, tapered, or is configured to have various shapes and configurations along the length of the stent.

In some examples, a device comprising an elongated catheter wherein said catheter comprises an expandable member (such as a balloon) located towards a distal end of said catheter, said balloon comprises a therapeutic composition comprises a factor Xa inhibitor, optionally an m-TOR inhibitor, and optionally a factor IIa inhibitor, said composition is coated onto the exterior surface of said expandable member or as a reservoir within the expandable member. In one example, the coating comprises said one or more agents and said one or more agents are contained in one or more polymeric material, one or more carriers, or one or more excipients, or combination thereof. In yet another example, the coating comprises one or more agents contained in microspheres or nanospheres. In yet another example, the one or more agents are contained in a hydrophilic coating, a contrast agent, or other type carriers, excipients, or combination thereof: in one example, the expandable member performs or more functions comprising delivering locally one or more agents, open a blocked lumen or vessel, occlude a lumen or vessel, or other functions.

In some examples, an implant comprising a therapeutic composition, wherein said composition is formulated to release a dose of a direct factor Xa inhibitor at an injury site sufficient to inhibit clot formation. In yet other examples, an implant comprising a therapeutic composition, wherein said composition is formulated to release a dose of a direct factor Xa inhibitor and a dose of a factor IIa inhibitor, at an injury site sufficient to inhibit clot formation. In one example, the implant sole function is to release said composition. In another example, the implant has one or more functions comprising opening a blocked vessel, replacing a body part, replacing a body organ, repairing a body part, replacing a body function, occluding a body part, maintaining a body lumen open, and/or delivering locally one or more agents. In some examples, the injury is due to mechanical injury. In other examples, the injury is due to one or more of inflammation, clot formation, platelet aggregation, cell proliferation, or other. In yet another example, the device is placed in a mammalian body prior to injury. In some examples, the device is placed in a mammalian body lumen. In other examples, the device is placed in mammalian body tissue. In a third example, the device is placed in a mammalian blood vessel.

In some examples, the injury is due to mechanical injury. In other examples, the injury is due to one or more of inflammation, clot formation, platelet aggregation, cell proliferation, or other. In yet another example, the device is placed in a mammalian body prior to injury. In some examples, the device is placed in a mammalian body lumen. In other examples, the device is placed in mammalian body tissue. In a third example, the device is placed in a mammalian blood vessel.

In yet other examples, an implant comprising a therapeutic composition, wherein said composition is formulated to release a dose of a direct factor Xa inhibitor and optionally a dose of a factor IIa inhibitor, at an injury site sufficient to inhibit clot formation, wherein said composition is formulated to commence release of one or both agents within 30 minutes, 1 hour, 3 hours, 6 hours, or 24 hours of said injury, and wherein said release is formulated to last for about 3 hours to about 6 months or longer.

In yet other examples, an implant comprising a therapeutic composition, wherein said composition is formulated to release a dose of a direct factor Xa inhibitor and a dose of a factor IIa inhibitor, at an injury site sufficient to inhibit or resolve one or more of inflammation, IEL injury, injury, smooth muscle cell proliferation, cell proliferation, clot formation, platelet activation, or platelet aggregation, wherein said clot formation comprises one or more of clot at the injured tissue site, clot at a blood vessel adjacent to said tissue site, clot at the implant surface (exterior and/or interior), or clot in the systemic blood circulation resulting from said tissue injury.

In another example of any of the examples in this application, the medical device structure comprise one or more surfaces comprising one or more internal (inner) surface, external surface, one or more side surfaces, and wherein one or more agents are coated on at least one surface of the device, preferably coated on an inner structure surface, or coated on an exterior surface of the device, preferably coated on the entire device structure surfaces. In yet another example of this aspect, the medical device structure has more than two surfaces, and wherein the one or more agents are coated on all or some of these surfaces. In yet another example of this aspect, the coating thickness may be uniform between surfaces or vary between surfaces of the device structure. In yet another example of this aspect, the device may have a partial or full covering or sleeve on one or more surfaces of the device (such as FIFE, Dacron, or other type material) wherein said material comprises the one or more agents.

In some examples, the therapeutic composition comprises a first and, or second layer comprise a drug/polymer matrix of the one or more agents. In one example, the first layer is configured for a burst release of the one or more agents, while the second layer is configured for an extended release of the one or more agents. In yet another example, the first and/or second layer are topcoat covering one or more drug agents wherein the one or more drug agents are formulated with an excipient or are formulated in a drug polymer matrix under said first and/or second layer coating. The coating of the matrix and the first or second layers maybe the same or different.

In another example of any of the examples in this application, a therapeutic composition comprising two or more active substances on at least one surface of the device is configured to be positioned adjacent to an injury site in the patient's body, wherein adjacent to comprises one or more of the following: next to, touching, deployed at, expanded at, pushing against, placed against, or other. In a preferred example, the active substances are a direct factor IIa inhibitor and a direct factor Xa inhibitor. In another example the active substances are a direct factor IIa inhibitor, a direct factor Xa inhibitor and an anti-proliferative. In yet another example, the active substances are one of Argatroban, Rivaroxaban or Apixaban, and Sirolimus or Sirolimus analogue.

The illustrative examples described are not meant to be limiting. Other examples may be utilized, and other changes may be made, or combined in whole or in part, without departing from the scope of the subject matter presented herein. It will be readily understood that the aspects of the present disclosure, as generally described herein, and illustrated in the figures, and detailed description, and in the examples, can be arranged, substituted, combined, separated, and designed in a wide variety of different configurations, all of which are explicitly contemplated herein.

These and other embodiments are described in further detail in the following description related to the appended drawing figures.

In one aspect, the present invention provides, a medical device comprising a combination of a structure and a therapeutic composition. The structure has at least one surface and is configured for internal use within a patient's body, where the surface is positioned adjacent an injury site in the patient's body. The therapeutic composition comprises two or more active substances including, a direct factor IIa inhibitor, and a direct factor Xa inhibitor. The therapeutic composition is positioned on or in the device to release the two or more active substances to the injury site to accelerate dissolution of or to inhibit one or more of inflammation, cell proliferation, internal elastic lamina (IEL) injury, fibrin formation, platelet aggregation, platelet activation, and clot formation. In one example, optionally, the composition further comprises an anti-proliferative agent. The therapeutic composition is positioned on or in the device to release the two or more active substances to the injury site to increase activated clotting time and/or extend the time it takes for blood to clot. In another example, the composition further comprises an anti-platelet agent. In another example, the composition comprises two or more compositions to control one or more of release rate, one or more drug release, release duration of the one or more drugs, or other.

In one aspect, the present invention provides, a medical device comprising a combination of a structure and a therapeutic composition. The structure has at least one surface and is configured for internal use within a patient's body, where the surface is positioned adjacent an injury site in the patient's body. The therapeutic composition comprises one or more active substances including, a direct factor IIa inhibitor and/or a direct factor Xa inhibitor. The therapeutic composition is positioned on or in the device to release the one or more active substances to the injury site to accelerate dissolution of or to inhibit one or more of inflammation, cell proliferation, internal elastic lamina (IEL) injury, fibrin formation, platelet aggregation, platelet activation, and clot formation. The composition comprises a burst release phase ranging from 1 hour to 28 days, and an extended release phase ranging from 30 days to 1 year.

In another aspect, the present invention provides, a medical device comprising a combination of a structure and a therapeutic composition. The structure has a surface is configured for internal use within a patient's body, where the surface is positioned adjacent an injury site in the patient's body. The therapeutic composition comprises three or more active substances including an anti-proliferative agent, a direct factor IIa inhibitor, and a direct factor Xa inhibitor. The therapeutic composition is formulated and is positioned on the device to locally release the three or more active substances to the injury site to inhibit or resolve one or more of inflammation, cell proliferation, internal elastic lamina (IEL) injury, fibrin formation, platelet aggregation, platelet activation, and clot formation.

In another example, the therapeutic composition may be positioned on an external surface portion of the device, may be positioned on an internal surface of the device, and/or may be positioned on both external and internal surfaces of the device.

In specific example, at least a rapid release portion of the therapeutic composition is formulated to locally release the two or three or more active substances to the injury site at a rate or a concentration sufficient to begin to inhibit or resolve one or more of inflammation, cell proliferation, internal elastic lamina (IEL) injury, fibrin formation, platelet aggregation, platelet activation, and clot formation, typically within about 3 hours to about 7 days or to about 28 days after the surface of the structure is positioned adjacent the injury site.

In specific example, at least an extended release portion of the therapeutic composition is formulated to locally release the two, three or more active substances to the injury site at a rate or a concentration sufficient to inhibit or resolve one or more of inflammation, cell proliferation, internal elastic lamina (IEL) injury, fibrin formation, platelet aggregation, platelet activation, and clot formation; and/or to extend time before clot formation, for a period of at least 1 day, for a period of at least one week, for a period of at least one month, for a period of at least three months, for a period of at least six months, or for a period of at least one year after the surface of the structure is positioned adjacent the injury site.

In specific example, the therapeutic composition will include at least a rapid release portion and an extended release portion, where the extended release portion will continue releasing at least some of the active substances after the rapid release portion has substantially stopped releasing the active substances.

In some instances, the therapeutic compositions of the present invention may be formulated to substantially simultaneously release the at least two, three or more active substances. For example, the therapeutic compositions of the present invention may be formulated to release the direct factor IIa inhibitor and the direct factor Xa inhibitor and the anti-proliferative substantially simultaneously.

In other instances, the therapeutic compositions of the present invention may be formulated to release the direct factor IIa inhibitor and the direct factor Xa inhibitor substantially simultaneously and to release of the anti-proliferative after release of the direct factor IIa inhibitor and the direct factor Xa inhibitor has commenced. For example, release of the of the anti-proliferative agent may commence in a period of 1 minute to 3 days, usually 3 hours to 1 day, after release of the direct factor IIa inhibitor and the direct factor Xa inhibitor has commenced.

In still other instances, the therapeutic compositions of the present invention may be formulated to commence release of the direct factor IIa inhibitor before commencing release of the direct factor Xa inhibitor. For example, the release of the of the direct factor Xa inhibitor may commence from 1 minute to 3 days, usually 3 hours to 1 day, after release of the direct factor IIa inhibitor has commenced.

In still other instances, the therapeutic compositions of the present invention may be formulated to commence release of the direct factor Xa inhibitor before commencing release of the direct factor IIa inhibitor. For example, release of the of the direct factor IIa inhibitor may commence from 1 minute to 3 days, usually 3 hours to 1 day, after release of the direct factor Xa inhibitor has commenced.

Exemplary direct factor IIa inhibitors suitable for incorporation into the therapeutic compositions of the present invention include at least one of argatroban, dabigatran, ximelagatran, melagatran, efegatran, inogatran, atecegatran metoxil (AZD-0837), hirudin, hirudin analogs, bivalirudin, desirudin, and lepirudin. Presently preferred is argatroban, r a salt, isomer, solvate, analog, derivative, metabolite, or prodrugs thereof:

Exemplary direct factor Xa inhibitors suitable for incorporation into the therapeutic compositions of the present invention include at least one of apixaban, betrixaban, edoxaban, otamixaban, razaxaban, rivaroxaban, (r)-n-(2-(4-(1-methylpiperidin-4-yl)piperazin-1-yl)-2-oxo-1-phenyl-ethyl)-1 h-indole-6-carboxamide LY-517717), daraxaban (YM-150), 2-[(7-carbamimidoylnaphthalen-2-yl)methyl-[4-(1-ethanimidoylpiperidin-4-yl)oxyphenyl]sulfamoyl]acetic acid (YM-466 or YM-60828), or eribaxaban (PD 0348292), carbamimidoyl-2-hydroxy-phenyl) 4-[5-(2,6-dimethyl-piperidin-1-yl)-pentyl]-3-oxo-3,4-dihydro-quinoxaline-6-carboxylic acid (PD0313052). Presently preferred are rivaroxaban and apixaban, or a salt, isomer, solvate, analog, derivative, metabolite, or prodrugs thereof.

Exemplary anti-proliferative agents suitable for incorporation into the therapeutic compositions of the present invention include at least m-tor inhibitors selected from a group consisting of sirolimus, biolimus, everolimus, myolimus, novolimus, ridaforolimus, temsirolimus, zotarolimus, or salts, isomers, solvates, analogs, derivatives, metabolites, or prodrugs thereof. Preferred m-tor inhibitors include sirolimus, or a salt, isomer, solvate, analog, derivative, metabolite, or prodrugs thereof.

Exemplary anti-proliferative agents suitable fir incorporation into the therapeutic compositions of the present invention also include paclitaxel, or a salt, isomer, solvate, analog, derivative, metabolite, or pro drug thereof, as well as antiplatelet drugs.

Preferred combinations of active agent pairs include argatroban as the direct factor IIa inhibitor and apixaban or rivaroxaban as the direct factor Xa inhibitor comprises.

In specific instances, the structure may comprise a scaffold having at least an outer surface, an inner surface, and one or more edge surfaces between the outer and inner surface. In such instances at least a portion of the outer surface may coated with the therapeutic composition, at least a portion of the inner surface may be coated with the therapeutic composition, at least a portion of the edge surfaces is coated with the therapeutic composition, and frequently two or three of such surfaces will be coated.

In specific instances, at least some of the surfaces, including the outer, inner, and edge surfaces, may have receptacles formed therein, and at least some of these receptacles may have therapeutic agent(s) therein. The receptacles may comprise one or more of wells, channels, holes, surface texture, and the like.

In specific instances, the therapeutic compositions may further comprise an excipient, an adjuvant, a polymeric carrier, or the like.

In specific instances, the three or more active substances may be mixed uniformly with each other. Alternatively or additionally, the three or more active substances may be layered separately from each other. Each layer may comprise an excipient mixed with the therapeutic agent, where the excipient(s) in two or more layers may the same or may be different in at least two of the three layers.

In specific instances, the, the devices may further comprise a control-release layer timed over the at least two, three or more active substances.

In specific instances, the therapeutic composition may include a base layer formed over a surface of the structure and an top layer formed over the base layer. The base layer and top layer may differ in at least some properties. For example, the base layer and top layer differ in at least one of drug dose, drug release rate, and drug release duration.

In preferred examples, the top layer of the therapeutic composition will be formulated to commence release of the active substances before commencing of the active substances from the base layer. For example, the active substances may be released from the top layer over a time period in the range from 1 hour to 7 days after the surface of the structure is positioned adjacent the injury site and/or the active substances may be release from the base layer over a time period in the range from 7 days to 12 months after the active substances have been substantially completely released from the top layer. For example, each of the base and top layers may comprise at least three active substances are mixed in a biodegradable polymeric matrix.

In a second aspect, the present invention provides a vascular prosthesis comprising a scaffold and a therapeutic composition. The scaffold has an outer surface, an inner surface, and one or more edge surfaces therebetween. The therapeutic composition is disposed on at least a portion of the outer surface, wherein the therapeutic composition comprises three or more active substances including an anti-proliferative agent, a direct factor IIa inhibitor, and a direct factor Xa inhibitor. The therapeutic composition includes at least a base layer and a top layer, wherein the top layer is formulated to release the at least three active substances in a bolus when exposed to a vascular environment and the base layer is formulated to release the at least three active substances over an extended time period when exposed to the vascular environment.

In specific instances, of the vascular prosthesis, the anti-proliferative agent comprises sirolimus, the direct factor IIa inhibitor comprises argatroban, and the direct factor Xa inhibitor comprises rivaroxaban. The top layer is typically formulated to release the at least three active substances over a period from 1 hour to 3 hours or over a period from 1 hour to 7 days or over a period of 1 hour to 28 days when exposed to a vascular environment, while the base layer is formulated to release the at least three active substances over a period of at least 28 days, preferably over a period of at least 3 months, and most preferably over a period of at least 6 months, when exposed to a vascular environment. Preferably, the anti-proliferative agent comprises sirolimus, the direct factor IIa inhibitor comprises argatroban, and the direct factor Xa inhibitor comprises rivaroxaban or Apixaban.

In a third aspect, the present invention provides a method for treating tissue injury in patients. The method comprises deploying a structure at a target tissue injury location in the patient's body lumen. A therapeutic composition is released from the deployed structure to the location of injury, where the therapeutic composition comprises at least a direct factor IIa inhibitor, a direct factor Xa inhibitor, and optionally an anti-proliferative agent.

The therapeutic composition may be positioned on an external surface of the device, on an internal surface of the device, or on both external and internal surfaces of the device.

The tissue injury may be caused by deploying the structure at the location or may preexists deploying the structure at the location.

In specific instances, the body lumen comprises a blood vessel and the therapeutic composition is formulated to locally release the at least two, three or more active substances to the injury site at a rate or a concentration sufficient to begin to inhibit or resolve one or more of inflammation, cell proliferation, internal elastic lamina (IEL) injury, fibrin formation, platelet aggregation, platelet activation, and clot formation or dissolution within about 3 hours to about 7 days after the structure is deployed.

In specific instances, the at least two, three or more active substances may be released to the injury site at a rate or a concentration sufficient to inhibit one or more of inflammation, cell proliferation, internal elastic lamina (IEL) injury, fibrin formation, platelet aggregation, platelet activation, and clot formation or dissolution for a period of at least 1 day, for a period of at least one week, for a period of at least one month, for a period of at least three months, for a period of at least six months, or for a period of at least one year after the surface of the structure is positioned adjacent the injury site.

In specific instances, the two, three or more active substances are released substantially simultaneously.

Alternatively or additionally, the direct factor IIa inhibitor and the direct factor Xa inhibitor are released substantially simultaneously and the anti-proliferative is released after the release of the direct factor IIa inhibitor and the direct factor Xa inhibitor has commenced. For example, the release of the of the anti-proliferative agent may commence in a period of 1 minute to 3 days, usually 6 hours to 1 day, after release of the direct factor IIa inhibitor and the direct factor Xa inhibitor has commenced.

Alternatively or additionally, the therapeutic composition may commences release of the direct factor IIa inhibitor before commencing release of the direct factor Xa inhibitor. For example, the release of the of the direct factor Xa inhibitor commences from 1 minute to 3 days, usually 6 hours to 1 day, after release of the direct factor IIa inhibitor has commenced.

Alternatively or additionally, the therapeutic composition may commence release of the direct factor Xa inhibitor before commencing release of the direct factor IIa inhibitor. For example, wherein the release of the of the direct factor IIa inhibitor commences from 1 minute to 3 days, usually 6 hours to 1 day, after release of the direct factor Xa inhibitor has commenced.

In some instances, the direct factor IIa inhibitor comprises at least one of argatroban, dabigatran, ximelagatran, melagatran, efegatran, inogatran, atecegatran metoxil (AZD-0837), hirudin, hirudin analogs, bivalirudin, desirudin, and lepirudin. In presently preferred instances, the direct factor IIa inhibitor comprises argatroban, or a salt, isomer, solvate, analog, derivative, metabolite, or prodrugs thereof:

In some instances, the direct factor Xa inhibitor comprises at least one of apixaban, betrixaban, edoxaban, otamixaban, razaxaban, rivaroxaban, (r)-n-(2-(4-(1-methylpiperidin-4-yl)piperazin-1-yl)-2-oxo-1-phenylethyl)-1h-indole-6-carboxamide (LY-517717), daraxaban (YM-150), 2-[(7-carbamimidoylnaphthalen-2-yl)methyl-[4-(1-ethanimidoylpiperidin-4-yl)oxyphenyl]sulfamoyl]acetic acid (YM-466 or YM-60828), or eribaxaban (PD 0348292), carbamimidoyl-2-hydroxy-phenyl) 4-[5-(2,6-dimethyl-piperidin-1-yl)-pentyl]-3-oxo-3,4-dihydro-quinoxaline-6-carboxylic acid (PD0313052). In a presently preferred example, the direct factor Xa inhibitor comprises rivaroxaban, or a salt, isomer, solvate, analog, derivative, metabolite, or prodrugs thereof. In a second preferred example, the direct factor Xa inhibitor comprises apixaban, or a salt, isomer, solvate, analog, derivative, metabolite, or prodrugs thereof:

In some instances, the anti-proliferative agent comprises an in-Tor inhibitor may be selected from a group consisting of sirolimus, biolimus, everolimus, myolimus, novolimus, ridaforolimus, temsirolimus, zotarolimus, or salts, isomers, solvates, analogs, derivatives, metabolites, or prodrugs thereof. A presently preferred anti-proliferative agent comprises sirolimus, or a salt, isomer, solvate, analog, derivative, metabolite, or prodrugs thereof.

In other instances, the anti-proliferative agent may comprises paclitaxel, or a salts, isomer, solvate, analog, derivative, metabolite, or prodrug thereof.

In still other instances, the anti-proliferative agent may comprise an antiplatelet drug.

Preferred combinations and pairings of active substances in the methods herein, comprise: the direct factor IIa inhibitor comprising (1) argatroban and the direct factor Xa inhibitor comprising apixaban and (2) the direct factor IIa inhibitor comprising argatroban, the direct factor Xa inhibitor comprises apixaban, and the anti-proliferative agent comprising sirolimus.

In some instances, the structure comprises a scaffold having at least an outer surface, an inner surface, and one or more edge surfaces between the outer and inner surfaces and wherein deploying comprises expanding the scaffold in the body lumen. Typically, at least a portion of the outer surface is coated with the therapeutic composition. Optionally, at least a portion of the inner surface is coated with the therapeutic composition. Further optionally, a portion of the edge surfaces is coated with the therapeutic composition.

In some instances, at least some of the surfaces may have receptacles formed therein and at least some of these receptacles have therapeutic agent therein wherein the receptacles may comprise one or more of wells, channels, holes, and surface texture.

In some instances, the release rates) of the active substances will be controlled. For example, excipients with different degradation or release rates can be added to different layers and/or combined with different active substances. Additionally or alternatively, a control-release layer may be formed over therapeutic composition to control the release of the three or more active substances.

In some, the therapeutic composition may include a base layer formal over the surface and a top layer formed over the base layer, wherein the base layer and top layer differ in at least some properties. In such instances, the therapeutic composition may be formulated to release the active substances substantially completely from the top layer before releasing the active substances from the base layer. For example, the active substances may be released from the top layer over a time period in the range from 1 hour to 7 days after the surface of the structure is positioned adjacent the injury site, and the active substances are released from the base layer over a time period in the range from 7 days to 12 months after the after the active substances have been substantially completely released from the top layer. In some instances, each of the base and top layers comprises the at least three active substances are mixed in a biodegradable polymeric matrix.

Often, the injury is at least partially caused before deployment of the structure, but more commonly deployment of the structure, e.g. stent expansion in an artery, causes the injury and wherein the therapeutic composition is formulated to release the direct factor IIa inhibitor, the direct factor Xa inhibitor, or the anti-proliferative agent before, during, and/or following the injury occurs. Specific examples include vascular wall injury during vascular interventions, including, angioplasty, atherectomy, stent placement, graft placement, and the like.

In other instances, injury occurs during placement, implantation, or other introduction of a temporary or non-temporary device which is selected from the group consisting of access devices, infusion devices, tools, surgical instruments and tools, implants, bodily implants, hip implants, shoulder implants, knee implants, organ implants, lumina) implants, vascular implants, stem-delivery systems, stents, stent-grafts, catheters, balloons, graft implants, grafts, aneurysm coils, valves, valve implants, shunts, left atrial appendage implants, foramen implants, leads, closure devices, clips, wound-closure devices and implants, sutures, patches, injection devices, needles inserted in the body, and needles inserted from outside the body.

As described herein, it was surprisingly found that fast release composition and/or a fast release rate and an extended release rate composition of factor Xa inhibitor (alone or in combination with release of an anti-proliferative agent) resulted in prolonged anti-coagulant effects (e.g., one or more of inhibition of fibrin, inhibition of thrombin formation, enhanced fibrin dissolution, enhancing thrombin inhibition, inhibition of clot formation, and/or extending time before clotting) compared to control and/or a slower release composition profile. The combination of a direct factor Xa inhibitor and a direct IIa inhibitor composition was also surprisingly found to improve one or more of inhibition of fibrin, inhibition of clot formation, and extend time before clotting, compared to either agent alone. Additionally, it was surprisingly found that the combination of a direct Xa inhibitor and a direct IIa inhibitor composition resulted in unexpected anti-proliferative effects (e.g., reduced cell proliferation) in combination, while each agent alone had little to no anti-proliferative effect. Furthermore, surprisingly, and unexpectedly, direct Xa inhibitor and a direct IIa inhibitor combination with an anti-proliferative agent composition, improved or enhanced the anti-proliferative effect compared to the anti-proliferative agent composition alone. It was also surprisingly found that the combination of an anti-proliferative agent with a direct Xa inhibitor and a direct IIa inhibitor composition enhanced inhibition or enhanced dissolution of one or more of the following: fibrin, clot formation, thrombin, platelet aggregation, platelet activation, inflammation, time before clotting, and injury; acutely, and/or within 3 hours to 7 days, and/or within 28 days, and/or within 90 days.

In one example, several anticoagulants delivered locally were tested in-vivo in an animal model including Heparin, Rivaroxaban (factor Xa inhibitor), and Argatroban (factor IIa inhibitor). It was an unexpected result that only Rivaroxaban formulation was shown to inhibit fibrin formation at 7 days.

In another example, two formulations of Rivaroxaban were tested in a local delivery in-vivo animal model, wherein one formulation comprised a taster release dose release within 7 days versus control within 7 days. It was unexpected result that the composition comprising faster release dose released within 7 days was more effective than control, within 7 days. The composition comprising faster dose formulation inhibited fibrin more effectively through 28 days compared to the 7 days slower release dose.

A surprising finding was that composition comprising the fast release of Rivaroxaban in combination with m-TOR inhibitor released locally was more elective at inhibiting fibrin at 7 days and 28 days as compared to control while a slower release formulation of Rivaroxaban in combination with m-TOR inhibitor was less effective at inhibiting fibrin formation at 28 days from implant.

A surprising finding was that a composition comprising Rivaroxaban released locally in combination with m-TOR inhibitor inhibits fibrin formation after injury. Many attempts using heparin, and other anticoagulants have failed to show such effects when combined with m-TOR inhibitors.

A surprising finding was that a composition comprising Rivaroxaban released locally in combination with Argatroban inhibited fibrin formation after injury.

A surprising finding was that a composition comprising Rivaroxaban released locally in combination with Argatroban inhibited smooth muscle cell proliferation after injury.

A surprising finding was that a composition comprising Rivaroxaban released locally in combination with Argatroban and an m-TOR inhibitor further inhibited smooth muscle cell proliferation after injury.

In one example, a device for use in a body lumen is configured to release locally a composition comprising factor Xa inhibitor, preferably Rivaroxaban, more preferably Apixaban, wherein said device is configured to release at least 89 μg, preferably at least 150 μg (micro-grams) of said factor Xa inhibitor, within 3 hours, within 12 hours, within 1 day, within 3 days, or within 7 days from time of injury.

In another example, a device for use in a body lumen is configured to release locally a composition comprising factor Xa inhibitor, preferably Rivaroxaban, more preferably Apixaban, wherein said device is configured to release at least 6.3614 per millimeter of device length, preferably release at least 10.714 per millimeter of device length, of said factor Xa inhibitor within 3 hours, within 12 hours, within 1 day, within 3 days, or within 7 days from time of injury.

In another example, a device for use in a body lumen is configured to release locally a composition comprising factor Xa inhibitor, preferably Rivaroxaban, more preferably Apixaban, wherein said device from time of injury to 3 hours, 12 hours, 1 day, 3 days, or to 7 days is configured to release 89 μg or more or 6.36 μg or more/mm of device length of said drug, preferably configured to release 150 μg or more or 10.7 μg/mm of device length or more of said drug.

In another unexpected finding that the combination of factor Xa inhibitor Apixaban and Argatroban combination was shown to enhance the SMC proliferation inhibition when released together with m-TOR inhibitor, sirolimus. Further finding showed Apixaban or rivaroxaban and Argatroban combination had synergistic effects of one or more of extending time before clotting of blood, anti-fibrin formation, or anti clot formation effects that was better than either alone.

In an unexpected finding, composition comprising of a factor Xa inhibitor Apixaban, factor IIa inhibitor Argatroban, and the M-Tor inhibitor Sirolimus exhibited more efficacy at inhibiting one or more of the following at 28 days and/or 90 day time points: cell proliferation, inflammation, injury, fibrin formation inhibition, clot formation, and fibrin dissolution acceleration; and/or extending time before clotting of blood, and or increasing ACT.

The composition comprising a combination of factor Xa inhibitor (Apixaban), a factor II inhibitor (argatroban) and an anti-proliferative (M-tor) formulation was surprisingly more effective than an anti-proliferative (M-tor) alone.

The composition comprising a combination of factor Xa inhibitor (Apixaban) and a factor II inhibitor (argatroban) was effective at inhibiting clot/thrombus formation.

The composition comprising a combination of factor Xa inhibitor and a factor IIa inhibitor had surprisingly synergistic effect in extending time before clotting, an/or enhance anticoagulation effect, and/or inhibit clot formation, at a concentration of 0.025 ng/mg for each drug and higher. In a preferred example, a composition comprising a combination of factor Xa inhibitor and factor IIa inhibitor configured to release over a period ranging from 7 days to 1 year, preferably ranging from 21 day to 1 year, more preferably ranging from 30 days to one year, wherein the tissue concentration adjacent to said composition ranges from 0.025 ng/mg for each of said drugs to 10 ng/mg over said period.

In some examples, the therapeutic composition comprises one or more anticoagulant agents that has an IC50 to inhibit factor Xa and factor II at a dose ranging from 0.0001 nM to 1000 nM, preferably at a dose ranging from 0.0001 nM to 100 nM, more preferably at a dose ranging from 0.0001 nM to 10 nM, and most preferably at a dose ranging from 0.0001 nM to 1 nM.

Other aspects and features of the present invention are set forth in the following numbered clauses.

Clause 1. A medical device, the device comprising:
a structure having an external surface configured for internal use within a patient's body; and
a therapeutic composition comprising one or more active substances including a direct factor Xa inhibitor disposed on the external surface of the structure,
wherein the external surface of the structure is configured to be positioned adjacent an injury site in the patient's body, and
wherein the therapeutic composition is formulated to locally release the one or more active substances to the injury site at a rate sufficient to generate a tissue concentration of about 2 ng/mg tissue to about 200 ng/mg tissue of the one or more active substances at the injury site within about 3 hours after the external surface of the structure is positioned adjacent the injury site.

Clause 2. The device of clause 1, wherein the therapeutic composition further comprises an anti-proliferative agent.

Clause 3. The device of clause 1 or 2, wherein the direct factor Xa inhibitor comprises apixaban, betrixaban, edoxaban, otamixaban, razaxaban, rivaroxaban, (r)-n-(2-(4-(1-methylpiperidin-4-yl)piperazin-1-yl)-2-oxo-1-phenylethyl)-1h-indole-6-carboxamide (LY-517717), daraxaban (YM-150), 2-[(7-carbamimidoylnaphthalen-2-yl)methyl-[4-(1-ethanimidoylpiperidin-4-yl)oxyphenyl]sulfamoyl]acetic acid (YM-466 or YM-60828), or eribaxaban (PD 0348292), or 2-(5-carbamimidoyl-2-hydroxy-phenyl) 4-[5-(2,6-dimethyl-piperidin-1-yl)-pentyl]-3-oxo-3,4-dihydro-quinoxaline-6-carboxylic acid (PD03130521.

Clause 4. The device of clause 3, wherein the direct factor Xa inhibitor comprises rivaroxaban, or a salt, isomer, solvate, analog, derivative, metabolite, or prodrugs thereof.

Clause 5. The device of clause 3, wherein the direct factor Xa inhibitor comprises apixaban, or a salt, isomer, solvate, analog, derivative, metabolite, or pro drugs thereof.

Clause 6. The device of clause 2, wherein the anti-proliferative agent comprises sirolimus, biolimus, everolimus, myolimus, novolimus, ridaforolimus, temsirolimus, zotarolimus, or salts, isomers, solvates, analogs, derivatives, metabolites, or prodrugs thereof.

Clause 7. The device of clause 6, wherein the anti-proliferative agent comprises sirolimus, or a salt, isomer, solvate, analog, derivative, metabolite, or prodrugs thereof.

Clause 8. The device of clause 2, wherein the direct factor Xa inhibitor comprises apixaban and the anti-proliferative agent comprises sirolimus.

Clause 9. The device of clause 1 or 2, wherein the therapeutic composition is formulated to release the one or more active substances at a rate of 1 μg/hour/mm device to about 30 μg/day/mm device.

Clause 10. The device of clause 1 or 2, wherein the therapeutic composition is formulated to begin releasing the one or more active substances within about 15 minutes after the external surface of the structure is positioned adjacent the injury site.

Clause 11. The device of clause 1 or 2, wherein the therapeutic composition is formulated to begin releasing the one or more active substances before the external surface of the structure is positioned adjacent the injury site.

Clause 12. The device of clause 1 or 2, wherein the therapeutic composition is formulated to release substantially all of the one or more active substances within about 1 to about 90 days.

Clause 13. The device of clause 12, wherein the therapeutic composition is formulated to release substantially all of the one or more active substances within about 7 days or about 28 days.

Clause 14. The device of clause 2, wherein the therapeutic composition is formulated to release the direct factor Xa inhibitor faster than the anti-proliferative agent.

Clause 15. The device of clause 1 or 2, wherein the therapeutic composition is formulated to release the one or more active substances at a rate sufficient to generate a tissue concentration at the injury site within a range of about 2 ng/mg to about 800 ng/mg within about 3 hours.

Clause 16. The device of clause 1 or 2, wherein the therapeutic composition is formulated to release the one or more active substances at a rate sufficient to generate a tissue concentration at the injury site within a range of about 10 ng/mg to about 100 ng/mg within about 3 hours.

Clause 17. The device of clause 1 or 2, wherein the therapeutic composition is formulated to release the one or more active substances at a rate sufficient to generate a tissue concentration at the injury site within a range of about 2 wing to about 100 ng/mg within about 24 hours.

Clause 18. The device of clause 17, wherein the therapeutic composition is formulated to release the one or more active substances at a rate sufficient to generate a tissue concentration at the injury site within a range of about 3 ng/mg to about 50 ng/mg within about 24 hours.

Clause 19. The device of clause 17, wherein the therapeutic composition is formulated to release the one or more active substances at a rate sufficient to generate a tissue concentration at the injury within a range of about 4 ng/mg to about 25 ng/mg within about 24 hours.

Clause 20. The device of clause 1 or 2, wherein the therapeutic composition is formulated to release the one or more active substances at a rate sufficient to generate a tissue concentration at the injury site within a range of about 1 ng/mg to about 30 ng/mg within about 7 days.

Clause 21. The device of clause 20, wherein the therapeutic composition is formulated to release the one or more active substances at a rate sufficient to generate a tissue concentration at the injury site within a range of about 1.5 ng/mg to about 20 ng/mg within about 7 days.

Clause 22. The device of clause 20, wherein the therapeutic composition is formulated to release the one or more active substances at a rate sufficient to generate a tissue concentration at the injury site within a range of about 2 ng/mg to about 25 ng/mg within about 7 days.

Clause 23. The device of clause 1 or 2, wherein the therapeutic composition is formulated to release the one or more active substances at a rate sufficient to generate a tissue concentration at the injury site within a range of about 0.5 ng/mg to about 30 ng/mg within about 28 days.

Clause 24. The device of clause 23, wherein the therapeutic composition is formulated to release the one or more active substances at a rate sufficient to generate a tissue concentration at the injury site within a range of about 1 ng/mg to about 20 ng/mg within about 28 days.

Clause 25. The device of clause 23, wherein the therapeutic composition is formulated to release the one or more active substances at a rate sufficient to generate a tissue concentration at the injury site within a range of about 1.5 ng/mg to about 25 ng/mg within about 28 days.

Clause 26. The device of clause 1 or 2, wherein the therapeutic composition is formulated to release the one or more active substances at a rate sufficient to generate a tissue concentration at a location proximal or distal a proximal end of the structure or a distal end of the structure, respectively, within a range of about 0.5 ng/mg to about 500 ng/mg within about 3 hours.

Clause 27. The deice of clause 26, wherein the therapeutic composition is formulated to release the one or more active substances at a rate sufficient to generate a tissue concentration at the location proximal or distal the proximal end of the structure or the distal end of the structure, respectively, within a range of about 1 ng/mg to about 35 ng/mg within about 3 hours.

Clause 28. The device of clause 26, wherein the therapeutic composition is formulated to release the one or more active substances at a rate sufficient to generate a tissue concentration at the location proximal or distal the proximal end of the structure or the distal end of the structure, respectively, within a range of about a range of about 1.5 ng/mg to about 30 ng/mg within about 3 hours.

Clause 29. The device of clause 1 or 2, wherein the therapeutic composition is formulated to release the one or more active substances at a rate sufficient to generate a tissue concentration at a location proximal or distal a proximal end of the structure or a distal end of the structure, respectively, within a range of about 0.2 ng/mg to about 25 ng/mg within about 24 hours.

Clause 30. The device of clause 29, wherein the therapeutic composition is formulated to release the one or more active substances at a rate sufficient to generate a tissue concentration at the location proximal or distal the proximal end of the structure or the distal end of the structure, respectively, within a range of about 0.25 ng/mg to about 20 ng/mg within about 24 hours.

Clause 31. The device of clause 29, wherein the therapeutic composition is formulated to release the one or more active substances at a rate sufficient to generate a tissue concentration at the location proximal or distal the proximal end of the structure or the distal end of the structure, respectively, within a range of about 0.3 ng/mg to about 10 ng/mg within about 24 hours.

Clause 32. The device of clause 2, wherein the therapeutic composition is formulated to release a larger dose of the direct factor Xa inhibitor than the anti-proliferative agent.

Clause 33. The device of clause 32, wherein the dose of the direct factor Xa inhibitor is about 1.25 to about 5 times larger than a dose of the anti-proliferative agent.

Clause 34. The device of clause 1 or 2, wherein the therapeutic composition is formulated to release a dose of the direct factor Xa inhibitor sufficient to generate a blood concentration of the direct factor Xa inhibitor which is smaller than a median maximum serum concentration ($C_{max}$) of the direct factor Xa inhibitor generated by systemic delivery of the direct factor Xa inhibitor to achieve the same tissue concentration at the injury site.

Clause 35. The device of clause 34, wherein the systemic delivery comprises a single oral dose, a daily oral dose, or a smallest oral dose of the direct factor Xa inhibitor.

Clause 36. The device of clause 34, wherein the blood concentration is larger than a median minimum serum concentration ($C_{min}$) of the direct factor Xa inhibitor generated by systemic delivery.

Clause 37. The device of clause 34, wherein the blood concentration is smaller than a median minimum serum concentration ($C_{min}$) of the direct factor Xa inhibitor generated by systemic delivery.

Clause 38. The device of clause 1 or 2, wherein the therapeutic composition is formulated to release a dose of the direct factor Xa inhibitor sufficient to generate a plasma drug level area under the curve (AUC (0-∞)) in ng·h/ml which is smaller than a median AUC (0-∞) in ng·h/ml of the direct factor Xa inhibitor generated by systemic delivery of the direct factor Xa inhibitor to achieve the same tissue concentration at the injury site.

Clause 39. The device of clause 2, wherein the therapeutic composition is formulated to release a dose of the anti-proliferative agent sufficient to generate a blood concentration of the anti-proliferative agent which is smaller than a median maximum serum concentration ($C_{max}$) of the anti-proliferative agent generated by systemic delivery of the anti-proliferative agent to achieve the same tissue concentration at the injury site.

Clause 40. The device of clause 39, wherein the systemic delivery comprises a single oral dose, a daily oral dose, or a smallest oral dose of the anti-proliferative agent.

Clause 41. The device of clause 39, wherein the blood concentration is larger than a median minimum serum concentration ($C_{min}$) of the anti-proliferative agent generated by systemic delivery.

Clause 42. The device of clause 39, wherein the blood concentration is smaller than a median minimum serum concentration ($C_{min}$) of the anti-proliferative agent generated by systemic delivery.

Clause 43. The device of clause 2, wherein the therapeutic composition is formulated to release a dose of the anti-proliferative agent sufficient to generate a plasma drug level urea under the curve (AUC (0-∞)) in ng·h/ml which is smaller than a median AUC (0-∞) in ng·h/ml of the anti-proliferative agent generated by systemic delivery of the anti-proliferative agent to achieve the same tissue concentration at the injury site.

Clause 44. The device of clause 1 or 2, wherein the therapeutic composition is formulated to release the one or more active substances at a rate within a range of about 5 µg/mm device to about 100 µg/mm device within about 3 hours.

Clause 45. The device of clause 1 or 2, wherein the therapeutic composition is formulated to release the one or more active substances at a rate within a range of about 5 µg/mm device to about 100 µglum device within about 12 hours.

Clause 46. The device of clause 1 or 2, wherein the therapeutic composition is formulated to release the one or more active substances at a rate within a range of about 5 µg/mm device to about 100 µg mm device within about 7 days.

Clause 47. The device of clause 1 or 2, the therapeutic composition is formulated to release the one or more active substances at a rate within a range of about 5 µg/mm device to about 100 µg/mm device within about 28 days.

Clause 48. The device of clause 1 or 2, wherein the therapeutic composition is formulated to release the one or more active substances at a dose within a range of about 1 µg/mm$^2$ device to about 12 µg/mm$^2$ device within about 3 hours.

Clause 49. The device of clause 1 or 2, wherein the therapeutic composition is formulated to release the one or more active substances at a dose within a range of about 1 µg/mm$^2$ device to about 12 µg/mm$^2$ device within about 12 hours.

Clause 50. The device of clause 1 or 2, wherein the therapeutic composition is formulated to release the one or more active substances at a dose within a range of about 1 µg/mm$^2$ device to about 12 µg/mm$^2$ device within about 7 days.

Clause 51. The device of clause 1 or 2, wherein the therapeutic composition is formulated to release the one or more active substances at a dose within a range of about 1 µg/mm$^2$ device to about 12 µg/mm$^2$ device within about 28 days.

Clause 52. The device of clause 1 or 2, wherein the therapeutic composition is formulated to release the one or more active substances at a rate sufficient to generate a tissue concentration of about 1 ng/mg at about 14 mm from the external surface of the structure within about 28 days.

Clause 53. The device of clause 2, wherein the therapeutic composition is formulated to release the direct factor Xa inhibitor and the anti-proliferative agent at the same rate.

Clause 54. The device of clause 2, wherein the therapeutic composition is formulated to release the direct factor Xa inhibitor, and the anti-proliferative agent at different rates.

Clause 55. The device of clause 54, wherein the release rate ratio of the direct factor Xa inhibitor to the anti-proliferative agent is within a range of about 3:2 to about 6:1.

Clause 56. The device of clause 54, wherein the release rate ratio of the direct factor Xa inhibitor to the anti-proliferative agent is within a range of about 3:2 to about 6:1 within about 3 hours, about 24 hours, about 7 days, or about 28 days.

Clause 57. The device of clause 1 or 54, wherein the therapeutic composition is formulated to release the direct factor Xa inhibitor at a rate of about 4 µg/hour/mm device to about 14 µg/day/mm device.

Clause 58. The device of clause 54, wherein the therapeutic composition is formulated to release the anti-proliferative agent at a rate of about 1 µg/hour/mm device to about 41 µg/day/mm device.

Clause 59. The device of clause 2, wherein the weight compositional ratio of the direct factor Xa inhibitor to the anti-proliferative agent in the therapeutic composition is about 5:2.

Clause 60. The device of clause 2, wherein the weight compositional ratio of the direct factor Xa inhibitor to the anti-proliferative agent in the therapeutic composition is within a range of about 5:1 to about 3:1.

Clause 61. The device of clause 1, wherein therapeutic composition comprises a coating disposed on the external surface of the structure, and wherein the coating comprises a first layer and a second layer.

Clause 62. The device of clause 61, wherein the first layer comprises the direct factor Xa inhibitor.

Clause 63. The device of clause 2, wherein therapeutic composition comprises a coating disposed on the external surface of the structure, and wherein the coating comprises a first layer and a second layer.

Clause 64. The device of clause 63, wherein the first layer comprises the anti-proliferative agent and the second layer comprises the direct factor Xa inhibitor.

Clause 65. The device of clause 64, further comprising a top layer or coat of the same or different material as the first layer or the second layer.

Clause 66. The device of clause 63, wherein the first layer comprises the direct factor Xa inhibitor and the anti-proliferative agent.

Clause 67. The device of clause 66, wherein the second layer comprises a top layer or coal of the same or different material as the first layer.

Clause 68. The device of clause 1 or 2, wherein therapeutic composition comprises a coating disposed on the external surface of the structure, and wherein the coating further comprises a biodegradable polymer carrier.

Clause 69. The device of clause 68, wherein the weight compositional ratio of the biodegradable polymer carrier to the one or more active substances is about 1:5 to about 3:2.

Clause 70. The device of clause 1 or 2, wherein therapeutic composition comprises a coating disposed on the external surface of the structure, and wherein the coating further comprises a non degradable polymer carrier.

Clause 71. The device of clause 1, wherein therapeutic composition comprises a coating disposed on the external surface of the structure, and wherein the coating comprises at least one layer of a polymeric material containing the direct factor Xa inhibitor.

Clause 72. The device of clause 1, wherein therapeutic composition comprises a coating disposed on the external surface of the structure, and wherein the coating consists of a single layer of a polymeric material which releasably contains the direct factor Xa inhibitor.

Clause 73. The device of clause 71 or 72, further comprising a top layer or coat comprising the same or different polymeric material.

Clause 74. The device of clause 71 or 72, wherein the direct factor Xa inhibitor is uniformly distributed in the polymeric material.

Clause 75. The device of clause 71 or 72, wherein the direct factor Xa inhibitor is non-uniformly distributed in the polymeric material.

Clause 76. The device of clause 2, wherein therapeutic composition comprises a coating disposed on the external surface of the structure, and wherein the coating comprises at least one layer of a polymeric material containing one or more of the direct factor Xa inhibitor and the anti-proliferative agent.

Clause 77. The device of clause 2, wherein therapeutic composition comprises a coating disposed on the external surface of the structure, and wherein the coating consists of a single layer of a polymeric material which releasably contains the direct factor Xa inhibitor and the anti-proliferative agent.

Clause 78. The device of clause 76 or 77, further comprising a top layer or coat comprising the same or different polymeric material.

Clause 79. The device of clause 76 or 77, wherein the direct factor Xa inhibitor, and the anti-proliferative agent are uniformly distributed in the polymeric material.

Clause 80. The device of clause 76 or 77, wherein the direct factor Xa inhibitor, and the anti-proliferative agent are non-uniformly distributed in the polymeric material.

Clause 81. The device of clause 76 or 77, wherein the one or more active substances is present in the polymeric material at weight ratios within a range of about 1:1 to about 6:1 of direct factor Xa inhibitor to anti-proliferative agent.

Clause 82. The device of any one of clauses 71-81, wherein the polymeric material is porous.

Clause 83. The device of clause 82, wherein the polymeric material has a porosity within a range of about 10 mm to about 10 µm.

Clause 84. The device of any one of clauses 71-83, wherein the polymeric material is non degradable.

Clause 85. The device of any one of clauses 71-83, wherein the polymeric material is biodegradable.

Clause 86. The device of clause 85, wherein the polymeric material has a degradation rate within a range of about 1 month to about 36 months.

Clause 87. The device of any one of clauses 71-83, wherein the polymeric material comprises a material selected from a group consisting of polyesters, polylactide, polyglycolide, poly(ε-caprolactone), polydioxanone, poly(hydroxyalkanoates), poly(L-lactide-co-D-lactide), poly(L-lactide-co-D,L-lactide), poly(D-lactide-co-D,L-lactide), poly(lactide-co-glycolide) (including 70:30 to 99:1 PLA-co-PGA, such as 85:15 PLA-co-PGA), poly(lactide-co-ε-caprolactone) (including 70:30 to 99:1 PLA-co-PCL, such as 90:10 PLA-co-PCL), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), and copolymers and combinations thereof, wherein lactide includes L-lactide, D-lactide and D,L-lactide.

Clause 88. The device of any one of clauses 71-83, wherein the polymeric material comprises a material selected from a group of non-degradable polymeric materials consisting of polyacrylates, polymethacrylates, poly(n-butyl methacrylate), poly(hydroxyethylmethacrylate), poly(styrene-b-isobutylene-b-styrene), phosphorylcholine polymer, poly(ethylene-co-vinyl acetate), poly(n-butyl methacryalte), blend of thermoplastic Silicone-Polycarbonate-urethane with poly n-butyl methacrylate, poly(vinylidene-co-hexafluoropropylene), Blend of polyvinylpyrolidone, poly(hexylmethacrylate)-co-polyvinylpyrrolidone-co-poly vinyl acetate, and poly(n-butyl methacrylate)-co-poly(vinyl acetate). Polystyrene-butylene styrene), poly(tyrosine-derived polycarbonate), polyamides, nylons, nylon 12, Dacron, Polyethylene terephthalate, polyethylene glycol), polyethylene oxide (PEO), polydimethylsiloxane, polyvinylpyrrolidone, ethylene-vinyl acetate, phosphorylcholine-containing polymers, poly(2-methacryloyloxyethylphosphorylcholine), poly(2-methacryloyloxyethylphosphorylcholine-co-butyl methacrylate), polyvinylpyridine block with poly methyl methacrylate (PMMA), poly N-(2-Hydroxypropyl) methacrylamide, Polyethylenimine (PEI), dextran, dextrin, chitosans, poly(L-lysine), and poly(aspartamides), polyamides, Polyethylene glycol (PEG), Silicones, poly(anhydride), poly ortho esters, polystyrene-b-polyvinylpyridine, poly(styrene)-poly(butadiene)-polyvinyl pyridine), polystyrene, poly(methacrylic acid), poly(styrene)-poly(ethylene oxide), poly(vinyl pyridine)-poly(butadiene)-poly(vinyl pyridine), and polystyrene)-poly(vinyl pyridine)-polyethylene oxide) and monomers, block polymers, polymer mixtures, copolymers, and combinations thereof.

Clause 89. The device of clause 1 or 2, wherein the therapeutic composition is disposed within a drug reservoir fluidly coupled to the external surface of the structure.

Clause 90. The device of clause 1 or 2, wherein the structure causes an injury at the injury site and wherein the therapeutic composition is formulated to release the one or more active substances before the injury occurs.

Clause 91. The device of clause 1 or 2, wherein the structure forms at least a portion of an implantable device.

Clause 92. The device of clause 1 or 2, wherein the structure forms at least a portion of a surgical tool.

Clause 93. The device of clause 1 or 2, wherein the structure forms at least a portion of a temporary or non-temporary device which is selected from the group consisting of access devices, infusion devices, tools, surgical instruments and tools, implants, bodily implants, hip implants, shoulder implants, knee implants, organ implants, luminal implants, vascular implants, scent-delivery systems, stents, stent-grafts, catheters, balloons, graft implants, grafts, aneurysm coils, valves, valve implants, shunts, left atrial appendage implants, foramen implants, leads, closure devices, clips, wound-closure devices and implants, sutures, patches, injection devices, needles inserted in the body, and needles inserted from outside the body.

Clause 94. The device of clause 93, wherein the device is a drug-coated balloon or a balloon reservoir.

Clause 95. The device of clause 94, wherein the therapeutic composition is formulated to release the one or more active substances at a rate of 1 µg/minute/mm device to about 100 µg/minute/mm device.

Clause 96. The device of clause 93, wherein the device is a catheter.

Clause 97. The device of clause 96, wherein the catheter is a diffusion catheter, infusion catheter, balloon-catheter, or weeping catheter.

Clause 98. The device of clause 93, wherein the device is a stein.

Clause 99. The device of clause 93, wherein the device is a surgical instrument or tool.

Clause 100. The device of clause 99, wherein the surgical instrument or tool is a surgical cutting instrument or knife.

Clause 101. The device of clause 93, wherein the device is expandable against the injury site.

Clause 102. The device of clause 93, wherein the device is configured to treat a blockage at the injury site.

Clause 103. The device of clause 1 or 2, wherein the injury site comprises one of more of a body part, a duct, an atrium of the heart, a ventricle of the heart, a heart, a heart valve, a valve, an aorta, a coronary artery, a vein, an artery, a tissue, a surface, a lumen wall, a vessel wall, a ship, a shoulder, or a knee.

Clause 104. A medical device, the device comprising:
 a structure having an external surface configured for internal use within a patient's body; and
 a therapeutic composition comprising two or more active substances including a direct factor Xa inhibitor and a direct factor IIa inhibitor,
 wherein the external surface of the structure is configured to be positioned adjacent an injury site in the patient's body, and
 wherein the therapeutic composition is formulated to locally release the two or more active substances to the injury site at a rate or a concentration sufficient to reduce cell proliferation at the injury site within about 3 hours to about 7 days after the external surface of the structure is positioned adjacent the injury site.

Clause 105. The device of clause 104, wherein the therapeutic composition further comprises an anti-proliferative agent.

Clause 106. The device of clause 104 or 105, wherein the direct factor IIa inhibitor comprises argatroban, dabigatran, ximelagatran, melagatran, efegatran, inogatran, atecegatran metoxil (AZD-0837), hirudin, hirudin analogs, bivalirudin, desirudin, or lepirudin.

Clause 107. The device of clause 106, wherein the direct factor IIa inhibitor comprises argatroban, or a salt, isomer, solvate, analog, derivative, metabolite, or prodrugs thereof.

Clause 108. The device of clause 104 or 105, wherein the direct factor Xa inhibitor comprises apixaban, betrixaban, edoxaban, otamixaban, razaxaban, rivaroxaban, (r)-n-(2-(4-(1-methylpiperidin-4-yl)piperazin-1-yl)-2-oxo-1-phenyl-ethyl)-1h-indole-6-carboxamide(LY-517717), daraxaban (YM-150), 2-[(7-carbamimidoylnaphthalen-2-yl)methyl-[4-(1-ethanimidoylpiperidin-4-yl)oxyphenyl]sulfamoyl]acetic acid (YM-466 of YM-60828), or eribaxaban (PD 0348292), or 2-(5-carbamimidoyl-2-hydroxy-phenyl) 4-[5-(2,6-dimethyl-piperidin-1-yl)-pentyl]-3-oxo-3,4-dihydro-quinoxaline-6-carboxylic acid (PD0313052).

Clause 109. The device of clause 108, wherein the direct factor Xa inhibitor comprises rivaroxaban, or a salt, isomer, solvate, analog, derivative, metabolite, or pro drug thereof.

Clause 110. The device of clause 108, wherein the direct factor Xa inhibitor comprises apixaban, or a salt, isomer, solvate, analog, derivative, metabolite, or prodrugs thereof.

Clause 111. The device of clause 105, wherein the anti-proliferative agent comprises sirolimus, biolimus, everolimus, myolimus, novolimus, ridaforolimus, temsirolimus, zotarolimus, or salts, isomers, solvates, analogs, derivatives, metabolites, or prodrugs thereof.

Clause 112. The device of clause 111, wherein the anti-proliferative agent comprises sirolimus, or a salt, isomer, solvate, analog, derivative, metabolite, or prodrugs thereof.

Clause 113. The device of clause 104 or 105, wherein the direct factor IIa inhibitor comprises argatroban and the direct factor Xa inhibitor comprises apixaban.

Clause 114. The device of clause 105, wherein the direct factor IIa inhibitor comprises argatroban, the direct factor Xa inhibitor comprises apixaban, and the anti-proliferative agent comprises sirolimus.

Clause 115. The device of clause 104 or 105, wherein the therapeutic composition is formulated to reduce cell proliferation compared to either the direct factor IIa inhibitor or the direct factor Xa inhibitor alone.

Clause 116. The device of clause 104 or 105, wherein the therapeutic composition is formulated to maintain reduced cell proliferation at the injury site for about 28 days after the external surface of the structure is positioned adjacent the injury site.

Clause 117. The device of clause 104 or 105, wherein the therapeutic composition is formulated to reduce smooth muscle cell proliferation at the injury site.

Clause 118. The device of clause 105, wherein the therapeutic composition is formulated to enhance an anti-proliferative activity of the anti-proliferative agent by about 10% to about 30% in aortic human smooth muscle cell culture compared to the anti-proliferative agent alone.

Clause 119. The device of clause 104 or 105, wherein the direct factor IIa inhibitor and the direct factor Xa inhibitor synergistically reduce clotting time as measured by ACT at a concentration of about 0.2 ng/mg or greater.

Clause 120. The device of clause 104 or 105, wherein the therapeutic composition is formulated to reduce fibrin formation within 7 days as measured by a mean fibrin score below 1 compared to low molecular weight heparin.

Clause 121. The device of clause 104 or 105, wherein the direct factor IIa inhibitor and the direct factor Xa inhibitor synergistically reduce late lumen loss (LLL) compared to the direct factor IIa inhibitor alone, the direct factor Xa inhibitor alone, or low molecular weight heparin alone.

Clause 122. The device of clause 104 or 105, wherein the therapeutic composition is formulated to release the two or more active substances at a rate of 1 µg/hour/mm device to about 30 µg/day/mm device.

Clause 123. The device of clause 104 or 105, wherein the therapeutic composition is formulated to release substantially all of the two or more active substances within about 1 to about 90 days.

Clause 124. The device of clause 123, wherein the therapeutic composition is formulated to release substantially all of the two or more active substances within about 7 days or about 28 days.

Clause 125. The device of clause 104 or 105, wherein the therapeutic composition is formulated to release a dose of the direct factor Xa inhibitor sufficient to generate a blood concentration of the direct factor Xa inhibitor which is smaller than a median maximum serum concentration ($C_{max}$) of the direct factor Xa inhibitor generated by systemic delivery of the direct factor Xa inhibitor to achieve the same tissue concentration at the injury site.

Clause 126. The device of clause 125, wherein the systemic delivery comprises a single oral dose, a daily oral dose, or a smallest oral dose of the direct factor Xa inhibitor.

Clause 127. The device of clause 125, wherein the blood concentration is larger than a median minimum serum concentration ($C_{min}$) of the direct factor Xa inhibitor generated by systemic delivery.

Clause 128. The device of clause 125, wherein the blood concentration is smaller than a median minimum serum concentration ($C_{min}$) of the direct factor Xa inhibitor generated by systemic delivery.

Clause 129. The device of clause 104 or 105, wherein the therapeutic composition is formulated to release a dose of the direct factor Xa inhibitor sufficient to generate a plasma drug level area under the curve (AUC (0-∞)) in ng·h/ml which is smaller than a median AUC (0-∞) in ng·h/ml of the direct factor Xa inhibitor generated by systemic delivery of the direct factor Xa inhibitor to achieve the same tissue concentration at the injury site.

Clause 130. The device of clause 104 or 105, wherein the therapeutic composition is formulated to release a dose of the direct factor IIa inhibitor sufficient to generate a blood concentration of the direct factor IIa inhibitor which is smaller than a median maximum serum concentration ($C_{max}$) of the direct factor IIa inhibitor generated by systemic delivery of the direct factor IIa inhibitor to achieve the same tissue concentration at the injury site.

Clause 131. The device of clause 125, wherein the systemic delivery comprises a single oral dose, a daily oral dose, or a smallest oral dose of the direct factor IIa inhibitor.

Clause 132. The device of clause 125, wherein the blood concentration is larger than a median minimum serum concentration ($C_{min}$) of the direct factor IIa inhibitor generated by systemic delivery.

Clause 133. The device of clause 125, wherein the blood concentration is smaller than a median minimum serum concentration ($C_{min}$) of the direct factor IIa inhibitor generated by systemic delivery.

Clause 134. The device of clause 104 or 105, wherein the therapeutic composition is formulated to release a dose of the direct factor IIa inhibitor sufficient to generate a plasma drug level area under the curve (AUC (0-∞)) in ng·h/ml which is smaller than a median AUC (0-∞) in ng·h/ml of the direct factor IIa inhibitor generated by systemic delivery of the direct factor IIa inhibitor to achieve the same tissue concentration at the injury site.

Clause 135. The device of clause 105, wherein the therapeutic composition is formulated to release a dose of the anti-proliferative agent sufficient to generate a blood concentration of the anti-proliferative agent which is smaller than a median maximum serum concentration ($C_{max}$) of the anti-proliferative agent generated by systemic delivery of the anti-proliferative agent to achieve the same tissue concentration at the injury site.

Clause 136. The device of clause 135, wherein the systemic delivery comprises a single oral dose, a daily oral dose, or a smallest oral dose of the anti-proliferative agent.

Clause 137. The device of clause 135, wherein the blood concentration is larger than a median minimum serum concentration ($C_{min}$) of the anti-proliferative agent generated by systemic delivery.

Clause 138. The device of clause 135, wherein the blood concentration is smaller than a median minimum serum concentration ($C_{min}$) of the anti-proliferative agent generated by systemic delivery.

Clause 139. The device of clause 105, wherein the therapeutic composition is formulated to release a dose of the anti-proliferative agent sufficient to generate a plasma drug level area under the curve (AUC (0-∞)) in ng·h/ml which is smaller than a median AUC (0-∞) in ng·h/ml of the anti-proliferative agent generated by systemic delivery of the anti-proliferative agent to achieve the same tissue concentration at the injury site.

Clause 140. The device of clause 104 or 105, wherein the therapeutic composition is formulated to release the two or more active substances at a rate within a range of about 5 μg/mm device to about 100 μg/mm device within about 3 hours.

Clause 141. The device of clause 104 or 105, wherein the therapeutic composition is formulated to release the two or more active substances at a rate within a range of about 5 μg/mm device to about 100 μg/mm device within about 12 hours.

Clause 142. The device of clause 104 or 105, wherein the therapeutic composition is formulated to release the two or more active substances at a rate within a range of about 5 μg/mm device to about 100 μg/mm device within about 7 days.

Clause 143. The device of clause 104 or 105, wherein the therapeutic composition is formulated to release the two or more active substances at a rate within a range of about 5 μg/mm device to about 100 μg/mm device within about 28 days.

Clause 144. The device of clause 104 or 105, wherein the therapeutic composition is formulated to release the two or more active substances at a dose within a range of about 1 μg/mm² device to about 12 μg/mm² device within about 3 hours.

Clause 145. The device of clause 104 or 105, therapeutic composition is formulated to release the two or more active substances at a dose within a range of about 1 μg/mm² device to about 12 μg/mm² device within about 12 hours.

Clause 146. The device of clause 104 or 105, wherein the therapeutic composition is formulated to release the two or more active substances at a dose within a range of about 1 μg/mm² device to about 12 μg/mm² device within about 7 days.

Clause 147. The device of clause 104 or 105, wherein the therapeutic composition is formulated to release the two or more active substance at a dose within a range of about 1 μg/mm² device to about 12 μg/mm² device within about 28 days.

Clause 148. The device of clause 104 or 105, wherein the therapeutic composition is formulated to release the two or more active substances at a rate sufficient to generate a tissue concentration of about log/mg at about 14 mm from the external surface of the structure within about 28 days.

Clause 149. The device of clause 104, wherein the therapeutic composition is formulated to release the direct factor IIa inhibitor and the direct factor Xa inhibitor at the same rate.

Clause 150. The device of clause 104, wherein the therapeutic composition is formulated to release the direct factor IIa inhibitor and the direct factor Xa inhibitor at different rates.

Clause 151. The device of clause 150, wherein the release rate ratio of the direct factor IIa inhibitor to the direct factor Xa inhibitor is within a range of about 0.7:1 to about 2:1.

Clause 152. The device of clause 150, wherein the release rate ratio of the direct factor IIa inhibitor to the direct factor Xa inhibitor is within a range of about 0.7:1 to about 2:1 within about 3 hours, about 24 hours, or about 7 days.

Clause 153. The device of clause 105, wherein the therapeutic composition is formulated to release the direct factor IIa inhibitor, the direct factor Xa inhibitor, and the anti-proliferative agent at the sane rate.

Clause 154. The device of clause 105, wherein the therapeutic composition is formulated to release the direct factor Xa inhibitor and the direct factor IIa inhibitor faster than the anti-proliferative agent.

Clause 155. The device of clause 154, wherein the dose of the direct factor Xa inhibitor or the direct factor IIa inhibitor is about 1 to about 6 times larger than a dose of the anti-proliferative agent.

Clause 156. The device of clause 105, wherein the therapeutic composition is formulated to release the direct factor IIa inhibitor, the direct factor Xa inhibitor, and the anti-proliferative agent at different rates.

Clause 157. The device of clause 156, wherein the release rate ratio of the direct factor IIa inhibitor to the direct factor Xa inhibitor to the anti-proliferative agent is within a range of about 1:1:1 to about 4:4:1.

Clause 158. The device of clause 150 or 156, wherein the therapeutic composition is formulated to release the direct factor IIa inhibitor at a rate of about 4 µg/hour/mm device to about 14 µg/day/mm device.

Clause 159. The device of clause 150 or 156, wherein the therapeutic composition is formulated to release the direct factor Xa inhibitor at a rate of about 4 µg/hour-mm device to about 14 µg/day/mm device.

Clause 160. The device of clause 156, wherein the therapeutic composition is formulated to release the anti-proliferative agent at a rate of about 1 µg/hour/mm device to about 4 µg/day/mm device.

Clause 161. The device of clause 104, wherein the weight compositional ratio of the direct factor IIa inhibitor to the direct factor Xa inhibitor in the therapeutic composition is about 1:1.

Clause 162. The device of clause 104, wherein the weight compositional ratio of the direct factor IIa inhibitor to the direct factor Xa inhibitor in the therapeutic composition is within a range of about 3:1 to about 1:3.

Clause 163. The device of clause 105, wherein the weight compositional ratio of the direct factor IIa inhibitor to the direct factor Xa inhibitor to the anti-proliferative agent in the therapeutic composition is about 5:5:2.

Clause 164. The device of clause 105, wherein the weight compositional ratio of the direct factor IIa inhibitor to the direct factor Xa inhibitor to the anti-proliferative agent in the therapeutic composition is within a range of about 6:6:1 to about 1:3:1.

Clause 165. The device of clause 104, wherein therapeutic composition comprises a coating disposed on the external surface of the structure, and wherein the coating comprises a first layer and a second layer.

Clause 166. The device of clause 165, wherein the first layer comprises the direct factor IIa inhibitor and the direct factor Xa inhibitor.

Clause 167. The device of clause 165, wherein the first layer comprises the direct factor IIa inhibitor and the second layer comprises the direct factor Xa inhibitor.

Clause 168. The device of clause 166 or 167, further comprising a top layer or coat of the same or different material as the first layer or the second layer.

Clause 169. The device of clause 105, wherein therapeutic composition comprises a coating disposed on the external surface of the structure, and wherein the coating comprises a first layer and a second layer.

Clause 170. The device of clause 169, wherein the first layer comprises the anti-proliferative agent, the direct factor IIa inhibitor, and the direct factor Xa inhibitor.

Clause 171. The device of clause 170, wherein the second layer comprises a top layer or coat of the same or different material as the first layer.

Clause 172. The device of clause 169, wherein the first layer comprises the anti-proliferative agent and the second layer comprises the direct factor IIa inhibitor and the direct factor Xa inhibitor.

Clause 173. The device of clause 169, wherein the first layer comprises the anti-proliferative agent and the direct factor Xa inhibitor and the second layer comprises the direct factor IIa inhibitor.

Clause 174. The device of clause 169, wherein the first layer comprises the direct factor IIa inhibitor and the direct factor Xa inhibitor and the second layer comprises the anti-proliferative agent.

Clause 175. The device of clause 174, wherein the first layer comprises apixaban and argatroban and the second layer comprises sirolimus.

Clause 176. The device of any one of clauses 172-175, further comprising a top layer or coat of the same or different material as the first layer or the second layer.

Clause 177. The device of clause 169, wherein the coating further comprises a third layer.

Clause 178. The device of clause 177, wherein the first layer comprises the direct factor IIa inhibitor, the second layer comprises the direct factor Xa inhibitor, and the third layer comprises the anti-proliferative agent.

Clause 179. The device of clause 177, further comprising a top layer or coat of the same or different material as the first layer, the second layer, or the third.

Clause 180. The device of clause 104 or 105, wherein therapeutic composition comprises a coating disposed on the external surface of the structure, and wherein the coating further comprises a biodegradable polymer carrier.

Clause 181. The device of clause 180, wherein the weight compositional ratio of the biodegradable polymer carrier to the two or more active substances is about 1:5 to about 3:2.

Clause 182. The device of clause 104 or 105, wherein therapeutic composition comprises a coating disposed on the external surface of the structure, and wherein the coating further comprises a non-degradable polymer carrier.

Clause 183. The device of clause 104, wherein therapeutic composition comprises a coating disposed on the external surface of the structure, and wherein the coating comprises at least one layer of a polymeric material containing one or more of the direct factor IIa inhibitor and the direct factor Xa inhibitor.

Clause 184. The device of clause 104, wherein therapeutic composition comprises a coating disposed on the external surface of the structure, and wherein the coating consists of a single layer of a polymeric material which releasably contains each of the direct factor IIa inhibitor and the direct factor Xa inhibitor.

Clause 185. The device of clause 183 or 184, further comprising a top layer or coat comprising the same or different polymeric material.

Clause 186. The device of clause 183 or 184, wherein the direct factor IIa inhibitor and the direct factor Xa inhibitor are uniformly distributed in the polymeric material.

Clause 187. The device of clause 183 or 184, wherein the direct factor IIa inhibitor and the direct factor Xa inhibitor are non-uniformly distributed in the polymeric material.

Clause 188. The device of clause 105, wherein therapeutic composition comprises a coating disposed on the external surface of the structure, and wherein the coating comprises at least one layer of a polymeric material containing one or more of the direct factor IIa inhibitor, the direct factor Xa inhibitor, and the anti-proliferative agent.

Clause 189. The device of clause 105, wherein therapeutic composition comprises a coating disposed on the external surface of the structure, and wherein the coating consists of a single layer of a polymeric material which releasably contains each of the direct factor IIa inhibitor, the direct factor Xa inhibitor, and the anti-proliferative agent.

Clause 190. The device of clause 188 or 189, further comprising a top layer or coat comprising the same or different polymeric material.

Clause 191. The device of clause 188 or 189, wherein the direct factor IIa inhibitor, the direct factor Xa inhibitor, and the anti-proliferative agent are uniformly distributed in the polymeric material.

Clause 192. The device of clause 188 or 189, wherein the direct factor IIa inhibitor, the direct factor Xa inhibitor, and the anti-proliferative agent are non-uniformly distributed in the polymeric material.

Clause 193. The device of clause 188 or 189, wherein the two or more active substances are present in the polymeric material at weight ratios of about 1:3:1; about 3:2:1; about 2:2:1; about 2:3:1; about 3:3:1; about 5:5:1; or about 6:6:1 of direct factor IIa inhibitor to direct factor Xa inhibitor to anti-proliferative agent.

Clause 194. The device of any one of clauses 183-193, wherein the polymeric material is porous.

Clause 195. The device of clause 194, wherein the polymeric material has a porosity within a range of about thin to about 10 μm.

Clause 196. The device of any one of clauses 183-193, wherein the polymeric material is non-degradable.

Clause 197. The device of any one of clauses 183-193, wherein the polymeric material is biodegradable.

Clause 198. The device of clause 197, wherein the polymeric material has a degradation rate within a range of about 1 month to about 36 months.

Clause 199. The device of any one of clauses 183-193, wherein the polymeric material comprises a material selected from a group consisting of polyesters, polylactide, polyglycolide, poly(ε-caprolactone), polydioxanone, poly (hydroxyalkanoates), poly(L-lactide-co-D-lactide), poly(L-lactide-co-D,L-lactide), poly(D-lactide-co-D,L-lactide), poly(lactide-co-glycolide) (including 70:30 to 99:1 PLA-co-PGA, such as 85:15 PLA-co-PGA), poly(lactide-co-ε-caprolactone) (including 70:30 to 99:1 PLA-co-PCL, such as 90:10 PLA-co-PCL), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), and copolymers and combinations thereof wherein lactide includes L-lactide, D-lactide and D,L-lactide.

Clause 200. The device of any one of clauses 183-193, wherein the polymeric material comprises a material selected from a group of non-degradable polymeric materials consisting of polyacrylates, polylmethacrylates, poly(n-butyl methacrylate), poly(hydroxyethylmethacrylate), poly (styrene-b-isobutylene-b-styrene), phosphorylcholine polymer, poly(ethylene-co-vinyl acetate), poly(n-butyl methacrylate), blend of thermoplastic Silicone-Polycarbonate-urethane with poly n-butyl methacrylate, poly(vinylidene-co-hexafluoropropylene), Blend of polyvinylpyrrolidone, poly(hexylmethacrylate)-co-polyvinylpyrrolidone-co-poly vinyl acetate, and poly(n-butyl methacrylate)-co-polyvinyl acetate), Polystyrene-butylene styrenes, poly(tyrosine-derived polycarbonate), polyamides, nylons, nylon 12, Dacron, Polyethylene terephthalate, poly(ethylene glycol), polyethylene oxide (PEO), polydimethylsiloxane, polyvinylpyrrolidone, ethylene-vinyl acetate, phosphorylcholine-containing polymers, poly(2-methacryloyloxyethylphosphorylcholine), poly(2-methacryloyloxyethylphosphorylcholine-co-butyl methacrylate), polyvinylpyridine block with poly methyl methacrylate (PMMA), poly N-(2-Hydroxypropyl) methacrylamide, Polyethylenimine (PEt), dextran, dextrin, chitosans, poly(L-lysine), and poly(aspartamides), polyamides, Polyethylene glycol (PEG), Silicones, poly(anhydride), poly ortho esters, polystyrene-b-polyvinylpyridine, poly(styrene)-poly(butadiene)-polyvinyl pyridine), poly(styrene-poly(methacrylic acid), poly(styrene)-polyethylene oxide), polyvinyl pyridine)-poly(butadiene)-poly(vinyl pyridine), and poly(styrene)-polyvinyl pyridine)-poly(ethylene oxide) and monomers, block polymers, polymer mixtures, copolymers, and combinations thereof.

Clause 201. The device of clause 104 or 105, wherein the therapeutic composition is disposed within a drug reservoir fluidly coupled to the external surface of the structure.

Clause 202. The device of clause 104 or 105, wherein the structure causes an injury at the injury site and wherein the therapeutic composition is formulated to release the two or more active substances before the injury occurs.

Clause 203. The device of clause 104 or 105, wherein the structure forms at least a portion of a temporary or non-temporary device which is selected from the group consisting of access devices, infusion devices, tools, surgical instruments and tools, implants, bodily implants, hip implants, shoulder implants, knee implants, organ implants, luminal implants, vascular implants, stent-delivery systems, stents, stent-grafts, catheters, balloons, graft implants, grafts, aneurysm coils, valves, valve implants, shunts, left atrial appendage implants, foramen implants, leads, closure devices, clips, wound-closure devices and implants, sutures, patches, injection devices, needles inserted in the body, and needles inserted from outside the body.

Clause 204. The device of clause 203, wherein the device is a drug-coated balloon or a balloon reservoir.

Clause 205. The device of clause 204, wherein the therapeutic composition is formulated to release the one or more active substances at a rate of μg/minute/mm device to about 100 μg/minute/mm device.

Clause 206. The device of clause 203, wherein the device is a catheter.

Clause 207. The device of clause 206, wherein the catheter is a diffusion catheter, infusion catheter, balloon-catheter, or weeping catheter.

Clause 208. The device of clause 203, wherein the device is a stent.

Clause 209. The device of clause 203, wherein the device is a surgical instrument or tool.

Clause 210. The device of clause 209, wherein the surgical instrument or tool is a surgical cutting instrument or knife.

Clause 211. The device of clause 203, wherein the device is expandable against the injury site.

Clause 212. The device of clause 203, wherein the device is configured to treat a blockage at the injury site.

Clause 213. The device of clause 104 or 105, wherein the injury site comprises one or more of a body part, a duct, an atrium of the heart, a ventricle of the heart, a heart, a heart valve, a valve, an aorta, a coronary artery, a vein, an artery, a tissue, a surface, a lumen wall, a vessel wall, a hip, a shoulder, or a knee.

Clause 214. A method of treating clotting in a patient, the method comprising:
  i. providing a structure having an external surface;
  ii. deploying the structure at a target location in the patient's body so as to cause an injury at the location; and
  iii. releasing from the external surface of the deployed structure to the location of injury in the patient's body therapeutically effective amounts of a therapeutic composition including at least a direct factor IIa inhibitor, a direct factor Xa inhibitor, and an anti-proliferative agent.

Clause 215. The method of clause 214, the direct factor IIa inhibitor comprises argatroban, the direct factor Xa inhibitor comprises apixaban, and the anti-proliferative agent comprises sirolimus.

Clause 216. The method of clause 214, wherein the therapeutic composition comprises a coating on the external surface of the structure and wherein releasing the therapeutic composition comprises releasing the therapeutic composition from the coating.

Clause 217. The method of clause 216, wherein the coating comprises one or more layers.

Clause 218. The method of clause 216, wherein the coating comprises a biodegradable porous matrix material, a degradable matrix material, or a non-degradable matrix material.

Clause 219. The method of clause 214, wherein the direct factor IIa inhibitor and the direct factor Xa inhibitor are released faster than the anti-proliferative agent.

Clause 220. The method of clause 214, wherein the direct factor IIa inhibitor and the direct factor Xa inhibitor enhance an anti-proliferative effect of the anti-proliferative agent.

Clause 221. The method of clause 214, wherein the therapeutic composition is disposed within a drug reservoir fluidly coupled to the external surface of the structure and wherein releasing the therapeutic composition comprises delivering the therapeutic from the drug reservoir to the external surface of the deployed structure.

Clause 222. The method of clause 214, wherein the injury is at least partially caused before deployment of the structure.

Clause 223. The method of clause 214, wherein deployment of the structure causes the injury and wherein the therapeutic composition is formulated to release the direct factor IIa inhibitor, the direct factor Xa inhibitor, or the anti-proliferative agent before the injury occurs.

Clause 224. The method of clause 214, wherein the structure forms at least a portion of a temporary or non-temporary device which is selected from the group consisting of access devices, infusion devices, tools, surgical instruments and tools, implants, bodily implants, hip implants, shoulder implants, knee implants, organ implants, luminal implants, vascular implants, stem-delivery systems, stents, stem-grafts, catheters, balloons, graft implants, grafts, aneurysm coils, valves, valve implants, shunts, left atrial appendage implants, foramen implants, leads, closure devices, clips, wound-closure devices and implants, sutures, patches, injection devices, needles inserted in the body, and needles inserted from outside the body.

Clause 225. The method of clause 224, wherein the device is a drug-coated balloon or a balloon reservoir.

Clause 226. The method of clause 225, wherein the therapeutic composition is formulated to release the one or more active substances at a rate of 1 μg/minute/mm device to about 100 μg/minute/mm device.

Clause 227. The method of clause 224, wherein the device is a catheter.

Clause 228. The method of clause 227, wherein the catheter is a diffusion catheter, infusion catheter, balloon-catheter, or weeping catheter.

Clause 229. The method of clause 224, wherein the device is a stmt.

Clause 230. The method of clause 224, wherein the device is a surgical instrument or tool.

Clause 231. The method of clause 230, wherein the surgical instrument or tool is a surgical cutting instrument or knife.

Clause 232. The method of clause 224, wherein deploying the structure comprises expanding the structure against the injury site.

Clause 233. The method of clause 224, wherein the target location comprises a blockage, and further comprising treating the blockage with the structure.

Clause 234. The method of clause 104 or 105, wherein the injury site is at a body part, a tissue, a surface, a lumen wall, or a vessel wall.

Clauses 235-300 have been intentionally lets open.

Clause 301. A medical device comprising:
  a. a structure having a surface, said structure configured for internal use within a patient's body and said surface configured to be positioned adjacent an injury site in the patient's body; and
  b. a therapeutic composition on the structure comprising three or more active substances including an anti-proliferative agent, a direct factor IIa inhibitor, and a direct factor Xa inhibitor;
  c. wherein the therapeutic composition is formulated and positioned on the device to locally release the three or more active substances to the injury site to inhibit one or more of inflammation, cell proliferation, internal elastic lamina (IEL) injury, fibrin formation, and clot formation.

Clause 301a. The device of clause 301, wherein the therapeutic composition is positioned on an external surface of the device.

Clause 301b. The device of clause 301, wherein the therapeutic composition is formulated and positioned on an internal surface of the device.

104761 Clause 301c. The device of clause 301, wherein the therapeutic composition positioned on both external and internal surfaces of the device.

Clause 302. The device of clause 301, wherein the therapeutic composition is formulated to locally release the three or more active substances to the injury site at a rate or a concentration sufficient to begin to inhibit one or more of inflammation, cell proliferation, internal elastic lamina (IEL) injury, fibrin formation, and clot formation within about 3 hours to about 7 days after the surface of the structure is positioned adjacent the injury site.

Clause 303. The device of clause 301 or 302, wherein the therapeutic composition is formulated to locally release the three or more active substances to the injury site at a rate or a concentration sufficient to inhibit one or more of inflammation, cell proliferation, internal elastic lamina (IEL) injury, fibrin formation, and clot formation for a period of at least 1 day, for a period of at least one week, for a period of at least one month, for a period of at least three months, for a period of at least six months, or for a period of at least one year after the surface of the structure is positioned adjacent the injury site.

Clause 304. The device of clause 301 to 303, wherein the therapeutic composition is formulated to substantially simultaneously release the three or more active substances.

Clause 305. The device of clause 301 to 303, wherein the therapeutic composition is formulated to release the direct factor IIa inhibitor and the direct factor Xa inhibitor substantially simultaneously and to release of the anti-proliferative after release of the direct factor IIa inhibitor and the direct factor Xa inhibitor has commenced.

Clause 306. The device of clause 305, wherein the release of the of the anti-proliferative agent commences in a period of 1 minute to 3 days, usually 3 hours to 1 day, after release of the direct factor IIa inhibitor and the direct factor Xa inhibitor has commenced.

Clause 307. The device of clause 301 to 303, wherein the therapeutic composition is formulated to commence release of the direct factor IIa inhibitor before commencing release of the direct factor Xa inhibitor Clause 308. The device of clause 307, wherein the release of the of the direct factor Xa inhibitor commences from 1 minute to 3 days, usually 3 haul to 1 day, after release of the direct factor IIa inhibitor has commenced.

Clause 309. The device of clause 301 to 303, wherein the therapeutic composition is formulated to commence release of the direct factor Xa inhibitor before commencing release of the direct factor IIa inhibitor Clause 310. The device of clause 309, wherein the release of the of the direct factor IIa inhibitor commences from 1 minute to 3 days, usually 3 hours to 1 day, after release of the direct factor Xa inhibitor has commenced.

Clause 311. The device of clause 301 to 310, wherein the direct factor IIa inhibitor comprises at least one of argatroban, dabigatran, ximelagatran, melagatran, efegatran, inogatran, atecegatran metoxil (AZD-0837), hirudin, hirudin analogs, bivalirudin, desirudin, and lepirudin.

Clause 312. The device of clause 311, wherein the direct factor IIa inhibitor comprises argatroban, or a salt, isomer, solvate, analog, derivative, metabolite, or prodrugs thereof.

Clause 313. The device of clause 312, wherein the direct factor Xa inhibitor comprises at least one of apixaban, betrixaban, edoxaban, otamixaban, razaxaban, rivaroxaban, (r)-n-(2-(4-(7-methylpiperidin-4-yl)piperazin-1-yl)-2-oxo-1-phenylethyl)-1h-indole-6-carboxamide (LY-517717), daraxaban (YM-150), 2-[(7-carbamimidoylnaphthalen-2-yl) methyl-[4-(1-ethanimidoylpiperidin-4-yl)oxyphenyl]sulfamoyl]acetic acid (YM-466 or YM-60828), or eribaxaban (PD 0348292), carbamimidoyl-2-hydroxy-phenyl) 4-[5-(2, 6-dimethyl-piperidin-1-yl)-pentyl]-3-oxo-3,4-dihydro-quinoxaline-6-carboxylic acid (PD0313052).

Clause 314. The device of clause 313, wherein the direct factor Xa inhibitor comprises rivaroxaban, or a salt, isomer, solvate, analog, derivative, metabolite, or prodrugs thereof.

Clause 315. The device of clause 313, wherein the direct factor Xa inhibitor comprises apixaban, or a salt, isomer, solvate, analog, derivative, metabolite, or prodrugs thereof.

Clause 316. The device of clause 301 to 315, wherein the anti-proliferative agent comprises an m-Tor inhibitor selected from a group consisting of sirolimus, biolimus, everolimus, myolimus, novolimus, ridaforolimus, temsirolimus, zotarolimus, or salts, isomers, solvates, analogs, derivatives, metabolites, or prodrugs thereof.

Clause 317. The device of clause 316, wherein the anti-proliferative agent comprises sirolimus, or a salt, isomer, solvate, analog, derivative, metabolite, or prodrugs thereof.

Clause 318. The device of clause 301 to 315, wherein the anti-proliferative agent comprises paclitaxel, or a salts, isomer, solvate, analog, derivative, metabolite, or prodrug thereof.

Clause 318a. The device of clause 301 to 315, wherein the anti-proliferative agent comprises an antiplatelet drug.

Clause 319. The device of clause 301 to 310, wherein the direct factor IIa inhibitor comprises argatroban and the direct factor Xa inhibitor comprises apixaban or rivaroxaban.

Clause 320. The device of clause 301 to 310, wherein the direct factor IIa inhibitor comprises argatroban, the direct factor Xa inhibitor comprises apixaban or rivaroxaban, and the anti-proliferative agent comprises sirolimus.

Clause 321. The device of clause 301 to 320, wherein the structure comprises a scaffold having at least an outer surface, an inner surface, and one or more edge surfaces between the outer and inner surfaces.

Clause 322. The device of clause 321, wherein at least a portion of the outer surface is coated with the therapeutic composition.

Clause 323. The device of clause 321 or 322, wherein at least a portion of the inner surface is coated with the therapeutic composition.

Clause 324. The device of clause 321 to 323, wherein a portion of the edge surfaces is coated with the therapeutic composition.

Clause 325. The device of clause 320 to 324, wherein at least some of the surfaces have receptacles formed therein and at least some of these receptacles have therapeutic agent therein.

Clause 326. The device of clause 325, wherein the receptacles comprise one or more of wells, channels, holes, and surface texture.

Clause 327. The device of clause 301 to 326, wherein the therapeutic composition further comprises an excipient.

Clause 327a. The device of clause 301 to 327, wherein the therapeutic composition further comprises an adjuvant.

Clause 327b. The device of clause 301 to 327a, wherein the therapeutic composition further comprises a polymeric carrier.

Clause 328. The device of clause 301 to 327b, wherein the three or more active substances are mixed uniformly with each other.

Clause 329. The device of clause 301 to 327b, wherein the three or more active substances are layered separately from each other.

Clause 330. The device of clause 329, wherein each layer comprises an excipient mixed with the therapeutic agent.

Clause 331. The device of clause 330, wherein each excipient is the same.

Clause 332. The device of clause 330, wherein at least two of the three excipients are different Clause 333. The device of clause 330 to 332, wherein the excipients are configured to control a release rate of one or more of the active substances.

Clause 334. The device of clauses 322 to 333, further comprising a control-release layer formed over the three or more active substances.

Clause 335. The device of clauses 301 to 334, further comprising a control-release layer formed over the three or more active substances.

Clause 336. The device of clauses 301 to 335, wherein the therapeutic composition includes an a base layer formed over a surface of the structure and an top layer formed over the base layer.

Clause 336a. The device of clause 336, wherein the base layer and top layer differ in at least some properties.

Clause 336b. The device of clause 336a, wherein the base layer and top layer differ in at least one of drug dose, drug release rate, and drug release duration.

Clause 337. The device of clause 336b, wherein the top layer of the therapeutic composition is formulated to commence release of the active substances before commencing of the active substances from the base layer.

Clause 338. The device of clause 337, wherein the active substances are released from the top layer over a time period in the range from 1 hour to 7 days after the surface of the structure is positioned adjacent the injury site.

Clause 339. The device of clause 338, wherein the active substances are released from the base layer over a time period in the range from 7 days to 12 months after the active substances have been substantially completely released from the top layer.

Clause 340. The device of clauses 336 to 339, wherein each of the base and top layers comprises the at least three active substances are mixed in a biodegradable polymeric matrix.

Clause 341. A vascular prosthesis comprising:
a scaffold having an outer surface, an inner surface, and one or more edge surfaces therebetween; and
a therapeutic composition on at least a portion of the outer surface, wherein the therapeutic composition comprises three or more active substances including an anti-proliferative agent, a direct factor IIa inhibitor, and a direct factor Xa inhibitor;
said therapeutic composition including at least a base layer and a top layer, wherein the top layer is formulated to release the at least three active substances in a bolus when exposed to a vascular environment and the base layer is formulated to release the at least three active substances over an extended time period when exposed to the vascular environment.

Clause 342. A vascular prosthesis as in clause 341, wherein the top layer is formulated to release the at least three active substances over a period from 1 hour to 3 hours when exposed to a vascular environment Clause 343. A vascular prosthesis as in clause 342, wherein the base layer is formulated to release the at least three active substances over a period of at least 28 days when exposed to a vascular environment Clause 344. A vascular prosthesis us in clause 341 to 343, wherein the anti-proliferative agent comprises sirolimus, the direct factor IIa inhibitor comprises argatroban, and a direct factor Xa inhibitor comprises rivaroxaban.

Clauses 345 to 350 have been intentionally left open.

Clause 351. A method for treating tissue injury in a patient, the method comprising:
deploying a structure at a target location in the patient's body lumen, said target location having a tissue injury; and
releasing a therapeutic composition from the deployed structure to the location of injury, wherein the therapeutic composition comprises at least a direct factor IIa inhibitor, a direct factor Xa inhibitor, and an anti-proliferative agent.

Clause 351a. The method of clause 351, wherein the therapeutic composition is positioned on an external surface of the device.

Clause 351b. The method of clause 351, wherein the therapeutic composition is formulated and positioned on an internal surface of the device.

Clause 351c. The method of clause 351, wherein the therapeutic composition positioned on both external and internal surfaces of the device.

Clause 351d. The method of clause 351, wherein the tissue injury is caused by deploying the structure at the location.

Clause 351e. The method of clause 351, wherein the tissue injury preexists deploying the structure at the location.

Clause 352. The method of clause 351, wherein the body lumen comprises a blood vessel and the therapeutic composition is formulated to locally release the three or more active substances to the injury site at a rate or a concentration sufficient to begin to inhibit one or more of inflammation, cell proliferation, internal elastic lamina (IEL) injury, fibrin formation, and clot formation within about 3 hours to about 7 days after the structure is deployed.

Clause 353. The method of clause 352, wherein the three or more active substances are released to the injury site at a rate or a concentration sufficient to inhibit one or more of inflammation, cell proliferation, internal elastic lamina (IEL) injury, fibrin formation, and clot formation for a period of at least 1 day, for a period of at least one week, for a period of at least one month, for a period of at least three months, for a period of at least six months, or for a period of at least one year after the surface of the structure is positioned adjacent the injury site.

Clause 354. The method of clause 351 to 353, wherein the three or more active substances are released substantially simultaneously.

Clause 355. The method of clause 351 to 353, wherein the direct factor IIa inhibitor and the direct factor Xa inhibitor are released substantially simultaneously and the anti-proliferative is released after the release of the direct factor IIa inhibitor and the direct factor Xa inhibitor has commenced.

Clause 356. The method of clause 355, wherein the release of the of the anti-proliferative agent commences in a period of 1 minute to 3 days, usually 6 hours to 1 day, after release of the direct factor IIa inhibitor and the direct factor Xa inhibitor has commenced.

Clause 357. The method of clause 351 to 353, wherein the therapeutic composition commences release of the direct factor IIa inhibitor before commencing release of the direct factor Xa inhibitor Clause 358. The method of clause 357, wherein the release of the of the direct factor Xa inhibitor commences from 1 minute to 3 days, usually 6 hours to 1 day, after release of the direct factor IIa inhibitor has commenced.

Clause 359. The method of clause 351 to 353, wherein the therapeutic composition commences release of the direct factor Xa inhibitor before commencing release of the direct factor IIa inhibitor Clause 360. The method of clause 359, wherein the release of the of the direct factor IIa inhibitor commences from 1 minute to 3 days, usually 6 hours to 1 day, after release of the direct factor Xa inhibitor has commenced.

Clause 361. The method of clause 351 to 360, wherein the direct factor IIa inhibitor comprises at least one of argatroban, dabigatran, ximelagatran, melagatran, efegatran, inogatran, atecegatran metoxil (AZD-0837), hirudin, hirudin analogs, bivalirudin, desirudin, and lepirudin.

Clause 362. The method of clause 361, wherein the direct factor IIa inhibitor comprises argatroban, or a salt, isomer, solvate, analog, derivative, metabolite, or prodrugs thereof.

Clause 363. The method of clause 362, wherein the direct factor Xa inhibitor comprises at least one of apixaban, betrixaban, edoxaban, otamixaban, razaxaban, rivaroxaban, (r)-n-(2-(4-(1-methylpiperidin-4-yl)piperazin-1-yl)-2-oxo-1-phenylethyl)-1h-indole-6-carboxamide (LY-517717), daraxaban (YM-150), 2-[(7-carbamimidoylnaphthalen-2-yl) methyl-[4-(1-ethanimidoylpiperidin-4-yl)oxyphenyl]sulfamoyl]acetic acid (YM-466 or YM-60828), or eribaxaban (PD 0348292). carbamimidoyl-2-hydroxy-phenyl) 4-[5-(2, 6-dimethyl-piperidin-1-yl)-pentyl]-3-oxo-3,4-dihydro-quinoxaline-6-carboxylic acid (PD0313052).

Clause 364. The method of clause 363, wherein the direct factor Xa inhibitor comprises rivaroxaban, or a salt, isomer, solvate, analog, derivative, metabolite, or prodrugs thereof.

Clause 365. The method of clause 363, wherein the direct factor Xa inhibitor comprises apixaban, or a salt, isomer, solvate, analog, derivative, metabolite, or prodrugs thereof.

Clause 366. The method of clause 351 to 365, wherein the anti-proliferative agent comprises an in-Tor inhibitor selected from a group consisting of sirolimus, biolimus, everolimus, myolimus, novolimus, ridaforolimus, temsirolimus, zotarolimus, or salts, isomers, solvate, analogs, derivatives, metabolites, or prodrugs thereof.

Clause 367. The method of clause 366, wherein the anti-proliferative agent comprises sirolimus, or a salt, isomer, solvate, analog, derivative, metabolite, or prodrugs thereof.

Clause 368. The method of clause 351 to 365, wherein the anti-proliferative agent comprises paclitaxel, or a salts, isomer, solvate, analog, derivative, metabolite, or prodrug thereof.

Clause 368a. The method of clause 351 to 365, wherein the anti-proliferative agent comprises an antiplatelet drug.

Clause 369. The method of clause 351 to 360, wherein the direct factor IIa inhibitor comprises argatroban and the direct factor Xa inhibitor comprises apixaban.

Clause 370. The method of clause 351 to 360, wherein the direct factor IIa inhibitor comprises argatroban, the direct factor Xa inhibitor comprises apixaban, and the anti-proliferative agent comprises sirolimus.

Clause 371. The method of clause 351 to 370, wherein the structure comprises a scaffold having at least an outer surface, an inner surface, and one or more edge surfaces between the outer and inner surfaces and wherein deploying comprises expanding the scaffold in the body lumen.

Clause 372. The method of clause 371, wherein at least a portion of the outer surface is coated with the therapeutic composition.

Clause 373. The method of clause 371 or 372, wherein at least a portion of the inner surface is coated with the therapeutic composition.

Clause 374. The method of clause 371 to 373, wherein a portion of the edge surfaces is coated with the therapeutic composition.

Clause 375. The method of clause 370 to 374, wherein at least some of the surfaces have receptacles formed therein and at least some of these receptacles have therapeutic agent therein.

Clause 376. The method of clause 375, wherein the receptacles comprise one or more of wells, channels, holes, and surface texture.

Clause 377. The method of clause 351 to 376, wherein the therapeutic composition further comprises an excipient.

Clause 378. The method of clause 351 to 377, wherein the three or more active substances are mixed uniformly.

Clause 379. The method of clause 351 to 377, wherein the three or more active substances are layered.

Clause 380. The method of clause 379, wherein each layer comprises an excipient mixed with the therapeutic agent.

Clause 381. The method of clause 380, wherein each excipient is the same.

Clause 382. The method of clause 380, wherein at least two of the three excipients are different Clause 383. The method of clause 380 to 382, wherein the excipients are configured to control a release rate of one or more of the active substances.

Clause 384. The method of clauses 382 to 383, further comprising a control-release layer formed over the three or more active substances.

Clause 385. The method of clauses 351 to 384, further comprising a control-release layer formed over the three or more active substances.

Clause 386. The method of clauses 351 to 385, wherein the therapeutic composition includes an base layer formed over the surface and an top layer formed over the base layer, wherein the base layer and top layer differ in at least some properties.

Clause 387. The method of clause 386, wherein the therapeutic composition is formulated to release active substances substantially completely from the top layer before releasing the active substances from the base layer.

Clause 388. The method of clause 387, wherein the active substances are released from the top layer over a time period in the range from 1 hour to 7 days after the surface of the structure is positioned adjacent the injury site.

Clause 389. The method of clause 388, wherein the active substances are released from the base layer over a time period in the range from 7 days to 12 months after the after the active substances have been substantially completely released from the top layer.

Clause 390. The method of clauses 386 to 389, wherein each of the base and top layers comprises the at least three active substances are mixed I a biodegradable polymeric matrix.

Clause 391. The method of clauses 351 to 390, wherein the injury is at least partially caused before deployment of the structure Clause 392. The method of clause 391, wherein deployment of the structure causes the injury and wherein the therapeutic composition is formulated to release the direct factor IIa inhibitor, the direct factor Xa inhibitor, or the anti-proliferative agent before the injury occurs.

Clause 393. The method of clause 351 to 392, wherein the structure forms at least a portion of a temporary or non-temporary device which is selected from the group consisting of access devices, infusion devices, tools, surgical instruments and tools, implants, bodily implants, hip implants, shoulder implants, knee implants, organ implants, luminal implants, vascular implants, stent-delivery systems, stents, stem-grafts, catheters, balloons, graft implants, grafts, aneurysm coils, valves, valve implants, shunts, left atrial appendage implants, foramen implants, leads, closure devices, clips, wound-closure devices and implants, sutures, patches, injection devices, needles inserted in the body, and needles inserted from outside the body.

Clause 394. The method of clause 393, wherein the device is a scent.

Clause 395. The method of clause 394, wherein deploying the structure comprises expanding the structure against the injury site.

The illustrative examples described are not meant to be limiting. Other examples may be utilized, and other changes may be made, or combined in whole or in part, without departing from the scope of the subject matter presented herein. It will be readily understood that the aspects of the present disclosure, as generally described herein, and illustrated in the figures, and detailed description, and in the examples, can be arranged, substituted, combined, separated, and designed in a wide variety of different configurations, all of which are explicitly contemplated herein.

The illustrative aspects, examples, or embodiments describes are not meant to be limiting. For example, the examples provided for an implantable scaffold comprising a scaffold structure having a surface configured to be expanded in the patient's body, can also apply to other devices described in this application.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows a side perspective view of a medical device example having a therapeutic coating disposed thereon, in accordance with examples;

FIG. 2A shows a side perspective view of a medical device example having a therapeutic coating disposed thereon, in accordance with examples;

FIG. 58 shows an example image of Elastin Trichrome stained sections of rapamycin apixaban and argatroban drug eluting stent and control DESyne X2 implanted vessels at the 3 month time point histology evaluation, in accordance with an example;

FIG. 6A shows a plot of HAoSMC cell proliferation in the presence of rapamycin and varying concentrations of apixaban, in accordance with examples;

FIG. 6B shows a plot of HAoSMC cell proliferation in the presence of rapamycin and varying concentrations of argatroban, in accordance with examples;

FIG. 6C shows a plot of HAoSMC cell proliferation in the presence of rapamycin and varying concentrations of apixaban and argatroban, in accordance with examples;

FIG. 6D shows a plot of HAoSMC cell proliferation in the presence of difference concentrations of apixaban, in accordance with examples;

FIG. 6E shows a plot of HAoSMC cell proliferation in the presence of difference concentrations of argatroban, in accordance with example;

DETAILED DESCRIPTION OF THE DISCLOSURE

Figure 1B:
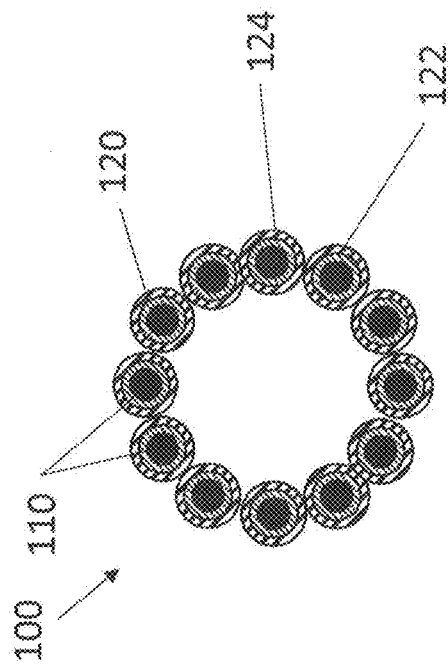
FIG. 1B shows a cross-sectional view of a medical device having a therapeutic coating comprising a first layer disposed thereon, in accordance with examples.

In the following detailed description, reference is made to the accompanying figures, which form a pan hereof. In the figures, similar symbols typically identify similar components, unless context dictates otherwise. The illustrative examples described in the detailed description, figures, and claims are not meant to be limiting. Other examples may be utilized, and other changes may be made, or combined in whole or in part, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain examples and examples are disclosed below, inventive subject matter extends beyond the specifically disclosed examples to other alternative examples and/or uses, and to modifications and equivalents thereof. Thus, the scope of the claims appended hereto is not limited by any of the particular examples described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain examples, however, the order of description should not be construed to imply that these operations are order dependent. Additionally, the structure, systems, and/or devices described herein may be embodied as integrated components or as separate components.

For purposes of comparing various examples, certain aspects and advantages of these examples are described. Not necessarily all such aspects or advantages are achieved by any particular example or embodiment. Thus, for example, various examples may be carried out in a manner that achieves or optimizes one advantage or group of advantages as taught herein without necessarily achieving other aspects or advantages as may also be taught or suggested herein.

Every example of the present invention may optionally be combined with any one or more of the other examples described herein. Every patent literature, and every non-patent literature, cited herein is incorporated herein by reference in its entirety.

The present invention disclosure is described in relation to drug-coated stents, drug-coated balloons, balloon reservoirs, heart implants, hip implants, knee implants, shoulder implants, and the like. However, one of skill in the art will appreciate that this is not intended to be limiting and the devices and methods disclosed herein may be used in other anatomical areas and in other surgical procedures or in other devices whether used as temporary devices or permanent devices.

As used herein, the term coagulation comprises one or more of thrombin formation, fibrin formation, platelet activation, platelet aggregation, and/or thrombus clot formation. Coagulation typically arises in response to a body part injury and/or to a foreign body such as a device. This may lead to one or more of inflammation, injury, blockage of a lumen or vessel partially or fully, degradation of the device function, formation of clot, and/or adverse clinical events. In some examples, any of the devices described herein may, at least partially, cause an injury to the tissue which may initiate the coagulation cascade.

As used herein, the term anti-coagulant refers to an agent that inhibits one or more of thrombin formation, fibrin formation, platelet activation (typically indirectly), platelet aggregation (typically indirectly), thrombus (clot) formation, thrombin dissolution, fibrin dissolution, or thrombus dissolution, thereby inhibiting one or more of blockage of a lumen or vessel partially or fully, degradation of the device function, formation of clot, and/or adverse clinical events.

Inhibiting one or more of thrombin formation, fibrin formation, platelet activation, and/or platelet aggregation enables the inhibition of one or more of blockage of a lumen or vessel partially or fully, degradation of the device function, formation of thrombus (clot) formation, inflammation, and/or adverse clinical events.

Described herein are devices and methods for locally delivering a therapeutic composition to a patient. The therapeutic composition includes one or more agents which inhibit one or more of thrombin, fibrin, and/or thrombus formation or promote one or more of thrombin, fibrin, and/or thrombus dissolution. In preferred examples, the therapeutic composition includes one or both of a direct Xa inhibitor and a direct IIa inhibitor. In another preferred example, an anti-proliferative agent may be added to the therapeutic composition of the direct Xa inhibitor and/or the direct IIa inhibitor. As described herein, it was surprisingly found that fast release formulation of factor Xa inhibitor (alone or in combination with release of an anti-proliferative agent) resulted in prolonged anti coagulant effects (e.g., one or more of inhibition of fibrin, inhibition of thrombin formation, enhanced fibrin dissolution, and/or enhancing thrombin inhibition) compared to control and/or a slower release composition profile. The combination of a direct Xa inhibitor and a direct IIa inhibitor formulation was also surprisingly found to improve inhibition of fibrin and/or inhibition of clot formation compared to either agent alone. Additionally, it was surprisingly found that the combination of a direct Xa inhibitor and a direct IIa inhibitor formulation resulted in unexpected anti-proliferative effects (e.g., reduced cell proliferation) in combination, while each agent alone had little to no anti-proliferative effect. Furthermore, surprisingly, and unexpectedly, direct Xa inhibitor and a direct IIa inhibitor combination with an anti-proliferative agent formulation, improved or enhanced the anti-proliferative effect compared to the anti-proliferative agent formulation alone. It was also surprisingly found that the combination of an anti-proliferative agent with a direct Xa inhibitor and a direct IIa inhibitor formulation enhanced inhibition or enhanced dissolution of one or more of the following: fibrin, clot formation, thrombin, platelet aggregation, platelet activation, inflammation, and injury; acutely, and or within 3 hours to 7 days, and/or within 28 days, and/or within 90 days. It was surprisingly found extending release of factor IIa inhibitor and/or a factor Xa inhibitor, inhibited one or more of clot formation, SMC proliferation, inflammation, and injury, wherein the extended release of the one or more drugs extended beyond 7 days, extended beyond 14 days, extended beyond 21 days, extended beyond 28 days, or extended beyond 3 months. It was surprisingly found extended release formulation comprising a factor IIa inhibitor and/or a factor Xa inhibitor, inhibited one or more of clot formation, SMC proliferation, inflammation, and injury, wherein the extended release of the one or more drugs extended beyond 7 days, extended beyond 14 days, extended beyond 21 days, extended beyond 28 days, or extended beyond 3 months.

In some examples, the devices described herein can be configured to release a factor Xa inhibiting agent to a mammalian body, lumen, tissue, and/or device surface prior to an injury to said tissue, concurrent with injury to said tissue, or after an initial injury to said tissue. The device is introduced into said mammalian body and advanced to said tissue site or body lumen. In some specific examples, the device is expanded against said tissue to release said agent. In other examples, the device is expanded against said tissue to perform a function such as opening up a vessel or lumen and to release said agent. In specific examples, the device is a stent or a balloon catheter. In yet another example, the device is placed adjacent to said tissue. In specific examples, the device releases said agent to a tissue segment adjacent to the device in the amount ranging from 0.01 ng/mg of tissue to 1000 ng/mg of tissue, preferably ranging from 0.1 ng/mg tissue to 500 ng/mg of tissue, more preferably ranging from 1 ng/mg of tissue to 150 ng/mg of tissue. In some other specific examples, the agent molecular weight ranges from 200 g/mol to 1500 g/mol, preferably ranges from 300 g/mol to 1000 g/mol, more preferably ranges from 350 g/mol to 500 g/mol. In some other examples, the device releases said agent prior to engaging (or coupling or contacting) of the device to the tissue site. In some specific examples, the device locally releases said agent to a tissue segment in the amount ranging from about 10 ng/mg to 200 ng/mg within about 3 hours from tissue injury and/or release of the agent to the tissue segment. In a preferred example, the adjacent tissue segment drug (e.g., tissue 5 mm proximal and 5 mm distal to the tissue segment) concentration range from about 0.1 ng/mg of tissue to about 100 ng/mg of tissue, preferably ranges from about 1 ng/mg of tissue to 100 ng/mg of tissue, at about 3 hours from tissue injury and/or release of the agent to the tissue segment. In a preferred example, the tissue concentration in the tissue segment at 3 hours after injury and/or release of said agent to the tissue segment ranges from about 100,000 times the $IC_{50}$ of factor Xa inhibition to 10,000,000 times the $IC_{50}$ of factor Xa inhibition, preferably ranges from 500,000 times to 5,000,000 times the $IC_{50}$ of factor Xa inhibition. The tissue concentration in the adjacent tissue segment (e.g., ±5 mm) at 3 hours after release of said agent to the tissue segment ranges from 100 times the $IC_{50}$ of factor Xa inhibition to 1,000,000 times the 1050 of factor Xa inhibition, preferably ranges from 1,000 times to 100,000 times the $IC_{50}$ of factor Xa inhibition. In a preferred example, the tissue concentration in the tissue segment at about 24 hours after injury and/or release of said agent to the tissue segment ranges from 100,000 times the $IC_{50}$ of factor Xa inhibition to 1000,000 times the $IC_{50}$ of factor Xa inhibition, preferably ranges from 1000 times to 20,000 times the $IC_{50}$ of factor Xa inhibition. The tissue concentration in the adjacent tissue segment (e.g., ±5 mm) at 24 hours after injury and/or release of said agent to the tissue segment ranges from 100 times the $IC_{50}$ of factor Xa inhibition to 1,000,000 times the $IC_{50}$ of factor Xa inhibition, preferably ranges from 1,000 times to 50,000 times the $IC_{50}$ of factor Xa inhibition. In another preferred example, the tissue concentration in the tissue segment at about 28 days after injury and/or release of said agent to the tissue segment ranges from 100 times the $IC_{50}$ of factor Xa inhibition to 100,000 times the $IC_{50}$ of factor Xa inhibition, preferably ranges from 500 times to 10,000 times the $IC_{50}$ of factor Xa inhibition. The tissue concentration in the adjacent tissue segment (e.g., =5 mm) at 28 days after injury and/or release of said agent to the tissue segment ranges from zero times the $IC_{50}$ of factor Xa inhibition to 100 time the $IC_{50}$ of factor Xa inhibition, preferably ranges from 10 times to 1,000 times the $IC_{50}$ of factor Xa inhibition. In a preferred specific example, the device releases a factor Xa inhibitor to a tissue site at about 3 hours after injury and/or release of agent to the tissue, wherein the tissue concentration in the tissue segment and in the adjacent tissue segment (e.g., ±5 mm front the tissue segment) is greater than the IC to inhibit factor Xa, preferably greater than 10 times the $IC_{50}$ to inhibit factor Xa, and more preferably greater than 1000 times the $IC_{50}$ to inhibit factor Xa. In a preferred specific example, the device releases a factor Xa inhibitor to a tissue site at about 24 hours after injury and/or release of agent to the tissue, wherein the tissue concentration in the tissue segment and in the adjacent tissue segment (±5 mm from the tissue segment) are greater than the $IC_{50}$ to inhibit factor Xa, preferably greater than 10 times the $IC_{50}$ to inhibit factor Xa, and more preferably greater than 1000 times the IC 50 to inhibit factor Xa. In a preferred example, the agent is rivaroxaban, apixaban, and/or analogs, derivatives, or salts thereof. In a most preferred example, the agent is apixaban.

In another example, the combination of apixaban and argatroban have an additive effect on thrombin formation inhibition or dissolution.

In some examples, a combination of factor IIa inhibitor and factor Xa inhibitor are released from a device to a mammalian body, lumen, tissue, and/or device surface after injury at sufficient concentrations in the tissue segment and adjacent tissue segments within about 3 hours after injury to inhibit thrombus (clot) formation. In a preferred example, the agents are apixaban and argatroban.

In some examples, the combination of apixaban and argatroban released from a device containing an mTOR inhibitor such as sirolimus maintains or enhances the antiproliferative effect of said mTOR at the tissue segment site while inhibiting thrombus formation at the said tissue segment site.

In some examples, the combination of apixaban and argatroban released from a device containing an mTOR inhibitor inhibits thrombus formation on the device surface.

In some examples, the device is coated or loaded with one or more agents comprising apixaban, argatroban and an mTOR inhibitor. The coating coats one or more surfaces of the device, preferably coating all surfaces of the device including the abluminal and luminal surfaces of the device. Alternatively, or in combination, structural elements of the device are loaded with the one or more agents. In a specific example, the one or more agents are contained in a drug polymer matrix, or contained in a polymer top layer or coat, or is coated as a top layer or coat. In a preferred example of a device configured to release two or more agents, the agents are contained in the same polymer matrix or a different polymer matrix, or one agent is in a polymer matrix while the other agent is under a top polymer coat. In yet another preferred example, the device contains three agents in the same polymer matrix. In another example, each of the drugs is contained in a separate polymer matrix. In yet another example, two of the agents are contained in one polymer matrix while the third agent is contained in a separate polymer matrix or a top layer or coat. In yet another example, the one or more agents are contained in the same polymer matrix and a top layer or coat of a polymer material covers the surface of the device.

In some examples, the device is a balloon catheter configured to release one or more agents comprising one or both of a factor Xa inhibitor and a factor IIa inhibitor, wherein in one example the balloon surface comprises the one or two agents directly or with excipient, contained in a polymer matrix, contained in micro or nano spheres, contained in hydrogels, or the like. In some examples, the balloon contains the one or two agents and is configured to release said agents into the tissue site through pores in the balloon. In a preferred example, the one or more agents are apixaban and argatroban. In another example the agents are rivaroxaban and argatroban.

It is an objective of this application to show factor Xa inhibitor and factor IIa inhibitor, and optionally in combination with an antiproliferative, inhibit or enhance dissolution of one or more of smooth muscle proliferation, thrombin formation, fibrin formation, clot formation, inflammation, blockage of a body lumen or vessel, degradation of a device function, and/or adverse clinical events. Anticoagulants have been successfully used in systemic application. Despite such success, anticoagulants had limited to no success when delivered locally.

While many of the examples described herein depict one or more active substances being coated on a device for local delivery of the one or more active substances, it will be understood by one of ordinary skill in the art that any of the devices described herein may locally delivery one or more of the active substances through any other means. For examples, one or more of the active substances may be coated, dipped, printed, deposited, painted, brushed, loaded, or otherwise disposed on one or more surfaces of the device for local delivery. In some examples, one or more of the active substances may be incorporated into the backbone structure of the device. Alternatively, or in combination, one or more of the active substances may be locally delivered via a drug reservoir coupled to the device. In some examples, one or more or the active substances may be coated or otherwise disposed directly onto one or more surfaces of the device. In some examples, one or more or the active substances may be coated or otherwise disposed on one or more surfaces of the device in a carrier such as a polymer matrix. In some examples, one or more of the active substances may be cross-linked with a polymer, or to itself, or to another drug (in order to be another active substance, e.g., after the links are broken in vivo). In some examples, the carrier may be an excipient, a polymer, or other types of material to facilitate applying or controlling the drug onto the device or controlling release of the drug from the device or protecting the drug from washing out during entry or deployment into the body. In some examples, the carrier may comprise a microsphere or a nanosphere.

FIG. 1A shows a side perspective view of an exemplary device 100 having a therapeutic coating 120 disposed thereon. In some examples, the device 100 may comprise a temporary or non-temporary device configured for use within a patient us described herein. For example, the device 100 may comprise a vascular stent 110 having a plurality of braided filaments or cut from a laser tube patterned into the stent. The device 100 may have an external surface configured for internal use within the patient's body. A therapeutic composition may be disposed on the external surface of the device 100. The therapeutic composition may comprise a coating 120 comprising one or more bioactive agents (also referred to herein as active substances) and optionally one or more carriers as described herein. The carrier may, for example, comprise a biodegradable or non-degradable polymer or matrix material as described herein. The therapeutic composition (e.g., the coating 120) may be formulated to locally release the one or more bioactive agents when positioned or implanted adjacent an injury site resulting from a surgery or intervention.

In some examples, the coating 120 may comprise a polymeric material as described herein.

In some examples, the coating 120 may comprise a therapeutic composition of bioactive agents including a direct factor IIa inhibitor, a direct factor Xa inhibitor, and/or an anti-proliferative agent. In some examples, the coating 120 may comprise a direct factor IIa inhibitor, a direct factor Xa inhibitor, and an anti-proliferative agent. In some examples, the coating 120 may comprise a direct factor IIa inhibitor and a direct factor Xa inhibitor but no anti-proliferative agent. In some examples, the coating 120 may comprise a direct factor Xa inhibitor and an anti-proliferative agent but no direct factor IIa inhibitor. In some examples, the coating 120 may comprise a direct factor Xa inhibitor but no direct factor IIa inhibitor or anti-proliferative agent.

When the therapeutic composition comprises a direct factor IIa inhibitor, a direct factor Xa inhibitor, and an anti-proliferative agent, the therapeutic composition may be present in the carrier material at weight ratios of 1:3:1, 3:2:1, 2:2:1, 2:3:1, 3:3:1, 5:5:1, or 6:6:1, respectively. In some examples, the weight compositional ratio of the direct factor IIa inhibitor to the direct factor Xa inhibitor to the anti-proliferative agent in the therapeutic composition may be about 5:5:2. In some examples, the weight compositional ratio of the direct factor IIa inhibitor to the direct factor Xa inhibitor to the anti-proliferative agent in the coating may be within a range of about 6:6:1 to 1:3:1.

When the therapeutic composition comprises a direct factor IIa inhibitor, a direct factor Xa inhibitor, and an anti-proliferative agent, the release rate ratio of the direct factor IIa inhibitor to the direct factor Xa inhibitor to the anti-proliferative agent may be about 1:1:1 to about 4:4:1. In some examples, the coating may be configured to release the direct factor IIa inhibitor, the direct factor Xa inhibitor, and the anti-proliferative agent at the same rate. In other examples, the coating may be configured to release the direct factor IIa inhibitor, the direct factor Xa inhibitor, and the anti-proliferative agent at different rates.

In some examples, the coating may be configured to release the direct factor IIa inhibitor at a rate of about 4 µg/hour/mm device 100 to about 14 µg/day/mm device 100.

In some examples, the coating may be configured to release the direct factor Xa inhibitor at a rate of about 4 µg/hour/mm device 100 to about 14 mg/day/rant device 100.

In some examples, the coating may be configured to release the anti-proliferative agent at a rate of about 1 µg/hour/mm device 100 to about 4 µg/day/mm device 100.

In some examples, the direct factor IIa inhibitor may have an inhibition potency for factor IIa ranging from about 0.001 nM to about 100 nM.

In some examples, the direct factor Xa inhibitor may have an inhibition potency for factor Xa ranging from about 0.001 nM to about 50 nM.

In some examples, the direct factor IIa inhibitor may comprise argatroban, or a salt, isomer, solvate, analog (including deuterated analog), derivative, metabolite, or prodrugs thereof.

In some examples, the direct factor Xa inhibitor may comprise apixaban, or a salt, isomer, solvate, analog (including deuterated analog), derivative, metabolite, or prodrugs thereof.

In some examples, the direct factor Xa inhibitor may comprise rivaroxaban, or a salt, isomer, solvate, analog (including deuterated analog), derivative, metabolite, or prodrugs thereof.

In some examples, the anti-proliferative agent may comprise rapamycin, or a salt, isomer, solvate, analog (including deuterated analog), derivative, metabolite, or prodrugs thereof.

In some examples, the direct factor Xa inhibitor may comprise apixaban, the direct factor IIa inhibitor may comprise argatroban, and the anti-proliferative agent may comprise rapamycin.

In some examples, the therapeutic composition is disposed on the external surface of the structure and on the internal surface of the structure. In some example, the therapeutic composition is disposed on the external surface (abluminal) of the structure, on the interior surface (luminal) of the structure, and on the side surface of the structure. In yet other examples, the therapeutic composition is disposed on one or more surfaces of the structure. In yet other examples, the therapeutic composition is disposed on all surfaces of the structure. In yet other examples, the therapeutic composition is disposed in a reservoir on or in the structure. In some examples, the therapeutic composition is disposed on the external surface of the structure.

FIG. 1B shows a cross-sectional view of a medical device 100 having a therapeutic coating 120 comprising a first layer 122 disposed thereon. In some examples, the device 100 may comprise a stent 110 having a first layer 122 of a coating 120 disposed thereon. The coating 120 may be disposed on an external surface of the stent 110 (e.g., on the abluminal surface of one or more filaments of the stent or struts of the stent), on an internal surface of the stent 110 (e.g., on the luminal surface of one or more filaments of the stent), or on both the external surface and the internal surface of the stent 110 (e.g., partially or fully surround one or more filaments of the stent). The first layer 122 of the coating 120 is shown fully coating each of the filaments of the stent 110. In some examples, the layer 122 is not on an external surface of the stent 110. The first layer 122 may comprise one or more bioactive agents. For example, the first layer 122 may comprise one bioactive agent, two bioactive agents, three bioactive agents, or more. In some examples, the first layer may comprise a direct factor IIa inhibitor, a direct factor Xa inhibitor, and/or an anti-proliferative agent, or any other agent described herein or known to one of ordinary skill in the an based on the teachings herein.

Figure 1C:
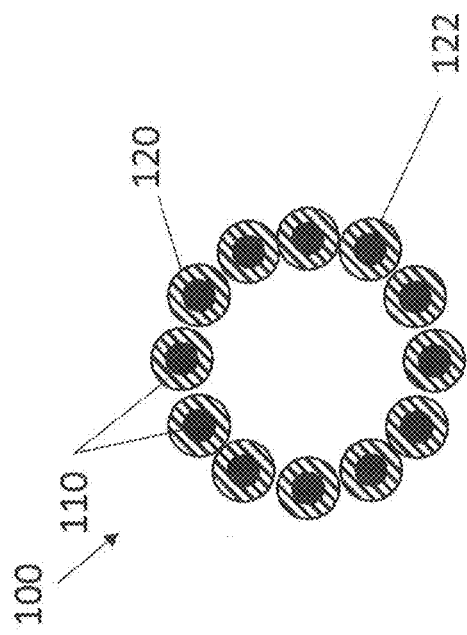
FIG. 1C shows a cross-sectional view of a medical device having a therapeutic coating comprising a first layer and a second disposed thereon, in accordance with examples.

FIG. 1C shows a cross-sectional view of a medical device 100 having a therapeutic coating 120 comprising a first layer 122 and a second layer 124 disposed thereon. The coating 120 may comprise a therapeutic composition of bioactive agents. The therapeutic composition may comprise one or more bioactive agents distributed within the first layer 122 and/or second layer 124.

In some examples, the first layer 122 or the second layer 124 may comprise one or more bioactive agents and the other layer may not comprise a bioactive agent.

In some examples, the first layer 122 may comprise one or more bioactive agents and the second layer may comprise one or more bioactive agents. The first layer 122 and the second layer 124 may be configured to release their respective bioactive agents at the same rate. Alternatively, the first layer 122 and the second layer 124 may be configured to release their respective bioactive agents at different rates.

In some examples, the first layer 122 may comprise a direct factor IIa inhibitor and the second layer 124 may comprise a direct factor Xa inhibitor. In some examples, the first layer 122 may comprise a direct factor Xa inhibitor and the second layer 124 may comprise a direct factor IIa inhibitor.

In some examples, the first layer 122 may comprise an anti-proliferative agent and the second layer 124 may comprise a direct factor IIa inhibitor and a direct factor Xa inhibitor.

In some examples, the first layer 122 may comprise a direct factor IIa inhibitor and a direct factor Xa inhibitor and the second layer may comprise an anti-proliferative agent.

In some examples, one or both of the layers 122, 124 may comprise a polymeric material as described herein. For example, the first layer 122 may comprise a polymeric material and the second layer 124 may not comprise a polymeric material. Alternatively, the first layer 122 may not comprise a polymeric material and the second layer 124 may comprise a polymeric material. Alternatively, both the first layer 122 and the second layer 124 may comprise the same or a different polymeric material and/or polymeric material concentration and/or formulation.

The first layer 122 and/or second layer 124 may be disposed on an external surface of the stent 110 (e.g., on the abluminal surface of one or more filaments of the stent), on an internal surface of the stent 110 (e.g., on the luminal surface of one or more filaments of the stent), or on both the external surface and the internal surface of the stent 110 (e.g., partially or fully surround one or more filaments of the stent). The first layer 122 and the second layer 124 of the coating 120 are shown fully coating each of the filaments of the stent 110. However, it will be understood by one of ordinary skill in the art that first layer 122 and the second layer 124 may coat the stent 110 differently. For example, the first layer 122 of the coating 120 may fully surround each of the filaments of the stent 110 while the second layer 124 may be applied only on one surface (e.g., luminal or abluminal) of the stent 110. In some examples, the layers 122, 124 are not on an external surface of the stent 110.

Figure 1D:
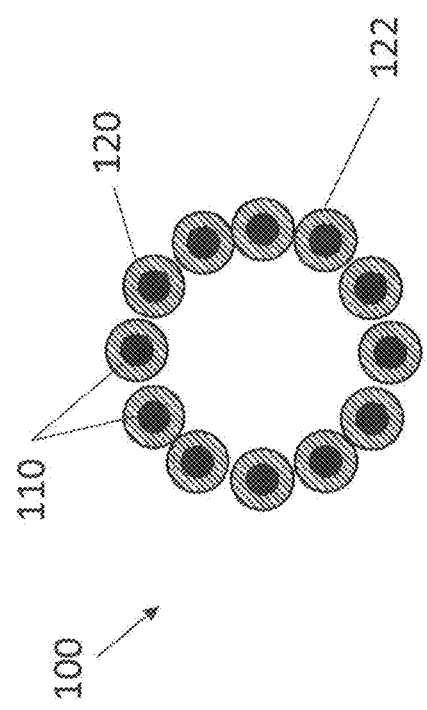
FIG. 1D shows a cross-sectional view of a medical device having a therapeutic coating comprising a first layer, a second layer, and a third layer disposed thereon, in accordance with examples.

FIG. 1D shows a cross-sectional view of a medical device 100 having a therapeutic coating 120 comprising a first layer 122, a second layer 124, and a third layer 126 disposed thereon. The coating 120 may comprise a therapeutic composition of bioactive agents. The therapeutic composition may comprise one or more bioactive agents distributed within the first layer 122, the second layer 124, and/or third layer 126.

In some examples, the first layer 122, the second layer 124, and/or the third layer 126 may comprise one or more bioactive agents and one or more of the other layers may not comprise a bioactive agent.

In some examples, the first layer 122 may comprise one or more bioactive agents, the second layer may comprise one or more bioactive agents, and the third layer 126 may comprise one or more bioactive agents. The first layer 122, the second layer 124, and the third layer 126 may be configured to release their respective bioactive agents at the same rate. Alternatively, two or more of the first layer 122, the second layer 124, or the third layer 126 may be configured to release their respective bioactive agents at different rates.

In some examples, the first layer 122 may comprise a direct factor IIa inhibitor, the second layer 124 may comprise a direct factor Xa inhibitor, and the third layer may comprise an anti-proliferative agent. In some examples, the first layer 122 may comprise a direct factor Xa inhibitor, the second layer 124 may comprise a direct factor IIa inhibitor, and the third layer may comprise an anti-proliferative agent.

In some examples, the first layer 122 may comprise an anti-proliferative agent, the second layer 124 may comprise a direct factor IIa inhibitor, and the third layer 124 may comprise a direct factor Xa inhibitor. In some examples, the first layer 122 may comprise an anti-proliferative agent, the second layer 124 may comprise a direct factor Xa inhibitor, and the third layer 124 may comprise a direct factor IIa inhibitor.

In some examples, one, two, or three of the layers 122, 124, 126 may comprise a polymeric material as described herein. For example, the first layer 122 may comprise a polymeric material, the second layer 124 may comprise a polymeric material, and the third layer 124 may not comprise a polymeric material. The layers 122, 124, 126 may comprise the same or a different polymeric material and/or polymeric material concentration and/or formulation.

The first layer 122, second layer 124, and/or third layer 126 may be disposed on an external surface of the stent 110 (e.g., on the abluminal surface of one or more filaments of the stent), on an internal surface of the stent 110 (e.g., on the lumina) surface of one or more filaments of the stem), or on both the external surface and the internal surface of the stent 110 (e.g., partially or fully surround one or more filaments of the stent). The first layer 122, the second layer 124, and third layer 126 of the coating 120 are shown fully coating each of the filaments of the stent 110. However, it will be understood by one of ordinary skill in the art that one or more of the first layer 122, the second layer 124, and the third layer 126 may coat the stent 110 differently. For example, the first layer 122 of the coating 120 may fully surround each of the filaments of the stent 110 while the second layer 124 may be applied to a first surface (e.g., luminal) and the third layer 126 may be applied to a second surface (e.g., abluminal) of the stent 110. In some examples, the layers 122, 124, 126 are not on an external surface of the stent 110.

It will be understood by one of ordinary skill in the art based on the description herein that any of the coatings 120 described herein may comprise any number of layers (122, 124, 126, etc.) desired and that the layers may comprise any number and combination of bioactive agents, carrier materials, etc. desired.

Figure 1E:
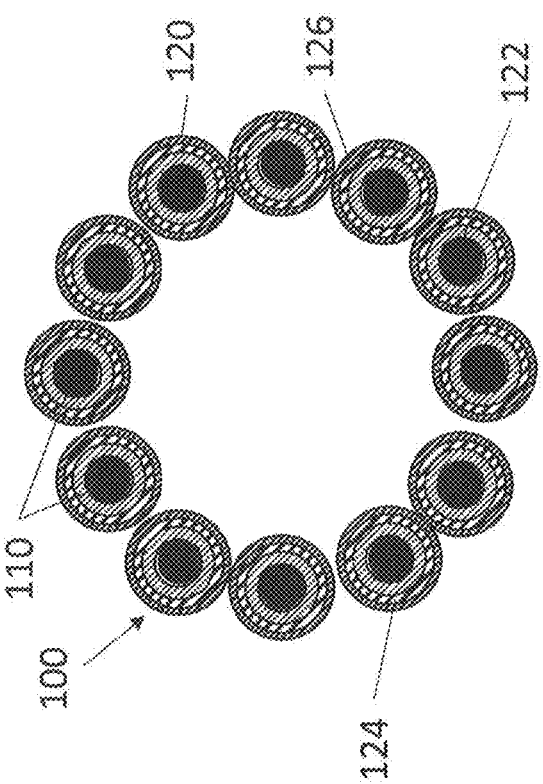
FIG. 1E shows a cross-sectional view of a medical device having a therapeutic coating comprising a single layer disposed thereon, in accordance with examples.

FIG. 1E shows a cross-sectional view of a medical device 100 having a therapeutic coating 120 comprising a single layer 122 disposed thereon. In some maniples, the therapeutic coating 120 may comprise a single layer 122 comprising a plurality of bioactive agents. For example, the single layer 122 may comprise a therapeutic composition of an anti-proliferative agent, a direct factor Xa inhibitor, and/or a direct factor IIa inhibitor us described herein. The bioactive agents may be uniformly distributed in a carrier material of the single layer 122. Alternatively, the bioactive agent, may be non-uniformly distributed in a carrier material of the single layer 122. In some examples, the carrier material is a polymeric material.

In some examples, the therapeutic composition may comprise a direct factor IIa inhibitor, a direct factor Xa inhibitor, and/or an anti-proliferative agent as described herein.

FIG. 2A shows a side perspective view of an exemplary device 100 having a therapeutic coating 120 disposed thereon. In some examples, the device 100 may comprise a temporary or non-temporary device configured for use within a subject as described herein. For example, the device 100 may comprise a drug-coated balloon 130 on a catheter 132. The coating 120 may comprise one or more bioactive agents and optionally one or more carriers as described herein. The carrier may, for example, comprise a biodegradable polymer or polymeric material as described herein. The coating 120 may be configured to locally release the one or more bioactive agents when positioned or implanted adjacent a site of a first substantial injury resulting from a surgery or intervention. Alternatively, the one or more active agents maybe incorporated into a reservoir within the balloon and released into the injury site by weeping of the agents through perforation in the balloon or when the balloon is inflated.

In some examples, the device may comprise a drug-eluting balloon configured to elute one or more of the bioactive agents or combinations described herein with or without the use of a coating 120. For example, one or more agents may be eluted by the drug-eluting stem and one or more agents may be coated on the drug-eluting stmt.

Figure 2C:
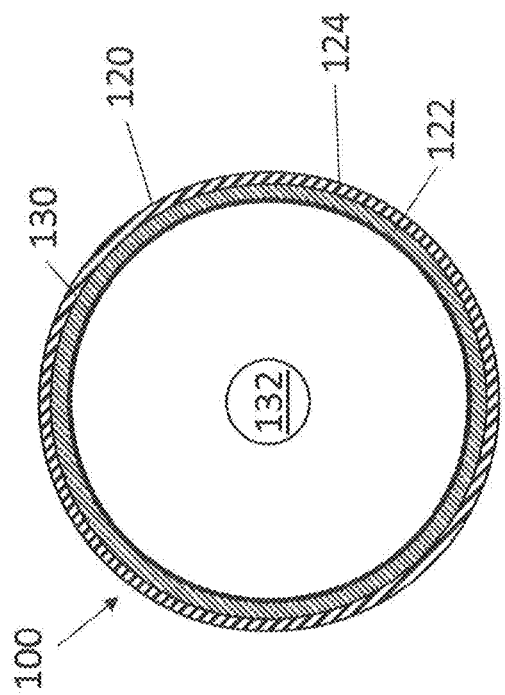
FIG. 2C shows a cross-sectional view of a medical device having a therapeutic coating comprising a first layer and a second disposed thereon, in accordance with examples.
Figure 2E:
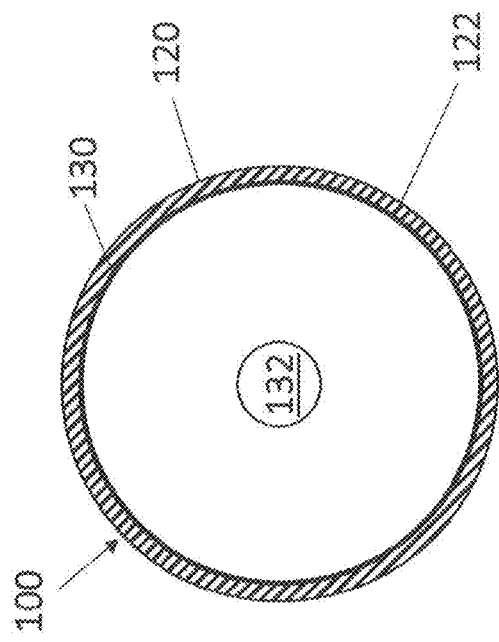
FIG. 2E shows a cross-sectional view of a medical device having a therapeutic coating comprising a single layer disposed thereon, in accordance with examples.
Figure 2B:
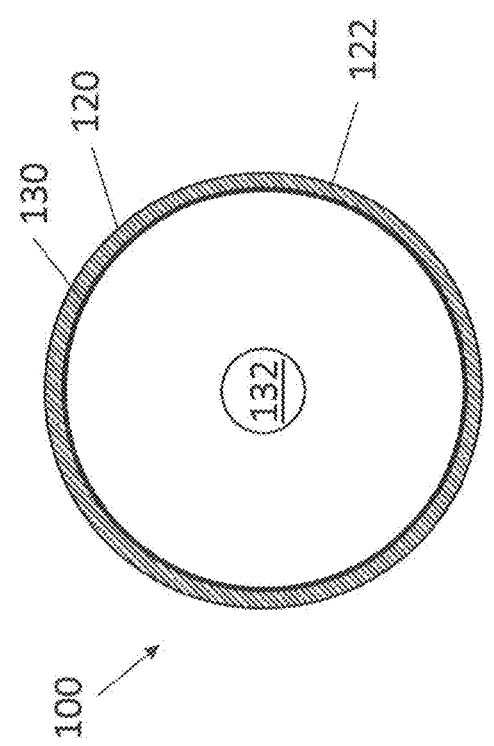
FIG. 2B shows a cross-sectional view of a medical device having a therapeutic coating comprising a first layer disposed thereon, in accordance with examples.

FIG. 2B shows a cross-sectional view of a medical device 100 having a therapeutic coating 120 comprising a first layer 122 disposed thereon. In some examples, the device 100 may comprise a drug-coated balloon 130 having a first layer 122 of a coating 120 disposed thereon. The first layer 122 may comprise one or more bioactive agents. For example, the first layer 122 may comprise one bioactive agent, two bioactive agents, three bioactive agents, or more. In some examples, the first layer may comprise a direct factor IIa inhibitor, a direct factor Xa inhibitor, and/or an anti-proliferative agent, or any other agent described herein or known to one of ordinary skill in the an based on the teachings herein. The first layer 122 may be substantially similar to any of the layers described herein (e.g., substantially similar to the layers described with respect to FIG. 1B).

FIG. 2C shows a cross-sectional view of a medical device 100 having a therapeutic coating 120 comprising a first layer 122 and a second layer 124 disposed thereon. The coating 120 may comprise a therapeutic composition of bioactive agents. The therapeutic composition may comprise one or more bioactive agents distributed within the first layer 122 and/or second layer 124. The first layer 122 and/or second layer 124 may be substantially similar to any of the layers described herein (e.g., substantially similar to the layers described with respect to FIG. 1d.

Figure 2D:
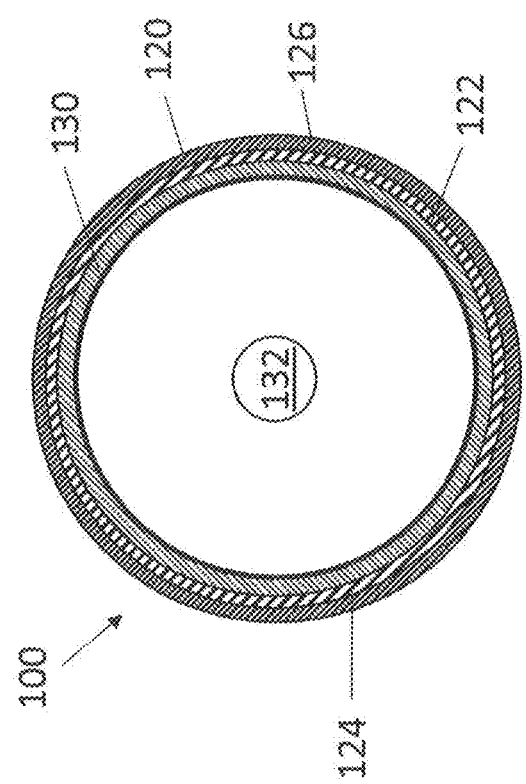
FIG. 2D shows a cross-sectional view of a medical device having a therapeutic coating comprising a first layer, a second layer, and a third layer disposed thereon, in accordance with examples.

FIG. 2D shows a cross-sectional view of a medical device 100 having a therapeutic coating 120 comprising a first layer 122, a second layer 124, and a third layer 126 disposed thereon. The coating 120 may comprise a therapeutic composition of bioactive agents. The therapeutic composition may comprise one or more bioactive agents distributed within the first layer 172, the second layer 124, and/or third layer 126. The first layer 122, second layer 124, and/or third layer 126 may be substantially similar to any of the layers described herein (e.g., substantially similar to the layers described with respect to FIG. 1D).

FIG. 2E shows a cross-sectional view of a medical device 100 having a therapeutic coating 120 comprising a single layer 122 disposed thereon. In some examples, the therapeutic coating 120 may comprise a single layer 122 comprising a plurality of bioactive agents. For example, the single layer 122 may comprise a therapeutic composition of an anti-proliferative agent, a direct factor Xa inhibitor, and/or a direct factor (a inhibitor as described herein. The bioactive agents may be uniformly distributed in a carrier material of the single layer 122. Alternatively, the bioactive agents may be non-uniformly distributed in a carrier material of the single layer 122. In some examples, the carrier material is a polymeric material.

In some examples, the drug coated balloon is to facilitate rapid and efficient uptake of drug by target tissue during transitory device deployment at a target site. The coated layers may be more than one.

In some examples, the layer may include a therapeutic agent and more than one excipient. For example, one excipient may sere to improve balloon adhesion of another excipient or excipient that are superior at promoting tissue uptake of drug and facilitate its rapid movement off the medical device during deployment and into target tissues.

In some examples, the therapeutic agent is rapidly released after the medical device is brought into contact with tissue and is readily absorbed.

In a further example, the balloon can optionally adopt carrier excipient to coat to facilitate drug transfer to the vessel wall and control release rate. A variety of carrier excipients and techniques can be used. The selected excipient could be contrast agent (i.e. iopromide), urea, dextrane, shellac, shelloic acid, keratosis (a naturally derived protein), Plasticizer (i.e. butyryl-tri-hexyl citrate, acetyl tributyl citrate, citrate ester, glycerol, other organic ester), hydrophilic space, Polyvinylpyrrolidone (PVP) and its hydrogels, Surfactants, Non-ionic surfactant Polysorbate/sorbitol (i.e. Tween20, Tween60 or Tween80), nordihydroguaiaretic acid (NDGA), hydrophobic excipient such as phospholipid, amphiphilic polymer such as Polyethylene glycol) (i.e PEG 8000), poly(ethylene oxide) (PEO) (molecular weight range from 100,000 to 10,000,000), Polyethylenimine (PEI) or polyaziridine linear or branched, amphiphilic block copolymers composed of poly(ethylene oxide) (PEO) as the hydrophilic block and poly(ether)s, poly(amino acid)s), hydrophobic polymer space, biodegradable polymers such as Poly DL lactide-co-glycolide, Poly L Lactide-co-caprolactone, durable polymers, individually or combinations thereof.

In some examples, the therapeutic agent in the coating solution is mTOR, such as novolimus or rapamycin.

In some examples, the therapeutic agent in the coating solution is a factor Xa inhibitor such as rivaroxaban or apixaban.

In another example, a factor Xa inhibitor, preferably Rivaroxaban, more preferably Apixaban released locally in combination with Argatroban from a balloon catheter to inhibit smooth muscle proliferation after vessel injury.

In some examples, the therapeutic agent may release to coronary Artery or Superficial Femoral Artery (SFA) or below the knee (BTK).

In further examples, each of the one or more agents that inhibit or enhance dissolution of fibrin formation and/or thrombus formation or promote fibrin dissolution and/or thrombus dissolution is released from a temporary device such as drug coated balloon, and optionally is administered locally, over a period of at least about 1 sec., 10 sec, 30 sec., 1 min., 2 min, or up to 10 minutes continuously or intermittently.

In still further examples, a substantial amount, or substantially all, of each of the fibrin formation inhibition, thrombus formation-inhibiting or fibrin or thrombus dissolution-promoting agent(s) is released from the device within about 1 min., 15 min., 30 min., 1 hr, 6 hr, 12 hr, 1 day, 2 days, 3 days, 1 week, 2 weeks, 3 weeks, 1 month, 2 months, 3 months, 4 months, 5 months, 6 months, 9 months, or 1 years. In a preferred example, the one or more agents comprising factor IIa inhibitor or factor Xa inhibitor are configured to substantially release over at least 28 day, preferably over at least 90 days, over at least 6 months, or over at least 1 year.

In some examples, each of the one or more active substances is released from a drug coated balloon at a rate sufficient to generate a tissue concentration of each of the agents within a range of about 1 ng/mg tissue to about 100 ng/mg tissue at the site of the first substantial injury within about 1-2 minutes of tissue contact.

In some examples, each of the one or more agents is released from a drug coated balloon sufficient to generate a tissue concentration of each of the agents last even beyond 7 to 28 days.

Figure 3A:
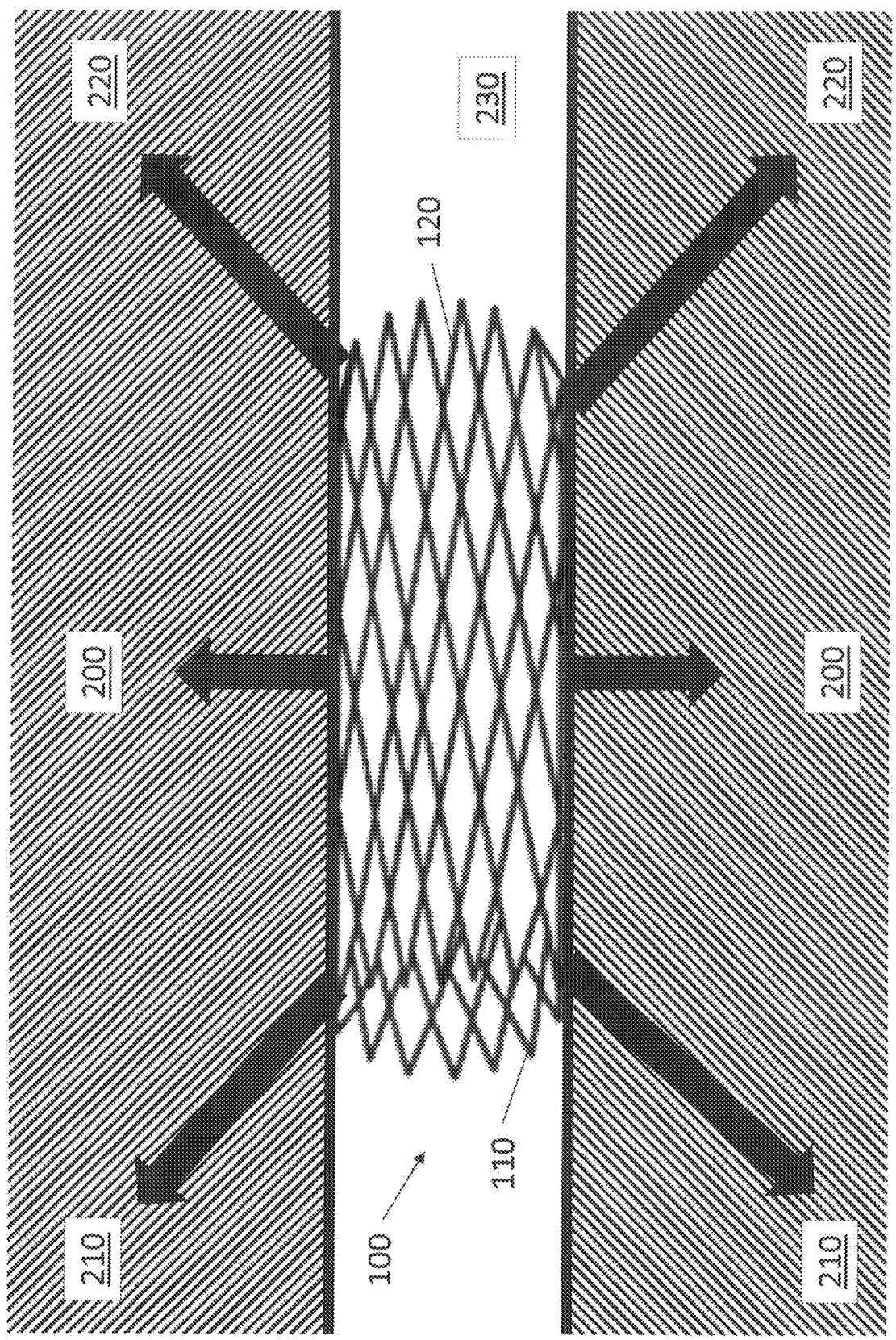
FIG. 3A shows a medical device having a therapeutic coating disposed adjacent an injury site for delivery of a therapeutic agent(s) to the tissue segment adjacent the medical device, to the device surface, and/or to the lumen adjacent to the device in accordance with examples.

FIG. 3A shows a medical device 100 having a therapeutic coating 120 disposed adjacent an injury site for delivery of a therapeutic agent(s) to the tissue segment 200. FIG. 3A is not drawn to scale. For example, the device 120 may comprise a stent 110 and a therapeutic coating 120 disposed thereon. In other examples, the device 100 may comprise a balloon or other device or instrument described herein (e.g., balloon 130 shown in FIG. 2A). The stent 110 may be configured to be positioned within a vessel adjacent to a vessel wall. When the device 100 is in contact with the vessel wall, the coating 120 may be configured to locally release the one or more bioactive agents therefrom to the tissue segment 200 at or adjacent the site of the first injury as indicated by the arrows in FIG. 3A. The coating 120 may be configured to locally release the one or more bioactive agents such that a tissue segment proximal to (e.g., adjacent tissue segment 210 within about 5 mm proximal to a proximal end of the device 100), adjacent to (e.g., tissue segment 200), and/or distal to (e.g., adjacent tissue segment 220 within about 5 mm distal to a distal end of the device 100) the device 100 achieves a therapeutic concentration of the one or more bioactive agents within about 30 minutes to about 4 hours of implantation. The device releases the drug to the tissue site, to the body lumen, to the device surface, and to the tissue adjacent to the device.

In some examples, the therapeutic coating 120 may be disposed on an abluminal side of the device 100. Alternatively, or in combination, the therapeutic coating 120 may be disposed on a luminal side of the device 100. In some embodiments, the coating 120 may locally release the one or more bioactive agents into a tissue segment 200 adjacent the abluminal side of the device 100, into an adjacent tissue segment 210 spaced proximally from the device 100, and/or into an adjacent tissue segment 220 spaced distally from the device 100. Alternatively, or in combination, the coating 120 may locally release the one or more bioactive agents into a body lumen 230. Delivery to the luminal side prevent device surface thrombus formation as well as release the one or more bioactive agents into the blood stream as described herein.

In some examples, the therapeutic coating 120 may locally release the one or more bioactive agents to the device surface, which may be disposed adjacent a tissue segment of interest. The coating 120 may release the one or more bioactive agents to the device surface in sufficient do a concentrations to inhibit platelet aggregation, thrombus, thrombin, and/or clot formation. The vicinity to the wall or tissue contacting blood should have sufficient drug concentration to inhibit platelet aggregation, fibrin, thrombin, and/or clot formation.

In some examples, the therapeutic coating 120 may locally release the one or more bioactive agents into the blood adjacent the tissue segment.

In some examples, the therapeutic coating 120 may be configured to release one or more of the agents at a dose substantially below a systemic therapeutic dose of each agent to minimize off-target effects. Preferably, the dose is at least about 5 times or more lower than the systemic dose or more preferably about 10 times or more lower than the systemic dose.

In many examples, a tissue segment is composed of the tissue segment coupled to the device releasing agent. For example, if the stem or balloon catheter is 20 mm in length, the tissue segment is 20 mm in length. In another specific example, the agent is released beyond the tissue segment. For example, when the tissue segment coupled to a device is 20 mm in length, the tissue adjacent to the tissue segment is called the adjacent tissue segment. In many cases the adjacent tissue segment ranges from 1 mm to 10 mm, preferably within a range from 1 mm to 5 mm, more preferably about 5 mm proximal and/or distal to the tissue segment, and most preferably is about 5 mm proximal and distal to the tissue segment.

As used herein, the term coating refers to one or more layers disposed on a surface of a device. In some examples, a single coating is applied to the device. In other examples, one or more coatings are used. In some examples, each component of the therapeutic composition is disposed within the same layer of the coating. In some examples, at least one component of the therapeutic composition is disposed in a different layer of the coating. In some examples, one or more component of the therapeutic composition is coated on all surfaces of the device. In some examples, one or more component of the therapeutic composition is coated on a single surface of the device. In some examples, one or more component of the therapeutic composition is coated on two or more surfaces of the device. In some examples, one or more component of the therapeutic composition is coated on at least four surfaces (e.g. an inner surface, an outer surface, a first side, and a second side) of the device. In some examples, one or more components of the therapeutic composition are not delivered by the coating. It will be understood by one of ordinary skill in the art that one or more components of any of the therapeutic compositions described herein as part of a coating may similarly be delivered locally to a tissue by infusion or direct injection, or by a device impregnated with one or more components of the therapeutic composition instead of or in addition to, the coatings described herein. For example, in some instances, the device can comprise one or more components of the therapeutic composition in a reservoir on or in the device. Alternatively, or in combination, the device can comprise one or more components of the therapeutic composition dispersed within the device structure.

Figure 3B:
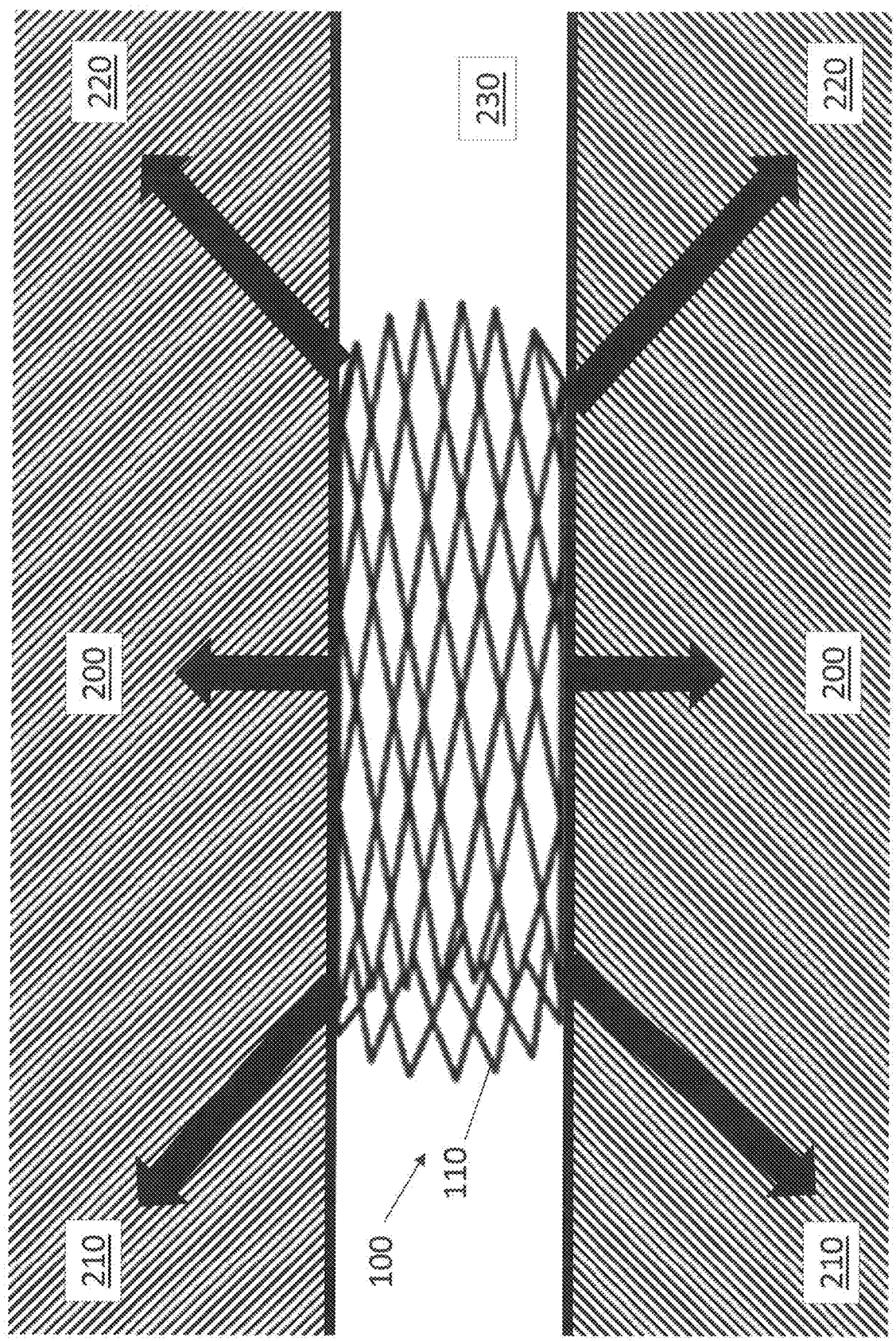
FIG. 3B shows a medical device disposed adjacent an injury site for delivery of a therapeutic agent(s) to the tissue segment adjacent the medical device, to the device surface, and/or to the lumen adjacent to the device in accordance with examples.

FIG. 38 shows a medical device 100 disposed adjacent an injury site for delivery of a therapeutic agent(s) to the tissue segment 200. FIG. 3B is not drawn to scale. For example, the device 120 may comprise a stent 110. The stent 110 may be substantially similar to any of the stents described herein except that it may not comprise a coating. Instead, the stent may be impregnated with the therapeutic composition and/or the scent may be coupled to a reservoir containing the therapeutic composition. In other examples, the device 100 may comprise a balloon with a reservoir, an infusion catheter, or other device or instrument described herein (e.g., balloon 130 shown in FIG. 2A). The stent 110 may be configured to be positioned within a vessel adjacent to a vessel wall. When the device 100 is in contact with the vessel wall, the therapeutic composition may locally release the one or more active substances therefrom to the tissue segment 200 at or adjacent the site of the first injury as indicated by the arrows in FIG. 313. The therapeutic composition may be formulated to locally release the one or more active substances such that a tissue segment proximal to (e.g., adjacent tissue segment 210 within about 5 mm proximal to a proximal end of the device 100), adjacent to (e.g., tissue segment 200), and/or distal to (e.g., adjacent tissue segment 220 within about 5 mm distal to a distal end of the device 100) the device 100 achieves a therapeutic concentration of the one or more bioactive agents within about 30 minutes to about 4 hours of implantation.

In some examples, the therapeutic composition may be formulated to release one or more of the agents at a dose substantially below a systemic therapeutic dose of each agent to minimize off-target effects. Preferably, the dose is at least about 5 times lower than the systemic dose or more preferably about 10 times lower than the systemic dose.

In many examples, a tissue segment is composed of the tissue segment coupled to the device releasing agent. For example, if the stent or balloon catheter is 20 mm in length, the tissue segment is 20 mm in length. In another specific example, the agent is released beyond the tissue segment. For example, when the tissue segment coupled to a device is 20 mm in length, the tissue adjacent to the tissue segment is called the adjacent tissue segment. In many cases the adjacent tissue segment ranges from 1 mm to 10 mm, preferably within a range from 1 mm to 5 mm, more preferably about 5 mm proximal and/or distal to the tissue segment, and most preferably is about 5 mm proximal and distal to the tissue segment.

Figure 4:
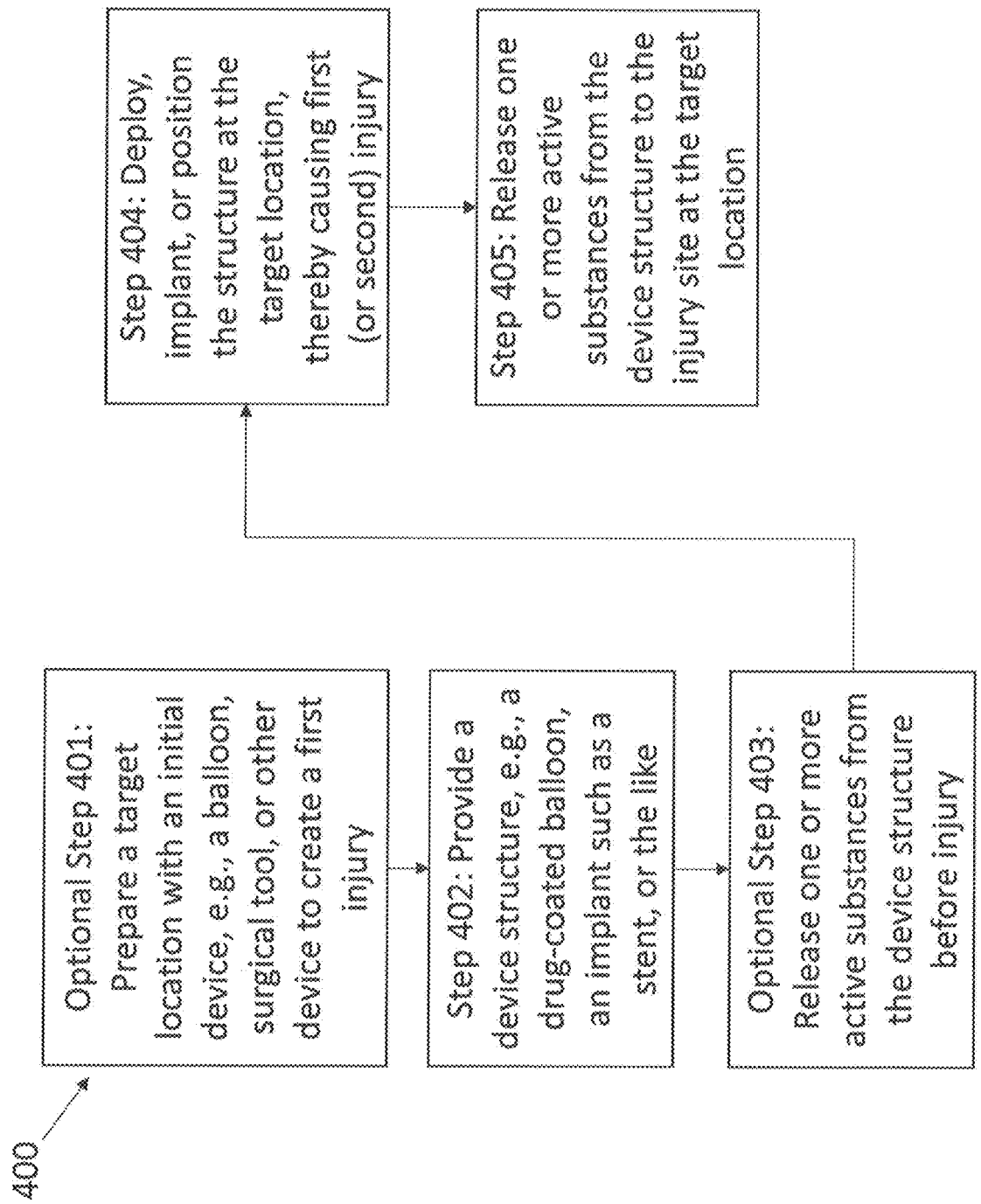
FIG. 4 shows a flowchart of a method of treating clotting in patient with a device, in accordance with examples.

FIG. 4 shows a flowchart of a method 400 of treating clotting in patient with a stent.

At Step 401, an optional injury may be caused at the target site. For example, a balloon may be positioned at a lesion (e.g., through a plaque) at the target site and expanded to prepare the target site (e.g., to open an artery) for the device (e.g., a stent). Alternatively, or in combination, a surgical tool or other device may create a first injury at the target site as described herein.

At Step 402, a device comprising a structure having an external surface may be provided. The device may comprise any of the devices described herein. For example, the device may comprise an implant (such as a stent) or a balloon. In some examples, the device may be a coated stent. In some examples, the device may be a catheter. In some examples, the device may be a coated balloon. In some examples, the device may be a balloon reservoir.

At Step 403, one or more active substances may optionally be released from the structure prior to the injury being caused. In some examples, one or more active substances may be released from the structure before, during placement at, and/or after placement at the target location. In some examples, the one or more active substances may be released from the structure prior to deployment of the structure (which subsequently may cause the injury) at the target location. In some examples, the one or more active substances may be released from the structure during deployment of the structure at the target location.

At Step 404, the structure may be deployed at a target location in a patient's body. In some examples, deployment of the structure may comprise expanding the structure against the target location and/or injury site. Deployment of the structure may cause an injury at the target location. In some examples, the injury is caused before deployment of the structure (e.g., with another device as described in optional Step 401). In some examples, deployment of the structure does not cause an injury to the target location.

At Step 405, one or more active substances may be released from the structure to the injury site. In some examples, one or more active substances may be released from the structure before, during placement at, and/or after placement at the injury site. In some examples, a therapeutic composition may comprise the one or more active substances. The one or more active substances may comprise a direct factor Xa inhibitor, a direct factor IIa inhibitor, and/or an anti-proliferative agent as described herein. For example, the one or more active substances may comprise apixaban, argatroban, and or sirolimus as described herein. In some examples, the direct factor Xa inhibitor and/or the direct factor IIa inhibitor may be released faster than the anti-proliferative agent. In some examples, the therapeutic composition may comprise a coating on the external surface of the structure. In some examples, the coating may comprise one or more layers as described herein. In some examples, the therapeutic composition may be disposed within a drug reservoir fluidly coupled to the external surface of the structure and delivering the therapeutic composition may comprise delivering the therapeutic composition from the drug reservoir to the external surface of the deployed structure, and to the tissue therefrom.

Although the steps above show a method 400 of treating clotting in a patient in accordance with examples, a person of ordinary skill in the art will recognize many variations based on the teaching described herein. The steps may be completed in a different order. Steps may be added or deleted. Some of the steps may comprise sub-steps. Many of the steps may be repeated as often as necessary to assemble at least a part of an article.

For example, in some examples Step 405 may occur in multiple steps such that one or more of a plurality of active substances are released from the therapeutic composition before one or more other of the plurality of active substances. For examples, the direct factor Xa inhibitor and/or the direct factor IIa inhibitor may be released before the anti-proliferative agent. Alternatively, or in combination, Step 405 may occur be Step 404 such that the structure releases one or more of the active substances before being positioned adjacent the injury site.

It will be understood by one of ordinary skill in the art that the methods described herein may be used for a wide range of devices. For example, method 400 may be adapted for placement of drug-coated (or drug infusion) scents, balloons, cardiac leads for pacemakers, grafts such as aortic grafts, shunts such as AV shunts, mitral/aortic valve replacement (where the drug is incorporated in the structure holding the valve or the valve or both), mitral repair devices such as, Mitra-clip (where the drug is incorporated in the clip), watchman device. Neuro device such as the Flow Diverter, Neuro coils, hip replacement devices, knee replacement devices, shoulder implants, or the like.

As used herein, the term "coating" refers to a layer of polymer and/or drug (or therapeutic agent or active agent) disposed on a surface of a device structure. The layer may comprise a polymer, a drug, or a combination of a drug and a polymer.

As used herein, the term "top layer or coat" refers to an outer-most layer of a coating. The top layer or coat may comprise a polymer, a drug (or therapeutic agent or active agent), or a combination of a drug and a polymer. The top layer or coat may comprise the same polymer or a different polymer as layers of coating disposed therebelow. The top layer or coat may comprise the same drug or a different drug(s) as layers of coating disposed therebelow.

As used herein, the term "matrix" refers to a mixture of a drug (or therapeutic agent or active agent) and a polymer.

The terms anti-thrombin, thrombin inhibiter, and thrombin formation inhibitor are used interchangeably herein. Also, the terms anti-fibrin, fibrin inhibitor, and fibrin formation inhibitor are used interchangeably herein.

As used herein, a direct factor Xa inhibitor refers to a direct, selective inhibitor of factor Xa that acts directly on factor Xa without using antithrombin as a mediator. The term "direct factor Xa inhibitor" is used herein interchangeably with the term "factor Xa inhibitor" or "anti-factor Xa". Direct factor Xa inhibitors inhibit thrombin formation and/or fibrin formation, thereby inhibiting clot formation. Direct factor Xa inhibitors include, but are not limited to, apixaban, betrixaban, edoxaban, otamixaban, razaxaban, rivaroxaban, (r)-n-(2-(4-(1-methylpiperidin-4-yl)piperazin-1-yl)-2-oxo-1-phenylethyl)-1h-indole-6-carboxamide (LY-517717), daraxaban (YM-150), or 2-[(7-carbamimidoylnaphthalen-2-yl)methyl]-[4-(1-ethanimidoylpiperidin-4-yl)oxyphenyl]sulfamoyl]acetic acid (YM-466 or YM-60828), or eribaxaban (PD 0348292), or 2-(5-carbamimidoyl-2-hydroxy-phenyl) 4-[5-(2,6-dimethyl-piperidin-1-yl)-pentyl]-3-oxo-3,4-dihydro-quinoxaline-6-carboxylic acid (PD0313052). Preferred direct Xa inhibitors include apixaban and rivaroxaban.

As used herein, a direct factor IIa inhibitor refers to a direct, selective inhibitor of factor IIa (also referred to herein as thrombin) which acts directly on factor IIa thrombin. The term "direct factor IIa inhibitor" is used herein interchangeably with the term "factor IIa inhibitor" or "anti-factor IIa". Direct factor IIa inhibitors inhibit thrombin formation and/or fibrin formation, thereby inhibiting clot formation. Direct thrombin factor IIa inhibitors include, but are not limited to, argatroban, dabigatran, ximelagatran, melagatran, efegatran, inogatran, atecegatran metoxil (AZD-0837), hirudin, hirudin analogs, bivalirudin, desirudin, and lepirudin. Preferred direct factor IIa inhibitors include argatroban.

As used herein, an anti-proliferative agent refers to anti-proliferative agents, anti-mitotic agents, cytostatic agents and anti-migratory agents which suppress cell growth, proliferation, and/or metabolism. Examples of anti-proliferative agents include without limitation inhibitors of mammalian target of rapamycin (mTOR), rapamycin (also called sirolimus), deuterated rapamycin, rapamycin prodrug TAFA93, 40-O-alkyl-rapamycin derivatives, 40-O-hydroxyalkyl-rapamycin derivatives, everolimus {40-O-(2-hydroxyethyl)-rapamycin}, 40-O-(3-hydroxy)propyl-rapamycin, 40-O-(2-(2-hydroxy)ethoxy)ethyl-rapamycin, 40-O-alkoxyalkyl-rapamycin derivatives, biolimus {40-O-(2-ethoxyethyl)-rapamycin}, 40-O-acyl-rapamycin derivatives, temsirolimus {40-(3-hydroxy-2-hydroxymethyl-2-methyl-propanoate)-rapamycin, or CCI-779 (temsirolimus), 40-O-phospho-containing rapamycin derivatives, ridaforolimus (40-dimethylphosphinate-rapamycin, or AP23573 (ridaforolimus, formerly known as deforolimus), 40(R or S)-heterocyclyl- or heteroaryl-containing rapamycin derivatives, zotarolimus {40-epi-(N1-tetrazolyl)-rapamycin, or ABT-578 (zotarolimus), 40-epi-(N2-tetrazolyl)-rapamycin, 32(R or S)-hydroxy-rapamycin, myolimus (32-deoxo-rapamycin), novolimus (16-O-desmethyl-rapamycin), taxanes, paclitaxel, docetaxel, cytochalasins, cytochalasins A through J, latrunculins, and salts, isomers, solvates, analogs (including deuterated analogs), derivatives, metabolites, and prodrugs thereof. The IUPAC numbering system for rapamycin is used herein. Preferred anti-proliferative agents include mTOR inhibitors and/or taxanes, or salts, isomers, solvates, analogs, derivatives, metabolites, or prodrugs thereof.

Table A provides non-limiting examples of derivatives of each of rapamycin, everolimus, biolimus, temsirolimus, ridaforolimus, zotarolimus, myolimus and novolimus.

TABLE A

Derivatives of rapamycin-type compounds

Derivatives of Each of Rapamycin, Everolimus, Biolimus, Temsirolimus, Ridaforolimus, Zotarolimus, Myolimus and Novolimus N7-oxide
2-hydroxy
3-hydroxy
4-hydroxy
5-hydroxy
6-hydroxy
11-hydroxy
12-hydroxy
13-hydroxy
14-hydroxy
23-hydroxy
24-hydroxy
25-hydroxy
31-hydroxy
35-hydroxy
43-hydroxy (11-hydroxymethyl)
44-hydroxy (17-hydroxymethyl)
45-hydroxy (23-hydroxymethyl)
46-hydroxy (25-hydroxymethyl)
47-hydroxy (29-hydroxymethyl)
48-hydroxy (31-hydroxymethyl)
49-hydroxy (35-hydroxymethyl)
17,18-dihydroxy
19,20-dihydroxy
21,22-dihydroxy
29,30-dihydroxy
10-phosphate
28-phosphate
40-phosphate
16-O-desmethyl
27-O-desmethyl
39-O-desmethyl
16,27-bis(O-desmethyl)
16,39-bis(O-desmethyl)
27,39-bis(O-desmethyl)
16,27,39-tris(O-desmethyl)
16-desmethoxy
27-desmethoxy
39-O-desmethyl-14-hydroxy
17,18-epoxide
19,20-epoxide
21,22-epoxide
29,30-epoxide
17,18-29,30-bis-epoxide
17,18-19,20-21,22-tris-epoxide
19,20-21,22-29,30-tris-epoxide
16-O-desmethyl-17,18-19,20-bis-epoxide
16-O-desmethyl-17,18-29,30-bis-epoxide
16-O-desmethyl-17,18-19,20-21,22-tris-epoxide
16-O-desmethyl-19,20-21,22-29,30-tris-epoxide
27-O-desmethyl-17,18-19,20-21,22-tris-epoxide
39-O-desmethyl-17,18-19,20-21,22-tris-epoxide
16,27-bis(O-desmethyl)-17,18-19,20-21,22-tris-epoxide
16-O-desmethyl-24-hydroxy-17,18-19,20-bis-epoxide
16-O-desmethyl-24-hydroxy-17,18-29,30-bis-epoxide
12-hydroxy and opened hemiketal ring It will be understood by one of ordinary skill in the art that the devices and methods described herein may be used in combination with one or more additional bioactive agents. Such agents optionally include anti-mitotic agents, cytostatic agents, anti-migratory agents, immunomodulators, immunosuppressants, anti-inflammatory agents, anti-ischemia agents, anti-hypertensive agents, vasodilators, anti-hyperlipidemia agents, anti-diabetic agents, anti-cancer agents, anti-tumor agents, anti-angiogenic agents, angiogenic agents, anti-chemokine agents, healing-promoting agents, anti-bacterial agents, anti-fungal agents, and combinations thereof. It is understood that a bioactive agent may exert more than one biological effect.

Use of anti-coagulants, or fibrin/thrombus formation-inhibiting agent(s) have surprisingly been found to also enhance or aid in inhibiting cell proliferation, smooth muscle cell proliferation, hyperplasia or restenosis (e.g., smooth muscle cell proliferation or hyperplasia), when two agents factor Xa inhibitor and factor IIa inhibitor (apixaban and argatroban) were tested in combination or additionally in combination with a third antiproliferative agent.

In a preferred example, a device releasing one or more factor Xa inhibitors, and/or one or more factor IIa inhibitors, and/or one or more antiproliferative agents, wherein said one or more agents inhibit thrombin formation and/or fibrin formation thereby inhibiting clot formation and smooth muscle cell proliferation.

In some examples, the injury to a tissue, surface, vessel/lumen wall, or other body part is the first substantial injury resulting from a surgery or intervention. In certain examples, the surgery or intervention is selected from the group consisting of vascular surgeries and interventions, cardiovascular surgeries and interventions, peripheral vascular surgeries and interventions, vascular grafting, vascular replacement, vascular angioplasty, thrombectomy, vascular stent placement, vascular laser therapy, coronary by-pass surgery, coronary angiography, coronary stent placement, carotid artery procedures, peripheral stent placement, organ transplants, artificial heart transplant, and plastic and cosmetic surgeries and interventions. In additional examples, the injury is the first substantial injury caused by the device delivering the one or more active substances, and optionally one or more other kinds of bioactive agents (e.g., anti-proliferative agents, anti-inflammatory agents, etc.). In some examples, a substantial injury to a tissue, surface, vessel/lumen wall or other body part results from contact of a device with the tissue, surface, vessel/lumen wall or other body part in a surgery or intervention (e.g., contact of the device causing damage to the endothelium lining a blood vessel, a surgical cutting instrument cutting a tissue, a deployed stent embedding into the wall of a blood vessel, etc.). In further examples, a substantial injury to a tissue, surface, vessel/lumen wall or other body part has a potential to elicit fibrin/thrombus formation, cell migration, cell proliferation or inflammation, or a combination thereof, at the site of injury or at an area adjacent thereto.

In some examples, the therapeutic composition is formulated to release the one or more active substances at a rate of 1 µg/second/mm device to about 50 µg/day/mm device, preferably at a rate of 1 µg/min/mm device to about 30 µg/day/mm device, more preferably at a rate of 1 µg/hour/mm device to about 30 µg/day/mm device.

In some examples, each of the one or more active substances is released from a temporary or non-temporary device at a rate within a range of about 1 µg/hour/mm device length to about 30 µg/day/mm device length, for example about 1 µg/hour/mm device length to about 20 µg/day/mm device length. In some examples, the therapeutic composition is formulated to release the one or more active substances at a rate of 1 µg/hour/mm device to about 20 µg/day/mm device. In some examples, the therapeutic composition may be formulated to release the one or more active substances at a rate within a range of about 1 µg/hour/mm device length to about 14 µg/hour/mm device length. In some examples, the therapeutic composition may be formulated to release the one or more active substances at a rate within a range bounded by any two of the following values: about 1 µg/hour/mm device length, about 2 µg/hour/mm device length, about 3 µg/hour/mm device length, about 4 µg/hour/mm device length, about 5 µg/hour-mm device length, about 6 µg/hour/mm device length, about 7 µg/hour/mm device length, about 8 µg/ hour/mm device length, about 9 µg/hour/mm device length, about 10 µg/hour/mm device length, about 11 µg/hour/mm device length, about 12 µg/hour/mm device length, about 13 µg/hour/mm device length, about 14 µg/hour/mm device length, about 15 µg/hour/mm device length, about 16 µg/hour/mm device length, about 17 µg/hour/min device length, about 18 µg/hour/mm device length, about 19 µg/hour/mm device length, about 20 µg/hour/mm device length, about 21 µg hour/mm device length, about 22 µg/hour/mm device length, about 23 µg/hour/mm device length, about 24 µg/hour/mm device length, about 25 µg/hour/mm device length, about 26 µg/hour/mm device length, about 27 µg/hour/mm device length, about 28 µg/hour/mm device length, about 29 µg/hour/mm device length, or about 30 µg/hour/mm device length.

In some examples, the therapeutic composition may be formulated not to release the one or more active substances until a predetermined time period has elapsed in order to ensure that the one or more active substances are released to the target tissue of interest and not during delivery of the structure to the target tissue. In some examples, the therapeutic composition may be formulated not to release the one or more active substances until the external surface of the structure is positioned adjacent the injury site. In some examples, the therapeutic composition is formulated not to release the one or more active substances for at least about 1 minute, about 5 minutes, about 30 minutes, about 1 hour, about 12 hours, or about 24 hours after introduction into the patient's body. In some examples, a removable cover or sheath may be disposed about the external surface of the structure in order to prevent release of the one or more active substances until the predetermined time period has elapsed. When the predetermined time period (e.g., 30 minutes, 1 hour, 12 hours, 24 hours, etc.) has elapsed, the cover or sheath may be removed and the therapeutic composition may be exposed, thereby beginning release of the one or more active substances.

In some examples, the therapeutic composition is formulated to begin releasing the one or more active substances within about 1 minute, 5, 10, 15, 20, 25, or 30 minutes after the external surface of the structure is positioned adjacent the injury site.

In some examples, substantially all of each of the one or more active substances is released from a temporary or non-temporary device within about 1 day to about 180 days or more, for example within about 1 day to about 90 days. In some examples, the therapeutic composition is formulated to release substantially all of the one or more active substances within about 7 days or about 28 days. In some examples, the therapeutic composition may be formulated to release substantially all of the one or more active substances within a range bounded by any two of the following value: 1 day, 3 days, 7 days, 14 days, 21 days, 28 days, 45 days, 90 days, 180 days, or more.

In some examples, the therapeutic composition is formulated to release substantially all of the one or more active substances within about 3 hours, about 6 hours, about 12 hours, about 1 day, or about 3 days. In some examples, the therapeutic composition is formulated to release at least 50%, at least 60%, or at least 70% of the one or more active substances within about 3 hours, about 6 hours, about 12 hours, about 1 day, about 3 days, about 7 days, or about 28 days.

In some examples, each of the one or more active substances is released from a temporary or non-temporary device at a rate sufficient to generate a tissue concentration of each of the agents within a range of about 5 ng/mg tissue to about 200 nm/mg tissue at the injury site within about 3 hours of tissue contact.

In some examples, the therapeutic composition is formulated to locally release the one or more active substances to the injury site at a rate sufficient to generate a tissue concentration of about 2 ng/mg tissue to about 800 ng/mg tissue, about 2 ng/mg tissue to about 200 ng/mg tissue, preferably at about 20 ng/mg tissue to about 200 ng/mg tissue, more preferably at about 40 ng/mg tissue to about 200 ng/mg tissue, of the one or more active substances at the injury site within about 3 hours after the external surface of the structure is positioned adjacent the injury site. In some examples, the therapeutic composition is formulated to release the one or more active substances at a rate sufficient to generate a tissue concentration at the injury site within a range of about 10 ng/mg tissue to about 100 ng/mg tissue. The therapeutic composition may be formulated to locally release the one or more active substances to the injury site at a rate sufficient to generate a tissue concentration of the one or more active substances at the injury site within about 3 hours after placement adjacent the injury site within a range bounded by any two of the following values: 2 ng/mg tissue, 5 ng/mg tissue, 10 ng/mg tissue, 20 ng/mg tissue, 30 ng/mg tissue, 40 ng/mg tissue, 50 ng/mg tissue, 60 ng/mg tissue, 70 ng/mg tissue, 80 ng/mg tissue, 90 ng/mg tissue, 100 ng/mg tissue, 110 ng/mg tissue, 120 ng/mg tissue, 130 ng/mg tissue, 140 ng/mg tissue, 150 ng/mg tissue, 160 ng/mg tissue, 170 ng/mg tissue, 180 ng/mg tissue, 190 ng/mg tissue, or 200 ng/mg tissue.

In another example, the device releases the one or more active substances from 1 microgram per mm of device length to 25 micrograms per mm of device length, and preferably releases said agent from 5 micrograms per mm of device length to 20 micrograms per mm of device length.

In some examples, the therapeutic composition is formulated to release the one or more active substances at a rate within a range of about 2 µg/mm device to about 100 µg/mm device, about 5 µg/mm device to about 100 µg/mm device, about 7 µg/mm device to about 100 µg/mm device, or about 10 µg/mm device to about 100 µg/mm device within about 3 hours, 12 hours, 1 day, 3 days, 7 days, 28 days, 90 days, or 180 days. In some examples, the therapeutic composition is formulated to release the one or more active substances at a rate within a range of about 5 µg/mm device to about 100 µg/mm device within about 3 hours. In some examples, the therapeutic composition is formulated to release the one or more active substances at a rate within a range of about 5 µg/mm device to about 100 µg/mm device within about 12 hours. In some examples, the therapeutic composition is formulated to release the one or more active substances at a rate within a range of about 5 µg/mm device to about 100 µg/mm device within about 7 days. In some examples, the therapeutic composition is formulated to release the one or more active substances at a rate within a range of about 5 µg/mm device to about 100 µg/mm$^2$ device within about 28 days.

In some examples, the therapeutic composition is formulated to release the one or more active substances at a dose within a range of about 0.5 µg/mm$^2$ device to about 15 µg/mm$^2$ device, or of about 1 µg/mm$^2$ device to about 12 µg/mm$^2$ device, or of about 2 µg/mm$^2$ device to about 12 µg/mm$^2$ device, or of about 5 µg/mm$^2$ device to about 12 µg/mm$^2$ device, or of about 7 µg/mm$^2$ device to about 12 µg/mm$^2$ device, within about 3 hours or about 12 hours or about 1 day or about 3 days or about 7 days. In some examples, the therapeutic composition is formulated to release the one or more active substances at a dose within a range of about 1 µg/mm² device to about 12 µg/mm² device within about 3 hours. In some examples, the therapeutic composition is formulated to release the one or more active substances at a dose within a range of about 1 µg/mm² device to about 12 µg/mm² device within about 12 hours. In some example, the therapeutic composition is formulated to release the one or more active substances at a dose within a range of about 1 µg/mm² device to about 12 µg/mm² device within about 7 days. In some examples, the therapeutic composition is formulated to release the one or more active substances at a dose within a range of about 1 µg/mm² device to about 12 µg/mm² device within about 28 days, about 90 days, or about 180 days.

In some examples, each of the one or more agents is released from a temporary or non-temporary device at a rate sufficient to generate a tissue concentration of each of the agents within a range of about 1 ne mg tissue at about 100 ng/mg tissue within about 28 days of tissue contact.

In some examples, the therapeutic composition is formulated to release the one or more active substances at a rate sufficient to generate a tissue concentration of about 0.5 ng/mg to about 10 ng/mg within the tissue adjacent to the device structure within about 28 days, about 90 days, or about 180 days.

In some examples, the therapeutic composition is formulated to release the one or more active substances at a rate sufficient to generate a tissue concentration at the injury site within a range of about 0.5 ng/mg to about 30 ng/mg within about 28 days. In some examples, the therapeutic composition is formulated to release the one or more active substances at a rate sufficient to generate a tissue concentration at the injury site within a range of about 1 ng/mg to about 20 ng/mg within about 28 days. In some examples, the therapeutic composition is formulated to release the one or more active substances at a rate sufficient to generate a tissue concentration at the injury site within a range of about 1.5 ng/mg to about 25 ng/mg within about 28 days.

In some examples, the therapeutic composition is formulated to release the one or more active substances at a rate sufficient to generate a tissue concentration at the injury site within a range of about 0.1 ng/mg to about 10 ng/mg within about 90 days or about 180 days.

In some examples, each of the one or more agents is released from a temporary or non-temporary device at the same rate. In other examples, one or more of the one or more agents that inhibit fibrin/thrombus formation or promote fibrin/thrombus dissolution and/or other bioactive agents is released from a temporary or non-temporary device at a different rate.

In some examples, the therapeutic composition is formulated to release the direct factor Xa inhibitor and/or the direct factor IIa inhibitor faster than the anti-proliferative agent.

In some examples, the therapeutic composition is formulated to release a larger dose of the direct factor Xa inhibitor than the anti-proliferative agent. In some examples, the dose of the direct factor Xa inhibitor is about 1.25 to about 5 times larger, about 1.5 to about 3 times larger, or about 1.5 to about 2.5 times larger than a dose of the anti-proliferative agent.

In some examples, the therapeutic composition is formulated to release the one or more active substances at a rate sufficient to generate a tissue concentration at a location proximal or distal a proximal end of the structure or a distal end of the structure, respectively (e.g., an adjacent tissue segment), within a range of about 0.5 ng/mg to about 500 ng/mg within about 3 hours. In some examples, the therapeutic composition is formulated to release the one or more active substances at a rate sufficient to generate a tissue concentration at the location proximal or distal the proximal end of the structure or the distal end of the structure, respectively (e.g., un adjacent tissue segment), within a range of about 1 ng/mg to about 35 ng/mg within about 3 hours. In some examples, the therapeutic composition is formulated to release the one or more active substances at a rate sufficient to generate a tissue concentration at the location proximal or distal the proximal end of the structure or the distal end of the structure, respectively (e.g., an adjacent tissue segment), within a range of about a range of about 1.5 ng/mg to about 30 ng/mg within about 3 hours. In some examples, the therapeutic composition is formulated to release the one or more active substances at a rate sufficient to generate a tissue concentration at the location proximal or distal to the proximal end of the structure or the distal end of the structure (e.g., within ±5 mm proximal or distal to an end of the structure), respectively, within a range of about 0.1 ng/mg to about 50 ng/mg, about 0.25 ng/mg to about 20 ng/mg, about 1 ng/mg to about 50 ng/mg, or about 3 ng/mg to about 50 ng/mg within about 3 hours.

In some examples, the therapeutic composition is formulated to release the one or more active substances at a rate sufficient to generate a tissue concentration at a location proximal or distal a proximal end of the structure or a distal end of the structure, respectively, within a range of about 0.2 ng/mg to about 25 ng/mg, about 2 ng/mg to about 25 ng/mg, or about 4 ng/mg to about 25 ng/mg within about 24 hours. In some examples, the therapeutic composition is formulated to release the one or more active substances at a rate sufficient to generate a tissue concentration at the location proximal or distal to the proximal end of the structure or the distal end of the structure (e.g., within mm proximal or distal to an end of the structure), respectively, within a range of about 0.1 ng/mg about 50 ng/mg, about 0.25 ng/mg to about 20 ng/mg, about 1 ng/mg to about 50 ng/mg, or about 3 ng/mg to about 50 ng/mg within about 24 hours. In some examples, the therapeutic composition is formulated to release the one or more active substances at a rate sufficient to generate a tissue concentration at the location proximal or distal the proximal end of the structure or the distal end of the structure, respectively, within a range of about 0.3 ng/mg to about 10 ng/mg within about 24 hours.

In some examples, the therapeutic composition is formulated to release a dose of the direct factor Xa inhibitor sufficient to generate a blood concentration of the direct factor Xa inhibitor which is smaller than a median maximum scrum concentration ($C_{max}$) of the direct factor Xa inhibitor generated by systemic delivery of the direct factor Xa inhibitor to achieve the same tissue concentration at the injury site. In other examples, the therapeutic composition is formulated to release a close of the direct factor Xa inhibitor sufficient to generate a blood concentration of the direct factor Xa inhibitor which is smaller than a median maximum serum concentration ($C_{max}$) of the direct factor Xa inhibitor generated by systemic delivery of the direct factor Xa inhibitor when taking one or more oral dose of said factor Xa inhibitor. In some examples, the systemic delivery comprises a single oral dose, a daily oral dose, or a smallest oral dose of the direct factor Xa inhibitor. In some examples, the blood concentration is larger than a median minimum serum concentration ($C_{min}$) of the direct factor Xa inhibitor generated by systemic delivery. In some examples, the blood concentration is smaller than a median minimum serum concentration ($C_{min}$) of the direct factor Xa inhibitor generated by systemic delivery. In some examples, the $C_{max}$ is measured using one of plasma blood, scrum blood, or whole blood. In other examples, the median $C_{max}$ is 80 ng/ml, or 123 ng/ml, or 171 ng/ml, or 321 ng/ml, or 480 ng/ml of blood.

In some examples, the therapeutic composition is formulated to release a dose of the direct factor Xa inhibitor sufficient to generate a plasma drug level area under the curve (AUC (0-24) or AUC (0-∞)) in ng·h/ml which is smaller than a median (AUC (0-24) or AUC (0-∞)) in ng·h/ml of the direct factor Xa inhibitor generated by systemic delivery of the direct factor Xa inhibitor to achieve the same tissue concentration at the injury site. In other examples, the therapeutic composition is formulated to release a dose of the direct factor Xa inhibitor sufficient to generate a plasma drug level area under the curve (AUC (0-24) or AUC (0-∞)) in ng·h/ml which is smaller than a median (AUC (0-24) or AUC (0-∞)) in ng·h/ml of the direct factor Xa inhibitor generated by systemic delivery of the direct factor Xa inhibitor when taking one or more oral dose of said factor Xa inhibitor. In some examples, the systemic delivery comprises a single oral dose, a daily oral dose, or a smallest oral dose of the direct factor Xa inhibitor. In some examples, the (AUC (0-24) or AUC (0 ∞)) is measured using one of plasma blood, serum blood, or whole blood. In other examples, the median (AUC (0-24) or AUC (0-∞)) is 724 ng·h/ml, or 1437 ng·h/ml, or 2000 ng·h/ml, or 4000 ng·h/ml.

In some examples, the therapeutic composition is formulated to release a dose of the anti-proliferative agent sufficient to generate a blood concentration of the anti-proliferative agent which is smaller than a median maximum serum concentration ($C_{max}$) of the anti-proliferative agent generated by systemic delivery of the anti-proliferative agent to achieve the same tissue concentration at the injury site. In some examples, the systemic delivery comprises a single oral dose, a daily oral dose, or a smallest oral dose of the anti-proliferative agent. In some examples, the blood concentration is larger than a median minimum serum concentration ($C_{min}$) of the anti-proliferative agent generated by systemic delivery. In some examples, the blood concentration is smaller than a median minimum serum concentration ($C_{min}$) of the anti-proliferative agent generated by systemic delivery. In some examples, the therapeutic composition is formulated to release a dose of the anti-proliferative agent sufficient to generate a plasma drug level area under the curve (AUC (0-∞)) in ng·h/ml which is smaller than a median AUC (0-∞) in ng·h/ml of the anti-proliferative agent generated by systemic delivery of the anti-proliferative agent to achieve the same tissue concentration at the injury site.

In some examples, the therapeutic composition is formulated to release a dose of the direct factor IIa inhibitor sufficient to generate a blood concentration of the direct factor IIa inhibitor which is smaller than a median maximum scrum concentration ($C_{max}$) of the direct factor IIa inhibitor generated by systemic delivery of the direct factor IIa inhibitor to achieve the same tissue concentration at the injury site. In other examples, the therapeutic composition is formulated to release a dose of the direct factor IIa inhibitor sufficient to generate a blood concentration of the direct factor IIa inhibitor which is smaller than a median maximum serum concentration ($C_{max}$) of the direct factor IIa inhibitor generated by systemic delivery of the direct factor IIa inhibitor when taking one or more oral dose of said factor IIa inhibitor. In some examples, the systemic delivery comprises a single oral dose, a daily oral dose, or a smallest oral dose of the direct factor IIa inhibitor. In some examples, the blood concentration is larger than a median minimum serum concentration ($C_{min}$) of the direct factor IIa inhibitor generated by systemic delivery. In some examples, the blood concentration is smaller than a median minimum serum concentration ($C_{min}$) of the direct factor IIa inhibitor generated by systemic delivery. In some examples, the $C_{max}$ is measured using one of plasma blood, scrum blood, or whole blood. In other examples, the median $C_{max}$ is 80 ng/ml, or 123 ng ml, or 171 ng ml, or 321 ng/ml, or 480 ng/ml of blood.

In some examples, the therapeutic composition is formulated to release a dose of the direct factor IIa inhibitor sufficient to generate a plasma drug level area under the curve (AUC (0-24) or AUC (0-∞)) in ng·html which is smaller than a median (AUC (0-24) or AUC (0-∞) in ng·h/ml of the direct factor IIa inhibitor generated by systemic delivery of the direct factor IIa inhibitor to achieve the same tissue concentration at the injury site. In other examples, the therapeutic composition is formulated to release a dose of the direct factor IIa inhibitor sufficient to generate a plasma drug level area under the curve (AUC (0-24) or AUC (0-∞)) in ng·h/ml which is smaller than a median (AUC (0-24) or AUC (0-∞)) in ng·h/ml of the direct factor IIa inhibitor generated by systemic delivery of the direct factor IIa inhibitor when taking one or more oral dose of said factor IIa inhibitor. In some examples, the systemic delivery comprises a single oral dose, a daily oral dose, or a smallest oral dose of the direct factor IIa inhibitor. In some examples, the (AUC (0-24) or AUC (0-∞)) is measured using one of plasma blood, serum blood, or whole blood. In other examples, the median (AUC (0-24) or AUC (0-∞)) is 724 ng·h/ml, or 1437 ng/ml, or 2000 ng·h/ml, or 4000 ng·h/ml.

In some examples, local delivery of one or more of the active substances may reduce the time a patient needs to spend on oral medications and/or obviate the need for such medications entirely.

In some examples, the dose of each of the one or more active substances for optional systemic administration on a one-time basis or over a certain time period described herein (e.g., 6 hr, 12 hr, 1 day, 2 days, 3 days, 1 week, 2 weeks, 3 weeks, 1 month, etc.) independently is at least about 1, 5, 10, 20, 50, 100 or 500 mg, or at least about 1, 5 or 10 g. in further examples, the amount of each of the one or more active substances loaded in and/or on a temporary or non-temporary device, or the amount of each such agent released from the device, independently is at least about 1, 10, 50, 100 or 500 μg, or at least about 1, 5, 10 or 20 mg. In certain examples, the amount of each of the fibrin/thrombus formation-inhibiting or fibrin/thrombus dissolution-promoting agents) loaded in and/or on the device, or the amount of each such agent released from the device, independently is about 1 μg to about 20 mg, or about 10 μg to about 10 mg, or about 50 μg to about 5 mg, or about 100 μg to about 1 mg, or about 100 μg to about 500 μg, or about 500 μg to about 1 mg.

In further examples, the concentration of each of the one or more active substances released from a temporary or non-temporary device, and optionally administered systemically in addition to locally, in blood or tissue at the site of injury or at an area adjacent thereto, and/or in blood or tissue adjacent to the device, independently is at least about 0.001, 0.01, 0.1, 1, 10, 50, 100 or 500 nM, or at least about 1, 10, 50, 100, 500 or 1000 μM. In certain examples, the concentration of each of the fibrin/thrombus formation-inhibiting or fibrin/thrombus dissolution-promoting agent(s) released from a temporary or non-temporary device, and optionally administered systemically in addition to locally, in blood or tissue at the site of injury or at an urea adjacent thereto, and/or in blood or tissue adjacent to the device, independently is about 0.01 or 0.1 nM to about 1000 μM, or about 0.1 or 1 nM to about 500 µM, or about 1 or 10 nM to about 100 µM, or about 50 nM to about 50 µM, or about 10 or 100 nM to about 10 µM, or about 100 nM to about 1 µM, or about 1 µM to about 10 µM.

In still further examples, the concentration of each of the one or more active substances released from a temporary or non-temporary device, and optionally administered systemically in addition to locally, in tissue at the site of injury or at an area adjacent thereto, and/or in tissue adjacent to the device, independently is at least about 0.01, 0.1, 1, 10, 50, 100 or 500 ng/gm tissue, or at least about 1, 10, 50, 100, 500 or 1000 µg/gm tissue. In certain examples, the concentration of each of the fibrin/thrombus formation-inhibiting or fibrin/thrombus dissolution-promoting agent(s) released from a temporary or non-temporary device, and optionally administered systemically in addition to locally, in tissue at the site of injury or at an area adjacent thereto, and/or in tissue adjacent to the device, independently is about 0.01 or 0.1 ng/gm tissue to about 1000 µg/gm tissue, or about 0.1 or 1 ng/gm tissue to about 500 µg/gm tissue, or about 1 or 10 ng/gm tissue to about 100 µg/gm tissue, or about 50 ng/gm tissue to about 50 µg/gm tissue, or about 10 or 100 ng/gm tissue to about 10 µg/gm tissue, or about 100 ng/gm tissue to about 1 µg/gm tissue, or about 1 µg/gm tissue to about 10 µg/gm tissue.

In additional examples, the concentration of each of the one or more active substances released from a temporary or non-temporary device (that may or may not cause an injury to a tissue, surface, vessel/lumen wall or other body part), and optionally administered systemically in addition to locally, in blood or tissue at the site of injury or at an area adjacent thereto, and/or in blood or tissue adjacent to the device, independently is at least about 0.001, 0.01, 0.1, 1, 10, 50, 100 or 500 nM, or at least about 1, 10, 50 or 100 µM, within about 1 day, 12 hr, 6 hr, 3 hr, 2 hr, 1 hr, 30 min., 15 min., 5 min, or 1 min. before, during and/or within about 1 day, 12 hr, 6 hr, 3 hr, 2 hr, 1 hr, 30 min., 15 min., 5 min, or 1 min. after delivery or deployment of the device and/or the injury. In further examples, the concentration of each of the one or more active substances released from a temporary or non-temporary device (that may or may not cause an injury to a tissue, surface, vessel/lumen wall or other body pant), and optionally administered systemically in addition to locally, in tissue at the site of injury or at an area adjacent thereto, and/or in tissue adjacent to the device, independently is at least about 0.01, 0.1, 1, 10, 50, 100 or 500 ng/gm tissue, or at least about 1, 10, 50 or 100 µg/gm tissue, within about 1 day, 12 hr, 6 hr, 3 hr, 2 hr, 1 hr, 30 min., 15 min., 5 min, or 1 min. before, during and/or within about 1 day, 12 hr, 6 hr, 3 hr, 2 hr, 1 hr, 30 min., 15 min., 5 min, or 1 min. after delivery or deployment of the device and/or the injury.

In some examples, the dose of each of the one or more optional other kinds of bioactive agents (e.g., anti-proliferative agents, anti-inflammatory agents, etc.) for optional systemic administration on a one-time basis or over a certain time period described herein (e.g., 6 hr, 12 hr, 1 day, 2 days, 3 days, 1 week, 2 weeks, 3 weeks, 1 month, etc.) independently is at least about 1, 5, 10, 20, 50, 100 or 500 mg, or at least about 1, 5 or 10 g. In additional examples, the amount of each of the one or more optional other kinds of bioactive agents (e.g., anti-proliferative agents, anti-inflammatory agents, etc.) loaded in and/or on a temporary or non-temporary device, or the amount of each such agent released from the device, independently is at least about 1, 10, 50, 100 or 500 µg, or at least about 1, 5, 10 or 20 mg. In certain examples, the amount of each of the optional other kind(s) of bioactive agent(s) loaded in and/or on the device, or the amount of each such agent released from the device, independently is about 1 µg to about 20 mg, or about 10 µg to about 10 mg, or about 50 µg to about 5 mg, or about 100 µg to about 1 mg, or about 100 µg to about 500 µg, or about 500 µg to about 1 mg, or about 50 µg to about 200 µg.

In further examples, the concentration of each of the one or more optional other kinds of bioactive agents (e.g., anti-proliferative agents, anti-inflammatory agents, etc.) released from a temporary or non-temporary device, and optionally administered systemically in addition to locally, in tissue at the site of injury or at an area adjacent thereto, and/or in tissue adjacent to the device, independently is at least about 0.01, 0.1, 1, 10, 50, 100 or 500 ng/gm tissue, or at least about 1, 10, 50, 100, 500 or 1000 µg/gm tissue. In certain examples, the concentration of each of the optional other kind(s) of bioactive agent(s) released from a temporary or non-temporary device, and optionally administered systemically in addition to locally, in tissue at the site of injury or at an area adjacent thereto, and/or in tissue adjacent to the device, independently is about 0.01 or 0.1 ng/gm tissue to about 1000 µg/gm tissue, or about 0.1 or 1 ng/gm tissue to about 500 µg/gm tissue, or about 1 or 10 ng/gm tissue to about 100 µg/gm tissue, or about 50 ng/gm tissue to about 50 µg/gm tissue, or about 10 or 100 ng/gm tissue to about 10 µg/gm tissue, or about 100 ng/gm tissue to about 1 µg/gm tissue, or about 1 µg/gm tissue to about 10 µg/gm tissue.

In some examples, the patient receiving one or more active substances (e.g., anti-coagulants) has a condition or is susceptible to a condition that renders the subject more susceptible to a vaso-occlusive event. In further examples, the subject has vascular disease or is susceptible to vascular disease. In certain examples, the vascular disease is selected from the group consisting of arteriosclerosis, cardiovascular disease, cerebrovascular disease, peripheral vascular disease, renovascular disease, mesenteric vascular disease, pulmonary vascular disease, and ocular vascular disease.

In additional examples, the patient has a condition or is susceptible to a condition selected from the group consisting of hyperlipidemia, hypercholesterolemia, hypertension, atherosclerosis, and diabetes. In certain examples, the patient is diabetic.

In some examples, measurements of blood or tissue described herein comprise one or more of mammalian blood or tissue, porcine blood or tissue, human blood or tissue, rabbit blood or tissue, rat blood or tissue, mouse blood or tissue, or the like.

One or more bioactive substances or agents can be delivered from any suitable medical device as described herein. The device can be a temporary device (e.g., a balloon, a catheter, a needle, a surgical knife or other surgical tool, a patch, etc.) or a non-temporary device (e.g., an implant, such as a stem, a graft, etc.). In some examples, the device is selected from the group consisting of temporary devices, non-temporary devices (including permanent devices), access devices, infusion devices, tools, surgical instruments and tools, implants, bodily implants, organ implants, hip implants, shoulder implants, knee implants, lumina) implants, vascular implants, stem-delivery systems, stents (including vascular stents, coronary stents and peripheral stents), stent-grafts, catheters (including infusion catheters, diffusion catheters, balloon-catheters, weeping catheters, and electrode catheters), balloons, graft implants, grafts (including aortic grafts, arterio-venous grafts and by-pass grafts), aneurysm coils (including abdominal aortic aneurysm coils and cerebral aneurysm coils), valves (including artificial heart valves), valve implants, shunts (including axius coronary shunts and cerebrospinal fluid shunts), left atrial appendage implants, foramen implants, leads (including endocardial leads), closure devices (including arterial and patent foramen ovule closure devices), clips (including anastomotic clips), wound-closure devices and implants, sutures, patches, injection devices, needles inserted in the body of a subject, and needles insert al from outside the body.

Non-limiting examples of surgical instruments and tools include surgical knives and mechanical cutters (e.g., scalpels, lancets, drill bits, rasps, scissors); other cutting instruments (e.g., microtomes, dermatomes, cryotomes, cutting laser guides) and ultrasound tissue disruptors; graspers (e.g., forceps); clamps, occluders and compressors (e.g., hemostats) for organs and tubular structures (e.g., blood vessels and other lumens); sealing devices (e.g., surgical staplers, LigaSure™ tissue-fusion devices); dilators and specula; retractors (e.g., those used to spread open skin, ribs and other tissues and body parts) and tyndallers (e.g., those used to wedge open brain tissue and other tissues); needles, tips and tubes (e.g., trocars) for introducing or removing material (e.g., fluids); scopes and probes (e.g., endoscopes, tactile probes); distractors, positioners and stereotactic devices; powered devices (e.g., drills); carriers and appliers for optical, electronic and mechanical devices; and measurement devices (e.g., rulers, calipers).

In some examples, the device contains the bioactive agent(s) in the body and/or on at least one surface of the device. In certain examples, the bioactive agent(s) are contained in one or more layers in the body and or at the surface of the device.

In further examples, the bioactive agent(s) are contained in one or more coatings disposed over the body of the device. The coating(s) can be disposed over any desired portions) and any desired surface(s) of the body of the device. As a non-limiting example, for a tubular vascular device such as a stent, the coating(s) can be disposed over the lumina) (lumen-facing) surface, the abluminal (tissue-facing) surface or the side surface(s) of the stent, or a combination thereof (e.g., all surfaces of the stent).

In additional examples, the device comprises the bioactive agent(s) in the body of the device and in one or more coatings disposed over the body of the device.

A temporary or non-temporary device can comprise openings in and/or on the body (including at the surface) of the device, and or in one or more coatings disposed over the body structure of the device. Examples of openings include without limitation pores (including partial pores and through pores), holes (including partial holes and through holes), voids, recesses, pits, cavities, trenches, reservoirs and channels. In some examples, a temporary or non-temporary device contains one or more anti-coagulant, and optionally one or more other kinds of bioactive agents (e.g., anti-proliferative agents, anti-inflammatory agents, etc.) in openings in and/or on the body (including at the surface) of the device, and/or in one or more coatings disposed over the body of the device.

The device may comprise one or more coatings disposed over an exterior surface of a structure of the device, as described herein. In some embodiments, the coating(s) may comprise a homopolymer, a copolymer, a mixture of homopolymers, a mixture of copolymers, or a mixture of a homopolymer and a copolymer. In some examples, the coating(s) comprise a soft or hydrophilic, or a softer or more hydrophilic, polymeric material. In further examples, the coating(s) comprise a polymeric material and an additive (e.g., a monomer of the polymeric material) that softens the polymeric material.

In some examples, the device has a first coating that comprises a biodegradable or non degradable polymeric material, or one or more bioactive agents, or both a biodegradable or non degradable polymeric material and one or more bioactive agents. In further examples, the device has a second coating that comprises a biodegradable or non-degradable polymeric material, or one or more bioactive agents, or both a biodegradable or non-degradable polymeric material and one or more bioactive agents, wherein the second coating optionally is disposed over the first coating. In additional examples, the device has a third coating that comprises a biodegradable or non-degradable polymeric material, wherein the third coating is disposed over the first coating and/or the second coating. In some examples, the third coating serves as a top layer or coat or diffusion barrier that controls release of one or more bioactive agents from inner coatings) anchor the body of the device.

In some examples, a bioactive agent that is intended to have an earlier or shorter time of action can be contained in an outer coating, on a surface uncovered by a coating, and/or in the body of the device closer to the surface, and a bioactive agent that is intended to have a later or longer time of action can be contained in an inner coating, in a coating covered by a barrier coating, on a surface covered by a coating, and/or in the body of the device farther from the surface. In further examples, a bioactive agent that is intended to have an earlier or shorter time of action is contained on a surface of the device, or contained in a coating on the device or in a layer of the body of the device which comprises a faster-degrading polymeric material, and a bioactive agent that is intended to have a later or longer time of action is contained within the device, or contained in a coating on the device or in a layer of the body of the device which comprises a slower-degrading or non-degrading polymeric material. In additional examples, a bioactive agent that is intended to have an earlier or shorter time of action is more soluble, and a bioactive agent that is intended to have a later or longer time of action is less soluble.

In certain examples, the concentration of a bioactive agent [e.g., anti-coagulant, anti-proliferative, etc.] in a coating comprising a polymeric material is at least about 10%, 20%, 30%, 40%, 50% or 60% by weight relative to the weight of the bioactive agent and the polymeric material.

In timber examples, the thickness (e.g., average thickness) of each of the coatings) independently is no more than about 20, 15, 10, 5, 3 or 1 micron.

In some examples, the coating(s) may comprise carrier material. Non-limiting examples of carrier materials include biodegradable polymeric materials, non-degradable polymeric materials, and other matrix materials.

In some examples, the carrier material may be porous. In certain examples, the porosity of each of the coating(s) of the carrier material may be within a range of about 10 nm to about 10 μm.

In some examples, the carrier material may be biodegradable. In certain examples, the carrier material may have a depredation rate within a range of about 1 month to about 36 months.

In some examples, the weight compositional ratio of the carrier material to the therapeutic composition of one or more bioactive agents may be within a range of about 1:5 to 3:2.

Non-limiting examples of polymeric materials that can compose the carrier material include polyesters, polylactide, polyglycolide, poly(ε-caprolactone), polydioxanone, poly (hydroxyalkanoates), poly(L-lactide-co-D-lactide), poly(L- lactide-co-D,L-lactide), poly(D-lactide-co-D,L-lactide), poly(lactide-co-glycolide) (including 70:30 to 99:1 PLA-co-PGA, such as 85:15 PLA-co-PGA), poly(lactide-co-ε-caprolactone) (including 70:30 to 99:1 PLA-co-PCL, such as 90:10 PLA-co-PCL), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), and copolymers and combinations thereof; wherein lactide includes L-lactide. D-lactide and D,L-lactide. The polymeric material may comprise a material selected from a group of non-degradable polymeric materials consisting of polyacrylates, polymethacrylates, poly(n-butyl methacrylate), poly(hydroxyethylmethacrylate), polyamides, nylons, nylon 12. Dacron, Polyethylene terephthalate, polyethylene glycol), polyethylene oxide (PEO), polydimethylsiloxane, polyvinylpyrrolidone, ethylene-vinyl acetate, phosphorylcholine-containing polymers, poly(2-methacryloyloxyethylphosphorylcholine), poly(2-methacryloyloxyethylphosphorylcholine-co-butyl methacrylate), and copolymers and combinations thereof.

Non-limiting examples of biodegradable polymeric materials that can compose the body of the device, a layer of the body, or a coating include polyesters, poly(α-hydroxyacids), polylactide, polyglycolide, poly(ε-caprolactone), polydioxanone, poly(hydroxyalkanoates), poly(hydroxypropionates), poly(3-hydroxypropionate), poly(hydroxybutyrates), poly(3-hydroxybutyrate), poly(4-hydroxybutyrate), poly(hydroxypentanoates), poly(3-hydroxypentanoate), poly(hydroxyvalerates), poly(3-hydroxyvalerate), poly(4-hydroxyvalerate), poly(hydroxyoctanoates), poly(3-hydroxyoctanoate), polysalicylate/polysalicylic acid, polycarbonates, poly(trimethylene carbonate), polyethylene carbonate), poly(propylene carbonate), tyrosine-derived polycarbonates, L-tyrosine-derived polycarbonates, polyiminocarbonates, poly(DTH iminocarbonate), poly(bisphenol A iminocarbonate), poly(amino acids), poly(ethyl glutamate), poly(propylene fumarate), polyanhydrides, polyorthoesters, poly(DETOSU-1,6HD), poly(DETOSU-t-CDM), polyurethanes, polyphosphazenes, polyamides, nylons, nylon 12, polyoxyethylated castor oil, poly(ethylene glycol), polyethylene oxide (PEO), polyvinylpyrrolidone, poly(L-lactide-co-D-lactide), ethylene-vinyl acetate, poly (L-lactide-co-D,L-lactide), poly(D-lactide-co-D,L-lactide), poly(lactide-co-glycolide) (including 70:30 to 99:1 PLA-co-PGA, such as 85:15 PLA-co-PGA), poly(lactide-co-ε-caprolactone) (including 70:30 to 99:1 PLA-co-PCL, such as 90:10 PLA-co-PCL), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), poly(glycolide-co-ethylene carbonate), poly(lactide-co-propylene carbonate), poly(glycolide-co-propylene carbonate), poly(lactide-co-2-methyl-2-carboxyl-propylene carbonate), poly(glycolide-co-2-methyl-2-carboxyl-propylene carbonate), poly(lactide-co-hydroxybutyrate), poly(lactide-co-3-hydroxybutyrate), poly(lactide-co-4-hydroxybutyrate), poly(glycolide-co-hydroxybutyrate), poly (glycolide-co-3-hydroxybutyrate), poly(glycolide-co-4-hydroxybutyrate), poly(lactide-co-hydroxyvalerate), poly (lactide-co-3-hydroxyvalerate), poly(lactide-co-4-hydroxyvalerate), poly(glycolide-co-hydroxyvalerate), poly (glycolide-co-3-hydroxyvalerate), poly(glycolide-co-4-hydroxyvalerate), poly(3-hydroxybutyrate-co-4-hydroxybutyrate), poly(hydroxybutyrate-co-hydroxyvalerate), poly(3-hydroxybutyrate-co-3-hydroxyvalerate), poly(3-hydroxybutyrate-co-4-hydroxyvalerate), poly(4-hydroxybutyrate-co-3-hydroxyvalerate), poly(4-hydroxybutyrate-co-4-hydroxyvalerate), poly(ε-caprolactone-co-fumarate), poly (ε-caprolactone-co-propylene fumarate), poly(ester-co-ether, poly(lactide-co-ethylene glycol), poly(glycolide-co-ethylene glycol), poly(r-caprolactone-co-ethylene glycol), polyester-co-amide), poly(DETOSU-1,6HD-co-DETOSU-t-CDM), poly(lactide-co-cellulose ester), poly(lactide-co-cellulose acetate), poly(lactide-co-cellulose butyrate), poly (lactide-co-cellulose acetate butyrate), poly(lactide-co-cellulose propionate), poly glycolide-co-cellulose ester), poly(glycolide-co-cellulose acetate), poly(glycolide-co-cellulose butyrate), poly(glycolide-co-cellulose acetate butyrate), poly(glycolide-co-cellulose propionate), poly(lactide-co-glycolide-co-ε-caprolactone), poly(lactide-co-glycolide-co-trimethylene carbonate), poly(lactide-co-ε-caprolactone-co-trimethylene carbonate), poly(glycolide-co-ε-caprolactone-co-trimethylene carbonate), poly(3-hydroxybutyrate-co-3-hydroxyvalerate-co-4-hydroxybutyrate), poly(3-hydroxybutyrate-co-4-hydroxyvalerate-co-4-hydroxybutyrate), collagen, casein, polysaccharides, cellulose, cellulose esters, cellulose acetate, cellulose butyrate, cellulose acetate butyrate, cellulose propionate, chitin, chitosan, dextran, starch, modified starch, and copolymers and combinations thereof, wherein lactide includes L-lactide, D-lactide and D,L-lactide.

Examples of non-degradable polymeric materials that can compose the body of the device, a layer of the body, or a coating include without limitation polyacrylates, polymethacrylates, poly(n-butyl methacrylate), poly(hydroxyethylmethacrylate), poly(styrene-b-isobutylene-b-styrene), phosphorylcholine polymer, polyethylene-co-vinyl acetate), poly (n-butyl methacrylate), blend of thermoplastic Silicone-Polycarbonate-urethane with poly n-butyl methacrylate, poly(vinylidene-co-hexafluoropropylene), Blend of polyvinylpyrrolidone, poly(hexylmethacrylate)-co-polyvinylpyrrolidone-co-poly vinyl acetate, and poly(n-butyl methacrylate)-co-poly(vinyl acetate), Poly(styrene-butylene styrene), poly(tyrosine-derived polycarbonate), polyamides, nylons, nylon 12, polyethylene glycol), polyethylene oxide (PEO), polydimethylsiloxane, polyvinylpyrrolidone, ethylene-vinyl acetate, phosphorylcholine-containing polymers, poly(2-methacryloyloxyethylphosphorylcholine), poly(2-methacryloyloxyethylphosphorylcholine-co-butyl methacrylate), polyvinylpyridine block with poly methyl methacrylate (PMMA), poly N-(2-Hydroxypropyl) methacrylamide, Polyethylenimine (PEI), dextran, dextrin, chitosans, poly(L-lysine), and poly(aspartamides), polyamides, Polyethylene glycol (PEG), Silicones, poly(anhydride), poly ortho esters, polystyrene-b-polyvinylpyridine, poly(styrene)-poly(butadiene)-polyvinyl pyridine), poly(styrene-poly(methacrylic acid), poly(styrene)-poly(ethylene oxide), poly(vinyl pyridine)-poly(butadiene)-poly(vinyl pyridine), and poly(styrene)-polyvinyl pyridine-poly(ethylene oxide) and copolymers and/or combinations thereof.

Non-limiting examples of corrodible metals and metal alloys that can compose the body of the device, a layer of the body, or a coating include cast ductile irons (e.g., 80-55-06 grade cast ductile iron), corrodible steels (e.g., AISI 1010 steel, AISI 1015 steel, AISI 1430 steel, AISI 5140 steel and AISI 8620 steel), melt-fusible metal alloys, bismuth-tin alloys (e.g., 40% bismuth-60% tin and 58% bismuth-42% tin), bismuth-tin-indium alloys, magnesium, magnesium alloys, tungsten alloys, zinc alloys, shape-memory metal alloys, and superelastic metal alloys. Examples of non-corrodible metals and metal alloys that can compose the body of the device, a layer of the body, or a coating include without limitation stainless steels (e.g., 316L stainless steel), cobalt-chromium alloys (e.g., L-605 and MP35N cobalt-chromium alloys), gold, molybdenum-rhenium alloys, nickel-titanium alloys, palladium, platinum, platinum-iridium alloys, tantalum, and alloys thereof.

In some examples, the device is coated. The coating layer may comprise a therapeutic agent and an additive. In some examples, the coating layer overlying an exterior surface of the exterior surface of the medical device consists essentially of the therapeutic agent and the additive.

In some examples, the additive is selected from PEG (polyethylene glycol), polyalkylene oxide, e.g., polyethylene oxide, polypropylene oxide, or a copolymer thereof (e.g., a polyethylene oxide-polypropylene oxide-polyethylene oxide copolymers), polyphenylene oxide, copolymers of PEG and polyalkylene oxide, poly (methoxyethyl methacrylate benzoate), poly (a methacryloyloxy one phosphatidylcholine), perfluorinated polyether, dextran or poly vinylpyrrolidone, poly (ethylene-vinyl acetate), polypeptides, water soluble surfactants, water soluble vitamins, and proteins, PEG fatty esters and alcohols, glycerol fatty esters, sorbitan fatty esters, PEGylation (PEG-drug conjugation). PEG glyceryl fatty esters. PEG sorbitan fatty esters, sugar fatty esters, PEG sugar esters, vitamins and derivatives, amino acids, multi amino acids and derivatives, peptides, polypeptides, oligomers, copolymers, block polymers, proteins, albumin, quaternary ammonium salts such as but not limited to benzalkonium chloride, benzethonium chloride, docecyl trimethyl ammonium bromide, sodium docecylsulfates, dialkyl methylbenzyl ammonium chloride, dialkylesters of sodium sulfonsuccinic acid, organic acids, salts and anhydrides and combinations thereof.

In one example, the device is drug coated balloon. The balloon can optionally adopt carrier excipient to coat to facilitate drug transfer to the vessel wall and control release rate. A variety of carrier excipients are not limited to contrast agent (i.e. iopromide), urea, dextrane, shellac, shelloic acid, keratosis (a naturally derived protein), Plasticizer (i.e. butyryl-tri-hexyl citrate, acetyl tributyl citrate, citrate ester, glycerol, other organic ester), hydrophilic space, Polyvinylpyrrolidone (PVP) and its hydrogels, Surfactants, Non-ionic surfactant Polysorbate/sorbitol (i.e. Tween20, Tween60 or Tween80), nordihydroguaiaretic acid (NDGA), hydrophobic excipient such as phospholipid, amphiphilic polymer such as Poly(ethylene glycol) (i.e. PEG K000), poly(ethylene oxide) (PEO) (molecular weight range from 100,000 to 10,000,000), Polyethylenimine (PEI) or polyaziridine linear or branched, amphiphilic block co-polymers composed of polyethylene oxide) (PEO) as the hydrophilic block and poly(ether)s, poly(amino acid)s), hydrophobic polymer space, biodegradable polymers such as Poly DL lactide-co-glycolide, Poly L Lactide-co-caprolactone, durable polymers, individually or combinations thereof.

In one example, several anticoagulants delivered locally were tested in-vivo in an animal model including Heparin, Rivaroxaban (factor Xa inhibitor), and Argatroban (factor IIa inhibitor). It was an unexpected result that only Rivaroxaban was shown to inhibit fibrin formation at 7 days.

In another example, two formulations of Rivaroxaban were tested in a local delivery in-vivo animal model, wherein one formulation comprised a faster release dose release within 7 days versus control within 7 days. It was unexpected result that the composition comprising faster release dose released within 7 days was more effective than control, within 7 days. The composition comprising faster dose inhibited fibrin more effectively through 28 days compared to 7 days with the composition comprising a slower release dose.

A surprising finding was that composition comprising the fast release of Rivaroxaban in combination with m-TOR inhibitor released locally was more effective at inhibiting fibrin at 7 days and 28 days as compared to control while a slower release formulation of Rivaroxaban in combination with m-TOR inhibitor was less effective at inhibiting fibrin formation at 28 days from implant.

A surprising finding was that a composition comprising Rivaroxaban released locally in combination with m-TOR inhibitor inhibits fibrin formation after injury. Many attempts using heparin, and other anticoagulants have failed to show such effects when combined with m-TOR inhibitors.

A surprising finding was that a composition comprising Rivaroxaban released locally in combination with Argatroban inhibited fibrin formation after injury.

A surprising finding was that a composition comprising Rivaroxaban released locally in combination with Argatroban inhibited smooth muscle cell proliferation after injury.

A surprising finding was that a composition comprising Rivaroxaban released locally in combination with Argatroban and an m-TOR inhibitor further inhibited smooth muscle cell proliferation after injury.

In one example, a device for use in a body lumen is configured to release locally a composition comprising factor Xa inhibitor, preferably Rivaroxaban, Inure preferably Apixaban, wherein said device is configured to release at least 8914, preferably at least 150 μg (micro-grans) of said factor Xa inhibitor, within 3 hours, within 12 hours, within 1 day, within 3 days, or within 7 days from time of injury.

In another example, a device for use in a body lumen is configured to release locally a composition comprising factor Xa inhibitor, preferably Rivaroxaban, more preferably Apixaban, wherein said device is configured to release at least 6.36 μg per millimeter of device length, preferably release at least 10.7 μg per millimeter of device length, of said factor Xa inhibitor within 3 hours, within 12 hours, within 1 day, within 3 days, or within 7 days from time of injury.

In another example, a device for use in a body lumen is configured to release locally a composition comprising factor Xa inhibitor, preferably Rivaroxaban, more preferably Apixaban, wherein said device from time of injury to 3 hours, 12 hours, 1 day, 3 days, or to 7 days is configured to release 89 μg or more or 6.36 μg or more/mm of device length of said drug, preferably configured to release 150 μg or more or 10.7 μg/mm of device length or more of said drug.

It was surprisingly found extended release formulation comprising a factor IIa inhibitor and/or a factor Xa inhibitor, inhibited one or more of clot formation, SMC proliferation, inflammation, and injury, wherein the extended release of the one or more drugs extended beyond 7 days, extended beyond 14 days, extended beyond 21 days, extended beyond 28 days, or extended beyond 3 months.

In another example, a device for use in a body lumen is configured to release locally a factor Xa inhibitor, preferably Rivaroxaban, more preferably Apixaban, wherein said device from time of injury to 3 hours, 12 hours, 1 day, 3 days, or to 7 days is configured to release from 89 μg to 150 μg of said drug, or release from 6.36 μg/mm of device length to 10.7 μg/mm of device length of said drug.

In another example, a device for use in a body lumen is configured to release locally a factor Xa inhibitor, preferably Rivaroxaban, more preferably Apixaban, wherein said device from time of injury to 3 hours, 12 hours, 1 day, 3 days, or to 7 days is configured to release from 89 μg to 150 μg or more of said drug, or release from 6.36 μg/mm of device length to 10.7 μg or more/mm of device length of said drug.

In another example, a device for use in a body lumen is configured to release locally a factor Xa inhibitor, preferably Rivaroxaban, more preferably Apixaban, wherein said device from time of injury to 3 hours, 12 hours, 1 day, 3 days, or to 7 days is configured to release from 89 μg or more to 150 μg of said drug, or release from 6.36 μg or more mm of device length to 10.7 μg/mm of device length of said drug.

In another example, a device for use in a body lumen is configured to release locally a factor Xa inhibitor, preferably Rivaroxaban, more preferably Apixaban, wherein said device from time of injury to 3 hours, 12 hours, 1 day, 3 days, or to 7 days is configured to release from 89 μg or more to 500 μg of said drug, or release from 6.36 μg or more mm of device length to 40 μg/mm of device length of said drug.

In another example, a device for use in a body lumen is configured to release locally a factor Xa inhibitor, preferably Rivaroxaban, more preferably Apixaban, wherein said device from time of injury to 28 days is configured to release at least 92 μg of said drug, preferably release at least 150 μg of said drug, more preferably release at least 200 μg of said drug, most preferably release at least 250 μg of said drug.

In another example, a device for use in a body lumen is configured to release locally a factor Xa inhibitor, preferably Rivaroxaban, more preferably Apixaban, wherein said device from time of injury to 28 days is configured to release at least 6.6 μg or more/mm of device length, preferably release at least 10.7 μg/mm of device length of said drug, more preferably release at least 14.3 μg/mm of device length of said drug, most preferably release at least 17.86 μg/mm of device length of said drug.

In another example, a device for use in a body lumen is configured to release locally a factor Xa inhibitor, preferably Rivaroxaban, more preferably Apixaban, wherein said device from time of injury to 28 days is configured to release from 92 μg to 300 μg.

In another example, a device for use in a body lumen is configured to release locally a factor Xa inhibitor, preferably Rivaroxaban, more preferably Apixaban, wherein said device from time of injury to 28 days is configured to release from 92 μg or more to 500 μg of said drug, or release from 6.6 μg or more/mm of device length to 40 μg/mm of device length of said drug.

In another example, a device for use in a body lumen is configured to release locally a factor Xa inhibitor, preferably Rivaroxaban, more preferably Apixaban, wherein the tissue concentration in the device segment (stented segment) by or at 3 hours ranges from 3.9 ng/mg of tissue to 200 ng/mg of tissue, preferably ranges from 3.9 ng/mg of tissue to 150 ng/mg of tissue. In other examples, the tissue concentration at 3 hours is at least 3.9 ng/mg of tissue, preferably at least 25 ng/mg of tissue, more preferably at least 50 ng/mg of tissue, and most preferred at least 75 ng/mg of tissue.

In another example, a device for use in a body lumen is configured to release locally a factor Xa inhibitor, preferably Rivaroxaban, more preferably Apixaban, wherein the tissue concentration in the device segment (stented segment) by or at 3 hours, 12 hours, 1 day, 3 days, or 7 days ranges from 3.9 ng/mg of tissue to 200 ng/mg of tissue, preferably ranges from 3.9 ng/mg of tissue to 150 ng/mg of tissue. In other examples, the tissue concentration at 3 hours, 12 hours, 1 day, 3 days, or at 7 days have tissue concentration of at least 3.9 ng/mg of tissue, preferably at least 25 ng/mg of tissue, more preferably at least 50 ng/mg of tissue, and most preferred at least 75 ng/mg of tissue.

In another example, a device for use in a body lumen is configured to release locally a factor Xa inhibitor, preferably Rivaroxaban, more preferably Apixaban, wherein the tissue concentration in the device segment (stented segment) by or at 28 days range from 1.69 ng/mg of tissue to 10 ng/mg of tissue, preferably ranges from 3.9 ng/mg of tissue to 5 ng/mg of tissue. In other examples, the tissue concentration at 28 days have tissue concentration of at least 1.69 ng/mg of tissue, preferably at least 3.6 ng/mg of tissue, more preferably at least 3.9 ng/mg of tissue, and most preferred at least 5 ng/mg of tissue.

In another example of any of the examples, a timepoint such as 3 hours, 1 day, 7 days, or 28 days refer to one of from time of injury, from time of release of drug, from time of implant releasing device, or from time of end procedure.

In another example of any of the example, a device is configured to release locally a factor Xa inhibitor to one or more of injured tissue segment, tissue segment adjacent to the device, adjacent tissue segment to the injured tissue segment, ±5 mm adjacent tissue to the injured tissue segment, 5 mm proximal adjacent tissue to the injured tissue segment, 5 mm distal adjacent tissue to the injured tissue segment, the device surface, to a body lumen wall, to a body lumen, to the abluminal surface of the device, to the luminal surface of the device.

In another example of any of the examples, from time of injury comprises one or more of time from injury by device releasing drug, time from injury by another device before device releasing drug, time from injury by another device 5, 10, 15, or 30 minutes before device releasing.

In some examples, the device for use in a body lumen wherein said device is configured to release one or more of factor Xa inhibitor wherein the dose ranges from 100 micrograms to 1000 micrograms, preferably ranging from 150 micrograms to 500 micrograms, more preferably ranging from 1511 micrograms to 300 micrograms.

In another example, a device for use in a body lumen is configured to release locally a factor Xa inhibitor, preferably Rivaroxaban, more preferably Apixaban, wherein said device is configured to release one or more factor Xa inhibitors wherein the drug dose ranges from 7.14 μg/mm of device length to 71 μg/mm of device length, preferably ranges from 10.71 μg/mm of device length to 35.7 μg/mm of device length, more preferably ranges from 10.71 μg/mm of device length to 21.4 μg/mm of device length.

In some examples, the device releasing factor Xa, preferably releasing Rivaroxaban, more preferably releasing Apixaban, wherein the device is configured to release said drug at a rate ranging from 88.9% to 99.7% from time of injury to 3 hours, 12 hours, 1 day, 3 days, or 7 days.

In some examples, the device releasing factor Xa, preferably releasing Rivaroxaban, more preferably releasing Apixaban, wherein the device is configured to release said drug at a rate ranging from 92% to 99.7% from time of injury to 28 days.

In some examples, the device releasing factor Xa, preferably releasing Rivaroxaban, more preferably releasing Apixaban, wherein the device is configured to release said drug at a rate ranging from 92% to 100% from time of injury to 28 days.

In another example the factor Xa inhibitor drug release rate composed of release of 100% by 28 days, preferably ranging from 90% to 100%, more preferably ranging from 95% to 100% by 28 days.

In another example, a device for use in a body lumen comprising a factor Xa inhibitor drug, wherein the drug is Rivaroxaban, preferably Apixaban, and wherein the device has a drug dose and wherein the drug is released at a rate ranging from 50% to 90%, preferably ranging from 55% to 85%, more preferably ranging from 60% to 80% of the drug dose within 3 hours, 12 hours, or 3 days from time of injury.

In another example, a device for use in a body lumen comprising a factor Xa inhibitor drug, wherein the drug is Rivaroxaban, preferably Apixaban, and wherein the device has a drug dose and wherein the drug is released at a rate ranging from 70% to 100%, preferably ranging from 80% to 99%, more preferably ranging from 85% to 99% of the drug dose within 3 hours, 12 hours, or 3 days from time of injury.

In another example, a device for use in a body lumen comprising a factor Xa inhibitor drug, wherein the drug is Rivaroxaban, preferably Apixaban, and wherein the device has a drug dose and wherein the drug is released at a rate ranging from 88% to 100%, preferably ranging from 92% to 100%, more preferably ranging from 85% to 99% of the drug dose within 7 days from time of injury.

In another example, a device for use in a body lumen comprising a factor Xa inhibitor drug, wherein the drug is Rivaroxaban, preferably Apixaban, and wherein the device has a drug dose and wherein the drug is released at a rate ranging from 12.86 µg to 200 µg, preferably ranging from 15 µg to 150 µg, more preferably ranging from 20 µg to 150 µg within an hour, within 3 hours, within 12 hours, within 3 days, or within 7 days from time of injury.

In some examples, a device for use in a body lumen wherein said device is configured to release one or more of factor Xa inhibitors within 28 day or more from time of injury wherein said release within 28 days ranges from 100 to 1000 micrograms, preferably ranges from 150 to 600 micrograms, more preferably ranges from 150 to 300 micrograms.

In another example, a device for use in a body lumen wherein said device is configured to release beyond 28 days one or more of factor Xa inhibitors, preferably Rivaroxaban, more preferably Apixaban, wherein said release beyond 28 days from time of injury ranges from 0.1 micrograms to micrograms, preferably ranges from 1 microgram to 25 micrograms, more preferably ranges from 1 microgram to 5 microgram.

In another example, a factor Xa inhibitor, preferably Rivaroxaban, more preferably Apixaban released locally from a device after injury wherein said drug inhibits fibrin formation, thrombin formation, and/or clot formation.

In another example, a factor Xa inhibitor, preferably Rivaroxaban, more preferably Apixaban released locally from a device after injury wherein said drug inhibits fibrin formation thereby inhibiting clot formation.

In another example, a factor Xa inhibitor, preferably Rivaroxaban, more preferably Apixaban in combination with Argatroban released from a device locally after injury wherein said drug combination inhibits smooth muscle cell proliferation.

In another example, a factor Xa inhibitor, preferably Rivaroxaban, more preferably Apixaban in combination with Argatroban released locally from a device after injury wherein said drug combination inhibits fibrin formation thereby inhibiting clot formation.

In another example, a factor Xa inhibitor, preferably Rivaroxaban, more preferably Apixaban in combination with Argatroban released locally from a device after injury wherein said drug combination inhibits fibrin formation or clot formation.

In another example, a factor Xa inhibitor, preferably Rivaroxaban, more preferably Apixaban released from a device locally at a dose of at least 150 µg within 7 days from implant (or from vessel injury) to inhibit fibrin formation, or to inhibit clot formation.

In another example, a factor Xa inhibitor, preferably Rivaroxaban, more preferably Apixaban released locally from a device after injury wherein said drug is released at a dose of at least 1.8 µg/mm within 7 days from vessel injury to inhibit clot formation or fibrin formation.

In another example, a factor Xa inhibitor, preferably Rivaroxaban, more preferably Apixaban released locally from a device after injury wherein said device releases said drug at a dose of at least 10.7 µg/mm of stem length within 7 days from vessel injury inhibiting clot formation or fibrin formation.

In another example, a factor Xa inhibitor, preferably Rivaroxaban, more preferably Apixaban released locally from a device after injury wherein the drug dose of at least 150 µg, or of at least 1.8 µg/mm$^2$, or at least 10.7 µg/mm of device length, are released from the device at a release rate of about 99.6% within 7 days from time of injury to inhibit fibrin formation or clot formation.

In another example, a factor Xa inhibitor, preferably Rivaroxaban, more preferably Apixaban released locally from a device after injury wherein the drug is released at a release rate of at least 70.9% when combined with Argatroban at a release rate of at least 96.9% within 7 days from from time of injury to inhibit fibrin formation or clot formation.

In another example, a factor Xa inhibitor, preferably Rivaroxaban, more preferably Apixaban released locally from a device after injury wherein said drug is released from said device at a dose of at least 100 µg, or at a dose of at least 1.2 µg/mm$^2$, or at a dose of at least 7.14 µg/mm of stent length, and at a release rate of at least 70.9% within 7 days when combined with Argatroban released from a stent at a dose of at least 100 µg, or at a dose of at least 1.2 µg/mm$^2$, or at a dose of at least 7.14 prim of stent length, and at a release rate of at least 96.9% within 7 days from device implantation to inhibit clot formation.

In another example, a factor Xa inhibitor, preferably Rivaroxaban, more preferably Apixaban released locally from a balloon catheter wherein said drug is released from said device at a dose of at least 500 µg, or at a dose of at least 10 µg/mm$^2$, or at a dose of at least 10 µg/mm of balloon length, within 10 seconds to 5 minutes after expansion of the balloon to inhibit clot formation.

In another example, a factor Xa inhibitor, preferably Rivaroxaban, more preferably Apixaban released locally from a balloon catheter to inhibit clot formation after vessel injury.

In another example, a factor Xa inhibitor, preferably Rivaroxaban, more preferably Apixaban released locally in combination with Argatroban from a balloon catheter to inhibit clot formation after vessel injury.

In another example, a factor Xa inhibitor, preferably Rivaroxaban, more preferably Apixaban released locally in combination with Argatroban from a balloon catheter to inhibit smooth muscle proliferation after vessel injury.

In another example, a factor Xa inhibitor, preferably Rivaroxaban, more preferably Apixaban released locally in combination with Argatroban and an m-TOR inhibitor from a balloon catheter to inhibit smooth muscle proliferation after vessel injury and/or clot formation.

In another example, a factor Xa inhibitor, preferably Rivaroxaban, more preferably Apixaban released locally in combination with Argatroban from an implant to inhibit fibrin or clot formation.

In another example, a factor Xa inhibitor, preferably Rivaroxaban, more preferably Apixaban released locally in combination with Argatroban from an implant to inhibit fibrin, clot formation, and or smooth muscle cell proliferation.

In another example, a factor Xa inhibitor, preferably Rivaroxaban, more preferably Apixaban released locally by an implant to inhibit clot formation.

In one example, a device delivery one or more drugs locally, wherein locally comprises delivering said one or more drugs to one or more of site specific location, to a vessel wall, adjacent to a vessel wall, in a body lumen, to a body organ, within a body organ, to the device surface in a body lumen, to a tissue, or to an injured tissue.

In another example, a factor Xa inhibitor, preferably Rivaroxaban, more preferably Apixaban is released locally in combination with an m-TOR inhibitor to inhibit fibrin formation or clot formation, or to inhibit fibrin formation or clot formation through 7 days, or to inhibit fibrin formation or clot formation through 28 days.

In another example, a factor Xa inhibitor, preferably Rivaroxaban, more preferably Apixaban is released locally from a device releasing said drug in combination with an m-TOR inhibitor at a dose of at least 88.9 µg, or a dose of at least 1.2 µg/mm$^2$, or a dose of at least 7.14 µg/mm of device length, within 7 days from vessel injury (or from implantation) to inhibit fibrin or clot formation.

In another example, a factor Xa inhibitor, preferably Rivaroxaban, more preferably Apixaban is released locally in combination with an m-TOR inhibitor from a stent at a rate of at least 92.5% within 28 days and a dose of at least 92.5 µg, or a dose of at least 1.1 µg/mm$^2$, or a dose of at least 6.6 µg/mm of stent length, within said 28 days after vessel injury (or from implantation) to inhibit clot formation.

In another example, a factor Xa inhibitor, preferably Rivaroxaban, more preferably Apixaban is released locally in combination with an m-TOR inhibitor is released at a rate of at least 88.9% within 7 days and a dose of at least 88.9 µg, or a dose of at least 1.2 µg/mm$^2$, or a dose of at least 7.14 µg/mm of stent length, was released within said 7 days from vessel injury for from implantation), and at a release rate of at least 92.5% within 28 days and a dose of at least 92.5 µg, or a dose of at least 1.1 µg/mm$^2$, or a dose of at least 6.6 µg/mm of stent length, is released within said 28 days from vessel injury (or from implantation) to inhibit clot formation.

In another example, a factor Xa inhibitor, preferably Rivaroxaban, more preferably Apixaban is released locally in combination with an m-TOR inhibitor from a stent at a rate of at least 68.1 µg, or at rate of 0.84 µg/mm$^2$, or a rate of at least 4.86 µg/mm of stent length, within 7 days after implantation to inhibit clot formation.

In another example, a factor Xa inhibitor, preferably Rivaroxaban, more preferably Apixaban is released locally in combination with an m-TOR inhibitor wherein tissue concentration of the factor Xa ranges from at least 3.96 ng/mg of tissue adjacent to the stented segment to at least 15 ng/mg of tissue adjacent to the stented segment, within or at 7 days, or within or 28 days from implant (or tissue injury)

In one example, Argatroban in combination with Rivaroxaban or Apixaban are configured to be released from a device locally in a body lumen wherein said drugs have the same or different dose and wherein the argatroban is configured to be released at a rate ranging from 70% to 99% within 3 hours, 3 days, or within 7 days, preferably configured to be released at a rate ranging from 80% to 99% within said 3 hours, 3 days, or within 7 day period, while the rivaroxaban or Apixaban are configured to be released at a rate ranging from 50% to 99% within 3 hours, 3 days, or within 7 day period, preferably released at a rate ranging from 60% to 99% within 3 hours, 3 days, or within 7 days.

In another example, Argatroban in combination with Rivaroxaban or Apixaban are configured to be released from a device locally in a body lumen wherein said drugs each have a dose ranging from 50 µg to 500 µg, or each has a dose ranging from 1.1 µg/mm$^2$ to 10 µg/mm$^2$, or each has a dose ranging from 3 µg/mm to 30 µg/mm of stent length, and wherein the argatroban is configured to be released at a rate ranging from 70% to 99% within 3 hours, 3 days, or within 7 days, preferably configured to be released at a rate ranging from 80% to 99% within said 3 hours, 3 days, or within 7 day period, while the rivaroxaban or Apixaban are configured to be released at a rate ranging from 50% to 99% within 3 hours, 3 days, or within 7 day period, preferably released at a rate ranging from 60% to 99% within 3 hours, 3 days, or within 7 days. The two drugs may be configured to release at same or similar release rate or different release rates, the two agents may have the same dose or different dose. In another example, a third antiproliferative drug is configured to be released from the device in combination with Argatroban and Rivaroxaban or Apixaban, at similar dose and release rate or different dose and release rate. In a specific example, the anti-proliferative drug is sirolimus or its analogs (including deuterated analog), metabolites, or salts.

In one example, a device delivery one or more drugs locally, wherein locally comprises delivery of said one or more drugs to one or more of site specific location, adjacent to a vessel wall, to a vessel wall, in a body lumen, to the device surface in a body lumen, to a tissue, to an injured tissue, wherein the local concentration of the one or more dugs maybe higher than in the systemic concentration of the one or more drugs.

In a preferred example, a device releasing factor Xa inhibitor in a body lumen wherein said device inhibits fibrin formation thereby inhibiting clot formation.

In another unexpected finding that the combination of factor Xa inhibitor Apixaban and Argatroban combination was shown to enhance the SMC proliferation inhibition when released together with m-TOR inhibitor, sirolimus. Further finding showed Apixaban or rivaroxaban and Argatroban combination had synergistic effects, anti-fibrin formation, or anti clot formation effects that was better than either alone.

In an unexpected finding, composition comprising of a factor Xa inhibitor Apixaban, factor IIa inhibitor Argatroban, and the M-Tor inhibitor Sirolimus exhibited more efficacy at inhibiting one or more of the following at 28 days and/or 90 day time points: cell proliferation, inflammation, injury, fibrin formation inhibition, clot formation, and fibrin dissolution acceleration.

The composition comprising a combination of factor Xa inhibitor (Apixaban), a factor 11 inhibitor (argatroban) and an anti-proliferative (M-tor) were surprisingly more effective than an anti-proliferative (M-tor) alone.

It was surprisingly found extended release formulation comprising a factor IIa inhibitor and/or a factor Xa inhibitor, inhibited one or more of clot formation, SMC proliferation, inflammation, and injury, wherein the extended release of the one or more drugs extended beyond 7 days, extended beyond 14 days, extended beyond 21 days, extended beyond 28 days, or extended beyond 3 months.

In another example, a device for use in a body lumen wherein said device is configured to release locally an effective dose of factor Xa inhibitor, preferably Rivaroxaban, more preferably Apixaban, wherein said dose is sufficient to inhibit one or more of thrombin formation, fibrin formation, and clot formation. In another example the device is configured to release in addition to the factor Xa inhibitor, release a factor IIa inhibitor, preferably Argatroban, wherein said dose are sufficient to inhibit one or more of thrombin formation, fibrin formation, and clot formation. In another example the device is configured to release in addition to the factor Xa inhibitor, release a factor IIa inhibitor, preferably Argatroban, wherein said dose are sufficient to inhibit one or more of thrombin formation, fibrin formation, clot formation, and smooth muscle cell proliferation. In another example the device is configured to release in addition to the factor Xa inhibitor, release a factor IIa inhibitor, preferably Argatroban, and in addition release of an anti-proliferative, preferably sirolimus, analogs (including deuterated analogs), metabolite, or salts, wherein said dose are sufficient to inhibit one or more of thrombin formation, fibrin formation, clot formation, and smooth muscle cell proliferation.

In one example, a device comprising a stem wherein said stem being expandable from a crimped configuration to an expanded configuration, wherein said stent comprises one or more expandable circumferential rings wherein adjacent rings are joined (or connected by one or more links), wherein said one or more rings comprise struts joined by crown. In one example, the stein is balloon expandable. In another example, the stent is self-expandable. In yet another example, the stent is non degradable. In another example, the stent is degradable. In yet another example, the scent is metallic, polymeric, or a hybrid of both. In yet another example, the stent is formed from a shape memory alloy such as nitinol. In another example, the stent is formed from a tubular body, from a sheet, from 3D printing, or a bent wire. In another example, the stent has a helical back bone. In one example, the stem is coated with one or more coating. In another example, the coating comprises one or more polymeric material. In yet another example, the polymeric material is coated as a matrix formed by mixing said one or more factor Xa inhibitors drugs, the said polymeric material, and one or more solvents, and spraying said mixture onto one or more stent surfaces, preferably spraying said mixture onto all stent surfaces. In yet some examples, the mixture is sprayed onto one or more surfaces such us abluminal surface of the stent or luminal surface of the stmt. In yet another example, a polymeric material is coated as a top layer or coat wherein the drug is coated onto the stent first and then a top layer or coat is coated on top of said drug to control release of said drug. Alternatively, or in addition, a top layer or coat may be coated on top of a drug/polymer matrix to control release of the drug. In yet another example, the drug is coated directly onto one or more surfaces of the stent. In another example, the drug is contained in stem material. In yet another example, the drug is contained in a reservoir on or in the stent. In yet another example, the drug and/or coating are applied to the stent by spraying, dipping, printing, or other methods known in the art. In one example the one or more factor Xa inhibitors are released in combination with one or more factor IIa inhibitor agents. In another example the one or more factor Xa inhibitors are released in combination with one or more factor IIa inhibitor agents and in combination with one or more antiproliferative agents.

In another example, a device comprising a catheter wherein said catheter comprises an expandable member at a distal segment of the catheter, wherein said expandable member outer surface comprises one or more factor Xa inhibitor drugs. In one example, the one or more drugs are contained in a drug polymer matrix. In another example, the one or more drugs are contained under a top layer or coat. In yet another example, the one or more drugs are contained within a polymer, a microsphere, a nanosphere, a carrier, an excipient, a hydrogel, or other. In yet another example, the drug is contained inside the expandable member and is released through holes or other means through the expandable member. In a preferred example, the expandable member is an expandable balloon. The one or more drugs in this example are released by or more means comprising friction when the expandable member is expanded against a vessel wall or tissue, diffusion gradient, creation of a reservoir at the vessel wall or tissue site, release of the drug, or other. In one example the one or more factor Xa inhibitors are released in combination with one or more factor IIa inhibitor agents. In another example the one or more factor Xa inhibitors are released in combination with one or more factor IIa inhibitor agents, and in combination with one or more antiproliferative agents.

In another example, a device comprising a catheter wherein said catheter comprises holes in the distal segment of the catheter, preferably on the abluminal surface of the catheter, wherein one or more factor Xa inhibitor drugs are released or injected through said holes. In another example, the one or more factor Xa inhibitors are released or injected through the distal end of the catheter. In yet another example, the catheter comprises two or more expandable members to prevent the one or more drugs from escaping into the systemic circulation, and wherein the one or more agents are released or injected in the space between said two or more expandable members. In one example the one or more factor Xa inhibitors are released in combination with one or more factor IIa inhibitor agents. In another example the one or more factor Xa inhibitors are released in combination with one or more factor IIa inhibitor agents, and in combination with one or more antiproliferative agents.

In another example, a device comprising an implant configured to be implanted in a body lumen wherein said body lumen comprises one or more of a vessel, duct, foramen, heart, heart valve, atrium, ventricle, aorta, or other, wherein said implant is configured to release one or more factor Xa inhibitors, and optionally in combination with one or more factor IIa inhibitors. The one or more drugs are coated onto the device surface, within or onto a sleeve covering one or more of one surface, all surfaces, part of the devices or all of the device surfaces, or in a reservoir on or in the device. In one example the one or more factor Xa inhibitors are released in combination with one or more factor IIa inhibitor agents. In another example the one or more factor Xa inhibitors are released in combination with one or more factor IIa inhibitor agents, and in combination with one or more antiproliferative agents.

In another example, a factor IIa inhibitor, preferably argatroban, released locally from a device, wherein said agent is released at a rate, concentrations, dose, duration, as any of the examples given in this application. In a preferred example, argatroban is released from a device over a period ranging from 28 days to 1 year, preferably over a period ranging from 90 days to one year. In yet another preferred example, argatroban is released from a device wherein argatroban is contained in a therapeutic composition and wherein the therapeutic composition comprises a first fast release rate and a second slower release rate.

In yet another example, a factor Xa inhibitor, preferably Apixaban or Rivaroxaban, released locally from a device, wherein said agent is released at a rate, concentrations, dose, duration, as any of the examples given in this application. In a preferred example, argatroban is released from a device over a period ranging from 28 days to 1 year, preferably over a period ranging from 90 days to one year. In yet another preferred example, argatroban is released from a device wherein argatroban is contained in a therapeutic composition and wherein the therapeutic composition comprises a first fast release rate and a second slower release rate.

EXPERIMENTAL EXAMPLES

Example 1: Preparation of Anticoagulant (Rivaroxaban, Argatroban, and Dalteparin) Eluting Stents Poly(n-butyl methacrylate) polymer was dissolved into dichloromethane (tetrahydrofuran (THF) was used for Dalteparin) at room temperature and vortexed until the polymer had uniformly dissolved/dispersed. Rivaroxaban was dissolved into dichloromethane at room temperature and vortexed until the drug was uniformly dissolved: dispersed. Argatroban (and Argatroban in combination with Rivaroxaban) was dissolved in Methanol and dichloromethane and vortexed at room temperature until the drug was uniformly dispersed/dissolved. Dalteparin was dissolved in water and THF until fully dissolved.

Each polymer solution and each drug solution were combined together (rivaroxaban to poly(n-butyl methacrylate) by weight ratio was 6:1), (Argatroban to poly(n-butyl methacrylate) by weight ratio was 3:4), (Dalteparin to poly (n-butyl methacrylate) by weight ratio was 2:3), and (Rivaroxaban in combination with Argatroban to Poly (n-butyl methacrylate) weight ratio was 3:2:2) according to the target drug dose of 150 µg for each drug (and 100 µg each for the rivaroxaban and Argatroban combination).

A microprocessor-controlled ultrasonic sprayer was used to coat each of the stents' 14 mm length uniformly with each of the drug polymer matrix solutions. After coating, the stents were placed in a vacuum chamber to remove the solvent. The stents were then mounted on balloon catheters and crimped. The catheters were then inserted in coils and packaged. The pouches were sterilized. The bare metal control stents were the same as the other stents without a drug or polymer coating.

Example 2: In Vivo Testing of Drug Eluting Stent with Different Drugs

The drug eluting stent systems containing different anticoagulants prepared as described in Example 1 were evaluated at 3 hours, 6 hours, 1 day, 3 days, 6 days, 7 days, or 28 days following implantation in a porcine coronary artery model.

The porcine model was chosen as this model has been used extensively for stent and angioplasty studies resulting in a large volume of data on the vascular response properties and its correlation to human vascular response (Schwartz et al. Circulation. 2002; 106:1867 1873). The animals were housed and cared for in accordance with the Guide for the Care and Use of Laboratory Animals as established by the National Research Council.

After induction of anesthesia, the left or right femoral artery was accessed using standard techniques and an arterial sheath was introduced and advanced into the artery. Vessel angiography was performed under fluoroscopic guidance, a 7 Fr. guide catheter was inserted through the sheath and advanced to the appropriate location where intracoronary nitroglycerin was administered. An appropriate implantation segment of coronary artery was randomly selected and a 0.014" guidewire inserted. Quantitative Coronary Angiography (QCA) was performed to document the results. The appropriately-sited stent was advanced to the deployment site. The balloon was inflated at a steady rate to a pressure sufficient to achieve a balloon to artery ratio of approximately 1.1 to 1.0 but less than 1.2:1.

Follow up angiography was performed at the designated timepoint for each of the animals. Lute lumen loss (LLL) can be expressed as:

$$LLL = \text{Post-stent minimum lumen diameter} - \text{Final minimum lumen diameter}$$

The LLL is an indicator of the amount smooth muscle cell (SMC) proliferation or inhibition. It is used to measure efficacy between drugs for SMC proliferation inhibition. The smaller the LLL, the better the efficacy of the drug.

Stented portions of coronary arteries were embedded in methyl methacrylate (MMA), then divided into a target of at least three blocks of approximately similar lengths for histology evaluation. Quantitative histopathological evaluation of stented artery sections was then performed and scored as indicated. For Fibrin formation, scores ranged from 0 to 3, with a score of 0 indicating absent or rare minimal spotting around struts of the stent, a score of 1 indicating the presence of fibrin in small amounts localized only around the struts, a score of 2 indicating the moderately abundant or denser presence of fibrin around and extending beyond the struts, and a score of 3 indicating the presence of abundant and dense fibrin and/or bridging of the fibrin between the struts. The mean score was calculated and reported. The mean of each section was then averaged to provide a mean fibrin score per stem. The smaller the fibrin score, the better efficacy.

The percentage and/or amount of each anticoagulant drug for or by each time point indicated were analyzed for each stem from the different devices in the example and the average drug tissue concentration reported.

Tissue concentrations and the amount of drug released from the stents were measured using stents implanted in porcine arteries for the drugs as indicated. The arteries at the designated time point were excised and a length of stented artery spanning from 5 mm proximal to the stented segment to 5 mm distal to the stented segment was cut. The stented artery was cut longitudinally with surgical scissors. The stents were separated from the tissue. The tissue content of each drug was analyzed using liquid chromatography mass spectroscopy (LCMS) and reported as a mean for each of the timepoint indicated. For drug remaining on each stent, each drug was extracted from the stent, measurer using HPLC, and reported as a mean for each of the timepoint indicated as drug released or drug remaining on a stein (where drug remaining is equal to 100% minus the percentage of drug released).

TABLE 1

Histopathology Scores, Quantitative Coronary Angiography data and PK data of Rivaroxaban, Argatroban, and Dalteparin (low molecular weight heparin) released from 14 mm stents at day 7.

| Stent coating information (n = 3 for each arm) | Fibrin score at day 7 | Cumulative Percent Release of drug by day 7 | Tissue concentration at day 7 (ng/mg) | LLL at day 7 | Injury | Inflammation | Diameter Stenosis from Coronary (%) |
|---|---|---|---|---|---|---|---|
| 150 µg Rivaroxaban & 25 µg Poly(n-butyl methacrylate) matrix coated stent | 0.72 ± 0.12 | 99.6% | 3.9 ± 0.6 | 0.31 ± 0.20 | 0.03 ± 0.04 | 1.15 ± 0.34 | 11.4 ± 2.5 |
| 150 µg Argatroban & 200 µg Poly(n-butyl methacrylate) matrix coated stent | 1.25 ± 0.87 | 47.7% | 5.7 ± 1.8 | 0.34 ± 0.20 | 0.08 ± 0.08 | 0.81 ± 0.46 | 2.4 ± 2.3 |
| 100 µg Argatroban and 100 µg Rivaroxaban in 150 µg Poly(n-butyl methacrylate) matrix coated stent | 0.80 ± 0.39 | 70.9% for Rivaroxaban 96.5% for Argatroban | 48.1 ± 43.6 for rivaroxaban 8.9 ± 6.3 for Argatroban | 0.04 ± 0.06 | 0.06 ± 0.07 | 1.11 ± 0.35 | 0.5 ± 0.9 |
| 150 µg Dalteparin(low molecular weight heparin) in 225 µg Poly(n-butyl methacrylate) matrix coated stent | 1.50 ± 0.82 | 98.3% | Not tested | 0.23 ± 0.20 | 0.05 ± 0.06 | 0.65 ± 0.30 | 3.7 ± 5.2 |
| Bare metal control stent (BMS) | 1.02 ± 0.35 | N/A | N/A | 0.17 ± 0.22 | 0.05 ± 0.08 | 0.77 ± 0.45 | 3.3 ± 1.7 |

As shown in Table 1, Rivaroxaban composition released from stents was more effective at inhibiting fibrin formation compared to bare metal control stents at 7 days, while Argatroban composition released from stenos or Dalteparin composition released from stenos were not more effective at inhibiting fibrin formation compared to bare metal control stents at 7 days.

As shown in Table 1, Rivaroxaban, Argatroban, or Dalteparin compositions released from stems as single agents had larger LLLs compared to control and thus were not more effective at inhibiting smooth muscle cell proliferation computed to bare metal control stents at 7 days.

As shown in Table 1, the combination of Rivaroxaban and Argatroban composition released from stents had a smaller LLL compared to control and thus was more effective at inhibiting smooth muscle cell proliferation compared to bare metal control stents at 7 days. Furthermore, the combination of Rivaroxaban and Argatroban composition released from stents was more effective at inhibiting fibrin for nation compared to bare metal control stents.

As shown in Table 1, Rivaroxaban composition comprising fast released from stents at a dose of about 150 µg within 7 days from implant (or from vessel injury) was more effective at inhibiting fibrin formation at or within 7 days.

As shown in Table 1, Rivaroxaban composition comprising fast released from stents at a dose of about 1.8 µg/mm2 within 7 days from implant (or from vessel injury) was more effective at inhibiting fibrin formation at or within 7 days.

As shown in Table 1, Rivaroxaban composition comprising fast released from stents at a dose of about 10.7 µg/mm of stent length within 7 days from implant (or from vessel injury) was more effective at inhibiting fibrin formation.

As shown in Table 1. Rivaroxaban composition comprising a dose of about 150 µg, and/or of about 1.8 µg/mm$^2$, and/or of about 10.7 µg/mm of device length, released from a stents device at a release rate comprising of about 99.5% within 7 days from implant (or from time of injury) was more effective at inhibiting fibrin formation.

As shown in Table 1. Rivaroxaban composition released from stents at a release rate comprising of about 70.9% within 7 days when combined with Argatroban composition at a release rate comprising of about 96.9% within 7 days from implant (or from time of injury) was more effective at inhibiting fibrin formation.

Table 1 shows Rivaroxaban composition release from a stem at a dose of about 100 µg, or at a dose comprising of about 1.2 µg/mm$^2$, and/or at a dose of about 7.14 µg/mm of stent length, at a release rate comprising of about 70.9% within 7 days when combined with Argatroban composition released from a stent at a dose comprising of about 100 µg, and/or at a dose of about 1.2 µg/mm$^2$, and/or at a dose of about 7.14 µg/mm of stent length, at a release rate comprising of about 96.5% within 7 days from implant (or from time of injury) was more effective at inhibiting fibrin formation.

Example 3: Preparation of Rivaroxaban and m-TOR Inhibitor Releasing Stent

Base coat of Novolimus (m-TOR inhibitor) and Poly (n-butyl methacrylate) matrix: Poly(n-butyl methacrylate) polymer was dissolved into dichloromethane at room temperature and vortex until the polymer had uniformly dissolved/dispersed. Novolimus was placed in another vial and dissolved in dichloromethane at room temperature until uniformly dissolved or dispersed. The polymer solution and drug solutions were mixed together and coated as a matrix (the drug to polymer weight ratio was 2:3 by weight).

Top layer or coat of Rivaroxaban and poly (n-butyl methacrylate) matrix: Poly n-butyl methacrylate) polymer was dissolved in dichloromethane at room temperature and vortex until the polymer had uniformly dissolved/dispersed. Rivaroxaban was dissolved into dichloromethane at room temperature and vortex until the drug was uniformly dissolved/dispersed. Each polymer solution and each drug solutions were mixed together as a matrix (rivaroxaban to poly(n-butyl methacrylate) by weight ratio was 6:1 for the rivaroxaban fast formulation without m-TOR). Rivaroxaban to poly (n-butyl methacrylate) ratio was 4:1 for the fast release formulation with m-TOR base coat matrix, and 2:1 for the slow release formulation with m-TOR base coat matrix according to the target drug dose of 100 µg Rivaroxaban and 25 µg poly(n-butyl methacrylate) for fast release formulation, and 100 µg Rivaroxaban and 50 µg poly(n-butyl methacrylate) for the slow release formulation.

A microprocessor-controlled ultrasonic sprayer was used to coat each of the stents' 14 mm length uniformly with each of the drug/polymer matrix solution with the base coat matrix first, placing the stents in vacuum chamber to remove the solvent, followed by the top layer or coat matrix. The scents were placed in a vacuum chamber again to remove the solvents. The stents were then mounted on balloon catheters and crimped. The catheters were then inserted in coils and packaged. The pouches were sterilized. The Novolimus (m-TOR inhibitor) stents controls (DES) consisted of only the base coat drug/polymer matrix, without the top layer or coat drug/polymer matrix, otherwise being the same as the other stents. The bare metal control stents (BMS) were the same as the other stents without a drug or polymer coating.

TABLE 2

Histopathology Scores, Quantitative Coronary Angiography data and PK of Rivaroxaban releasing 14 mm stents at day 7 and at day 28.

| Time point | Stent coating information n = 5 for each arm for each time point | Fibrin score | Cumulative percent release of drug | Tissue concentration (ng/mg) | Late lumen loss(mm) | Injury score | Inflammation score | Diameter stenosis (%) |
|---|---|---|---|---|---|---|---|---|
| Day 7 (n = 5) | 25 µg Poly(n-butyl methacrylate) & 150 µg Rivaroxaban matrix | 0.79 ± 0.14 | 99.7% | 3.95 ± 1.57 | 0.26 ± 0.24 | 0.07 ± 0.05 | 1.19 ± 0.26 | 8.5 ± 5.2 |
| | 66 µg Novolimus (m-TOR inhibitor) and 100 µg Poly(n-butyl methacrylate) matrix as a base coat then 100 µg Rivaroxban and 25 µg Poly(n-butyl methacrylate) matrix as a top coat | 1.16 ± 0.60 | 88.9% | 6.18 ± 5.37 | 0.21 ± 0.26 | 0.17 ± 0.09 | 1.32 ± 0.22 | 5.5 ± 5.9 |
| | 66 µg Novolimus (m-TOR inhibitor) and 100 µg Poly(n-butyl methacrylate) matrix as a base coat then 100 µg Rivaroxban and 50 µg Poly(n-butylmethacrylate) matrix as a top coat | 1.18 ± 0.53 | 68.1% | 8.56 ± 3.56 | 0.23 ± 0.22 | 0.26 ± 0.19 | 1.48 ± 0.13 | 4.1 ± 3.6 |
| | 66 µg Novolimus (m-TOR inhibitor) and 100 µg Poly(n-butyl methacrylate) matrix (DES) control | 1.51 ± 0.71 | — | — | 0.13 ± 0.15 | 0.20 ± 0.13 | 1.32 ± 0.51 | 9.0 ± 7.3 |
| | Bare metal control (BMS) | 1.35 ± 0.41 | — | — | 0.05 ± 0.09 | 0.13 ± 0.07 | 1.22 ± 0.30 | 5.4 ± 3.4 |
| Day 28 (n = 5) | 25 µg Poly(n-butyl methacrylate) & 150 µg Rivaroxaban matrix | 0.07 ± 0.05 | 100% | 3.93 ± 2.43 | 0.62 ± 0.21 | 0.25 ± 0.16 | 0.73 ± 0.24 | 22.7 ± 8.7 |
| | 66 µg Novolimus (m-TOR inhibitor) and 100 µg Poly(n-butyl methacrylate) matrix as a base coat then 100 µg Rivaroxban and 25 µg Poly(n-butyl methacrylate) matrix as a top coat | 1.06 ± 0.46 | 92.5% | 14.61 ± 17.68 | 0.88 ± 0.96 | 0.68 ± 0.57 | 1.04 ± 0.70 | 38.9 ± 36.0 |
| | 66 µg Novolimus (m-TOR inhibitor) and 100 µg Poly(n-butyl methacrylate) matrix as a base coat then 100 µg Rivaroxban and 50 µg Poly(n-butyl methacrylate) matrix as a top coat | 1.49 ± 0.37 | 72.7% | 15.23 ± 8.12 | 0.84 ± 0.73 | 0.53 ± 0.58 | 0.72 ± 0.86 | 22.4 ± 20.8 |
| | 66 µg Novolimus (m-TOR inhibitor) and 100 µg Poly(n-butyl methacrylate) matrix (DES) control | 1.37 ± 0.44 | — | — | 0.88 ± 0.21 | 0.55 ± 0.33 | 0.79 ± 0.80 | 24.8 ± 13.9 |

As shown in Table 2, Rivaroxaban composition comprising fast released formulation from a stent was more effective at inhibiting fibrin formation compared to control at 7 days and/or at 28 days when it was released at a faster rate formulation.

As shown in Table 2, Rivaroxaban composition released from a stent was more effective at inhibiting fibrin formation compared to control at 7 days and/or at 28 days when it was released at a rate comprising of about 88.9% within 7 days and/or when a dose of about 88.9 μg, and/or a dose of about 1.2 μg mm$^2$, and/or a dose of about 7.14 μg/mm of stent length, was released within 7 days from vessel injury (or from implantation).

As shown in Table 2, Rivaroxaban formulation released from a stent was more effective at inhibiting fibrin formation compared to control at 7 days and/or at 28 days when it was released at a rate comprising of about 92.5% within 28 days and/or when a dose of about 92.5 μg, and/or a dose of about 1.1 μg/mm$^2$, or a dose of about 6.6 μg/mm of stem length, was released at or within 28 days from vessel injury (or from implantation).

As shown in Table 2, Rivaroxaban composition released from a stent was more effective at inhibiting fibrin, formation compared to control at 7 days and/or at 28 days when it was released at a rate comprising of 88.9% within 7 days and/or when a dose of 88.9 μg, and/or a dose of 1.2 μg/mm, and/or a dose of 7.14 μg/mm of stent length, was released within 7 days after vessel injury (or from implantation), and/or at a rate comprising of about 92.5% within 28 days and/or when a dose of about 92.5 μg, and/or a dose of about 1.1 μg/mm$^2$, and/or a dose of about 6.6 μg/mm of stem length, was released within 28 days after vessel injury (or from implantation).

As shown in Table 2, Rivaroxaban composition released in combination with an m-TOR inhibitor from a stent was more effective at inhibiting fibrin formation compared to control at 7 days and/or at 28 days when it was released in a faster formulation rate in accordance with the experiment.

As shown in Table 2, Rivaroxaban composition released in combination with an m-TOR formulation inhibitor from a stent was more effective at inhibiting fibrin formation compared to control at 7 days and/or at 28 days when Rivaroxaban composition was released at a rate comprising of about 88.9 μg, or a dose of about 1.2 μg/mm$^2$, or a dose of about 7.14 μg/mm of stent length, within 7 days, and/or released at a rate comprising of about 92.5 μg, and/or a dose of about 1.1 μg/mm$^2$, and/or a dose of about 6.6 μg/mm of stent length, within 28 days.

As shown in Table 2. Rivaroxaban composition released in combination with an m-TOR inhibitor formulation from a stent was more effective at inhibiting fibrin formation compared to control at 7 days when Rivaroxaban composition was released at a rate comprising of about 68.1 μg, or at rate comprising of 0.84 μg/mm$^2$, and/or at a rate comprising of about 4.86 μg/mm of stent length, within 7 days.

As shown in Table 2, Rivaroxaban tissue concentration ranges from at least 3.96 ng/mg of tissue adjacent to the stented segment to at least 15 ng/mg of tissue adjacent to the stented segment, within or at 7 days, or within or 28 days from implant (or tissue injury)

It was reported that Rivaroxaban IC$_{50}$ for factor Xa inhibition to be about 21 nM or 0.0092 ng/mg. As shown in Table 2, the tissue concentration for Rivaroxaban was at least 426 times Rivaroxaban IC 50 tar factor Xa inhibition.

TABLE 3

Tissue concentration of Rivaroxaban and Argatroban at 7 days show multiple folds higher (or times higher) than IC50 for Anti-factor Xa/IIa and antiplatelet for the respective drugs.

| | Rivaroxaban* | | Argatroban** | |
| --- | --- | --- | --- | --- |
| Stent coated with combination of Rivaroxaban and Argatroban | Tissue concentration at day 7 in folds higher than IC50 of anti-Factor Xa | Tissue concentration at day 7 in folds higher than IC50 of anti-platelet | Tissue concentration at day 7 in folds higher than IC50 of anti-Factor IIa | Tissue concentration at day 7 in folds higher than IC50 of anti-platelet |
| 100 μg Argatroban and 100 μg Rivaroxaban in Poly(n-butyl methacrylate) matrix | 5253 | 354 | 835 | 1223 |

*Rivaroxaban IC50 for Anti-Factor Xa is 21 nM or 0.00916 ng/mg
*Rivaroxaban IC50 for Tissue factor generated antiplatelet is 312 nM or 0.136 ng/mg
**Argatroban IC50 for Anti-Factor IIa is 21 nM or 0.0107 ng/mg
**Argatroban IC50 for Tissue factor generated antiplatelet is 79 nM or 0.04 ng/mg

*Rivaroxaban IC50 for Anti-Factor Xa is 21 nM or 0.00916 ng/mg
*Rivaroxaban IC50 for Tissue factor generated antiplatelet is 312 nM or 0.136 ng/mg
**Argatroban IC50 for Anti-Factor IIa is 21 nM or 0.0107 ng/mg
**Argatroban 1050 for Tissue factor generated antiplatelet is 79 nM or 0.04 ng/mg Table 3 shows the tissue PK data for Rivaroxaban and Argatroban at or by or within 7 days from implants of stented vessels. It shows Rivaroxaban and Argatroban has therapeutic tissue concentrations in the tissue segment up to 7 days. Table 0.3 is Rivaroxaban and Argatroban concentration (ng/mg) in the tissue of treated area of the implanted device fold higher than ICS) for anti-Factor Xa or Anti-Factor IIa and anti-platelet. It shows that Rivaroxaban and Argatroban in tissue concentrations have several order of magnitudes, has from 2 to 4 orders of magnitude of tissue concentration for each of the drugs compared to their in the treated tissue segments up to 7 days, therefore inhibiting or enhancing dissolution of one or more of cell proliferation, fibrin formation, or clot formation on the device surfaces, the stented segment tissue, and or the tissue adjacent to the stented segment.

Example 4: Preparation of Anticoagulant/Anticoagulant2/mTOR Eluting Stents

Poly(L-lactide acid-co-glycolic acid) polymer was dissolved into dichloromethane at room temperature and vortex until the polymer had uniformly dissolved/dispersed. Sirolimus and anticoagulants (Apixaban or Rivaroxaban and Argatroban) were placed in a vial and dissolved in dichloromethane or dichlormethane/Methanol at room temperature and vortex until all the drug was uniformly dissolved/dispersed.

Each polymer solution and each drug (or combined drugs) solutions were combined together (SS7 arm anticoagulant (Apixaban to Argatroban was 1:1) to poly(L-lactide acid-co-glycolic acid) matrix by weight ratio was 3:1 as a base coat and Siroliums to poly(L-lactide acid-co-glycolic acid) matrix by weight ratio was 2:3 and coated as a top coat), (SS9 arm Siroliums and anticoagulant Apixaban and Argatroban was (1:1:1) to poly(L-lactide acid-co-glycolic acid) by weight ratio was 5:2 on matrix), (SS15 arm Sirolimus and Apixaban and Argatroban were combined in a ratio of (1:1:1) with poly(L-lactide acid-co-glycolic acid) by weight ratio which was (1:2) (by weight of 23 µg Sirolimus, 23 µg Apixaban and 23 µg Argatroban combined with 138 µg poly(L-lactide acid-co-glycolic acid)) and mixed together, and coated as a base coat (drug, polymer matrix as a base coat). In addition, Sirolimus and Apixaban and Argatroban were combined in the ratio of (3:4:4) with poly(L-lactide acid-co-glycolic acid) by weight ratio which was (5:3) and coated as a top layer or coat (drug/polymer matrix top layer or coat), (by weight of 71 µg Sirolimus, 94 µg Apixaban and 94 µg Argatroban and combined with 155 µg poly(L-lactide acid-co-glycolic acid) and coated as a top layer or coat, for cumulative total target drug dose of 117 µg for each anticoagulant and 94 µg for Sirolimus for a 14 mm stent length, (Slider II Arm1 (SS16) Sirolimus and Rivaroxaban and Argatroban were combined together in the ratio of (1:1:1) and were combined with poly(L-lactide acid-co-glycolic acid) by weight ratio which was (1:2) and coated as a base coat (drug/polymer matrix as base coat). In addition, Sirolimus and Rivaroxaban and Argatroban were combined in the ratio of (3:4:4) and combined with poly(L-lactide acid-co-glycolic acid) by weight ratio was (5:3) and coated as a top layer or coat (drug/polymer matrix as top layer or coat), (by weight of 23 µg Sirolimus, 23 µg Rivaroxaban and 23 µg Argatroban and 138 µg poly(L-lactide acid-co-glycolic acid) mixed together and coated as base coat; and by weight of 71 µg Sirolimus, 94 µg Rivaroxaban and 94 µg Argatroban and 155 µg poly(L-lactide acid-co-glycolic acid) mix together in a matrix and coated as top layer or coat, for a total target drug dose of 117 µg for each anticoagulant and 94 µg for Sirolimus for a 14 mm stent length, (Slider 11 Arm2 (SS17) Sirolimus and Rivaroxaban and Argatroban were combined in a ratio of (4:1:1) and combined with poly(L-lactide acid-co-glycolic acid) by weight ratio which was (1:1) and coated as a base coat (drug/polymer matrix as base coat). In addition. Rivaroxaban and Argatroban were combined in a ratio of (1:1) and combined with poly(L-lactide acid-co-glycolic acid) by weight ratio which was (5:3) and coated as a top layer or coat on the stent (drug/polymer matrix us a top layer or coat), (by weight of 94 µg Sirolimus, 23 µg Rivaroxaban and 23 µg Argatroban and 140 µg poly(L-lactide acid-co-glycolic acid) mixed together and coated as base coat; and by weight of 94 µg Rivaroxaban and 94 µg Argatroban and 113 µg poly(L-lactide acid-co-glycolic acid) were mixed together and coated as top layer or coat, for a total target drug dose of 117µg for each anticoagulant and 94 µg for Sirolimus for a 14 mm stent length. The preceding doses for SS7, SS9, SS15, SS16, and SS17 were for 14 mm stent lengths. Drug and polymer doses are adjusted accordingly for each stent length. Control was 14 mm stent length eluting 65 µg Novolimus (m-TOR inhibitor). A microprocessor controlled ultrasonic sprayer was used to coat each of the stents' 14 mm length uniformly with each of the drug/polymer matrix solution. After coating, the stents were placed in a 70° C. oven for about 2 hours to remove the solvent. The stents wore then mounted on balloon catheters and crimped. The catheters were then inserted in coils and packaged. The pouches were sterilized.

The following tables 4A-4K describe results from in vivo testing for the following arms of SS7, SS9, SS15, SS16, and SS17 from example 4.

TABLE 4A

In-vivo cumulative percent drug release profile of Rapamycin, Apixaban/Rivaroxaban and Argatroban in stented segments.

| Sample Matrix | Sample Size | Time period | 1 H | 3 H | 24 H | 6 D | 7 D | 28 D | 90 D |
|---|---|---|---|---|---|---|---|---|---|
| SS7 Argatroban/ Apixaban/ Sirolimus | n = 1 | Apixaban, % Argatroban, % Sirolimus, % | N/A N/A N/A | 30 91 50 | 91 99 70 | 98 98 69 | 99 99 73 | 99 99 77 | N/A N/A N/A |
| SS9 Argatroban/ Apixaban/ Sirolimus | n = 1 | Apixaban, % Argatroban, % Sirolimus, % | N/A N/A N/A | 68 79 60 | 97 98 91 | 98 98 93 | 98 98 94 | 99 99 97 | N/A N/A N/A |
| SS15 Argatroban/ Apixaban/ Sirolimus | n = 5 | Apixaban, % Argatroban, % Sirolimus, % | 49 51 44 | 61 63 55 | 77 77 71 | N/A N/A N/A | 80 80 81 | 84 (n = 3) 84 (n = 3) 90 (n = 3) | 87 (n = 3) 86 (n = 3) 97 (n = 3) |
| SS16 Argatroban/ Rivaroxaban/ Sirolimus | n = 5 | Rivaroxaban, % Argatroban, % Sirolimus, % | 36 35 29 | 47 49 44 | 83 82 73 | N/A N/A N/A | 86 85 87 | 89 87 94 | N/A N/A N/A |
| SS17 Argatroban/ Rivaroxaban/ Sirolimus | n = 5 | Rivaroxaban, % Argatroban, % Sirolimus, % | 65 78 8 | 71 80 18 | 86 86 63 | N/A N/A N/A | 92 91 77 | 94 93 87 | N/A N/A N/A |

N/A: Not available

Table 4A: SS7 and SS9 provide a therapeutic composition where about 90% of the factor Xa and factor IIa inhibitors are released from the stent within 24 hours. It also shows that these agents are released substantially completely within about 28 days.

Table 4A: SS15, SS16, and SS17 provide therapeutic compositions where each composition providing a bolus drug release from time of injury and/or implant, and an extended drug release from time of injury and/or implant for each of Apixaban, Rivaroxaban, and Argatroban.

Table 4A: SS15 provides a therapeutic composition providing a bolus drug release phase (or formulation) from time of injury and/or implant and an extended drug release phase (or formulation) from time of injury and/or implant for the combination of Apixaban and Argatroban, wherein the bolus drug release occurs within an hour, within 3 hours, or within 24 hours, from tune of injury and/or implant; and the extended drug release extends beyond 7 day, extends beyond 28 days, or extends beyond 90 days from time of injury and/or implant.

Table 4A: SS15 provides a therapeutic composition a bolus drug release phase (or formulation) from time of injury and/or implant and an extended drug release phase (or formulation) from time of injury and/or implant for the combination of Apixaban. Argatroban, and Sirolimus, wherein the bolus drug release occurs within an hour to within 24 hours from time of injury and/or implant and the extended drug release extends beyond 7 day, extends beyond 28 days, or extends beyond 90 days from time of injury and/or implant.

Table 4A: SS15 provides a therapeutic composition providing a bolus drug release phase (or formulation) from time of injury and/or implant and an extended drug release phase (or formulation) from time of injury and/or implant for the combination of Apixaban and Argatroban, wherein the bolus drug release occurs within an hour from time of injury and/or implant and wherein Apixaban bolus release is about 49% within an hour and wherein Argatroban bolus release is about 51% within an hour and the extended drug release of each of the drugs is about 80% within 7 days, about 84% within 28 days, and about 86% within 90 days from time of injury and/or implant. In this arm, the drugs are released or commence release substantially about the same time.

Table 4A: SS16 and SS17 provide therapeutic composition providing a bolus drug release phase (or formulation) from time of injury and/or implant and an extended drug release phase (or formulation) from time of injury and/or implant for the combination of Rivaroxaban and Argatroban, wherein the bolus drug release occurs within an hour to within 24 hours from time of injury and/or implant and the extended drug release extends beyond 7 day, or extends beyond 28 days from time of injury and/or implant.

Table 4A: SS16 provides a therapeutic composition providing a bolus drug release phase (or formulation) from time of injury and/or implant and an extended drug release phase (formulation) from time of injury and/or implant for the combination of Rivaroxaban. Argatroban, and Sirolimus, wherein the bolus drug release occurs within un hour to within 24 hours from time of injury and/or implant and the extended drug release extends beyond 7 day, or extends beyond 28 days from time of injury and/or implant. In this arm, the drugs are released or commence release substantially about the same time.

Table 4A: SS16 and SS17 provide therapeutic compositions providing a bolus drug release phase (or formulation) from time of injury and or implant and an extended drug release phase (or formulation) from time of injury and/or implant for the combination of Rivaroxaban and Argatroban, wherein the bolus drug release occurs within an hour to within 24 hours from time of injury and/or implant and wherein Rivaroxaban bolus release ranges from 36% to 68% within an hour and wherein Argatroban bolus release ranges from 35% to 78% within an hour and the extended drug release of each of the drugs ranges from 85% to 92% for Rivaroxaban within 7 days, 86%-91% for Argatroban within 7 days, ranges from 89%-94% within 28 days for Rivaroxaban and 87%-93% for Argatroban from time of injury and/or implant to within 28 days.

Table 4A: SS16 and SS17 formulations each has one formulation providing a bolus drug release and another formulation providing an extended drug release for the combination of Rivaroxaban and Argatroban, wherein the bolus drug release occurs within an hour to within 24 hours of injury or implantation and the extended drug release extends beyond 7 day, or extends beyond 28 days.

Table 4A: SS16 and SS17 shows multiple formulations providing a bolus drug release formulation and an extended drug release formulation for the combination of each of Rivaroxaban and Argatroban, wherein the extended release extends beyond 7 day, or extends beyond 28 days.

Table 4A: SS15, SS16, and SS17 Provides therapeutic compositions comprising two drugs/polymer formulations each, wherein each formulation contains at least two drugs: a factor Xa inhibitor and a factor IIA inhibitor. A third drug being an M-tor inhibitor is present in each of the formulations except in SS17 where it is present in only one formulation (base formulation) configured to delay the release of M-tor in SS17 providing a smaller bolus within the first hour for M-tor. Ali formulations provide an extended release of the drugs beyond 7 days, or beyond 28 days. Arm SS17 factor IIa inhibitor and factor Xa inhibitor commence release prior to the anti-proliferative which was intended/configured to delay commence of its release compared to the other two drugs.

TABLE 4B

Tissue drug concentration (ng/mg) of Apixaban, Rivaroxaban, Argatroban and Rapamycin in the stented segment tissue at the indicated time points following implantation.

| Sample | Sample Size | Time period | 1 H | 3 H | 24 H | 6 D | 7 D | 28 D | 90 D |
|---|---|---|---|---|---|---|---|---|---|
| SS7 | n = 1 | Apixaban | N/A | 102.9 | 16.5 | 0.07 | 0.03 | 0.12 | N/A |
| Argatroban/ | | Argatroban | N/A | 54 | 0.75 | 0.09 | 0.05 | 0.15 | N/A |
| Apixaban/ | | Sirolimus | N/A | 7.34 | 4.46 | 1.38 | 0.73 | 1.79 | N/A |
| Sirolimus | | | | | | | | | |
| SS9 | n = 1 | Apixaban | N/A | 91.8 | 4.17 | 0.28 | 2.65 | 1.69 | N/A |
| Argatroban/ | | Argatroban | N/A | 123.1 | 0.18 | 0.33 | 2.54 | 1.76 | N/A |
| Apixaban/ | | Sirolimus | N/A | 40.57 | 0.93 | 1.61 | 3.24 | 2.48 | N/A |

TABLE 4B-continued

Tissue drug concentration (ng/mg) of Apixaban, Rivaroxaban, Argatroban and Rapamycin in the stented segment tissue at the indicated time points following implantation.

| Sample Matrix | Sample Size | Time period | 1 H | 3 H | 24 H | 6 D | 7 D | 28 D | 90 D |
|---|---|---|---|---|---|---|---|---|---|
| Sirolimus SS15 Argatroban/ Apixaban/ Sirolimus | n = 5 | Apixaban | 66.94 ± 27.33 | 25.31 ± 11.21 | 13.25 ± 10.17 | NA | 1.15 ± 0.52 | 1.28 ± 0.47 (n = 3) | 3.05 ± 1.77 (n = 3) |
| | | Argatroban | 71.37 ± 31.32 | 27.65 ± 15.00 | 15.64 ± 12.08 | NA NA | 1.41 ± 0.69 | 1.69 ± 0.64 (n = 3) | 3.74 ± 1.89 (n = 3) |
| | | Sirolimus | 43.22 ± 14.73 | 23.37 ± 6.88 | 29.17 ± 18.65 | | 1.54 ± 0.35 | 1.67 ± 0.22 (n = 3) | 1.28 ± 0.07 (n = 3) |
| SS16 Argatroban/ Rivaroxaban/ Sirolimus | n = 5 | Rivaroxaban | 48.75 ± 25.52 | 21.48 ± 5.80 | 3.67 ± 5.59 | N/A | 0.31 ± 0.24 | 0.34 ± 0.27 | N/A |
| | | Argatroban | 61.87 ± 24.60 | 32.81 ± 10.96 | 3.80 ± 4.87 | N/A | 0.42 ± 0.32 | 0.52 ± 0.37 | N/A |
| | | Sirolimus | 45.10 ± 14.77 | 38.30 ± 9.29 | 9.18 ± 5.69 | N/A | 1.46 ± 0.38 | 0.94 ± 0.19 | N/A |
| SS17 Argatroban/ Rivaroxaban/ Sirolimus | n = 5 | Rivaroxaban | 38.31 ± 16.08 | 26.23 ± 23.50 | 1.31 ± 0.28 | N/A | 1.07 ± 1.88 | 0.52 ± 0.63 | N/A |
| | | Argatroban | 11.80 ± 2.69 | 8.06 ± 3.48 | 1.19 ± 0.46 | N/A | 1.35 ± 2.41 | 0.67 ± 0.87 | N/A |
| | | Sirolimus | 21.34 ± 7.51 | 27.32 ± 6.86 | 10.85 ± 3.55 | N/A | 3.80 ± 4.86 | 1.73 ± 1.52 | N/A |

Table 4B shows drug concentration in tissue adjacent to the stented segment for each of the drugs: Apixaban of about 67 ng/mg within one hour, of about 25 ng/mg tissue within 3 hours, of about 1.15 ng/mg tissue within 7 days, 1.28 ng/mg tissue within 28 days, and of about 3 ng/mg tissue within 90 days from time of injury and/or implant; Rivaroxaban of about 38 ng/mg, or of about 49 ng/mg within one hour, of about 21 ng/mg, or of about 26 ng/mg tissue within 3 hours, of about 0.3 ng/mg, or of about 1.1 ng/mg tissue within 7 days, of about 0.34 ng/mg, or of about 0.52 ng/mg tissue within 28 days, from time of injury and/or implant; Argatroban of about 12 ng/mg, of about 62 ng/mg tissue, or of about 71 ng/mg tissue within 1 hour, of about 8 ng/mg tissue, of about 33 ng/mg tissue, or of about 27 ng/mg tissue within 3 hours, of about 0.42 ng/mg tissue, of about 1.35 ng/mg tissue, or of about 1.41 ng/mg tissue within 7 days, of about 0.52 ng/mg tissue, of about 0.67 ng/mg tissue, or of about 1.69 ng/mg tissue within 28 days, and of about 3.74 ng/mg tissue within 90 days from time of injury and or implant; and Sirolimus of about 21 ng/mg tissue, of about 45 ng/mg tissue, or of about 43 ng/mg tissue within one hour, of about 27 ng/mg tissue, or about 38 ng/mg tissue, or of about 24 ng/mg tissue within 3 hours, of about 1.46 ng/mg tissue, of about 3.8 ng/mg tissue, or of about 1.54 ng/mg tissue within 7 days, of about 0.94 ng/mg tissue, of about 1.73 ng/mg tissue, or of about 1.67 ng/mg tissue within 28 days, and of about 1.28 ng/mg tissue within 90 days, front time of tissue injury and or implant.

TABLE 4C

In Vivo drug remaining on stent (μg) and average cumulative percentage releases (%) of Apixaban, Rivaroxaban, Argatroban and Sirolimus in the stent at the indicated time points following implantation.

| | Sample matrix* (n = 5) | | | | | | | | |
|---|---|---|---|---|---|---|---|---|---|
| | SS15 Argatroban/Apixaban/ Sirolimus in base coat and in topcoat | | | SS16 Argatroban/Rivaroxaban/ Sirolimus in base coat and in topcoat | | | SS17 Argatroban/Rivaroxaban/ Sirolimus in base coat and in topcoat | | |
| Time | Drug remaining on stent, μg & percentage released (%) | | | | | | | | |
| (hrs) | Apixaban | Argatroban | Sirolimus | Rivaroxaban | Argatroban | Sirolimus | Rivaroxaban | Argatroban | Sirolimus |
| 0 | 119 | 123 | 96 | 120 | 119 | 90 | 121 | 121 | 96 |
| 1 H | 61 ± 4.8 (49%) | 60 ± 5.5 (51%) | 54 ± 2.8 (44%) | 76 ± 7.1 (36%) | 77 ± 59.2 (35%) | 63 ± 4.7 (29%) | 43 ± 3.5 (65%) | 26 ± 0.8 (78%) | 88 ± 1.5 (8%) |
| 3 H | 46 ± 5.2 (61%) | 46 ± 5.1 (63%) | 43 ± 3.9 (55%) | 64 ± 9.5 (47%) | 61 ± 13.9 (49%) | 50 ± 6.1 (44%) | 34 ± 5.1 (71%) | 24 ± 1.9 (80%) | 79 ± 3.5 (18%) |
| 24 H | 27 ± 3.6 (77%) | 28 ± 1.4 (77%) | 28 ± 0.8 (71%) | 21 ± 4.8 (83%) | 21 ± 1.6 (82%) | 24 ± 7.1 (73%) | 17 ± 5.9 (86%) | 17 ± 3.8 (86%) | 36 ± 7.3 (63%) |
| 7 D | 24 ± 1.4 (80%) | 25 ± 1.0 (80%) | 18 ± 0.3 (81%) | 16 ± 2.5 (86%) | 18 ± 1.7 (85%) | 12 ± 1.2 (87%) | 9 ± 0.3 (92%) | 11 ± 0.4 (91%) | 22 ± 0.5 (77%) |
| 28 D | 19 ± 0.9 (84%) | 20 ± 6.1 (84%) | 9 ± 0.3 (90%) | 14 ± 1.0 (89%) | 15 ± 0.8 (87%) | 5 ± 0.4 (94%) | 7 ± 0.4 (94%) | 9 ± 0.7 (93%) | 13 ± 0.7 (87%) |
| 90 D | 16 ± 1.6 (87%) | 17 ± 0.6 (86%) | 3 ± 0.1 (97%) | N/A | N/A | N/A | N/A | N/A | N/A |

N/A: Not available
*SS15 28 D and 90 D (n = 3)

TABLE 4D

In Vivo drug concentration (ng/mg) in the tissue within 5 mm proximal and 5 mm distal
(tissue adjacent to the stented segment) to the stented segment.

| Sample Matrix (Sample Size) | Drug | 1-Hour | | 3-Hour | | 1 Day | | 6 Day | |
|---|---|---|---|---|---|---|---|---|---|
| | | Proximal | Distal | Proximal | Distal | Proximal | Distal | Proximal | Distal |
| SS115 (n = 5 except 28 D & 90 D n = 3) | Apixaban, ng/mg | 7.86 ± 3.01 | 3.53 ± 1.95 | 5.15 ± 1.59 | 6.77 ± 2.22 | 0.14 ± 0.08 | 0.36 ± 0.29 | N/A | N/A |
| | Argatroban, ng/mg | 8.57 ± 3.66 | 3.84 ± 2.42 | 5.43 ± 2.67 | 6.46 ± 3.14 | 0.05 ± 0.03 | 0.17 ± 0.09 | N/A | N/A |
| | Sirolimus, ng/mg | 2.82 ± 1.15 | 1.66 ± 0.78 | 3.52 ± 0.51 | 3.81 ± 0.61 | 0.12 ± 0.11 | 3.18 ± 3.01 | N/A | N/A |
| SS16 (Slider II Arm 1 (n = 5)) except 3 H n = 4, 28 d n = 6) | Rivaroxaban, ng/mg | 2.63 ± 1.14 | 6.51 ± 2.45 | 1.72 ± 0.53 | 2.16 ± 0.83 | 0.09 ± 0.03 | 0.09 ± 0.02 | N/A | N/A |
| | Argatroban, ng/mg | 3.74 ± 1.93 | 7.87 ± 3.04 | 2.48 ± 0.36 | 2.63 ± 0.87 | 0.07 ± 0.03 | 0.09 ± 0.03 | N/A | N/A |
| | Sirolimus, ng/mg | 2.30 ± 1.22 | 5.25 ± 1.62 | 2.62 ± 0.82 | 3.78 ± 0.81 | 0.18 ± 0.06 | 1.10 ± 0.44 | N/A | N/A |
| SS17 (Slider II Arm 2 (n = 5 except 3 H n = 4, 28 d n = 6) | Rivaroxaban, ng/mg | 1.52 ± 0.70 | 2.61 ± 1.38 | 3.00 ± 1.50 | 2.72 ± 1.66 | 0.09 ± 0.05 | 0.07 ± 0.02 | N/A | N/A |
| | Argatroban | 0.65 ± 0.23 | 0.91 ± 0.51 | 0.68 ± 0.28 | 0.87 ± 0.52 | 0.04 ± 0.01 | 0.03 ± 0.01 | N/A | N/A |
| | Sirolimus, ng/mg | 1.39 ± 0.83 | 1.81 ± 0.83 | 2.49 ± 1.02 | 3.95 ± 3.09 | 0.26 ± 0.27 | 0.86 ± 0.48 | N/A | N/A |

| Sample Matrix (Sample Size) | Drug | 7 Day | | 28 Day | | 90 Day | |
|---|---|---|---|---|---|---|---|
| | | Proximal | Distal | Proximal | Distal | Proximal | Distal |
| SS115 (n = 5 except 28 D & 90 D n = 3) | Apixaban, ng/mg | 0.01 ± 0.01 | 0.01 ± 0.01 | 0.04 (n = 1) BQL (n = 2) | 0.02 (n = 1) BQL (n = 2) | 0.0003 ± 0.0002 (n = 2) BQL (n = 1) | 0.0002 ± 0.0001 (n = 3) |
| | Argatroban, ng/mg | 0.01 ± 0.01 | 0.01 ± 0.003 | 0.04 (n = 1) BQL (n = 2) | 0.02 (n = 1) BQL (n = 2) | 0.008 (n = 1) BQL (n = 2) | 0.0006 ± 0.0004 (n = 2-) BQL (n = 1) |
| | Sirolimus, ng/mg | 0.02 ± 0.01 | 0.27 ± 0.11 | 0.02 ± 0.01 | 0.14 ± 0.04 | 0.01 ± 0.01 | 0.02 ± 0.01 |
| SS16 (Slider II Arm 1 (n = 5)) except 3 H n = 4, 28 d n = 6) | Rivaroxaban, ng/mg | BQL | BQL | 0.02 (n = 1); BQL (n = 5) | 0.02 (n = 1); BQL (n = 5) | N/A | N/A |
| | Argatroban, ng/mg | BQL | BQL | BQL | BQL | N/A | N/A |
| | Sirolimus, ng/mg | 0.04 ± 0.03 | 0.55 ± 0.22 | 0.05 ± 0.05 (n = 4); BQL (n = 2) | 0.11 ± 0.05 | N/A | N/A |
| SS17 (Slider II Arm 2 (n = 5 except 3 H n = 4, 28 d n = 6) | Rivaroxaban, ng/mg | 0.01 (n = 1); BQL (n = 4) | 0.01 (n = 1) BQL (n = 4) | 0.02 ± 0.001 (n = 2); BQL (n = 4) | BQL | N/A | N/A |
| | Argatroban | BQL | BQL | BQL | BQL | N/A | N/A |
| | Sirolimus, ng/mg | 0.01 (n = 3); BQL (n = 2) | 0.34 ± 0.21 | 0.03 ± 0.02 (n = 4); BQL (n = 2) | 0.13 ± 0.06 | N/A | N/A |

BQL: Below Quantification Limit
N/A: Not Available

TABLE 4E

In Vivo Apixaban concentration (ng/mg) in the stented segment tissue and adjacent segments of 5 mm proximal and 5 mm distal to the implanted device.

| Stent (Sample Size) | 1 hour | 3 hours | 1 day | 6 days | 7 days | 28 days | 90 days |
|---|---|---|---|---|---|---|---|
| Apixaban in treated area tissue content, ng/mg | | | | | | | |
| SS15 (n = 5) | 66.94 ± 27.33 | 25.31 ± 11.21 | 13.25 ± 10.17 | N/A | 1.15 ± 0.52 | 1.28 ± 0.47 (n = 3) | 3.05 ± 1.77 (n = 3) |
| Apixaban in Proximal tissue content, ng/mg | | | | | | | |
| SS15 (n = 5) | 7.86 ± 3.01 | 5.15 ± 1.59 | 0.14 ± 0.08 | N/A | 0.01 ± 0.01 | 0.04 (n = 1) BQL (n = 2) | 0.0003 ± 0.0002 (n = 2) BQL (n = 1) |
| Apixaban in Distal tissue content, ng/mg | | | | | | | |
| SS15 (n = 5) | 3.53 ± 1.95 | 6.77 ± 2.22 | 0.36 ± 0.29 | N/A | 0.01 ± 0.01 | 0.02 (n = 1) BQL (n = 2) | 0.0002 ± 0.0001 (n = 3) |

BQL: Below Quantification Limit

TABLE 4F

In Vivo Rivaroxaban concentration (ng/mg) in the stented segment tissue and adjacent segments of 5 mm proximal and 5 mm distal to the implanted device.

| Stent (Sample Size) | 1 hour | 3 hours | 1 day | 7 days | 28 days |
|---|---|---|---|---|---|
| Rivaroxaban in treated area tissue content, ng/mg | | | | | |
| SS16: Slider II Arm1 (n = 5 except 3 H n = 4, 28 d n = 6) | 48.75 ± 25.52 | 21.48 ± 5.80 | 3.67 ± 5.59 | 0.31 ± 0.24 | 0.34 ± 0.27 |
| SS17: Slider II Arm2 (n = 5 except 3 H n = 4, 28 d n = 6) | 38.31 ± 16.08 | 26.23 ± 3.50 | 1.31 ± 0.28 | 1.07 ± 1.88 | 0.52 ± 0.63 |
| Rivaroxaban in Proximal tissue content, ng/mg | | | | | |
| SS16: Slider II Arm1 (n = 5 except 3 H n = 4, 28 d n = 6) | 2.63 ± 1.14 | 1.72 ± 0.53 | 0.09 ± 0.03 | BQL | 0.02 (n = 1); BQL (n = 5) |
| SS17: Slider II Arm2 (n = 5 except 3 H n = 4, 28 d n = 6) | 1.52 ± 0.70 | 3.00 ± 1.50 | 0.09 ± 0.05 | 0.01 (n = 1); BQL (n = 4) | 0.02 ± 0.001 (n = 2); BQL (n = 4) |
| Rivaroxaban in Distal tissue content, ng/mg | | | | | |
| SS16: Slider II Arm1 (n = 5 except 3 H n = 4, 28 d n = 6) | 6.51 ± 2.45 | 2.16 ± 0.83 | 0.09 ± 0.02 | BQL | 0.02 (n = 1); BQL (n = 5) |
| SS17: Slider II Arm2 (n = 5 except 3 H n = 4, 28 d n = 6) | 2.61 ± 1.38 | 2.72 ± 1.66 | 0.07 ± 0.02 | 0.01 (n = 1); BQL (n = 4) | BQL |

BQL: Below Quantification Limit
N/A: Not Available

TABLE 4G

In Vivo Argatroban concentration (ng/mg) in the stented segment tissue and adjacent tissue segment of 5 mm proximal and 5 mm distal to the implanted device.

| Stent (Sample Size) | 1 hour | 3 hours | 1 day | 6 days | 7 days | 28 days | 90 days |
|---|---|---|---|---|---|---|---|
| Argatroban in treated tissue content, ng/mg | | | | | | | |
| SS7 (n = 1) | N/A | 54.00 | 0.75 | 0.09 | 0.05 | 0.15 | N/A |
| SS9 (n = 1) | N/A | 123.10 | 0.18 | 0.33 | 2.54 | 1.76 | N/A |
| SS15 (n = 5) | 71.37 ± 31.32 | 27.65 ± 15.00 | 15.64 ± 12.08 | N/A | 1.41 ± 0.69 | 1.69 ± 0.64 (n = 3) | 3.74 ± 1.89 (n = 3) |
| SS16: Slider II Arm1 (n = 5 except 3 H n = 4, 28 d n = 6) | 61.87 ± 24.60 | 32.81 ± 10.96 | 3.80 ± 4.87 | N/A | 0.42 ± 0.32 | 0.52 ± 0.37 | N/A |
| SS17: Slider II Arm2 (n = 5 except 3 H n = 4, 28 d n = 6) | 11.80 ± 2.69 | 8.06 ± 3.48 | 1.19 ± 0.46 | N/A | 1.35 ± 2.41 | 0.67 ± 0.87 | N/A |
| Argatroban in Proximal tissue content, ng/mg | | | | | | | |
| SS7 (n = 1) | N/A | 13.39 | BQL | BQL | BQL | BQL | N/A |
| SS9 (n = 1) | N/A | 1.27 | BQL | BQL | BQL | BQL | N/A |
| SS15 (n = 5) | 8.57 ± 3.66 | 5.43 ± 2.67 | 0.05 ± 0.03 | N/A | 0.01 ± 0.01 | 0.04 (n = 1) BQL (n = 2) | 0.0008 (n = 1) BQL (n = 2) |
| SS16: Slider II Arm1 (n = 5 except 3 H n = 4, 28 d n = 6) | 3.74 ± 1.93 | 2.48 ± 0.36 | 0.07 ± 0.03 | N/A | BQL | BQL | N/A |
| SS17: Slider II Arm2 (n = 5 except 3 H n = 4, 28 d n = 6) | 0.65 ± 0.23 | 0.68 ± 0.28 | 0.04 ± 0.01 | N/A | BQL | BQL | N/A |
| Argatroban in Distal tissue content, ng/mg | | | | | | | |
| SS7 (n = 1) | N/A | 5.20 | BQL | BQL | BQL | BQL | N/A |
| SS9 (n = 1) | N/A | 11.33 | BQL | N/A | BQL | BQL | N/A |
| SS15 (n = 5) | 3.84 ± 2.42 | 6.46 ± 3.14 | 0.17 ± 0.09 | N/A | 0.01 ± 0.003 | 0.02 (n = 1) BQL (n = 2) | 0.0006 ± 0.0004 (n = 2) BQL (n = 1) |
| SS16: Slider II Arm1 (n = 5 except 3 H n = 4, 28 d n = 6) | 7.87 ± 3.04 | 2.63 ± 0.87 | 0.09 ± 0.03 | N/A | BQL | BQL | N/A |
| SS17: Slider II Arm2 (n = 5 except 3 H n = 4, 28 d n = 6) | 0.91 ± 0.51 | 0.87 ± 0.52 | 0.03 ± 0.01 | N/A | BQL | BQL | N/A |

BQL: Below Quantification Limit
N/A: Not available

TABLE 4H

In Vivo Rapamycin concentration (ng/mg) in the tissue of treated segment (stented segment) and adjacent tissue segment of 5 mm proximal and 5 mm distal to the implanted device.

| Stent (Sample Size) | 1 hour | 3 hours | 1 day | 6 days | 7 days | 28 days | 90 days |
|---|---|---|---|---|---|---|---|
| Sirolimus in treated tissue content, ng/mg | | | | | | | |
| SS7 (n = 1) | N/A | 7.34 | 4.46 | 1.38 | 0.73 | 1.79 | N/A |
| SS9 (n = 1) | N/A | 40.57 | 0.93 | 1.61 | 3.24 | 2.48 | N/A |
| SS15 (n = 5) | 43.22 ± 14.73 | 23.37 ± 6.88 | 29.17 ± 18.65 | N/A | 1.54 ± 0.35 | 1.67 ± 0.22 (n = 3) | 1.28 ± 0.07 (n = 3) |
| SS16: Slider II Arm1 (n = 5 except 3 H n = 4, 28 d n = 6) | 45.10 ± 14.77 | 38.30 ± 9.29 | 9.18 ± 5.69 | N/A | 1.46 ± 0.38 | 0.94 ± 0.19 | N/A |
| SS17: Slider II Arm2 (n = 5 except 3 H n = 4, 28 d n = 6) | 21.34 ± 7.51 | 27.32 ± 6.86 | 10.85 ± 3.55 | N/A | 3.80 ± 4.86 | 1.73 ± 1.52 | N/A |
| Sirolimus in Proximal tissue content, ng/mg | | | | | | | |
| SS7 (n = 1) | N/A | 3.21 | BQL | 0.14 | BQL | 0.01 | N/A |
| SS9 (n = 1) | N/A | 0.38 | 0.58 | BQL | 0.15 | 0.1 | N/A |
| SS15 (n = 5) | 2.82 ± 1.15 | 3.52 ± 0.51 | 0.12 ± 0.11 | N/A | 0.02 ± 0.01 | 0.02 ± 0.01 (n = 3) | 0.01 ± 0.01 (n = 3) |

TABLE 4H-continued

In Vivo Rapamycin concentration (ng/mg) in the tissue of treated segment (stented segment) and adjacent tissue segment of 5 mm proximal and 5 mm distal to the implanted device.

| Stent (Sample Size) | 1 hour | 3 hours | 1 day | 6 days | 7 days | 28 days | 90 days |
|---|---|---|---|---|---|---|---|
| SS16: Slider II Arm1 (n = 5 except 3 H n = 4, 28 d n = 6) | 2.30 ± 1.22 | 2.62 ± 0.82 | 0.18 ± 0.06 | N/A | 0.04 ± 0.03 | 0.05 ± 0.05 (n = 4); BQL (n = 2) | N/A |
| SS17: Slider II Arm2 (n = 5 except 3 H n = 4, 28 d n = 6) | 1.39 ± 0.83 | 2.49 ± 1.02 | 0.26 ± 0.27 | N/A | 0.01 (n = 3); BQL (n = 2) | 0.03±0.02 (n = 4); BQL (n = 2) | N/A |
| Sirolimus in Distal tissue content, ng/mg | | | | | | | |
| SS7 (n = 1) | N/A | 1.86 | 0.99 | 0.69 | 0.46 | 0.14 | N/A |
| SS9 (n = 1) | N/A | 6.56 | 1.88 | 0.39 | 0.61 | 0.21 | N/A |
| SS15 (n = 5) | 1.66 ± 0.78 | 3.81 ± 0.61 | 3.18 ± 3.01 | N/A | 0.27 ± 0.11 | 0.14 ± 0.04 (n = 3) | 0.02 ± 0.01 (n = 3) |
| SS16: Slider II Arm1 (n = 5 except 3 H n = 4, 28 d n = 6) | 5.25 ± 1.62 | 3.78 ± 0.81 | 1.10 ± 0.44 | N/A | 0.55 ± 0.22 | 0.11 ± 0.05 | N/A |
| SS17: Slider II Arm2 (n = 5 except 3 H n = 4, 28 d n = 6) | 1.81 ± 0.83 | 3.95 ± 3.09 | 0.86 ± 0.48 | N/A | 0.34 ± 0.21 | 0.13 ± 0.06 | N/A |

BQL: Below Quantification Limit
N/A: Not available

TABLE 4I

Tissue concentration of Rivaroxaban, Argatroban and Sirolimus number of orders of magnitude higher than IC50 for Anti-factor Xa/IIa or anti-cell proliferation for the respective drugs in the tissue of treated segment and adjacent tissue segment of 5 mm proximal and 5 mm distal to the implanted device for SS15.

| Ratio of Tissue content to IC50 | 1 Hour | | | 3 Hours | | | 1 Day | | |
|---|---|---|---|---|---|---|---|---|---|
| | Proximal | Treated | Distal | Proximal | Treated | Distal | Proximal | Treated | Distal |
| Apixaban | 215142 | 1821895 | 95316 | 141612 | 688998 | 185185 | 3813 | 362200 | 9804 |
| Argatroban | 806 | 6693 | 356 | 506 | 2587 | 609 | 5 | 1462 | 16 |
| Sirolimus | 28000 | 432000 | 17000 | 35000 | 234000 | 38000 | 1200 | 292000 | 31800 |

| Ratio of Tissue content to IC50 | 7 Days | | | 28 Days | | | 3 month | | |
|---|---|---|---|---|---|---|---|---|---|
| | Proximal | Treated | Distal | Proximal | Treated | Distal | Proximal | Treated | Distal |
| Apixaban | 272 | 31318 | 272 | 1089 | 34858 | 545 | 8 | 83061 | 5 |
| Argatroban | 1 | 132 | 1 | 4 | 158 | 2 | 0 | 351 | 0 |
| Sirolimus | 200 | 15400 | 2700 | 200 | 16700 | 1400 | 100 | 12800 | 200 |

*IC50 of Apixaban for anti-Xa 0.08 nM or 0.00004 ng/mg
*IC50 of Argatroban for anti-IIa 21 nM or 0.01 ng/mg
*IC50 of Sirolimus for cell proliferation 0.1 nM or 0.0001 ng/mg

TABLE 4J

Tissue concentration of Rivaroxaban, Argatroban and Sirolimus number of orders of magnitude higher than IC50 for Anti-factor Xa/IIa or anti- cell proliferation for the respective drugs in the tissue of treated segment and adjacent tissue segment of 5 mm proximal and 5 mm distal to the implanted device for Slider II Arm1.

| Ratio of Tissue content to IC50 | 1 Hour | | | 3 Hours | | | 1 Day | | | 7 Days | | | 28 days | | |
|---|---|---|---|---|---|---|---|---|---|---|---|---|---|---|---|
| | Proximal | Treated | Distal | Proximal | Treated | Distal | Proximal | Treated | Distal | Proximal | Treated | Distal | Proximal | Treated | Distal |
| Rivaroxaban | 286 | 5299 | 708 | 187 | 2335 | 235 | 10 | 399 | 10 | N/A | 34 | N/A | 2 | 37 | 2 |
| Argatroban | 351 | 5800 | 738 | 232 | 3076 | 247 | 7 | 356 | 8 | N/A | 39 | N/A | N/A | 49 | N/A |
| Rapamycin | 23000 | 451000 | 52500 | 26200 | 383000 | 37800 | 1800 | 91800 | 11000 | 400 | 14600 | 5500 | 500 | 9400 | 1100 |

*IC50 of Rivaroxaban for anti-Xa 21 nM or 0.0092 ng/mg
*IC50 of Argatroban for anti-IIa 21 nM or 0.01 ng/mg
*IC50 of Sirolimus for cell proliferation 0.1 nM or 0.0001 ng/mg

TABLE 4K

Tissue concentration of Rivaroxaban, Argatroban and Sirolimus number of orders of magnitude higher than IC50 for Anti-factor Xa/IIa or anti- cell proliferation for the respective drugs in the tissue of treated segment and adjacent tissue segment of 5 mm proximal and 5 mm distal to the implanted device for Slider II Arm2.

| Ratio of Tissue content to IC50 | 1 Hour | | | 3 Hours | | | 1 Day | | | 7 Days | | | 28 days | | |
|---|---|---|---|---|---|---|---|---|---|---|---|---|---|---|---|
| | Proximal | Treated | Distal | Proximal | Treated | Distal | Proximal | Treated | Distal | Proximal | Treated | Distal | Proximal | Treated | Distal |
| Rivaroxaban | 165 | 4164 | 284 | 326 | 2851 | 296 | 10 | 142 | 8 | 1 | 116 | 1 | 2 | 57 | N/A |
| Argatroban | 61 | 1106 | 85 | 64 | 756 | 82 | 4 | 112 | 3 | N/A | 127 | N/A | N/A | 63 | N/A |
| Rapamycin | 13900 | 213400 | 18100 | 24900 | 273200 | 39500 | 2600 | 108500 | 8600 | 100 | 38000 | 3400 | 300 | 17300 | 1300 |

IC50 of Rivaroxaban for anti-Xa 21 nM or 0.0092 ng/mg
IC50 of Argatroban for anti-IIa 21 nM or 0.01 ng/mg
IC50 of Sirolimus for cell proliferation 0.1 nM or 0.0001 ng/mg Tables 4D-4K show that all three drugs Apixaban, argatroban, and rapamycin maintain therapeutic tissue concentrations in the tissue segment up to 28 days, up to 90 days or longer, and furthermore achieve therapeutic tissue concentration in the adjacent tissue segment (±5 mm from the tissue segment such as Proximal and distal) at 1 hour, 3 hours and/or up to 1 day. This can be important to inhibit thrombus formation in the stented segment, the device surface, and in the tissue adjacent to the stented segment as in many cases such tissue is injured by balloon deployment or stent edges.

Taking Apixaban IC50 for factor Xa inhibition to be about 0.08 nM or 0.00004 ng/mg; Rivaroxaban IC50 for factor Xa inhibition to be about 21 nM or 0.0092 ng mg; Argatroban IC50 for factor IIa inhibition to be about 21 nM or 0.01 ng/mg; Sirolimus IC50 for cell proliferation to be about 0.1 nM, or 0.0001 ng/mg. Table 4I-Table 4K are the tissue concentration of Apixaban or Rivaroxaban, Argatroban and Sirolimus are several order of magnitude higher (or times higher) than IC50 for Anti-factor Xa, anti-IIa, or anti-cell proliferation for the respective drugs in the tissue of treated segment and adjacent tissue segment of 5 mm proximal and 5 mm distal to the implanted device. It shows that Apixaban, Rivaroxaban. Argatroban and/or Sirolimus in tissue concentrations have one or more order of magnitudes higher concentration at the times specified, has from 1 to 6 orders of magnitude of tissue concentration for each of the drugs compared to their IC50, in the treated tissue segments up to 28 days, or up to 90 days.

Example 5: In Vivo Animal Study of Anticoagulant1/Anticoagulant2/mTOR Elating Stents (Scaffolds)

The test drug eluting stent systems containing anticoagulants were prepared as described in Example 4 and were evaluated at 28 days and 90 days following implantation in a porcine coronary artery. The control device was the Novolimus (m-Tor) eluting DESyne X2 stem.

The porcine artery was chosen as this model has been used extensively for stem and angioplasty studies resulting in a large volume of data on the vascular response properties and its correlation to human vascular response (Schwartz et al, Circulation. 2002; 106:1867 1873). The animals were housed and cared for in accordance with the Guide for the Care and Use of Laboratory Animals as established by the National Research Council.

All animals were pretreated with aspirin (325 mg) and Clopidogrel (75 mg) per oral dose beginning at least 3 days prior to the intervention and continuing for the duration of the study. After induction of anesthesia, the left or right femoral artery was accessed using standard techniques and an arterial sheath was introduced and advanced into the artery. Vessel angiography was performed under fluoroscopic guidance, a 7 Fr. guide catheter was inserted through the sheath and advanced to the appropriate location where intracoronary nitroglycerin was administered. An appropriate implantation segment of coronary artery was randomly selected and a 0.014" guidewire inserted. Quantitative Coronary Angiography (QCA) was performed to document the results. The appropriately sized stent (3.0×14 mm or 3.5×14 mm) was advanced to the deployment site. The balloon was inflated at a steady rite to a pressure sufficient to achieve a balloon to artery ratio of approximately 1.1 to 1.0 but less than 1:2:1. Pressure was maintained tier approximately 10 seconds before the balloon was deflated. Each pig was implanted with 3 test devices and one control device in the coronary arteries. Each time point a whole blood was drawn from animals for blood drug concentration test.

Follow up angiography imaging was performed at the designated endpoint for each of the animals. Quantitative coronary angiographic analysis was performed and the average percent diameter stenosis values and late lumen loss for the test arms and control DESyne X2 for the 28 days and 3-month time points are shown in Table 5A.

Upon completion of follow-up angiography imaging, the animals were euthanized. The hearts were harvested from each animal. Any myocardial lesions or unusual observations were reported. The coronary arteries were perfused with 10% buffered formalin at 100 to 120 mm Hg with the animal's ear tag until processed for histology.

Figure 5A:
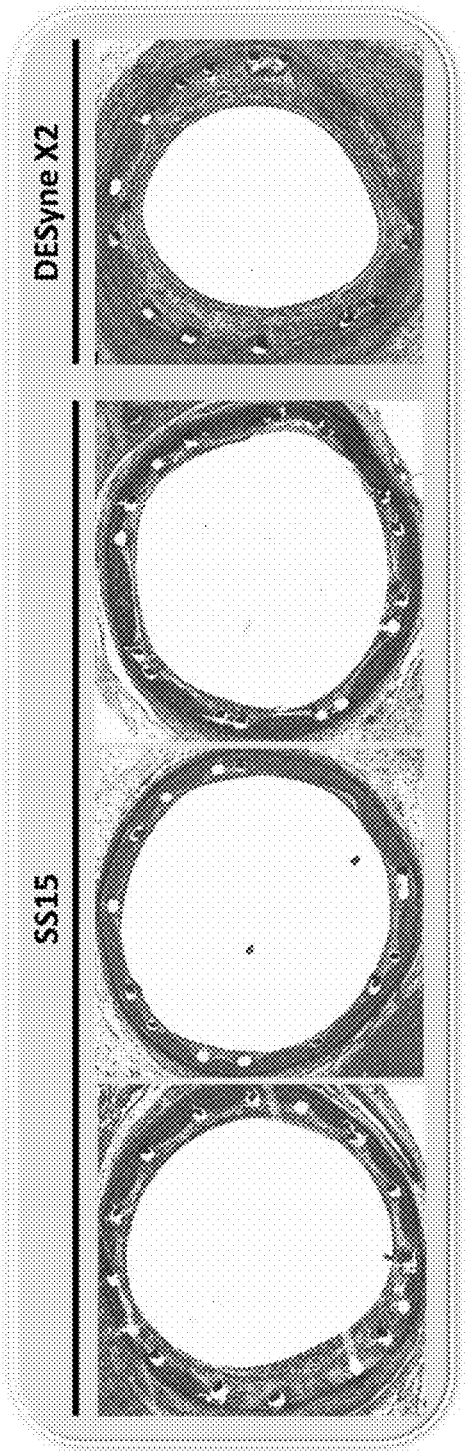
FIG. 5A shows an example image of Elastin Trichrome stained sections of rapamycin apixaban and argatroban drug eluting stent and control DESyne X2 implanted vessels at the 28 day time point histology evaluation, in accordance with an example.
Figure 5B:
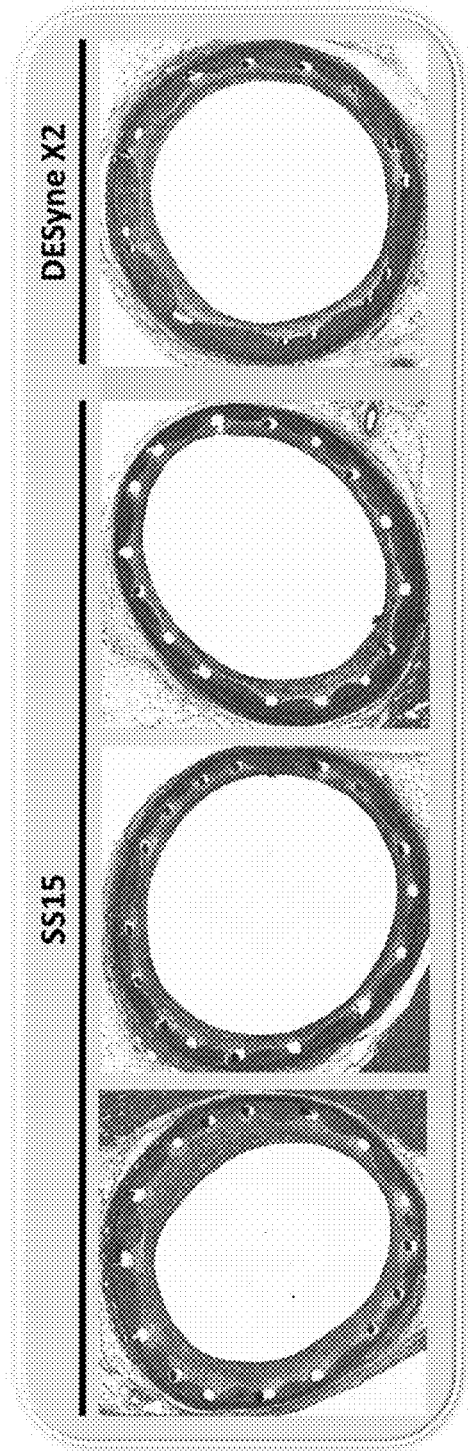

Stented portions of coronary arteries were embedded in methyl methacrylate (MMA), then divided into a target of three blocks of approximately similar length (about 4 mm), identified as proximal, mid and distal segments. From three blocks, 3 to 5 cuts were made for histology evaluation. Images examples of Elastin Trichrome stained sections of Slider (SS15) and DESyne X2 implanted vessels at the 28 days and 3-month time points are shown in FIGS. 5A and 5B.

Quantitative histopathological evaluation of stented artery sections was then performed and scored as indicated. The mean of each section was recorded and then averaged to provide a mean score per stent for the different parameters (Table 5A). The smaller the score, the better the efficacy.

Fibrin (strut-by-strut)
0=absent, or rare minimal spotting around struts
1=fibrin in small amounts, localized only around struts
2=fibrin moderately abundant or denser, extending beyond struts
3=abundant, dense fibrin, bridging between struts
Each strut in the section was scored; the mean fibrin score for each section was calculated and reported. The mean of the section means was calculated and reported, providing a mean fibrin score per stent.

Injury Based on Schwartz et al. J am Coll Cardiol 1992; 19:267-274, (Strut-by-Strut):
0=IEL intact
1=IEL lacerated
2=media completely lacerated
3=EEL lacerated
Each strut in the section as scored and the mean injury score for each section was calculated and reported. The mean of the section means was calculated and reported, providing a mean injury score per stent.

Inflammation (Strut-by-Strut)
0=no or very few (≤3) inflammatory cells around strut
1=few (~4-10) inflammatory cells around strut
2=many (>10) inflammatory cells around strut, can extend into but does not efface surrounding tissue
3=many (>10) inflammatory cells, effacing surrounding tissue
Each strut in the section was scored and the mean inflammation score for each section was calculated and reported. The mean of the section means was calculated and reported, providing a mean inflammation score per device.

TABLE 5A

Histopathology Scores and Quantitative Coronary Angiography data Apixaban/Rivaroxaban, Argatroban and Sirolimus releasing 14 mm stents at 7 days, 28 days and 3 month

| Time Point | Device | Injury | Inflammation | Fibrin | Diameter Stenosis % | LLL, mm |
|---|---|---|---|---|---|---|
| 7 Day | SS7 (n = 1) | 0.15 | 1.52 | 0.62 | N/A | N/A |
|  | SS9 (n = 1) | 0.61 | 1.66 | 0.44 | N/A | N/A |
| 28 Day | SS7 (n = 1) | 0.21 | 0.49 | 0.94 | 16.7 | 0.71 |
|  | SS9 (n = 1) | 0.36 | 0.32 | 0.64 | 21.3 | 0.76 |
|  | SS15 (n = 3) | 0.38 ± 0.34 | 0.62 ± 0.12 | 1.67 ± 0.38 | 19.8 ± 4.1 | 0.45 ± 0.15 |
|  | DESyne X2 (n = 1) | 1.34 | 1.83 | 1.87 | 51.6 | 1.14 |
|  | SS16 (Slider II Arm1, n = 6) | 0.91 ± 0.95 | 1.52 ± 1.03 | 1.90 ± 0.26 | 19.4 ± 13.8 | 0.72 ± 0.32 |
|  | DESyne X2 (n = 2) | 1.17 ± 1.60 | 1.97 ± 1.46 | 1.32 ± 1.11 | 36.6 ± 27.3 | 0.99 ± 0.48 |
|  | SS17 (Slider II Arm2, n = 6) | 1.01 ± 0.47 | 1.46 ± 0.43 | 1.88 ± 0.48 | 33.1 ± 12.8 | 0.86 ± 0.34 |
|  | DESyne X2 (n = 2) | 0.87 ± 0.74 | 1.59 ± 0.95 | 1.93 ± 0.31 | 21.9 ± 11.6 | 0.71 ± 0.62 |
| 3 Month | SS15 (n = 3) | 0.15 ± 0.18 | 0.52 ± 0.19 | 0.08 ± 0.06 | 18.2 ± 9.3 | 0.25 ± 0.29 |
|  | DESyne X2 (n = 1) | 0.43 | 0.59 | 0.76 | 22.3 | 0.52 |

LLL is an indicator of the amount cell proliferation or inhibition potency. It is used to measure efficacy between drugs for proliferation inhibition in mammalian arteries. The smaller the LLL, the better the efficacy of the drug.

As shown in Table 5A, SS15 composition providing the combination of Sirolimus, Apixaban and Argatroban released from stents had a smaller LLL compared to control which only had m-TOR inhibitor (Novolimus) and thus was unexpectedly more effective at inhibiting smooth muscle cell proliferation compared to Novolimus releasing scents at 28 days, and at 90 days. This was an unexpected finding for the test SS15 scents in comparison to the control DESyne X2 stents at the 28-day time point and/or at 90 days.

In an unexpected finding, SS15 stents composition eluting Apixaban, Argatroban, and the M-Tor inhibitor rapamycin exhibited more efficacy at inhibiting one or more of the following at 28 days and/or 90 day time points: cell proliferation, inflammation, injury, fibrin formation inhibition, and fibrin dissolution acceleration.

The LLL is an indicator of the amount cell proliferation or inhibition potency. It is used to measure efficacy between drugs for proliferation inhibition in mammalian arteries. The smaller the LLL, the better the efficacy of the drug.

As shown in Table 5A, SS16 shows the combination of Sirolimus, Rivaroxaban and Argatroban released from stents had a smaller LLL compared to control which only had m-TOR inhibitor (Novolimus) and thus was unexpectedly more effective at inhibiting smooth muscle cell proliferation compared to Novolimus releasing stents at 28 days.

As shown in Table 5A, SS17 composition configured to delay the release and tissue concentration of rapamycin within the first 1 hour and/or within the first 3 hours by incorporating rapamycin in the base coating shows the combination of Sirolimus, and/or lower tissue concentration of Rivaroxaban and Argatroban within at least the first hour showed less inhibition of SMC proliferation at 28 days.

TABLE 5B

Whole Blood PK Results of Apixaban/Argatroban/Sirolimus Eluting Stents from SS15
(from study with SS15; target dose Apixaban/Argatroban/Sirolimus = 117/117/94; n = 5)

| Time | Apixaban (ng/mL) | | | | | Argatroban (ng/mL) | | | | | Sirolimus (ng/mL) | | | | |
|---|---|---|---|---|---|---|---|---|---|---|---|---|---|---|---|
| Points | 1 H | 3 H | 1 D | 7 D | 28 D | 1 H | 3 H | 1 D | 7 D | 28 D | 1 H | 3 H | 1 D | 7 D | 28 D |
| Pre-implant | BQL | BQL | BQL | BQL | BQL | BQL | BQL | BQL | BQL | BQL | BQL | BQL | BQL | BQL | BQL |
| Post $1^{st}$ implant | 0.441 | 0.71 | 4.02 | 0.16 | 0.30 | 1.36 | 2.02 | 4.44 | 0.58 | 0.66 | 0.70 | 0.59 | 2.52 | 0.69 | 0.32 |
| Post $2^{nd}$ implant | 0.95 | 1.17 | 3.51 | 0.77 | 0.44 | 3.16 | 4.35 | 5.74 | 4.41 | 1.83 | 1.90 | 1.94 | 4.16 | 2.13 | 1.06 |
| Post $3^{rd}$ implant | 1.8 | 2.18 | 4.29 | 1.31 | 0.91 | 6.71 | 7.59 | 9.26 | 7.85 | 3.72 | 3.30 | 3.74 | 7.08 | 3.28 | 2.49 |
| Post $4^{th}$ implant | 2.56 | 2.91 | 5.01 | 1.72 | 1.65 | 10.2 | 11.0 | 11.4 | 10.9 | 7.33 | 4.80 | 5.22 | 8.06 | 4.17 | 4.73 |
| Post $5^{th}$ implant | 3.27 | 3.55 | 5.84 | 2.12 | 2.45 | 13.4 | 13.3 | 14.5 | 12.8 | 10.3 | 6.71 | 7.13 | 9.98 | 4.75 | 5.91 |
| 15 min. | 3.91 | 4.60 | — | — | — | 17.8 | 21.7 | — | — | — | 8.77 | 11.3 | — | — | — |
| 30 min. | 4.78 | 5.20 | 8.69 | — | — | 22.7 | 24.6 | 22.6 | — | — | 11.2 | 12.3 | 17.2 | — | — |
| 45 min. | 6.29 | — | — | — | — | 28.9 | — | — | — | — | 13.4 | — | — | — | — |
| 60 min. (1 hr) | 6.32 | 6.28 | 9.91 | — | — | 28.2 | 29.0 | 24.4 | — | — | 12.8 | 12.7 | 21.3 | — | — |
| 90 min. | — | 7.26 | — | — | — | — | 31.1 | — | — | — | — | 13.7 | — | — | — |
| 120 min. (2 hr) | — | 7.76 | 12.7 | — | — | — | 28.5 | 20.7 | — | — | — | 12.8 | 21.3 | — | — |
| 150 min. | — | 7.38 | — | — | — | — | 28.9 | — | — | — | — | 12.4 | — | — | — |
| 180 min. (3 hr) | — | 6.89 | 12.8 | — | — | — | 20.4 | 16.9 | — | — | — | 9.32 | 14.0 | — | — |
| 4 hr | — | — | 13.3 | — | — | — | — | 12.9 | — | — | — | — | 12.4 | — | — |
| 5 hr | — | — | 14.7 | — | — | — | — | 9.25 | — | — | — | — | 11.0 | — | — |
| 6 hr | — | — | 13.3 | — | — | — | — | 7.02 | — | — | — | — | 10.5 | — | — |
| 24 hr (Day 1) | — | — | 1.51 | — | — | — | — | 0.383 | — | — | — | — | 2.65 | — | — |
| Day 7 | — | — | — | BQL | — | — | — | — | BQL | — | — | — | — | 0.384 | — |
| Day 28 | — | — | — | — | BQL | — | — | — | — | BQL | — | — | — | — | BQL |

Note.
Blood volume in porcine model is about 40%-50% of adult human. Thus drug concentrations in human would typically be lower than the figures shown in table 5B.

TABLE 5C

Whole Blood PK Results of Rivaroxaban/Argatroban/Sirolimus Eluting Stents from SS16
(Rivaroxaban Arm1; target dose Rivaroxaban/Argatroban/Sirolimus = 117/117/94;
n = 5 except D28 n = 6)

| Time | Rivaroxaban (ng/mL) | | | | Argatroban (ng/mL) | | | | Sirolimus (ng/mL) | | | |
|---|---|---|---|---|---|---|---|---|---|---|---|---|
| Points | 1 H | 1 D | 7 D | 28 D | 1 H | 1 D | 7 D | 28 D | 1 H | 1 D | 7 D | 28 D |
| Pre-implant | BQL | BQL | BQL | BQL | BQL | BQL | BQL | BQL | BQL | BQL | BQL | BQL |
| Post $1^{st}$ implant | 0.72 | 1.14 | 1.07 | 0.69 | 1.96 | 2.94 | 2.22 | 1.89 | 0.52 | 0.69 | 0.66 | 0.48 |
| Post $2^{nd}$ implant | 1.34 | 2.16 | 2.14 | 1.44 | 5.05 | 6.92 | 5.91 | 4.76 | 1.56 | 1.47 | 1.75 | 1.29 |
| Post $3^{rd}$ implant | 2.10 | 2.57 | 2.94 | 2.17 | 10.3 | 10.1 | 10.2 | 8.22 | 3.53 | 2.22 | 3.35 | 2.32 |
| Post $4^{th}$ implant | 2.67 | 3.36 | 3.52 | 2.80 | 15.0 | 17.2 | 13.6 | 11.69 | 4.69 | 3.41 | 4.69 | 3.59 |
| Post $5^{th}$ implant | 2.92 | 4.32 | 3.95 | 3.33 | 18.9 | 19.9 | 19.1 | 14.42 | 6.15 | 5.37 | 7.24 | 5.08 |
| Post $6^{th}$ implant | — | — | — | 4.32 | — | — | — | 19.05 | — | — | — | 6.58 |

TABLE 5C-continued

Whole Blood PK Results of Rivaroxaban/Argatroban/Sirolimus Eluting Stents from SS16
(Rivaroxaban Arm1; target dose Rivaroxaban/Argatroban/Sirolimus = 117/117/94;
n = 5 except D28 n = 6)

| Time Points | Rivaroxaban (ng/mL) | | | | Argatroban (ng/mL) | | | | Sirolimus (ng/mL) | | | |
|---|---|---|---|---|---|---|---|---|---|---|---|---|
| | 1 H | 1 D | 7 D | 28 D | 1 H | 1 D | 7 D | 28 D | 1 H | 1 D | 7 D | 28 D |
| 15 min. | 3.32 | 4.05 | — | — | 23.5 | 22.8 | — | — | 8.38 | 6.92 | — | — |
| 30 min. | 3.34 | 3.76 | — | — | 27.5 | 27.0 | — | — | 10.1 | 8.56 | — | — |
| 45 min. | 3.68 | 3.47 | — | — | 31.9 | 31.5 | — | — | 10.9 | 9.93 | — | — |
| 60 min. (1 hr) | 4.08 | 2.61 | — | — | 31.1 | 31.5 | — | — | 11.2 | 10.7 | — | — |
| 90 min. | — | 2.43 | — | — | — | 30.8 | — | — | — | 12.3 | — | — |
| 120 min. (2 hr) | — | 2.30 | — | — | — | 26.6 | — | — | — | 12.1 | — | — |
| 150 min. | — | 2.08 | — | — | — | 26.6 | — | — | — | 11.7 | — | — |
| 180 min. (3 hr) | — | 1.95 | — | — | — | 25.1 | — | — | — | 10.3 | — | — |
| 4 hr | — | 1.23 | — | — | — | 18.4 | — | — | — | 7.62 | — | — |
| 5 hr | — | 1.11 | — | — | — | 13.5 | — | — | — | 6.89 | — | — |
| 6 hr | — | 1.03 | — | — | — | 11.0 | — | — | — | 6.09 | — | — |
| 24 hr (Day 1) | — | BQL | — | — | — | 1.92 | — | — | — | 2.14 | — | — |
| Day 7 | — | — | BQL | — | — | — | BQL | — | — | — | 0.44 | — |
| Day 28 | — | — | — | BQL | — | — | — | BQL | — | — | — | BQL |

Note.
Blood volume in porcine model is about 40%-50% of adult human. Thus drug concentrations in human would typically be lower than the figures shown in table 5C.

TABLE 5D

Whole Blood PK Results of Rivaroxaban/Argatroban/Sirolimus Eluting Stents from SS17
Rivaroxaban/Argatroban/Sirolimus = 117/117/94; n = 5 except D28 n = 6)

| Time Points | Rivaroxaban (ng/mL) | | | | Argatroban (ng/mL) | | | | Sirolimus (ng/mL) | | | |
|---|---|---|---|---|---|---|---|---|---|---|---|---|
| | 1 H | 1 D | 7 D | 28 D | 1 H | 1 D | 7 D | 28 D | 1 H | 1 D | 7 D | 28 D |
| Pre-implant | BQL | BQL | BQL | BQL | BQL | BQL | BQL | BQL | BQL | BQL | BQL | BQL |
| Post 1st implant | 3.77 | 3.62 | 3.18 | 3.20 | 11.7 | 11.1 | 11.0 | 14.05 | BQL | 0.11 | BQL | BQL |
| Post 2nd implant | 5.27 | 6.16 | 5.90 | 5.79 | 20.5 | 24.7 | 25.9 | 32.44 | 0.17 | 0.36 | BQL | 0.06 |
| Post 3rd implant | 9.27 | 11.4 | 8.41 | 8.66 | 41.3 | 45.2 | 44.3 | 52.20 | 0.28 | 0.44 | 0.22 | 0.21 |
| Post 4th implant | 10.9 | 16.7 | 10.8 | 9.02 | 54.4 | 59.6 | 63.2 | 65.75 | 0.47 | 0.91 | 0.77 | 0.46 |
| Post 5th implant | 12.5 | 22.3 | 12.0 | 10.70 | 65.7 | 70.3 | 73.6 | 79.38 | 0.98 | 1.38 | 1.08 | 0.69 |
| Post 6th implant | — | — | — | 13.42 | — | — | — | 96.18 | — | — | — | 1.20 |
| 15 min. | 10.8 | 24.0 | — | — | 73.4 | 67.2 | — | — | 2.11 | 2.88 | — | — |
| 30 min. | 8.44 | 20.1 | — | — | 51.9 | 51.7 | — | — | 2.79 | 4.65 | — | — |
| 45 min. | 7.82 | 19.5 | — | — | 42.4 | 46.5 | — | — | 3.96 | 5.35 | — | — |
| 60 min. (1 hr) | 7.54 | 18.5 | — | — | 38.3 | 44.2 | — | — | 4.32 | 6.97 | — | — |
| 90 min. | — | 15.0 | — | — | — | 32.9 | — | — | — | 8.08 | — | — |
| 120 min. (2 hr) | — | 11.6 | — | — | — | 25.8 | — | — | — | 8.12 | — | — |
| 150 min. | — | 11.3 | — | — | — | 20.5 | — | — | — | 7.97 | — | — |
| 180 min. (3 hr) | — | 8.39 | — | — | — | 16.3 | — | — | — | 7.10 | — | — |
| 4 hr | — | 3.74 | — | — | — | 9.30 | — | — | — | 5.63 | — | — |
| 5 hr | — | 3.90 | — | — | — | 6.78 | — | — | — | 6.80 | — | — |
| 6 hr | — | 3.10 | — | — | — | 5.40 | — | — | — | 6.30 | — | — |
| 24 hr (Day 1) | — | 0.16 | — | — | — | 0.48 | — | — | — | 2.92 | — | — |
| Day 7 | — | — | BQL | — | — | — | 0.36 | — | — | — | 0.49 | — |
| Day 28 | — | — | — | BQL | — | — | — | BQL | — | — | — | 0.66 |

Note.
Blood volume in porcine model is about 40%-50% of adult human. Thus drug concentrations in human would typically be lower than the figures shown in table 5D.

Tables 5B, 5C, and 5D show although local (tissue adjacent to the device) concentrations of Apixaban, Rivaroxaban, and Argatroban reached therapeutic levels, the systemic blood concentrations for each of the drugs were below one or more of the following to achieve systemic therapeutic concentrations: systemic Cmax, Systemic Cmean, Systemic Ctrough. These tables also show that each of these agents reached BQL levels within one of the following: 1 day, 7 days, 28 days, or 90 days Example 6: Anti-Proliferative Activity of Apixaban, Argatroban and Rapamycin Combination Anti-proliferative activity of Apixaban, Argatroban, and Rapamycin was tested in Human Aortic SMC (HAoSMC, ATCC, PCS-100-012). Cell proliferation assay was done in 96-well format. Low passage cells were trypsinized and seeded in 96 well plates at a density of ~4000 cells/well. The cells are allowed to attach overnight in a $CO_2$ incubator. Next day, the medium was removed and replaced with fresh complete medium containing various concentrations of the test compounds. The final concentration of vehicle (DMSO) in the test medium was 0.1%. After adding test compounds, the cells were incubated for 72 hours. Following this period, the medium was removed and then added fresh medium (100 µl) containing CellTiter Aqueous (lx concentration final) to the wells and incubated for 2 hours in the CO2 incubator. At the end of incubation measured fluorescence with a plate-reader. Controlled incubations with untreated cells and blank incubations containing only medium were included and tested similarly. Based on the cell viability assay the percentage inhibition of the cell proliferation was determined at the different concentrations of the drug tested.

The cell proliferation assay was performed with different concentrations of Apixaban and Argatroban when combined with Rapamycin. Following the cell proliferation assay as indicated earlier, the percent cell proliferation inhibition was determined, and the assay results plotted to determine the IC50 for the different drug combinations and shown in FIG. 6A-6E.

FIGS. 6A-6C show HAoSMC proliferation inhibition in the presence of different drug combinations. The data shows the combination of Apixaban, Argatroban surprisingly and unexpectedly enhanced the anti-proliferative effects of rapamycin on smooth muscle cell proliferation as measured by cell proliferation test when Apixaban and Argatroban were combined with rapamycin, i.e the combination of Apixaban, Argatroban. and rapamycin were more potent than rapamycin alone at inhibiting SMS proliferation.

FIGS. 6D and 6E show HAoSMC proliferation in presence of different concentrations of Apixaban or Argatroban. In order to determine if Apixaban or Argatroban independently had inhibitory effect on the proliferation of HAoSMC, a proliferation assay in the presence of either of these two drugs at different concentrations were tested as described earlier. Various concentration of Apixaban alone or Argatroban alone had small to no inhibition of HAoSMC proliferation was observed as shown in FIGS. 6D-6E.

Example 7: Activated Clotting Time (ACT) Evaluation of Apixaban, Argatroban or a Combination of Apixaban and Argatroban The activated clotting time (ACT) evaluation of anticoagulants was performed in Calcium-reconstituted sheep blood and recorded employing the Hemochron® Response device.

The ACT measurements were made in citrated sheep blood. 1.9 ml of citrated sheep blood was added to a test tube containing an activator (Hemochron@Celite@ ACT tubes, Lot F8FTE026 from Accriva Diagnostics, Inc.). A target amount of drug solution was then added into the test tube. The test tube was gently swirled so that the blood and drug was well-mixed. 0.1 ml of 0.3M calcium chloride was then added. The tube was gently shaken before being inserted into the Hemochron Response detector. The ACT read out was recorded and reported. The ACT of the control blood in the absence of any drug as first determined to establish a baseline. Then ACT was determined in the presence of different concentrations of the drug as a single component. Selected drug combinations, were then tested to evaluate for potential synergy in action between the two drugs.

As shown in FIGS. 7A-7D, the clotting time was observed to be significantly extended or increased at a higher drug combination concentrations. The Apixaban/Argatroban combination achieved ACT levels that were higher than the sum of the individual ACT values, indicating a synergistic effect between these drug combinations. This may be particularly important when delivering these drugs locally (adjacent to injured tissue) to inhibit clot formation. The figures are presented in ng/mg wherein the density of blood and tissue are approximately the same.

Figure 7A:
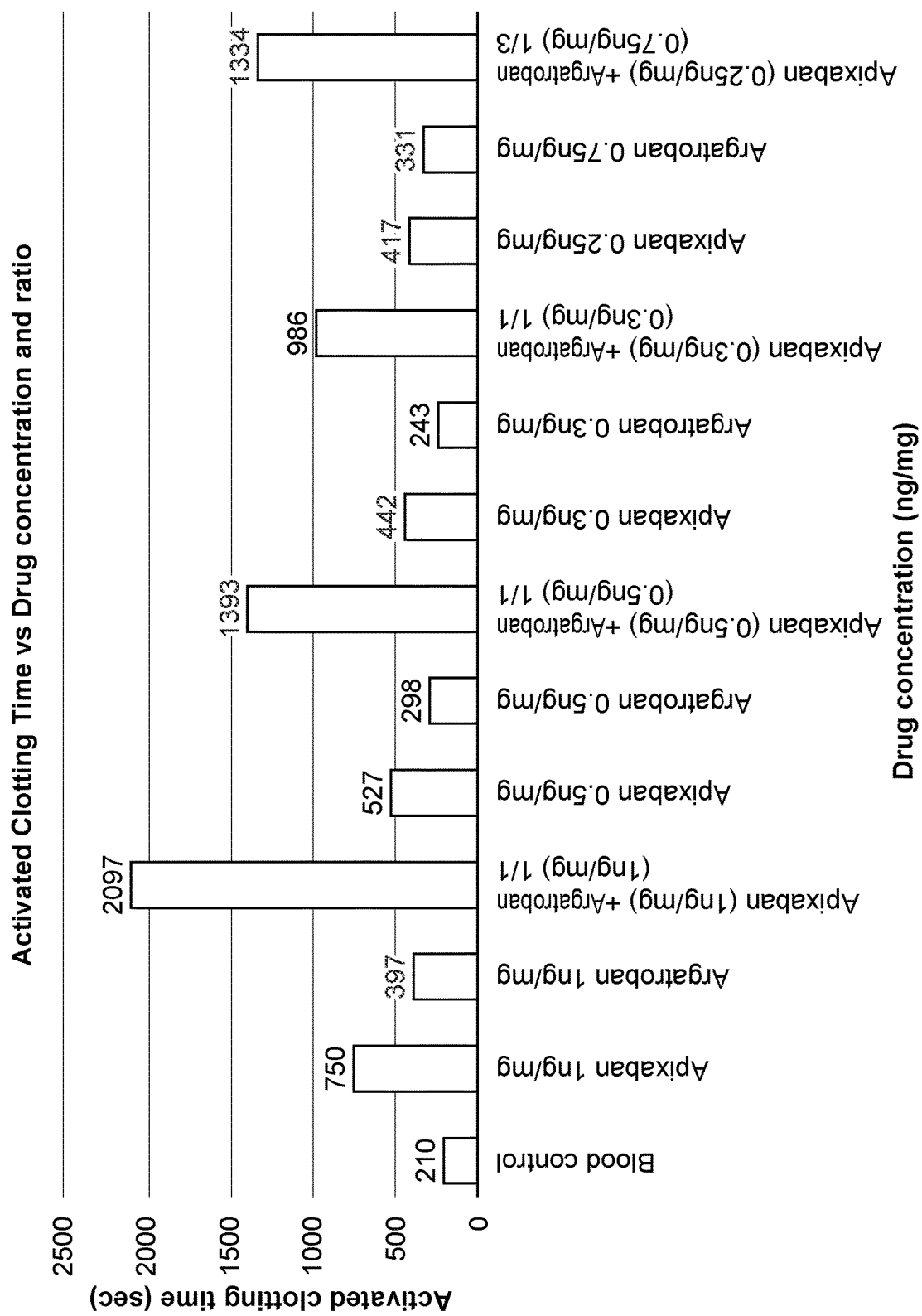
FIG. 7A shows a plot of activated clotting time (ACT) versus drug concentration, in accordance with examples.
Figure 7B:
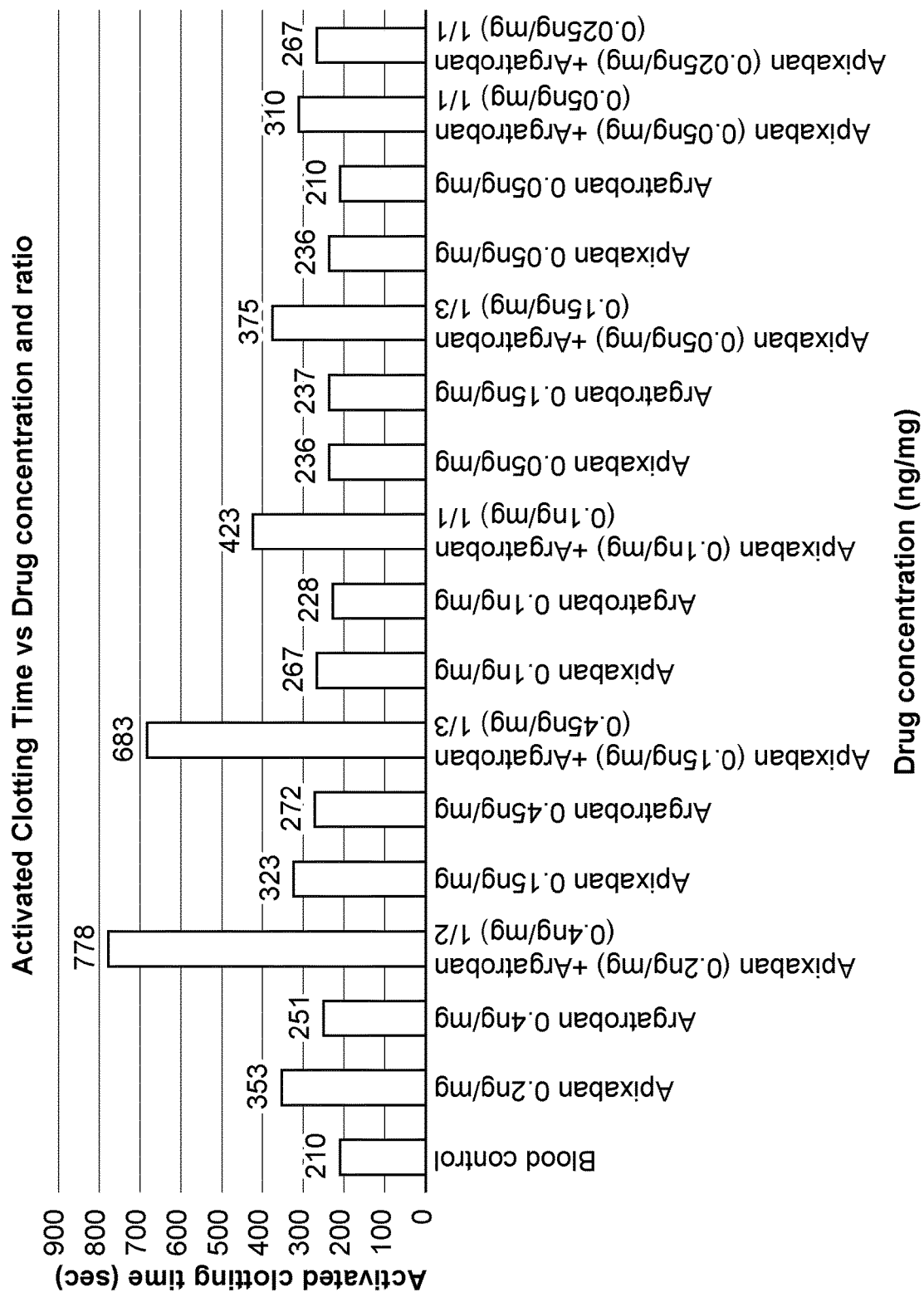
FIG. 7B shows a plot of activated clotting time (ACT) versus drug concentration, in accordance with examples.

It was found, unexpectedly, that the combination drug concentrations of 0.025 ng/mg for each Apixaban and Argatroban drug extended the ACT by a larger time (as shown in FIG. 7B).

Figure 7C:
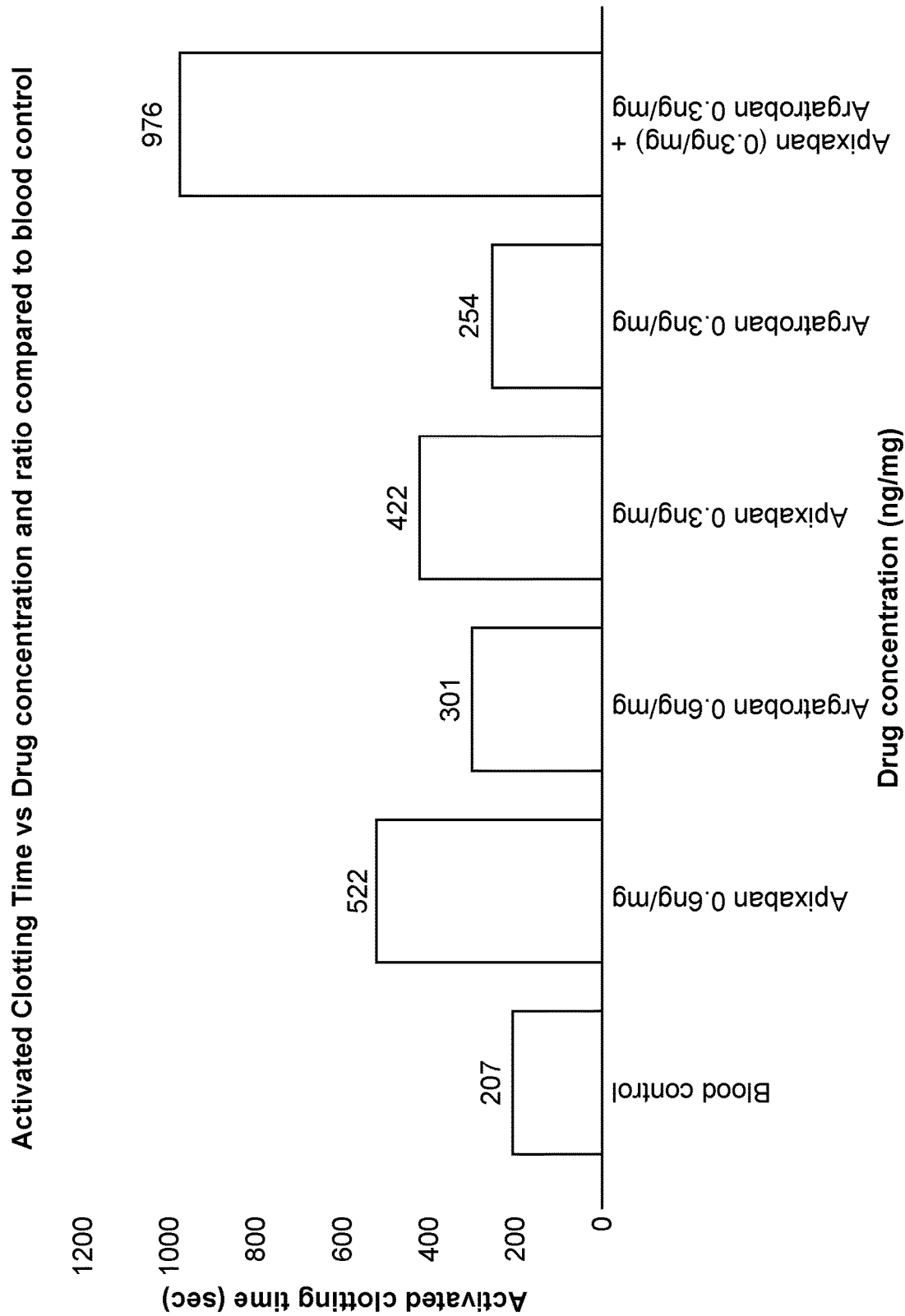
FIG. 7C shows a plot of activated clotting time (ACT) versus drug concentration, showing the synergistic effects of apixaban in combination with argatroban, in accordance with examples.
Figure 7D:
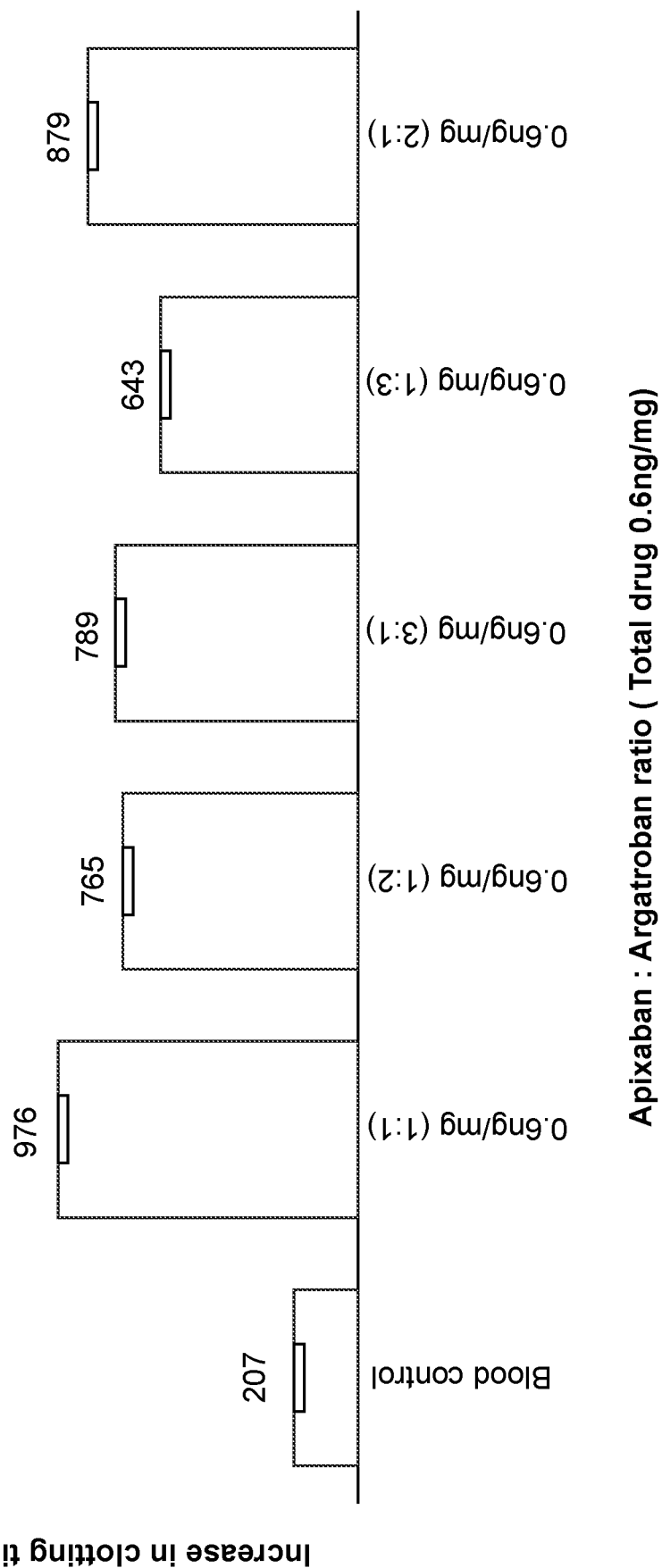
FIG. 7D shows a plot of various synergistic effects of drug combination ratios between apixaban and argatroban, in accordance with examples.

It was found, unexpectedly, that the combination drug concentrations of 0.3 ng/mg for each drug (0.6 ng/mg total) extended the ACT by a larger time (i.e., was more effective) than the ACT for each individual drug at 0.6 ng/mg concentration (ACT of 976 for the combination versus 522 for Apxaban versus 301 for Argatroban as shown in FIG. 7C).

FIG. 7C further shows, unexpectedly, that the combination drug concentrations of 0.3 ng/mg for each drug (0.6 ng/mg total) extended the ACT by a larger time (i.e., was more effective) than the ACT for the sum of each individual drug ACT at 0.3 ng/mg or at 0.6 ng/mg concentration. (ACT of 976 for the combination versus 676 (for the sum of individual drugs having 0.3 ng mg concentrations).

It is important to note that drug tissue concentrations for factor Xa inhibitors like Rivaroxiban or Apixaban alone or in combination with factor IIa Argatraban to have sufficient tissue concentrations in the stented tissue segment and in the adjacent tissue segment to have therapeutic levels for each drug to be larger than 0.02 ng/mg, larger than 0.1 ng/mg, preferably larger than 0.2 ng/mg of tissue, preferably 0.3 ng/mg of tissue, more preferably larger than 1 ng/mg of tissue at or within 3 hours after implantation, or at or within 1 day after implantation, to inhibit clot formation.

It was also shown that the combination of Apixaban and argatroban with m-TOR inhibitor inhibited thrombus formation in a shunt model (e.g., as in Example 8).

Example 8: Ex Vivo Testing of Drug Eluting Stunt Compared with 2 Anticoagulants and mTOR Eluting Stents The thrombogenicity of a drug eluting stem system with two anticoagulant Apixaban and Argatroban in combination with rapamycin at two different loading drug doses was evaluated at 1 hour in an arteriovenous ex vivo shunt in a porcine model wherein the devices were deployed in a blood compatible polymeric tubing.

The control stents were 16-o-demethyl rapamycin m-TOR inhibitor (Novolimus) drug eluting coronary stent (DESyne, Elixir) and m-TOR inhibitor Zotarolimus eluting coronary stem (Resolute, Medtronic. USA).

The test arm for this experiment were SS9, SS9*, and SS10* and were manufactured as follows: Each polymer solution and each drug solutions were combined together ((Sirolimus and anticoagulant Apixaban and Argatroban was 1:1:1) to poly(L-lactide acid-co-glycolic acid) by weight ratio was 5:2 matrix) according to the target drug dose of 235 μg for each anticoagulant and 94 μg for Sirolimus for SS9, SS9* test arm was about ⅓ of each of the drugs dose as follows: Sirolimus and anticoagulant Apixaban and Argatroban was 1:1:1) to poly(L-lactide acid-co-glycolic acid) by weight ratio was 5:2 on matrix) according to the target drug dose of 78.3 μg for each anticoagulant and 31.3 μg for Sirolimus, and SS10* arm was Sirolimus and anticoagulant Apixaban and Argatroban was 1:1:3) to poly(L-lactide acid-co-glycolic acid) by weight ratio was 5:2 matrix) according to the target drug dose of 39.2 μg for Apixaban and 117.5 μg for Argatroban and 31.3 μg for Sirolimus.

A microprocessor controlled ultrasonic sprayer was used to coat each of the stents 14 mm length uniformly with each of the drug/polymer matrix solution. After coating, the stents were placed in a 70° C. oven for about 2 hours to remove the solvent. The stents were then mounted on balloon catheters and crimped. The catheters were then inserted in coils and packaged. The pouches were sterilized.

The ex-vivo shunt model to evaluate thrombogenicity has been extensively employed to evaluate the biocompatibility of different drug eluting stents (Waksman et al. Circ Cardiovasc Interv. 2017; 10:e004762, Otsuka et al. J Am Coll Cardiol Intv 2015; 8:1248-60, Lipinski et al. EuroInterv 2018; Jaa-369 2018) The animals were housed and cared for in accordance with the Guide for the Care and Use of Laboratory Animals us established by the National Research Council.

Figure 8:
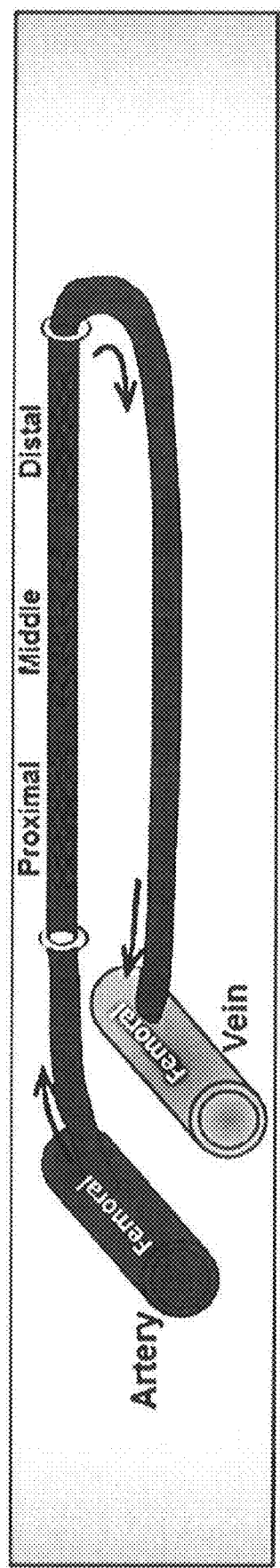
FIG. 8 shows a schematic illustration of an acute shunt model, in accordance with examples.

The two pigs that were employed in this study did not receive any aspirin or clopidogel pretreatment. Further all procedures were performed in the absence of any anticoagulant including heparin. After induction of anesthesia, an arterial bypass shunt from the femoral artery to the femoral vein was created. Schematic illustration of the acute shunt model is shown in FIG. 8. Blood flow was established through the shunt. Flow rates through the shunt was continuously monitored during the procedure with a flow probe that was placed on the shunt tubing proximal to the arterial flow.

In the first pig three control devices were deployed in the first shunt and the blood flow through the shunt was performed for a period of 1 hour. Following perfusion, the shunt tubing containing the stents was rinsed with saline and then fixed in situ with 10% buffered formalin in order to capture the thrombus, if any, that are deposited on the stent surface.

Similar procedure with 3 shunts with only one stem SS9* or SS9 in each shunt was tested with a perfusion time of 1 hour for each of the shunts.

In the second pig three control devices were deployed in the first shunt and the blood flow through the shunt was performed for a period of 1 hour. Following perfusion, the shunt tubing containing the stents was rinsed with saline and then fixed in situ with 10% buffered formalin in order to capture the thrombus, if any, that are deposited on the stent surface.

Similar procedure with 2 shunts with only one stem SS10* in each shunt was tested with a perfusion time of 1 hour for each of the shunts.

Promptly following perfusion in each of the shunts, the tubing containing the stents was gently rinsed with saline under gravity flow and then fixed in situ with 10% buffered formal in in order to anchor the thrombus, if any, that are deposited on the stein surface.

Figure 9:
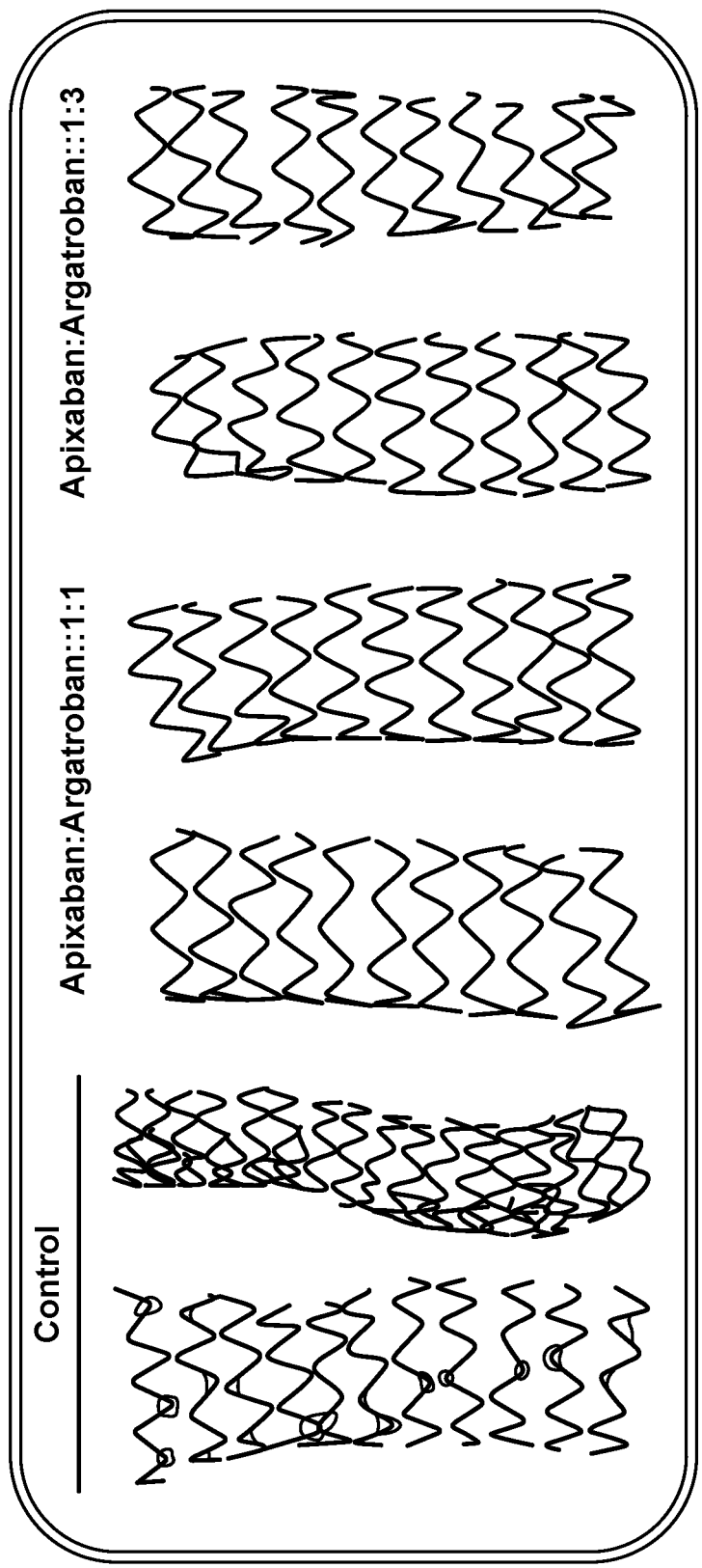
FIG. 9 shows low magnification images of a luminal surface of control stents (left) and test stents (middle and right), in accordance with examples.

The stents were then removed from the tubing and bisected longitudinally. Low magnification photographs of the luminal side of two halves of the control and test stents were recorded. Images of the luminal surface of the control and test stents following perfusion are shown in FIG. 9.

Figure 10:
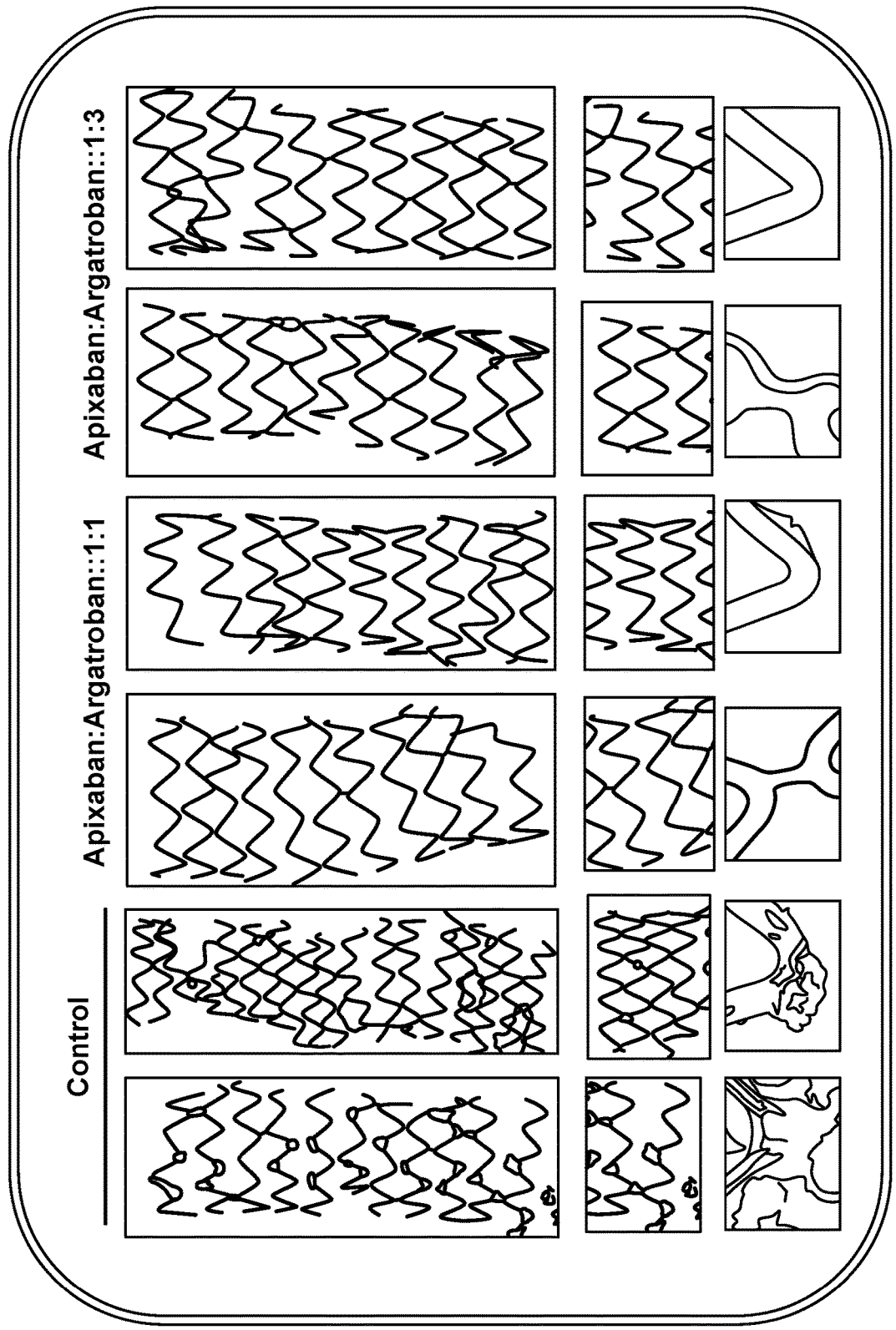
FIG. 10 shows low magnification (top and middle) and high magnification (bottom) SEM images of a luminal surface of control stents (left) and test stents (middle and right), in accordance with examples.

The two halves of the stents were then processed for scanning electron microscopy (SEM) so as to examine the thrombus on the luminal side of the stent. Low (15×) and high (200×) magnification images of the stem surface were captured to evaluate the extent of thrombus deposition on the luminal surface of the stmt. Low and high magnification SEM images of the luminal surface of the control and test stents are shown in FIG. 10.

Significant number of thrombus was observed on the luminal surface (inner surface) of the control DES stents as seen on the low and high magnification SEM images whereas there was little or no thrombus deposits on the test stents with combinations of Apixaban and Argatroban and m-TOR. The number of thrombus deposits on the control and test stents as evaluated from SEM images are shower in Table 6. The data shows that the combinations of Apixaban and argatroban and m-TOR inhibited thrombus formation in the shunt model better than control.

Table 6 shows several therapeutic compositions of factor Xa inhibitor, factor IIa, and M-tor inhibitor releasing steals had less thrombus (clot formation) compared to M-Tor inhibitor alone releasing stents.

The composition comprising a combination of factor Xa inhibitor, a factor 11 inhibitor and an anti-proliferative were surprisingly more effective than the anti-proliferative alone.

TABLE 6

Thrombus deposits on the control and test stents as evaluated from SEM images

| Animal # | Control/Test DES | Device | Number of Thrombus deposits |
|---|---|---|---|
| 1 | Control | DESyne-1 | 18 |
|  |  | DESyne-2 | 40 |
|  |  | Resolute | 14 |
|  | Test-Apixaban:Argatroban(1:1) | SS9* | 4 |
|  |  | SS9* | 0 |
|  |  | SS9 | 3 |
| 2 | Control | DESyne-1 | 17 |
|  |  | DESyne-2 | 17 |
|  |  | Resolute | 15 |
|  | Test-Apixaban:Argatroban(1:3) | SS10* | 2 |
|  |  | SS10* | 2 |

Example 9 Preparation of Anticoagulant or mTOR Inhibitors Coated Balloon

Rivaroxaban, Apixaban, Novolimus, or Rapamycin were dissolved into dichloromethane at room temperature and vortex until the drug was uniformly dissolved/dispersed; Ethylene Vinyl Acetate/Polyvinylpyrrolidone (MW=1.3M) was dissolved into 6.25% methanol in dichloromethane at room temperature and vortex until the polymer had uniformly dissolved/dispersed (100% Dichloromethane was used for Polyethylene oxide (MW=8M)).

Each polymer solution and each drug solutions were combined together (rivaroxaban to Ethylene vinyl acetate Polyvinylpyrrolidone (MW=1.3M) by weight ratio was 2:1:1 for SV300), (Apixaban to Polyethylene oxide (MW=8M)/Polyvinylpyrrolidone (MW=1.3M)/Butylated hydroxytoluene by weight ratio was 2/1/1/0.01 for VGR), (Novolimus to Ethylene vinyl acetate/Polyvinylpyrrolidone (MW=1.3M) by weight ratio was 2:1:1 NEV250 and NEV200), and (Rapamycin to Ethylene vinyl acetate/Polyvinylpyrrolidone (MW=1.3M) by weight ratio was 2:1:1 for REV200) according to the target drug dose of 300 µg for rivaroxaban in SV300, 800 µg for Apixaban in VGR, 250 mg for Novoliums in NEV250, 200 µg for Novoliums in NEV200 and 200 µg for Rapamycin in REV200.

A microprocessor controlled ultrasonic sprayer was used to coal each of the balloon 14 mm or 18 mm length uniformly (as shown in Table 7) with each of the drug/polymer matrix solutions. Balloons were inflated prior to coating and held by a rotating fixture. A rotational motor rotated the catheter and balloon 360 degrees while a mandrel and a clamp securely held the catheter tail in place and rotate. The coating parameter was adjusted to ideal coating texture and the morphology and the profile of the interface between drug and balloon surface. After coating, the balloons were placed in a vacuum chamber to remove the solvent. The balloons were then tri-folded before putting on the protective sheath. The balloon catheters were then inserted in coils and packaged. The pouches were sterilized.

Example 10: In Vivo Pharmacokinetics of Drug Eluting Balloon with Anticoagulant

The pharmacokinetics of the drug eluting balloon systems with anticoagulant of Example 9 were evaluated in porcine coronary/internal thoracic arteries in the non-diseased porcine coronary artery model. The balloon (e.g., the balloon of a balloon-catheter of a stent-delivery system) was advanced to a site to be treated (e.g., an occluded or weakened section of a blood vessel to be opened up or supported by a stent) in the body of a subject and inflated to a desired inflation diameter. Before, during, and/or after inflation of the balloon, the balloon released the therapeutic composition to, into, or at the treatment site, or to, into, or at an area adjacent thereto, by any suitable mechanism (e.g., concentration gradient, diffusion, pressure, or mechanical force, or a combination thereof). Safety of the device was evaluated at the 7- and 28-day time points following treatment in the coronary arteries and the tissue pharmacokinetics were evaluated following treatment in the coronary/thoracic arteries at the 7 and 28 day time points. Following treatment with the 14 mm length test drug coated balloon or the control plain balloon, an 18 mm length drug eluting balloon was deployed over the balloon treated segment of the coronary/thoracic artery. The tissue concentration is shown in ng/mg tissue.

The coated balloons were evaluated for drug delivery efficiency in an animal study. Drug transfer of the coated balloons into arterial segments were evaluated using harvested pig arteries. The arterial wall was separated after animal study. The arterial walls were then stored in an individual labeled vial. All samples were kept on dry ice until stored in the −80° C. freezer. All samples were then frozen to 70° C. prior to being analyzed. The tissue was extracted with Acetonitrile/methanol for Rivaroxaban, Apixaban, Novolimus and Rapamycin. The tissue content of Rivaroxaban, Apixaban, Novolimus and Rapamycin from the different drug coated balloon were analyzed using liquid chromatography mass spectroscopy (LCMS) with corresponding reference standards.

TABLE 7

Coated Balloon tissue concentration in vivo by different time period.

| Balloon type | Balloon Coating information | Artery type | Drug | Time period | Tissue concentration |
|---|---|---|---|---|---|
| SV300 18 mm Balloon | 300 µg Rivaroxaban in 150 µg Ethylene vinyl acetate and 150 µg Polyvinylpyrrolidone (MW = 1.3M) matrix | Coronary Artery | Rivaroxaban | 15 min | 1.23 ± 0.37 (n = 4) |
| | | Superficial Femoral Artery (SFA) | Rivaroxaban | 15 min | 40.58 ± 64.71 (n = 4) |
| VGR 14 mm Balloon | 800 µg Apixaban in 400 µg Polyethylene oxide (MW = 8M), 400 µg Polyvinylpyrrolidone (MW = 1.3M) and 4 µg Butylated hydroxytoluene matrix | Coronary Artery | Apixaban | Acute | 60.09 ± 80.49 (n = 2) |
| | | | | 1 D | 0.08 ± 0.08 (n = 3) |
| | | | | 7 D | 0.0001 ± 0.0001 (n = 3) |
| | | | | 28 D | 0.003 ± 0.005 (n = 3) |
| NEV250 18 mm Balloon | 250 µg Novolimus in 125 µg Ethylene vinyl acetate and 125 µg Polyvinylpyrrolidone (MW = 1.3M) matrix | Coronary Artery | Novolimus | 6 H | 6.52 ± 3.68 (n = 3) |
| | | | | 3 D | 3.77 ± 1.62 (n = 3) |
| | | | | 7 D | 1.47 ± 0.37 (n = 3) |
| | | Superficial Femoral Artery (SFA) | Novolimus | 6 H | 5.94 ± 3.66 (n = 4) |
| | | | | 3 D | 4.4 ± 1.95(n = 4) |
| | | | | 7 D | 1.16 ± 0.23 (n = 4) |
| NEV200 14 mm Balloon | 200 µg Novolimus in 100 µg Ethylene vinyl acetate and 100 µg Polyvinylpyrrolidone | Coronary Artery | Novolimus | 7 D | 0.60 ± 0.64(n = 7) |
| REV200 14 mm Balloon | 200 µg Rapamycin in 100 µg Ethylene vinyl acetate and 100 µg Polyvinylpyrrolidone | Coronary Artery | Rapamycin | 7 D | 1.45 ± 1.23(n = 8) |

As shown in Table 7, Rivaroxaban tissue concentration of tissue adjacent to the balloon treated segment ranges from at least 1.23 ng/mg within or at 15 min in coronary artery tissue to at least 40.58 ng/mg in Superficial Femoral Artery (SFA) tissue, within or at 15 minutes; Apixaban tissue concentration of tissue adjacent to the balloon treated segment in coronary artery tissue ranges from at least 60.09 ng/mg at acute to at least 0.08 ng/mg within or at 1 day to at least 0.0001 ng/mg within or at 7 days to at least 0.003 ng/mg within or at 28 days; Novolimus tissue concentration of tissue adjacent to the balloon treated segment in coronary artery tissue ranges from at least 6.52 ng/mg within or at 6 hours to at least 3.77 ng/mg within or at 3 day to at least 1.47 ng/mg within or at 7 days; Novolimus tissue concentration of tissue adjacent to the balloon treated segment in Superficial Femoral Artery (SFA) tissue ranges from at least 5.94 ng/mg within or at 6 hours to at least 4.4 ng/mg within or at 3 day to at least 1.16 ng/mg within or at 7 days; Rapamycin tissue concentration of tissue adjacent to the balloon treated segment in coronary artery tissue ranges from at least 1.45 ng/mg within or at 7 days. Rivaroxaban, Apixaban, Novolimus or Rapamycin released locally sufficiently from a coated balloon catheter to inhibit smooth muscle proliferation after vessel injury at sufficient tissue concentration up to 7 days.

Example 11: Preparation of Anticoagulant Eluting Value Implant or Part of the Implant not Covered by a Sleeve with Carrier A valve or valve repair implant or part of the implant comprising the valve is coated with a coating containing anticoagulant Apixaban or Rivaroxaban and Argatroban.

Poly (L-lactide acid-co-glycolic acid) polymer is dissolved into dichloromethane at room temperature and vortex until the polymer had uniformly dissolved/dispersed. Anticoagulant (Apixaban or Rivaroxaban & Argatroban) are placed in a vial and dissolved in dichloromethane/Methanol at room temperature and vortex until all the drug was uniformly dissolved/dispersed.

Each polymer solution and each drug solutions are combined together (anticoagulant (Apixaban or Rivaroxaban & Argatroban with weight ratio 1 to 1) to poly (L-lactide acid-co-glycolic acid) by weight ratio was 3:1) according to the target drug dose.

The valve, and/or valve repair implant, and/or at least part of the implant comprising the valve optionally undergo surface treatment if the surface is not porous (i.e. plasma treatment or other surface friction treatment).

A microprocessor controlled ultrasonic sprayer was used to coat the valve of the drug containing carrier solution to the entire surface of the implant or part of the surface. After coating, the implant is placed in a 70° C. oven for about 2 hours to remove the residue solvent. The transcatheter valve or valve repair implant is then mounted on the delivery catheter. The catheters is then inserted in coils and packaged. The pouches were sterilized.

Example 12: Preparation of Anticoagulant Eluting Value Implant or Part of the Implant Covered by a Sleeve with Carrier A valve or valve repair implant or part of the implant covered by a sleeve can have a polymer coating containing anticoagulant Apixaban or Rivaroxaban, Argatroban or a combination of both on top, part of, or adjacent to the sleeve made from ePTFE, Dacron, knitted or weaved fabric, or those known in the art.

The sleeve is infused with a polymer coating in a solvent solution with anticoagulant Apixaban or Rivaroxaban, Argatroban or a combination of both drugs and drug solution into the said sleeve and said solvent is allowed to evaporate leaving either polymer coating or drug in the pores of the sleeve. The sleeve is placed prior to being attached to the valve or valve repair implant or after it has been attached to the implant.

Poly (L-lactide acid-co-glycolic acid) polymer is dissolved into dichloromethane at room temperature and vortex until the polymer is uniformly dissolved/dispersed. Anticoagulant (Apixaban or Rivaroxaban & Argatroban) is placed in a vial and dissolved in dichloromethane/Methanol at room temperature and vortex until all the drug is uniformly dissolved/dispersed.

Each polymer solution and each drug solutions is combined together (anticoagulant (Apixaban or Rivaroxaban and Argatroban with weight ratio 1 to 1) to poly (L-lactide acid-co-glycolic acid) by weight ratio was 3:1) according to the target drug dose.

The sleeve optionally undergoes surface treatment if the surface is not porous (i.e. plasma treatment or other friction surface treatment). After surface treatment, the coating is spray coated or dip coated. The coating can be inside the sleeve or dipped onto the sleeve or coated on the sleeve.

When spray coated, a microprocessor controlled ultrasonic sprayer is used to coat the sleeve containing drug excipient solution to the entire surface of the implant. After coating, the sleeve is placed in a 70° C. oven for about 2 hours to remove the residue solvent. The sleeve is then attached to the valve or valve repair implant if not prior to being attached to the implant. The valve or valve repair implant with sleeve attached is then mounted on the delivery catheter. The transcatheter valve or valve repair device is then inserted in a coil and packaged. The pouches were sterilized.

Example 13: Preparation of Drug Eluting Stent Having Anticoagulant Argatroban Crosslinked with Poly N-(2-Hydroxypropyl) Methacrylamide by Ester Linker Example 13 includes methods for applying chemically crosslinked polymers and anticoagulant onto stent. The reactive polymer and anti-coagulant can be reacted and purified before making the coating solution or can be mixed together with initiator, then coated one layer for slow release of anticoagulant.

Figure 11:
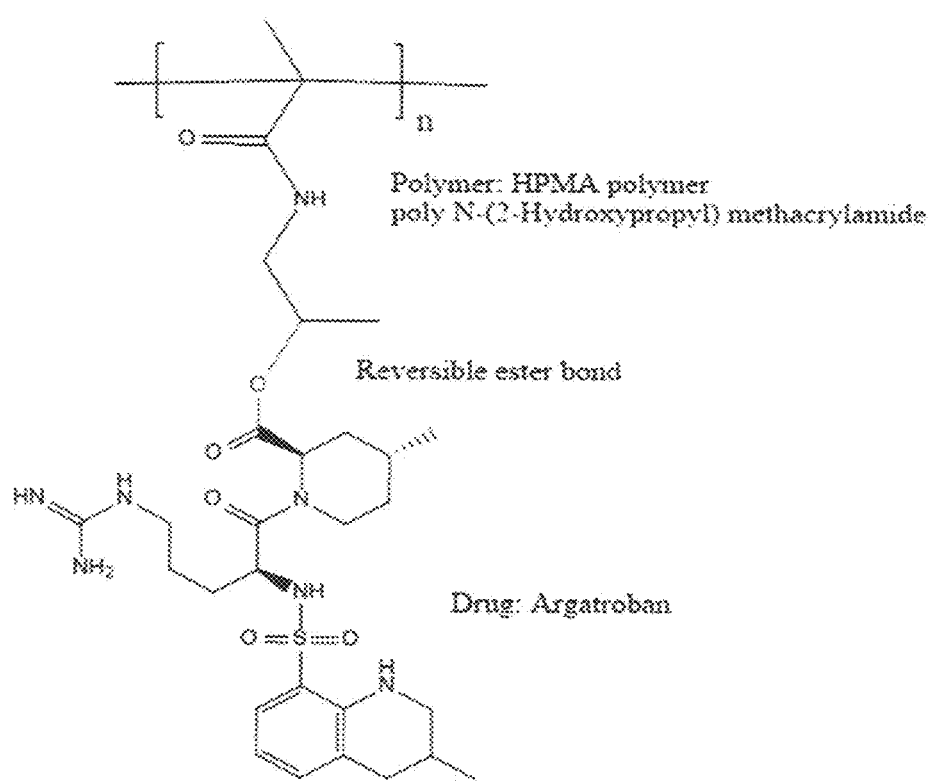
FIG. 11 shows a reaction scheme of Argatroban with poly N-(2-Hydroxypropyl) methacrylamide, in accordance with examples.

Anticoagulant (Apixaban or Rivaroxaban, Argatroban, Rivaroxaban etc.) is conjugated with biocompatible polymers via a reversible covalent bond, which can slowly release anticoagulant in a controlled manner. For example, argatroban is linked to poly N-(2-Hydroxypropyl) methacrylamide by a reversible ester bond as show in FIG. 11. When this ester bond is hydrolyzed, the drug (argatroban) is released.

Argatroban reacted with poly N-(2-Hydroxypropyl) methacrylamide is dissolved in THF. This polymer solution is air sprayed onto a stainless-steel coronary stent by a microprocessor controlled ultrasonic sprayer until a target weight achieved. After coating, the stents is placed in a 70° C.; oven for about 2 hours to remove the solvent. The stents are then mounted on balloon catheters and crimped. The catheters are then inserted in coils and packaged. The pouches are sterilized.

In Vivo, when Argatroban-poly N-(2-Hydroxypropyl) methacrylamide ester bond is hydrolyzed, the drug (argatroban) will be released.

Example 14: Preparation of Drug Eluting Stent Having Anticoagulant Argatroban Crosslinked with PAMAM-OH Dendrimer by Ester Linker PAMAM-OH dendrimer (generation 2) and Argatroban (1 to 1.2 mole ratio) are dissolved in THF, 4-Dimethylaminopyridine (DMAP) 1% was added as catalyst. The reaction mixture stirred overnight followed by purification. The purified Argatroban-PAMAM-OH dendrimer is dissolved in Tetrahydrofuran (THF). This polymer solution is air sprayed onto a stainless-steel coronary stem by a microprocessor controlled ultrasonic sprayer until a target weight achieved. After coating, the stents are placed in a 70° C. oven fix about 2 hours to remove the solvent. The stents are then mounted on balloon catheters and crimped. The catheters are then inserted in coils and packaged. The pouches were sterilized.

In Vivo, when Argatroban crosslinked with PAMAM-OH dendrimer ester bond is hydrolyzed, the drug (argatroban) will be released.

Example 15: Preparation of Drug Eluting Stent Having Anticoagulant and Polymer Microsphere Anticoagulant (Apixaban, Argatroban, Rivaroxaban etc.) are embodied within biocompatible materials (such as polymers, metals, ceramics, natural plant and/or animal materials). The polymers can be selected from polyesters (poly lactic acid, poly glycolic acid, Polyurethanes), Poly methyl methacrylate (PMMA), poly N-(2-Hydroxypropyl) methacrylamide, Polyethylenimine (PEI), dextran, dextrin, chitosans, poly(L-lysine), and poly(aspartamides), polyethylene, polypropylene, polyamides, Polyethylene glycol (PEG), Polytetrafluoroethylene (PTFE), Silicones, poly(anhydride), poly ortho esters etc. Anticoagulant (Apixaban, Argatroban. Rivaroxaban etc.) with polymers to form drug-polymer nano particles, microsphere, polymeric micelles as the polymer drug delivery systems, which can have high drug loading capacity in the hydrophobic core especially for hydrophobic drugs, and rapid cellular uptake facilitated by their nano-size characteristics.

0.5 mL of poly(D,L-lactide) dichloromethane solution (0.5% w/v) and anticoagulant (rivaroxaban, apixaban or argatroban) dichloromethane solution (0.5% w/v) are slowly added dropwise to polyvinyl alcohol water solution (5% w/w) with magnetic stirring at 1000-1500 rpm. These dispersions are continue stirred for 2 hours at 40° C. and 200 rpm until the microspheres are very small (ie less than 1 μm in diameter) to form colloids and therefore the suspension does not settle under gravity. This polymer-anticoagulant suspension is dip coated multiple times to the stem surface until target drug weight achieved. The stent is air dried first then the stents are placed in a 70° C. oven for about 4 hours to remove the solvent. The stents are then mounted on balloon catheters and crimped. The catheters are then inserted in coils and packaged. The pouches were sterilized.

Example 16: Preparation and Use of Anticoagulant-Impregnated Balloon

A balloon made of a biodegradable or non-degradable polymeric material (e.g., a nylon) and having openings (e.g., pores, holes, etc.) in the body and/or at the surface of the balloon is immersed in a mixture containing a fibrin/thrombus formation-inhibiting or fibrin/thrombus dissolution-promoting agent (e.g., an anticoagulant, such as rivaroxaban or a derivative thereof, or a fibrinolytic or thrombolytic agent, such as a plasminogen activator) and a solvent, and optionally another kind of bioactive agent (e.g., an anti-proliferative agent, such as rapamycin or a derivative thereof, or an anti-inflammatory agent). The balloon can optionally have one or more coatings comprising a fibrin/thrombus formation-inhibiting or fibrin/thrombus dissolution-promoting agent and/or another kind of bioactive agent and can optionally have a coating comprising no bioactive agent.

The balloon (e.g., the balloon of a balloon-catheter of a stent-delivery system) is advanced to a site to be treated (e.g., an occluded or weakened section of a blood vessel to be opened up or supported by a stent) in the body of a subject and is inflated to a desired inflation diameter. Before, during and/or after inflation of the balloon, the balloon releases the fibrin/thrombus formation-inhibiting or fibrin/thrombus dissolution-promoting agent and the optional other kind of bioactive agent (e.g., an anti-proliferative agent or an anti-inflammatory agent) to, into or at the treatment site, or to, into or at an area adjacent thereto, by any suitable mechanism (e.g., concentration gradient, diffusion, pressure or mechanical force, or a combination thereof).

Example 17: Preparation and Use of Anticoagulant-Coated Catheter

A first mixture containing a fibrin/thrombus formation-inhibiting or fibrin/thrombus dissolution-promoting agent (e.g., an anticoagulant, such as rivaroxaban or a derivative thereof, or a fibrinolytic or thrombolytic agent, such as a plasminogen activator) and a solvent, and optionally a biodegradable or non-degradable polymeric material and/or another kind of bioactive agent (e.g., an anti-proliferative agent, such as rapamycin or a derivative thereof, or an anti-inflammatory agent), is applied (e.g., by spraying or dipping) to a catheter made of a biodegradable or non-degradable polymeric material (e.g., a nylon or a polyether block amide, such as PEBAX®) to form a first coating on the catheter. The first coating can cover any surfaces (e.g., the exterior surface, any other surfaces or all surfaces) of the catheter.

Optionally, a second mixture containing another kind of bioactive agent (e.g., an anti-proliferative agent, such as rapamycin or a derivative thereof, or an anti-inflammatory agent) and a solvent, and optionally a biodegradable or non-degradable polymeric material and/or a fibrin/thrombus formation-inhibiting or fibrin/thrombus dissolution-promoting agent (e.g., an anticoagulant, such as rivaroxaban or a derivative thereof, or a fibrinolytic or thrombolytic agent, such as a plasminogen activator), is applied to the catheter (e.g., by spraying or dipping) to form a second coating on the catheter. The optional second coating can cover any surfaces (e.g., the exterior surface, any other surfaces or all surfaces) of the catheter. The first mixture and the optional second mixture can be applied to the catheter in any order.

Optionally, a third mixture containing a biodegradable or non-degradable polymeric material and a solvent is applied to the catheter (e.g., by spraying or dipping) to form a third coating over the first coating and the optional second coating. The optional third coating can be, e.g., a top layer or coat or a diffusion barrier that controls release of the fibrin thrombus formation-inhibiting or fibrin/thrombus dissolution-promoting agent and the optional other kind of bioactive agent from the first coating and the optional second coating. The optional third coating can cover the exterior surface or any other surfaces, or all surfaces, of the catheter.

The coated catheter is optionally heated to stabilize the coatings) and is placed in a container (e.g., a pouch) and sterilized (e.g., by exposure to e-beam radiation).

The catheter (e.g., the catheter of a stent-delivery system) is advanced to a site to be treated (e.g., an occluded or weakened section of a blood vessel to be opened up or supported by a stent) in the body of a subject. Before, while and/or after the catheter is positioned at the treatment site or at an area adjacent thereto, the catheter releases the fibrin/thrombus formation-inhibiting or fibrin/thrombus dissolution-promoting agent and the optional other kind of bioactive agent (e.g., an anti-proliferative agent or an anti-inflammatory agent) to, into or at the treatment site, or to, into or at an area adjacent thereto, by any suitable mechanism (e.g., concentration gradient, diffusion, pressure or mechanical force, or a combination thereof).

Example 18: Preparation and Use of Anticoagulant-Impregnated Catheter

A catheter (e.g., an infusion catheter) made of a biodegradable or non-degradable polymeric material (e.g., a nylon or a polyether block amide, such as PEBAX®) and having openings (e.g., pores, holes, etc.) in the body and/or at the surface of the catheter is immersed in a mixture containing a fibrin/thrombus formation-inhibiting or fibrin/thrombus dissolution-promoting agent (e.g., an anticoagulant, such as rivaroxaban or a derivative thereof, or a fibrinolytic or thombolytic agent, such as a plasminogen activator) and a solvent, and optionally another kind of bioactive agent (e.g., an anti-proliferative agent, such as rapamycin or a derivative thereof, or an anti-inflammatory agent). The catheter can optionally have one or more coatings comprising a fibrin/thrombus formation-inhibiting or fibrin/thrombus dissolution-promoting agent and/or another kind of bioactive agent, and can optionally have a coating comprising no bioactive agent, as described in Example 22.

The catheter (e.g., the catheter of a stent-delivery system) is advanced to a site to be treated (e.g., an occluded or weakened section of a blood vessel to be opened up or supported by a stent) in the body of a subject. Before, while and/or after the catheter is positioned at the treatment site or at an area adjacent thereto, the catheter releases the fibrin/thrombus formation-inhibiting or fibrin/thrombus dissolution-promoting agent and the optional other kind of bioactive agent (e.g., an anti-proliferative agent or an anti-inflammatory agent) to, into or at the treatment site, or to, into or at an area adjacent thereto, by any suitable mechanism (e.g., concentration gradient, diffusion, pressure or mechanical force, or a combination thereof).

Example 19: Preparation and Use of Anticoagulant-Coated Balloon-Catheter

A first mixture containing a fibrin/thrombus formation-inhibiting or fibrin/thrombus dissolution-promoting agent (e.g., an anticoagulant, such as rivaroxaban or a derivative thereof, or a fibrinolytic or thrombolytic agent, such as a plasminogen activator) and a solvent, and optionally a biodegradable or non-degradable polymeric material and/or another kind of bioactive agent (e.g., an anti-proliferative agent, such as rapamycin or a derivative thereof, or an anti-inflammatory agent), is applied (e.g., by spraying or dipping) to the balloon portion and/or the catheter portion of a balloon-catheter made of a biodegradable or non-degradable polymeric material (e.g., a nylon) to form a first coating on the balloon portion and/or the catheter portion. The first coating can cover any surfaces (e.g., the exterior surface, any other surfaces or all surfaces) of the balloon and/or the catheter.

Optionally, a second mixture containing another type of bioactive agent (e.g., an anti-proliferative agent, such as rapamycin or a derivative thereof, or an anti-inflammatory agent) and a solvent, and optionally a biodegradable or non-degradable polymeric material and/or a fibrin/thrombus formation-inhibiting or fibrin/thrombus dissolution-promoting agent (e.g., an anticoagulant, such as rivaroxaban or a derivative thereof, or a fibrinolytic or thrombolytic agent, such as a plasminogen activator), is applied to the balloon portion and/or the catheter portion (e.g., by spraying or dipping) to form a second coating on the balloon portion and/or the catheter portion. The optional second coating can cover any surfaces (e.g., the exterior surface, any other surfaces or all surfaces) of the balloon and/or the catheter. The first mixture and the optional second mixture can be applied to the balloon portion and/or the catheter portion in any order.

Optionally, a third mixture containing a biodegradable or non-degradable polymeric material and a solvent is applied to the balloon portion and/or the catheter portion (e.g., by spraying or dipping) to form a third coating over the first coating and the optional second coating. The optional third coating can be, e.g., a top layer or coat or a diffusion barrier that controls release of the fibrin thrombus formation-inhibiting or fibrin/thrombus dissolution-promoting agent and the optional other kind of bioactive agent from the first coating and the optional second coating. The optional third coating can cover the exterior surface or any other surfaces, or all surfaces, of the balloon and/or the catheter.

The coated balloon-catheter is optionally heated to stabilize the coating(s) and is placed in a container (e.g., a pouch) and sterilized (e.g., by exposure to e-beam radiation).

The balloon-catheter (e.g., the balloon-catheter of a stent-delivery system) is advanced to a site to be treated (e.g., an occluded or weakened section of a blood vessel to be opened up or supported by a stent) in the body of a subject, and the balloon is inflated to a desired inflation diameter. Before, during and/or after inflation of the balloon, the balloon portion and/or the catheter portion of the balloon-catheter releases the fibrin/thrombus formation-inhibiting or fibrin/thrombus dissolution-promoting agent and the optional other kind of bioactive agent (e.g., an anti-proliferative agent or an anti-inflammatory agent) to, into or at the treatment site, or to, into or at an area adjacent thereto, by any suitable mechanism (e.g., concentration gradient, diffusion, pressure or mechanical force, or a combination thereof).

Example 20: Preparation and Use of Anticoagulant-Impregnated Balloon-Catheter

The balloon portion and/or the catheter portion of a balloon-catheter (e.g., a weeping catheter) made of a biodegradable or non-degradable polymeric material (e.g., a nylon) and having openings (e.g., pores, holes, etc.) in the body and/or at the surface of the balloon and/or the catheter is immersed in a mixture containing a fibrin/thrombus formation-inhibiting or fibrin/thrombus dissolution-promoting agent (e.g., an anticoagulant, such as rivaroxaban or a derivative thereof, or a fibrinolytic or thrombolytic agent, such as a plasminogen activator) and a solvent, and optionally another type of bioactive agent (e.g., an anti-proliferative agent, such as rapamycin or a derivative thereof, or an anti-inflammatory agent). The balloon portion and/or the catheter portion of the balloon-catheter can optionally have one or more coatings comprising a fibrin/thrombus formation-inhibiting or fibrin/thrombus dissolution-promoting agent and/or another kind of bioactive agent, and can optionally have a coating comprising no bioactive agent, as described in Example 24.

The balloon-catheter (e.g., the balloon-catheter of a steno-delivery system) is advanced to a site to be treated (e.g., an occluded or weakened section of a blood vessel to be opened up or supported by a stem) in the body of a subject, and the balloon is inflated to a desired inflation diameter. Before, during and/or after inflation of the balloon, the balloon portion and/or the catheter portion of the balloon-catheter releases the fibrin/thrombus formation-inhibiting or fibrin/thrombus dissolution-promoting agent and the optional other kind of bioactive agent (e.g., an anti-proliferative agent or an anti-inflammatory agent) to, into or at the treatment site, or to, into or at an area adjacent thereto, by any suitable mechanism (e.g., concentration gradient, diffusion, pressure or mechanical force, or a combination thereof).

Example 21: Use of Anticoagulant-Delivering Infusion Catheter

An infusion catheter contains one or more lumens for delivering one or more drugs. The infusion catheter (e.g., the catheter of a stet-delivery system) is advanced to a site to be treated (e.g., an occluded or weakened section of a blood vessel to be opened up or supported by a stent) in the body of a subject. Before, while and/or after the catheter is positioned at the treatment site or at an area adjacent thereto, a first mixture containing a fibrin/thrombus formation-inhibiting or fibrin/thrombus dissolution-promoting agent (e.g., an anticoagulant, such as rivaroxaban or a derivative thereof, or a fibrinolytic or thrombolytic agent, such as a plasminogen activator) and a solvent (e.g., saline), and optionally another kind of bioactive agent (e.g., an anti-proliferative agent, such as rapamycin or a derivative thereof, or an anti-inflammatory agent), is injected through one or more drug-delivering lumens of the catheter. Before, while and/or after the catheter is positioned at the treatment site or at an area adjacent thereto, a second mixture containing another kind of bioactive agent (e.g., an anti-proliferative agent or an anti-inflammatory agent) and a solvent (e.g., saline), and optionally a fibrin/thrombus formation-inhibiting or fibrin/thrombus dissolution-promoting agent, optionally is injected through one or more drug-delivering lumens of the catheter. The catheter delivers the fibrin/thrombus formation-inhibiting or fibrin/thrombus dissolution-promoting agent and the optional other kind of bioactive agent (e.g., an anti-proliferative agent or an anti-inflammatory agent) to, into or at the treatment site, or to, into or at an area adjacent thereto.

Example 22: Preparation and Use of Anticoagulant-Coated Surgical Instrument

A surgical instrument (e.g., a cutting instrument, such as a knife) made of a biodegradable or non-degradable metal or metal alloy (e.g., stainless steel) optionally undergoes surface treatment (e.g., microblasting) to improve adhesion of a coating (e.g., a polymeric coating) to a metal surface.

A first mixture containing a fibrin/thrombus formation-inhibiting or fibrin thrombus dissolution-promoting agent (e.g., an anticoagulant, such as rivaroxaban or a derivative thereof, or a fibrinolytic or thrombolytic agent, such as a plasminogen activator) and a solvent, and optionally a biodegradable or non-degradable polymeric material and or another kind of bioactive agent (e.g., an anti-proliferative agent, such as rapamycin or a derivative thereof, or an anti-inflammatory agent), is applied to the surgical instrument (e.g., by dipping or spraying) to form a first coating on the surgical instrument. The first coating can cover the exterior surface, any other surfaces or all surfaces of the surgical instrument.

Optionally, a second mixture containing another kind of bioactive agent (e.g., an anti-proliferative agent, such as rapamycin or a derivative thereof, or an anti-inflammatory agent) and a solvent, and optionally a biodegradable or non-degradable polymeric material and/or a fibrin/thrombus formation-inhibiting or fibrin/thrombus dissolution-promoting agent (e.g., an anticoagulant, such as rivaroxaban or a derivative thereof, or a fibrinolytic or thrombolytic agent, such as a plasminogen activator), is applied to the surgical instrument (e.g., by dipping or spraying) to form a second coating on the surgical instrument. The optional second coating can cover the exterior surface, any other surfaces or all surfaces of the surgical instrument. The first mixture and the optional second mixture can be applied to the surgical instrument in any order.

Optionally, a third mixture containing a biodegradable or non-degradable polymeric material and a solvent is applied to the surgical instrument (e.g., by dipping or spraying) to form a third coating over the first coating and the optional second coating. The optional third coating can be, e.g., a top layer or coat or a diffusion barrier that controls release of the fibrin/thrombus formation-inhibiting or fibrin thrombus dissolution-promoting agent and the optional other kind of bioactive agent from the first coating and the optional second coating. The optional third coating can cover the exterior surface, any other surfaces or all surfaces of the surgical instrument.

The coated surgical instrument is optionally heated to stabilize the coating(s) and is placed in a container (e.g., a pouch) and sterilized (e.g., by exposure to e-beam radiation).

The surgical instrument (e.g., a cutting instrument, such as a knife) is advanced to a site in the body of a subject undergoing a surgery or intervention (e.g., a tissue to be cut or treated). Before, while and/or after the surgical instrument is positioned at the treatment site or at an area adjacent thereto, or before, while and/or after the surgical instrument contacts the tissue to be treated, the surgical instrument releases the fibrin/thrombus formation-inhibiting or fibrin/thrombus dissolution-promoting agent and the optional other kind of bioactive agent (e.g., an anti-proliferative agent or an anti-inflammatory agent) to, into or at the treatment site, or to, into or at an area adjacent thereto, by any suitable mechanism (e.g., concentration gradient, diffusion, pressure or mechanical force, or a combination thereof).

Example 23: Preparation and Use of Anticoagulant-Impregnated Surgical Instrument A surgical instrument made of a biodegradable or non-degradable metal or metal alloy (e.g., stainless steel) and having openings (e.g., pores, holes, etc.) in the body and/or at the surface of the surgical instrument is immersed in a mixture containing a fibrin/thrombus formation-inhibiting or fibrin/thrombus dissolution-promoting agent (e.g., an anti-coagulant, such us rivaroxaban or a derivative thereof, or a fibrinolytic or thrombolytic agent, such as a plasminogen activator) and a solvent, and optionally another kind of bioactive agent (e.g., an anti-proliferative agent, such as rapamycin or a derivative thereof, or an anti-inflammatory agent). The surgical instrument can optionally undergo surface treatment, can optionally have one or more coatings comprising a fibrin/thrombus formation-inhibiting or fibrin/thrombus dissolution-promoting agent and/or another kind of bioactive agent, and can optionally have a coating comprising no bioactive agent.

The surgical instrument (e.g., a cutting instrument, such as a knife) is advanced to a site in the body of a subject undergoing a surgery or intervention (e.g., a tissue to be cut or treated). Before, while and/or after the surgical instrument is positioned at the treatment site or at an area adjacent thereto, or before, while and/or after the surgical instrument contacts the tissue to be treated, the surgical instrument releases the fibrin/thrombus formation-inhibiting or fibrin/thrombus dissolution-promoting agent and the optional other kind of bioactive agent (e.g., an anti-proliferative agent or an anti-inflammatory agent) to, into or at the treatment site, or to, into or at an area adjacent thereto, by any suitable mechanism (e.g., concentration gradient, diffusion, pressure or mechanical force, or a combination thereof).

Example 24: Use of Anticoagulant-Delivering Infusion Surgical Instrument

An infusion surgical instrument [e.g., a cutting instrument (e.g., a knife) or an injection device (e.g., a needle)] contains one or more lumens for delivering one or more drugs. The surgical instrument is advanced to a site in or on the body of a subject undergoing a surgery or intervention (e.g., a tissue to be cut or treated). Before, while and/or after the surgical instrument is positioned at the treatment site or at an area adjacent thereto, or before, while and/or after the surgical instrument contacts the tissue to be treated, a first mixture containing a fibrin-thrombus formation-inhibiting or fibrin/thrombus dissolution-promoting agent (e.g., an anticoagulant, such as rivaroxaban or a derivative thereof, or a fibrinolytic or thrombolytic agent, such as a plasminogen activator) and a solvent (e.g., saline), and optionally another kind of bioactive agent (e.g., an anti-proliferative agent, such as rapamycin or a derivative thereof, or an anti-inflammatory agent), is injected through one or more drug-delivering lumens of the surgical instrument. Before, while and/or after the surgical instrument is positioned at the treatment site or at an area adjacent thereto, or before, while and/or after the surgical instrument contacts the tissue to be treated, a second mixture containing another kind of bioactive agent (e.g., an anti-proliferative agent or an anti-inflammatory agent) and a solvent (e.g., saline), and optionally a fibrin/thrombus formation-inhibiting or fibrin/thrombus dissolution-promoting agent, optionally is injected through one or more drug-delivering lumens of the surgical instrument. The surgical instrument delivers the fibrin/thrombus formation-inhibiting or fibrin/thrombus dissolution-promoting agent and the optional other kind of bioactive agent (e.g., an anti-proliferative agent or art anti-inflammatory agent) to, into or at the treatment site, or to, into or at an area adjacent thereto.

Example 25 Preparation of mTOR Inhibitors and/or Anticoagulant Coated Balloon with Excipient The balloon can optionally adopt carrier excipient to coat to facilitate drug transfer to the vessel wall and control release rate. A variety of carrier excipients and techniques can be used. The selected excipient could be contrast agent (i.e. iopromide), urea, dextrane, shellac, shelloic acid, keratosis (a naturally derived protein), Plasticizer (i.e. butyryl-tri-hexyl citrate, acetyl tributyl citrate, citrate ester, glycerol, other organic ester), hydrophilic space, Polyvinylpyrrolidone (PVP) and its hydrogels. Surfactants, Non-ionic surfactant Polysorbate/sorbitol (i.e. Tween20, Tween60 or Tween84), nordihydroguaiaretic acid (NDGA), hydrophobic excipient such as phospholipid, amphiphilic polymer such as Polyethylene glycol) (i.e PEG 8000), polyethylene oxide) (PEO) (molecular weight range from 100.000 to 10,000,000), Polyethylenimine (PEI) or polyaziridine linear or branched, amphiphilic block co-polymers composed of poly (ethylene oxide) (PEO) as the hydrophilic block and poly (ether)s, poly(amino acid)s), hydrophobic polymer space, biodegradable polymers such as Poly DL lactide-co-glycolide, Poly L Lactide-co-caprolactone, durable polymers, individually or combinations thereof.

A balloon made of a biodegradable or non-degradable polymeric material (e.g., a nylon) and having openings (e.g., pores, holes, etc.) in the body and/or at the surface of the balloon was used. The drug was selected from a mixture containing a mTOR inhibitors/Anticoagulant1/Anticoagulant2. The mTOR inhibitors was selected from Sirolimus, Novolimus, temsirolimus, zotarolimus and everolimus etc. The anticoagulants were selected from Apixaban, Argatraban, rivaroxaban or a derivative thereof, and/or a fibrinolytic or thrombolytic agent, such as a plasminogen activator) individually or combinations thereof. For example, Siroliums and Anticoagulant1/Anticoagulant2 (Apixaban and Argatroban) were placed in a vial and dissolved in dichloromethane or dichloromethane/Methanol combination at 2 to 10 mg/ml. The carrier excipient was dissolved in a proper solvent. The solution and drug solutions were combined at a target ratio of 3 to 1, 1 to 1, 2 to 1, or 1 to 3 ratios according to the target drug loading. Further dilution with dichloromethane was conducted if needed. Optionally anti-solvent was used to control the coating morphology of particles and drug release rate.

Optionally the balloon can undergo physical surface treatment before coated such that the surface has microspores, micro-holes, or chemical surface treatment before coated such that the balloon materials have photo-link or other chemical function group that can be reacted under UV or other techniques to easy coating. After surface treatment, the coating can be spray coat or dip coat or use other coating techniques (i.e. 3D printer).

The coating can optionally cover any surfaces (e.g., the exterior surface, any other surfaces or all surfaces) of the balloon. The coating solution can be homogeneous or non-homogeneous such as suspension or emulsions.

The coated balloon can optionally combine multi-strategies (e.g., electrospinning, plasma treatment. Layer-by-Layer Self-Assembly or a combination thereof) to form finely controlling structural, mechanical, and surface properties. With tuned coating techniques and solvent removal technique, the produces powder particles can be optionally homogenous, porous, and uniform in size and shape. The morphology of particles could be micro-crystalline, nanoparticles, Nano-encapsulated to provide release rate control.

When spray coat, a microprocessor controlled ultrasonic sprayer was used to apply the drug containing drug solution to cover any surface of a balloon. A mandrel was placed through catheter tips and underneath an ultrasonic spray nozzle (Micromist System with Ultrasonic Atomizing Nozzle Sprayer, Sono-Tek, N.Y.), which was rotating at 80 rpm and move longitudinally at a rate of 0.050 inches/ minutes. The coating parameter can optionally adjusted to ideal coating texture and the morphology and the profile of the interface between drug and balloon surface.

After coating, the balloon was placed in a vacuum chamber to remove the residue solvent. Optionally the coated balloon can be tri-folded to protect coated drug with a folded and/or wrapped balloon thereon to a pre-annealing step to induce a fold/wrap memory in the resulting pre-annealed balloon and/or coated balloon has a protector which need to peel off before use.

The balloon catheter was then inserted in a coil and packaged. The pouch was sterilized by Ethylene oxide or E-beam. The pouch was further packaged in a toil pouch with oxygen scavengers and nitrogen purge and vacuum sealed.

The balloon (e.g., the balloon of a balloon-catheter of a balloon-delivery system) was advanced to a site to be treated (e.g., an occluded or weakened section of a blood vessel to be opened up or supported by a balloon) in the body of a subject and was inflated to a desired inflation diameter. Before, during and/or after inflation of the balloon, the balloon releases the fibrin/thrombus formation-inhibiting or fibrin/thrombus dissolution-promoting agent and the optional other kind of bioactive agent (e.g., an anti-proliferative agent or an anti-inflammatory agent) to, into or at the treatment site, or to, into or at an area adjacent thereto, by any suitable mechanism (e.g., concentration gradient, diffusion, pressure or mechanical force, or a combination thereof).

Example 26: Preparation of Drug Coated Balloon Having Anticoagulant and Polymer Microsphere Anticoagulant (Apixaban, Argatroban, Rivaroxaban etc.) are embodied within biocompatible materials (such as polymers, metals, ceramics, albumin, liposome, natural plant and/or animal materials). The polymers can be selected from polyesters (poly lactic acid, poly glycolic acid, poly lactic acid-co-glycolic acid, poly lactic acid-co-caprolactone, poly ethylene glycol-block-poly caprolactone, Polyurethanes etc.), Poly methyl methacrylate (PMMA), poly N-(2-Hydroxypropyl) methacrylamide, Polyethylenimine (PEI), dextran, dextrin, chitosans, poly(L-lysine), and poly(aspartamides), polyethylene, polypropylene, polyamides. Polyethylene glycol (PEG), Silicones, poly(anhydride), poly ortho esters etc. Anticoagulant (Apixaban, Argatroban, Rivaroxaban etc.) with polymers to form drug-polymer nano particles, microsphere, polymeric micelles as the polymer drug delivery systems, which can have high drug loading capacity in the hydrophobic core especially for hydrophobic drugs, and rapid cellular uptake facilitated by their micro nano-size characteristics.

0.5 mL of poly(D,L-lactide) dichloromethane solution (0.5% w/v) and anticoagulant (rivaroxaban, apixaban or argatroban) dichlormethane solution (0.5% w/v) are slowly added dropwise to polyvinyl alcohol water solution (5% w/w) with magnetic stirring at 1000-1500 rpm. These dispersions are continue stirred for 2 hours at 40° C. and 200 rpm until the microspheres are very small (ie less than 1 μm in diameter) to form colloids and therefore the suspension does not settle under gravity. This polymer-anticoagulant suspension is dip coated multiple times to the balloon surface until target drug weight achieved. After coating, the balloons were air dried first then were placed in a vacuum chamber to remove the solvent. The balloons were then tri-fielded before putting on the protective sheath. The balloon catheters were then inserted in coils and packaged. The pouches were sterilized.

Example 27: Preparation of Drug Coated Balloon Having Anticoagulant and Polymer Self-Assembly Hollow Nanoparticles Anticoagulant (Apixaban, Argatroban, Rivaroxaban etc.) are monodispersed within hollow polymer nanoparticle. The polymers with molecular range from 100K to 10K (optimally from 40k to 20K) can be selected from block degradable polymers of poly lactic acid, poly glycolic acid, poly lactic acid-co-glycolic acid, poly lactic acid-co-caprolactone, poly ethylene glycol-block-poly caprolactone etc., or block non-degradable polymers selected from Polyvinylpyridine block with Poly methyl methacrylate (PMMA), poly N-(2-Hydroxypropyl) methacrylamide, Polyethylenimine (PEI), dextran, dextrin, chitosans, poly(L-lysine), and poly(aspartamides), polyamides, Polyethylene glycol (PEG), Silicones, poly(anhydride), poly ortho esters, polystyrene-b-polyvinylpyridine, poly(isoprene)-b-polyvinyl pyri dine), poly(vinyl pyridine)-b-poly(styrene)-b-polyvinyl pyridine), polystyrene)-b-polyvinyl pyridine)-b-poly(styrene), poly(styrene-b-poly(acrylic acid), poly(styrene)-b-poly(butadiene)-b-poly(vinyl pyridine), poly(styrene-b-poly (methacrylic acid), poly(styrene)-b-polyethylene oxide), poly(butadiene)-b-poly(acrylic acid), poly(butadiene)-b-poly(ethylene oxide), poly(vinyl pyridine)-b-poly(butadiene)-b-polyvinyl pyridine), poly(ethylene)-b-poly(ethylene oxide), and poly(styrene)-b-poly(vinyl pyridine)-b-poly (ethylene oxide) etc. Anticoagulant (Apixaban, Argatroban, Rivaroxaban etc.) with polymers to form drug-polymer nano particles as the polymer drug delivery systems, which can have high drug loading capacity in the hydrophobic core especially for hydrophobic drugs, and rapid cellular uptake facilitated by their nano-size characteristics.

Polyethylene glycol)-block-poly(4-vinyl pyridine) or poly(styrene)-block-poly(4-vinyl pyridine) or other poly(4-vinyl pyridine) block polymers is dissolved in DMF or 1,4-dioxane to prepare a solution of 5 mg/ml; this solution is added to solutions containing varied amount of Azo compounds in the same solvent (the monomer molar ratio of 4-vinyl pyridine:Azo compounds from 1:0.2 to 1:2). Azo compounds are selected from Metanil Yellow, Orange II sodium salt, 2,2'-Dihydroxyazobenzene,2-(4-Hydroxyphenylazo) benzoic acid,5-[(2-Carboxyphenyl) azo]-2-hydroxybenzoic acid, Olsalazine, 5-[(4-aminophenyl)azo]-2-hydroxy-Benzoic acid as hydrogen bonding agent for self-assembly. After stirring and reflux overnight, the self-assembly nanoparticles were collected by centrifuging. Using ethanol wash to remove hydrogen bonding agent results in monodisperse hollow nanoparticles with tunable hollow cavity size and internal surface reactivity. The resulting nanoparticles are redispersed in chloroform and mixed with anticoagulant (rivaroxaban, apixaban or argatroban) solution in the same solvent; the balloon can be coated with this solution by dip- or spin-coating method to the balloon surface until target drug weight achieved with anticoagulant (rivaroxaban, apixaban or argatroban) is hydrogen bonding with this hollow nanoparticle polymers.

After coating, the balloons were air dried first then were placed in a vacuum chamber to remove the solvent. The balloons were then tri-folded before putting on the protective sheath. The balloon catheters were then inserted in coils and packaged. The pouches were sterilized.

Example 28: Preparation of Drug Coated Balloon Having Colocalized Synergized Delivery of m-TOR and Paclitaxel Self-Assembly Hollow Nanoparticles m-TOR (sirolimus, biolimus, everolimus, myolimus, novolimus, ridaforolimus, temsirolimus, zotarolimus, or salts, isomers, solvates, analogs, derivatives, metabolites etc.) and paclitaxel are embodied within hollow polymer nanoparticles. The polymers with molecular range from 100K to 10K (optimally from 40k to 20K) can be selected from block degradable polymers of poly lactic acid, poly glycolic acid, poly lactic acid-co-glycolic acid, poly lactic acid-co-caprolactone, poly ethylene glycol-block-poly caprolactone etc., or block non-degradable polymers selected from Polyvinylpyridine block with Poly methyl methacrylate (PMMA), poly N-(2-Hydroxypropyl) methacrylamide, Polyethylenimine (PEI), dextran, dextrin, chitosans, poly(L-lysine), and poly(aspartamides), polyamides, Polyethylene glycol (PEG), Silicones, poly(anhydride), poly ortho esters, polystyrene-b-polyvinylpyridine, poly(isoprene)-b-polyvinyl pyridine), poly(vinyl pyridine)-b-poly (styrene)-b-poly(vinyl pyridine), polystyrene)-b-polyvinyl pyridine)-b-poly(styrene), polystyrene-b-poly(acrylic acid), poly(styrene)-b-poly(butadiene)-b-poly(vinyl pyridine), polystyrene-b-poly(methacrylic acid), poly(styrene)-b-poly (ethylene oxide), poly(butadiene)-b-poly(acrylic acid), poly (butadiene)-b-poly(ethylene oxide), poly(vinyl pyridine)-b-poly(butadiene)-b-polyvinyl pyridine), poly(ethylene)-b-polyethylene oxide), and poly(styrene)-b-poly(vinyl pyridine)-b-polyethylene oxide). M-TOR with paclitaxel and polymers to form drug-polymer nano particles as the polymer drug delivery systems, which can have high drug loading capacity in the hydrophobic core especially for hydrophobic drugs, and rapid cellular uptake facilitated by their nano-size characteristics.

Poly(ethylene glycol)-block-poly(4-vinyl pyridine) or poly(styrene)-block-poly(4-vinyl pyridine) or other poly(4-vinyl pyridine) block polymers is dissolved in DMF or 1,4-dioxane to prepare a solution of 5 mg/ml; this solution is added to solutions containing varied amount of Azo compounds in the same solvent (the monomer molar ratio of 4-vinyl pyridine:Azo compounds from 1:0.2 to 1:2). Azo compounds are selected from Metanil Yellow. Orange 11 sodium salt, 2,2'-Dihydroxyazobenzene,2-(4-Hydroxyphenylazo) benzoic acid,5-[(2-Carboxyphenyl) azo]-2-hydroxybenzoic acid, Olsalazine, 5-[(4-aminophenyl) azo]-2-hydroxy-Benzoic acid as hydrogen bonding agent. After stirring and reflux overnight, the nanoparticles were collected by centrifuging. Using ethanol wash to remove hydrogen bonding agent results in self-assembly monodisperse hollow nanoparticles with tunable hollow cavity size and internal surface reactivity. The resulting nanoparticles are redispersed in chloroform and mixed with m-TOR and paclitaxel (ranging from 3:1 to 1:3 by weight) solution in the same solvent; the balloon can be coated with this solution by dip- or spin-coating method to the balloon surface until target drug weight achieved with m-TOR and paclitaxel are hydrogen bonding with this self-assembly hollow nanoparticle.

After coating, the balloons were air dried first then were placed in a vacuum chamber to remove the solvent. The balloons were then tri-folded before putting on the protective sheath. The balloon catheters were then inserted in coils and packaged. The pouches were sterilized.

Example 29: Preparation of Anticoagulant and/or mTOR Coated Sleeve in a Covered Stent A stent covered by a sleeve can have a polymer coating containing anticoagulant and/or a combination with mTOR on top, part of, and/or adjacent to the sleeve made from polymer selected from non-degradable polymers such as polytetrafluoroethylene, fluorinated ethylene propylene, Dacron, polyethylene terephthalate, polyurethanes, polycarbonate, polypropylene, Pebax, polyethylene and biological polymers such as modified cellulose, collagen, fibrin, and elastin, and biodegradable polymer such as poly(alpha-hydroxy acid), poly-L-lactide (PLEA), poly-D-lactide (PDLA), polyglycolide (PGA), polydioxanone, polycaprolactone (PCL), polygluconate, polylactic acid-polyethylene oxide copolymers, poly(hydroxybutyrate), polyanhydride, polyphosphoester, or poly(aminoacides), knitted or weaved fabric material or film material which have been previously cast by brushing, dipping, electrospun or electrospray technique or other means onto the metallic bare or polymer stent, or those known in the art, which coated with anticoagulant and/or mTOR. The sleeve surface can be porous or non-porous.

The sleeve can be infused with a polymer coating in a solvent solution with anticoagulant such as Apixaban, Rivaroxaban, Argatroban or a combination with mTOR such as rapamycin, everolimus, biolimus, temsirolimus, ridaforolimus, zotarolimus, myolimus and novolimus drug solution into the said sleeve and said solvent can evaporate leaving either polymer coating or drug in the pores of the sleeve. This process also applicable to stent graft.

Poly (L-lactide acid-co-glycolic acid) polymer is dissolved into dichloromethane at room temperature and vortex until the polymer is uniformly dissolved/dispersed. Anticoagulant (Apixaban or Rivaroxaban & Argatroban) is placed in a vial and dissolved in dichloromethane/Methanol at room temperature and vortex until all the drug is uniformly dissolved-dispersed.

Each polymer solution and each drug solutions is combined anticoagulant (Apixaban of Rivaroxaban & Argatroban and/or mTOR with weight ratio 1 to 1 or other ratio) to poly (L-lactide acid-co-glycolic acid) by weight ratio was 3:1 or other ratio according to the target drug dose.

The sleeve can optionally undergo surface treatment if the surface is not porous (i.e. plasma treatment or other friction surface treatment). After surface treatment, the coating could be spray coated or dip coated. The coating can be inside the sleeve or dipped onto the sleeve or coated on the sleeve.

When spray coated, a microprocessor controlled ultrasonic sprayer is used to coat the sleeve containing drug/ excipient solution to the entire surface of the implant. After coating, the sleeve is placed in a 70° C. oven for about 2 hours to remove the residue solvent. The covered stent is then mounted on the delivery catheter and then is inserted in a coil and packaged. The pouches were sterilized.

When a feature or element is herein referred to us being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the present disclosure. For example, as used herein, the singular forms "a", "an" and "the" are intended to include the plural forms us well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below". "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature element from another feature/element. Thus, a first feature/element discussed below could be termed a second feature element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is ±0.1% of the stated value (or range of values), ±1% of the stated value (or range of values), ±2% of the stated value (or range of values), ±5% of the stated value tor range of values), ±10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. An implant comprising:
a structure for implantation in a patient's body comprising:
a first therapeutic composition comprising a first drug formulation including at least one drug selected from the group consisting of a direct factor IIa inhibitor and a direct factor Xa inhibitor; and
a second therapeutic composition comprising a second drug formulation including at least one drug selected from the group consisting of a direct factor IIa inhibitor and a direct factor Xa inhibitor;
wherein the first therapeutic composition is formulated for a rapid release of the first drug formulation into an implanted environment and the second therapeutic composition is formulated for an extended release of the second drug formulation into the implanted environment, and
wherein the second therapeutic composition is layered over a surface of the implantable structure and the first therapeutic composition is layered over at least a portion of the second therapeutic composition and wherein the first and second therapeutic compositions each comprise a polymer and wherein the first therapeutic composition has a first drug-to-polymer weight ratio and the second therapeutic composition has a second drug-to-polymer weight ratio, wherein the first drug-to-polymer weight ratio is in a range from 5:1 to 1:3.

2. The implant of claim 1, wherein the implantable structure comprises a metal or a polymer scaffold which is non-degradable in the implanted environment.

3. The implant of claim 1, wherein the implantable structure comprises a metal or polymer scaffold which is degradable in the implanted environment.

4. The implant of claim 1, wherein at least one of the first drug formulation and the second drug formulation comprises both a direct factor IIa inhibitor and a direct factor Xa inhibitor.

5. The implant of claim 4, wherein the first drug formulation and the second drug formulation each comprise both a direct factor IIa inhibitor and a direct factor Xa inhibitor.

6. The implant of claim 1, wherein the first drug formulation is configured to release the at least one drug at a mean rate in a range from 1 µg/day to 10 µg/hour over a first time period in a range from 3 hours to 28 days after implantation.

7. The implant of claim 1, wherein the second formulation is configured to release the at least one drug of the second formulation at a mean rate not exceeding 2 µg/hour over a 24-hour period following implantation.

8. The implant of claim 4, further comprising an anti-proliferative agent.

9. The implant of claim 5, further comprising an anti-proliferative agent.

10. The implant of claim 1, wherein the first therapeutic composition and the second therapeutic composition are configured to delay start of release of the second drug formulation for a time period after release of the first drug has started.

11. The implant of claim 10, wherein the first therapeutic composition is configured to dissolve over the time period to expose the second therapeutic composition and allow release of the second drug formulation.

12. The implant of claim 1, wherein a sacrificial layer is present over at least one of the first therapeutic composition and the second therapeutic composition or between the first therapeutic composition and the second therapeutic composition to delay release of one or more drugs from either or both of the first therapeutic composition and the second therapeutic compositions.

13. The implant of claim 1, wherein a diffusion-rate controlling layer is present over at least one of the first therapeutic composition and the second therapeutic composition or between the first therapeutic composition and the second therapeutic composition to control a release rate of one or more drugs from either or both of the first therapeutic composition and the second therapeutic compositions.

14. The implant of claim 1, wherein the polymer of the first and/or second therapeutic composition is degradable when implanted in a patient's body and configured to release the first and/or second drug formulation at least partly by dissolution of the polymer when exposed to the implanted environment.

15. The implant of claim 14, wherein the polymer of one of the therapeutic compositions dissolves at a faster rate than does the polymer of the other therapeutic composition in the implanted environment.

16. The implant of claim 8, wherein the polymer of the at least first and/or second therapeutic composition is non-degradable when implanted in the patient's body and configured to release the first and/or second drug formulation at least partly by a diffusion mechanism through the polymer when exposed to the implanted environment.

17. The implant of claim 1, wherein the polymer is configured to release the first and/or second drug formulation through a combination of dissolution of and diffusion through the polymer when exposed to the implanted environment.

18. The implant of claim 1, further comprising an anti-proliferative agent.

19. The implant of claim 8, 9 or 18, wherein the anti-proliferative agent is present in the first drug formulation, in the second drug formulation and/or a third therapeutic composition or any combination thereof, which composition(s) are formulated to release the anti-proliferative drug into an implanted environment when the structure is present in the implanted environment.

20. The implant of claim 1, wherein the first drug formulation and/or the second drug formulation comprises a direct factor IIa inhibitor and the direct factor IIa inhibitor comprises at least one of argatroban, dabigatran, ximelagatran, melagatran, efegatran, inogatran, atecegatran metoxil (AZD-0837), hirudin, bivalirudin, desirudin, and lepirudin.

21. The implant of claim 20, wherein the direct factor IIa inhibitor comprises argatroban, or a salt, isomer, solvate, derivative, metabolite, or prodrugs thereof.

22. The implant of claim 21, wherein the first drug formulation and/or the second drug formulation comprise a direct factor Xa inhibitor comprising at least one of apixaban, betrixaban, edoxaban, otamixaban, razaxaban, rivaroxaban, (r)-n-(2-(4-(1-methylpiperidin-4-yl)piperazin-1-yl)-2-oxo-1-phenylethyl)-1h-indole-6-carboxamide (LY-517717), daraxaban (YM-150), 2-[(7-carbamimidoylnaphthalen-2-yl)methyl-[4-(1-ethanimidoylpiperidin-4-yl)oxyphenyl] sulfamoyl] acetic acid (YM-466 or YM-60828), or eribaxaban (PD 0348292), carbamimidoyl-2-hydroxy-phenyl) 445-(2,6-dimethyl-piperidin-1-yl)-pentyl]-3-oxo-3,4-dihydro-quinoxaline-6-carboxylic acid (PD0313052).

23. The implant of claim 22, wherein the direct factor Xa inhibitor comprises apixaban, or a salt, isomer, solvate, derivative, metabolite, or prodrugs thereof or rivaroxaban, or a salt, isomer, solvate, derivative, metabolite, or prodrugs thereof.

24. The implant of claim 8, 9, or 18, wherein the anti-proliferative agent comprises an mTOR inhibitor selected from a group consisting of sirolimus, biolimus, everolimus, myolimus, novolimus, ridaforolimus, temsirolimus, zotarolimus, or salts, isomers, solvates, derivatives, metabolites, or prodrugs thereof.

25. The implant of claim 8, 9, or 18, wherein the anti-proliferative agent comprises sirolimus, or a salt, isomer, solvate, derivative, metabolite, or prodrugs thereof or paclitaxel, or a salt, isomer, solvate, derivative, metabolite, or prodrug thereof.

26. The implant of claim 8, 9, or 18, further comprising openings in one or more of the layers comprising a reservoir of one or more of the drugs and/or anti-proliferative agents present in the layer(s).

27. The implant of claim 1, wherein each of the first and second therapeutic compositions comprises the same polymer.

28. The implant of claim 1, further comprising a third composition comprising a layer which comprises a polymer and optionally one or more drugs.

29. An implant comprising:
an implantable structure having a surface configured to be expanded in the patient's vasculature;
a first therapeutic composition comprising a first drug formulation including at least argatroban and analogs thereof and a direct factor Xa inhibitor including at least one of (1) apixaban and (2) rivaroxaban configured to rapidly release the first drug formulation into a vascular environment; and
a second therapeutic composition comprising a second drug formulation including at least argatroban and a direct factor Xa inhibitor including at least one of (1) apixaban and (2) rivaroxaban in a polymer configured for extended release of the second drug formulation into the vascular environment;
wherein the second therapeutic composition is layered over the surface of the implantable structure and the first therapeutic composition is layered over the second therapeutic composition and
wherein the first and second therapeutic compositions each comprise a polymer and wherein the first therapeutic composition has a first drug-to-polymer weight ratio and the second therapeutic composition has a second drug-to-polymer weight ratio, wherein the first drug-to-polymer weight ratio is in a range from 5:1 to 1:3.

30. The implant of claim 1 or 29, wherein the polymer of the first therapeutic composition is degradable or non-degradable and the polymer of the second therapeutic composition is degradable or non-degradable.

31. The implant of claim 30, wherein the first and/or second therapeutic composition comprises a degradable polymer, said degradable polymer comprising one or more selected from the group consisting of polylactic acids, polyglycolic acids, polylactic acid-co-glycolic acids, polylactic acid-co-caprolactones, polyethylene glycol-block-poly caprolactone, dextran, dextrin, chitosans, poly(L-lysine), degradable poly(anhydrides), poly ortho esters, and copolymers and combinations thereof.

32. The implant of claim 30, wherein the first and/or second therapeutic composition comprises a non-degradable polymer, said non-degradable polymer comprising one or more selected from the group consisting of polyacrylates, polymethacrylates, poly(n-butyl methacrylate), poly(hydroxyethylmethacrylate), polyamides, nylons, nylon 12, dacron, polyethylene terephthalate, poly(ethylene glycol), polyethylene oxide (PEO), polyethylenimine (PEI), polydimethylsiloxane, polyvinylpyrrolidone, polyvinylpyridine block with poly methyl methacrylate (PMMA), ethylene-vinyl acetate, poly(styrene-block-isobutylene-block-styrene), phosphorylcholine-containing polymers, poly(2-methacryloyloxyethylphosphorylcholine), poly(2-methacryloyloxyethylphosphorylcholine-co-butyl methacrylate), poly(hexyl methacrylate)-co-vinyl pyrrolidone-co-vinyl acetate, and copolymers and combinations thereof.

33. The implant of claim 1, 4, 5, 8, 9, 18, or 29, further comprising an anti-platelet agent.

34. The implant of claim 1 or 29, wherein the polymers of the first and second therapeutic compositions comprise the same or different polymers and/or either the first, second, or both therapeutic compositions include one or more additional polymers.

35. The implant of claim 34, wherein the first and second therapeutic compositions have one or more additional drugs.

36. The implant of claim 1, 4, 5, 8, 9, or 29, wherein the first therapeutic compositions comprises more than one drug, wherein the drugs in the first therapeutic compositions have the same or different release rates.

37. The implant of claim 1, 4, 5, 8, 9, or 29, wherein the second therapeutic composition comprises more than one drug, wherein the drugs in the second therapeutic composition have the same or different release rates.

38. The implant of claim 1 or 29, wherein the first therapeutic composition is configured to release a bolus of at least one drug within 24 hours of exposure to an implant environment.

39. The implant of claim 1 or 29, wherein the first and/or second therapeutic compositions may comprises a carrier or other material to control the release of the one or more drugs, to facilitate the application of the compositions to the implant, and/or to protect the one or more drugs from washing out during deployment of the implant.

40. The implant of claim 39, wherein the carrier or other material comprises collagen, casein, keratosis, a polysaccharide, chitin, chitosan, dextran, starch, a microsphere, a nanosphere, and/or a hydrogel.

41. The implant of claim 28, wherein the first, second and/or third compositions optionally comprise a plurality of different release rates for at least one drug.

42. The implant of claim 1 or 29, further comprising additional layers, which optionally include a drug.

43. The implant of claim 1, 4, 5, 8, 9, 18, or 29, wherein the second drug-to-polymer weight ratio is in a range from 5:2 to 1:5.

44. The implant of claim 1, 4, 5, 8, 9, 18 or 29, wherein the implant contains three or more drugs optionally layered separately from each other.

45. The implant of claim 35, wherein when more than one drugs is contained in the first therapeutic composition, the drugs are mixed together and/or when more than one drugs is in the second therapeutic composition, the drugs are mixed together.

46. The implant of claim 1 or 29, further comprising an overlaying polymer layer optionally including one or more drugs.

47. The implant of claim 1 or 29, wherein the surface comprises one or more of an external surface, an inner surface, or a side surfaces of said structure.

48. The implant of claim 1 or 29, wherein the structure is expandable from a crimped configuration to an expanded configuration.

* * * * *

UNITED STATES PATENT AND TRADEMARK OFFICE
CERTIFICATE OF CORRECTION

PATENT NO. : 11,654,036 B2
APPLICATION NO. : 17/402357
DATED : May 23, 2023
INVENTOR(S) : John Yan et al.

It is certified that error appears in the above-identified patent and that said Letters Patent is hereby corrected as shown below:

In the Specification

Column 7, Line 31: Replace "argatraban" with "argatroban"
Column 7, Line 32: Replace "rivaroaxaban" with "rivaroxaban"
Column 7, Line 36: Replace "argatraban" with "argatroban"
Column 7, Line 36: Replace "rivaroaxaban" with "rivaroxaban"
Column 8, Line 1: Replace "argatraban" with "argatroban"
Column 8, Line 2: Replace "rivaroaxaban" with "rivaroxaban"
Column 8, Line 4: Replace "argatraban" with "argatroban"
Column 8, Line 5: Replace "rivaroaxaban" with "rivaroxaban"
Column 8, Line 8: Replace "argatraban" with "argatroban"
Column 8, Line 12: Replace "rivaroaxaban" with "rivaroxaban"
Column 8, Line 17: Replace "argatraban" with "argatroban"
Column 8, Line 20: Replace "rivaroaxaban" with "rivaroxaban"
Column 21, Line 2: Replace "stem-delivery" with "stent-delivery"
Column 21, Line 10: Replace "stem" with "stent"
Column 31, Line 61: Replace "stem-grafts" with "stent-grafts"
Column 32, Line 9: Replace "stmt" with "stent"
Column 33, Line 58: Replace "stem" with "stent"
Column 41, Line 63: Replace "stem-delivery" with "stent-delivery"
Column 59, Line 67: Replace "stem-delivery" with "stent-delivery"
Column 60, Line 1: Replace "stem-grafts" with "stent-grafts"
Column 60, Line 20: Replace "stmt" with "stent"
Column 66, Line 60: Replace "stem-grafts" with "stent-grafts"
Column 77, Line 17: Replace "stem" with "stent"
Column 78, Line 10: Replace "stem" with "stent"
Column 78, Line 11: Replace "stmt" with "stent"
Column 80, Line 67: Replace "stem" with "stent"
Column 94, Line 15: Replace "stem" with "stent"
Column 94, Line 52: Replace "stem" with "stent"

Signed and Sealed this
Twenty-fourth Day of October, 2023

Katherine Kelly Vidal
*Director of the United States Patent and Trademark Office*

CERTIFICATE OF CORRECTION (continued)
U.S. Pat. No. 11,654,036 B2

Column 94, Line 58: Replace "stem-delivery" with "stent-delivery"
Column 107, Line 26: Replace "stem" with "stent"
Column 107, Line 27: Replace "stem" with "stent"
Column 107, Line 41: Replace "stem" with "stent"
Column 107, Line 50: Replace "stmt" with "stent"
Column 107, Line 58: Replace "stem" with "stent"
Table 2 between Columns 113 and 114: Replace 4 instances of "Rivaroxban" with "Rivaroxaban"
Column 115, Line 51: Replace "stem" with "stent"
Column 132, Line 50: Replace "stem" with "stent"
Column 132, Line 52: Replace "stem" with "stent"
Column 140, Line 36: Replace "Apxaban" with "Apixaban"
Column 140, Line 62: Replace "stem" with "stent"
Column 141, Line 4: Replace "stem" with "stent"
Column 141, Line 55: Replace "stem" with "stent"
Column 141, Line 65: Replace "stem" with "stent"
Column 142, Line 14: Replace "stem" with "stent"
Column 142, Line 16: Replace "stmt" with "stent"
Column 147, Line 17: Replace "stem" with "stent"
Column 147, Line 56: Replace "stem" with "stent"
Column 151, Line 12: Replace "stem" with "stent"
Column 162, Line 26: Replace "Ha" with "IIa"
Column 110, Line 44: Replace "stem" with "stent"
Column 110, Line 48: Replace "stem" with "stent"
Column 111, Line 38: Replace "stems" with "stents"
Column 112, Line 37: Replace "stem" with "stent"
Column 115, Line 39: Replace "stem" with "stent"
Column 140, Line 46: Replace "argatraban" with "argatroban"
Column 154, Line 25: Replace "argatraban" with "argatroban"